(12) United States Patent
Jiang et al.

(10) Patent No.: US 11,686,190 B2
(45) Date of Patent: Jun. 27, 2023

(54) 4D QUANTITATIVE AND INTELLIGENT DIAGNOSIS METHOD AND SYSTEM FOR SPATIO-TEMPORAL EVOLUTION OF OIL-GAS RESERVOIR DAMAGE TYPES AND EXTENT

(71) Applicants: China University of Petroleum (Beijing), Beijing (CN); CNPC Chuanqing Drilling Engineering Company Limited, Chengdu (CN); CNPC ENGINEERING TECHNOLOGY R&D COMPANY LIMITED, Beijing (CN)

(72) Inventors: Guancheng Jiang, Beijing (CN); Yinbo He, Beijing (CN); Tengfei Dong, Beijing (CN); Chunyao Peng, Beijing (CN); Lili Yang, Beijing (CN); Xiaohu Luo, Beijing (CN); Xuwu Luo, Karamay (CN); Xing Liang, Beijing (CN); Bin Tan, Beijing (CN); Yong Wang, Beijing (CN); Daqi Fu, Beijing (CN); Tie Geng, Beijing (CN); Qihua Ran, Chengdu (CN); Xiaobo Liu, Beijing (CN); Rongchao Cheng, Beijing (CN); Zenglin Wang, Dongying (CN); Gang Chen, Dongying (CN); Honghao Zhu, Beijing (CN); Yizheng Li, Beijing (CN); Li Zhao, Karamay (CN); Kaixiao Cui, Beijing (CN)

(73) Assignees: China University of Petroleum (Beijing), Beijing (CN); CNPC Chuanqing Drilling Engineering Company Limited, Chengdu (CN); CNPC ENGINEERING TECHNOLOGY R&D COMPANY LIMITED, Beijing (CN)

( * ) Notice: Subject to any disclaimer, the term of this patent is extended or adjusted under 35 U.S.C. 154(b) by 0 days.

(21) Appl. No.: 17/864,224

(22) Filed: Jul. 13, 2022

(65) Prior Publication Data
US 2023/0026538 A1 Jan. 26, 2023

Related U.S. Application Data

(63) Continuation of application No. PCT/CN2021/114851, filed on Aug. 26, 2021.

(30) Foreign Application Priority Data

Aug. 26, 2020 (CN) .......................... 202010873143.9

(51) Int. Cl.
*G01N 11/00* (2006.01)
*E21B 47/00* (2012.01)
(Continued)

(52) U.S. Cl.
CPC ............ *E21B 47/006* (2020.05); *E21B 43/20* (2013.01); *E21B 47/06* (2013.01); *G01N 11/00* (2013.01);
(Continued)

(58) Field of Classification Search
CPC ........ E21B 47/006; E21B 47/06; E21B 43/20; E21B 2200/20; E21B 49/00; G01N 11/00;
(Continued)

(56) References Cited

FOREIGN PATENT DOCUMENTS

CN 103806904 A 5/2014
CN 105181927 A 12/2015
(Continued)

OTHER PUBLICATIONS

Zou et al., Investigating Reservoir Pressure Transmission for Three Types of Coalbed Methane Reservoirs in the Qinshui Basin in Shan'xi Province, China, 2013, Petroleum Geoscience, vol. 19, pp. 375-383 (Year: 2013).*

(Continued)

Primary Examiner — Toan M Le
(74) *Attorney, Agent, or Firm* — Calfee Halter & Griswold LLP

(57) ABSTRACT

A 4D quantitative and intelligent diagnosis method for spatio-temporal evolution of oil-gas reservoir damage types and extent includes: determining a characteristic parameter characterizing reservoir damage by each of a plurality of factors based on a spatio-temporal evolution simulation equation of reservoir damage by each of the plurality of factors; and determining an effective characteristic parameter characterizing the damage extent of the reservoir based on the characteristic parameter characterizing reservoir damage by each of the plurality of factors. The method quantitatively simulate the characteristic parameters of reservoir damage caused by the various factors and a total characteristic parameter of the reservoir damage.

17 Claims, 40 Drawing Sheets

(51) Int. Cl.
    *E21B 43/20* (2006.01)
    *E21B 47/06* (2012.01)
    *G01N 13/00* (2006.01)
    *G01N 15/08* (2006.01)
(52) U.S. Cl.
    CPC ......... *G01N 13/00* (2013.01); *G01N 15/0826* (2013.01); *E21B 2200/20* (2020.05); *G01N 2011/0093* (2013.01); *G01N 2013/003* (2013.01)

(58) Field of Classification Search
    CPC .............. G01N 13/00; G01N 15/0826; G01N 2011/0093; G01N 2013/003; G16C 10/00; G06F 2111/10; G06F 2113/08; G06F 30/20
    See application file for complete search history.

(56) References Cited

FOREIGN PATENT DOCUMENTS

| | | |
|---|---|---|
| CN | 108240955 A | 7/2018 |
| CN | 108804779 A | 11/2018 |
| CN | 109594982 A | 4/2019 |
| CN | 109946436 A | 6/2019 |
| CN | 110376112 A | 10/2019 |

OTHER PUBLICATIONS

English Translation of International Search Report from PCT/CN2021/114851 dated Oct. 28, 2021 (3 pages).
Jiang et al. Quantitative Prediction Method of Water Blocking Damage in Low and Extra-Low Permeability Reservoir) Petroleum Drilling Techniques, vol. 40, No. 1, Jan. 31, 2012, p. 69-73 (English Abstract).
Wang et al. Mathematical Models Forecasting the Formation Impairment Induced FR-OM Drilling Fluid Drilling & Production Technology Dec. 31, 2002 , pp. 6 and 80-83 (English Abstract).
Yi et al. Numerical Simulation of Reservoir Damage by Oil/Water Emulsification Based on Hydrodynamic Instability[J]. Drilling Fluid & Completion Fluid, 2017, 34(6): pp. 22-128. doi: 10.3969/j.issn.1001-5620.2017.06.02 with English abstract.
Li et al., A review of the current status of induced seismicity monitoring for hydraulic fracturing in unconventional tight oil and gas reservoirs, Fuel, vol. 242, 2019, pp. 195-210.

\* cited by examiner

4D QUANTITATIVE AND INTELLIGENT DIAGNOSIS METHOD AND SYSTEM FOR SPATIO-TEMPORAL EVOLUTION OF OIL-GAS RESERVOIR DAMAGE TYPES AND EXTENT

CROSS REFERENCE TO RELATED APPLICATIONS

This application is a bypass continuation of PCT/CN2021/114851, filed Aug. 26, 2021, which claims benefits of Chinese patent application 202010873143.9 filed on Aug. 26, 2020, which is hereby incorporated by reference in its entirety.

FIELD OF THE INVENTION

The present invention relates to the technical field of oilfield exploration, in particular to a 4D quantitative and intelligent diagnosis method and system for spatio-temporal evolution of oil-gas reservoir damage types and extent.

BACKGROUND OF THE INVENTION

In various stages of oilfield exploration and development, due to the influence of a variety of internal and external factors, the original physical, chemical, thermodynamic and hydrodynamic equilibrium of a reservoir change, which inevitably causes a reduction in reservoir internal permeability in regions close to a well wall and even regions far from the well wall of the reservoir to clog flowing of fluid so as to cause reservoir damage and a well production decline, or even "kill" the reservoir, such that an oil-gas well produces no oil or gas. The causes of reservoir damage are diverse and complex. Especially during production, a storage-permeability space, surface wettability, a hydrodynamic field, a temperature field, rock types, etc. of reservoir rock continuously change, such that the damage mechanism changes over time, and the damage lasts for a long period and covers a wide range, and is more complex and superimposed. Once reservoir damage occurs, corresponding declogging measures must be taken according to reservoir damage to restore fluid flow channels, so as to increase oil-gas well production and water well injection capacity.

Usually, there are various causes and types of oil-gas reservoir damage, and multiple types of damage coexist, each type causing a different extent of oil-gas reservoir damage. It is very difficult but very important to determine which types (several or more than a dozen types) on earth lead to the oil-gas reservoir damage, the damage extent caused by each damage type or a contribution rate of each damage type to a total damage extent, a damaged zone radius and a total damaged zone radius due to each damage type, a spatio-temporal evolution law of oil-gas reservoir damage by each damage type, etc. It is indispensable not only for avoiding the occurrence of oil-gas reservoir damage for wells in normal production to increase production (or injection capacity), taking unclogging measures for wells that have stopped production to restore production, and taking protective measures for wells facing stop of production to extend the production life, but also for improving the precision of numerical simulation of oil pools and accurately predicting "sweet spots", etc. It is of great significance not only for strong theoretical significance, but also for a high practical value.

Currently, methods for diagnosing reservoir damage can be divided into field diagnostic methods and indoor evaluation methods. The field diagnostic methods include a well testing method. Although the well testing method can quantitatively provide important parameters such as skin factor, clogging ratio, and additional pressure drop that characterize a damage extent of a reservoir in a preset region of a well to be diagnosed, the skin factor characterized thereby is associated with other parameters. In other words, the skin factor obtained by the well testing method not only reflects a true reservoir damage characteristic, but is also an overall manifestation of various aspects and factors (i.e., it is the sum of a true damage skin factor and a pseudo-skin factor composed of a well deviation skin factor, a reservoir shape skin factor, a partial penetration skin factor, a non-Darcy flow skin factor, a perforation skin factor and the like), and the skin factor must be decomposed to obtain the true damage skin factor. The indoor evaluation method includes a core flow test method. The core flow test method uses a permeability change before and after core displacement to get a damage extent, and is suitable for studying reservoir damage by single-factor, but it is difficult to reflect reservoir damage laws on a larger scale. Moreover, as indoor core experiment conditions are idealized, cores used for evaluation are in an original state, and dynamic changes of reservoir properties cannot be taken into account, experimental results differ greatly from the real damage of the downhole reservoir. That is to say, so far, researches in China and other countries for decades have not achieved accurate quantitative and rapid diagnosis on reservoir damage causes, types and extent, not to mention spatio-temporal evolution diagnosis, which has become a key and major difficult problem at core of the strategy of "increasing reserves and production" in the international arena.

SUMMARY OF THE INVENTION

An objective of the present invention is to provided a 4D quantitative and intelligent diagnosis method and system for spatio-temporal evolution of oil-gas reservoir damage types and extent, which can quantitatively simulate characteristic parameters of reservoir damage caused by relevant factors and a total characteristic parameter of the reservoir damage, so that the oil-gas reservoir damage of an oil-gas production well or an injection well in various stages or aspects of exploration and development is "transparent, digitized, dynamic, visualized and intelligentized" in the spatial and temporal domains, and an experience of being personally on the scene is achieved, thereby, for a well without reservoir damage, performing quantitative prediction of reservoir damage and spatio-temporal deduction of damage laws, which is of scientific guidance significance for preventing or avoiding reservoir damage, and formulating development plans for oil pools and subsequent well stimulation measures, and for a well with reservoir damage, also performing quantitative diagnosis of reservoir damage and spatio-temporal deduction of damage laws, which is of very great significance for achieving optimal design of a declogging measure and improvement or restoration of oil-gas well production and water well injection capacity. Therefore, this makes the present invention be an indispensable technology in exploration and development of oil-gas pools.

To achieve the above objective, in a first aspect, the present invention provides a method for determining a damage extent of a reservoir, including: based on a spatio-temporal evolution simulation equation of reservoir damage by each of a plurality of factors, determining a characteristic parameter characterizing reservoir damage by each of the plurality of factors, wherein the reservoir is located in a preset region of a well to be diagnosed; and determining an effective characteristic parameter characterizing the damage extent of the reservoir based on the characteristic parameter characterizing reservoir damage by each of the plurality of factors.

By adopting the above technical solution, according to the present invention based on the spatio-temporal evolution simulation equation of reservoir damage by each of the plurality of factors, a characteristic parameter characterizing reservoir damage by each of the plurality of factors are creatively determined; and the effective characteristic parameter characterizing the damage extent of the reservoir is determined based on the characteristic parameter characterizing reservoir damage by each of the plurality of factors. Thus, by using the spatio-temporal evolution simulation equations of reservoir damage by the relevant factors, the characteristic parameters (such as permeability) of reservoir damage caused by the factors respectively and a total characteristic parameter (such as total permeability or effective permeability) of reservoir damage caused by the plurality of relevant factors can be quantitatively simulated. Therefore performing quantitative prediction of reservoir damage and spatio-temporal deduction of damage laws of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

In a second aspect, the present invention further provides a system for determining a damage extent of a reservoir, including: a first parameter determination device configured to, based on a spatio-temporal evolution simulation equation of reservoir damage by each of a plurality of factors, determine a characteristic parameter characterizing reservoir damage by each of the plurality of factors, wherein the reservoir is located in a preset region of a well to be diagnosed; and a second parameter determination device configured to determine an effective characteristic parameter characterizing the damage extent of the reservoir based on the characteristic parameter characterizing reservoir damage by each of the plurality of factors.

The system for determining the damage extent of the reservoir has the same advantages as the above method for determining the damage extent of the reservoir with respect to the prior art, which will not be described in detail here.

Correspondingly, in a third aspect, the present invention further provides a machine-readable storage medium that stores instructions which are configured to cause a machine to execute the method for determining a damage extent of a reservoir.

Other features and advantages of embodiments of the present invention will be described in detail in the subsequent section of detailed description of the embodiments.

BRIEF DESCRIPTION OF DRAWINGS

The accompanying drawings are used to provide further understanding of the embodiments of the present invention and form part of the specification, and are used, together with the following detailed description of the embodiments, for explaining the embodiments of the present invention, but do not limit the embodiments of the present invention. In the drawings.

DETAILED DESCRIPTION OF THE EMBODIMENTS

The specific implementations of the present invention will be described in detail below with reference to the accompanying drawings. It should be understood that the specific implementations described here are only used for illustrating and explaining the present invention, instead of limiting the present invention.

During development of an oilfield, different types of reservoir damage are produced by various reasons, resulting in lower production or even shutdown of oil wells and reduction of water injection capacity of water wells to cause huge economic losses to the oilfield. Implementing declogging on a damaged reservoir is an important measure to increase the production and improve the recovery ratio. However, an optimized decision of the declogging measure must be based on quantitative diagnosis of a reservoir damage type and extent. Due to a long period and a wide range of the reservoir damage during oilfield development, and more complexity and superimposition of the damage, the diagnosis of the reservoir damage is more difficult, so far, there is a lack of diagnosis methods and technology with high accuracy and practicality at home and abroad, so it is impossible to quantitatively diagnose the proportion of each damage type in a total damage extent of a well to be diagnosed, and even more impossible to achieve quantitative simulation of spatio-temporal evolution.

For the complex mechanism and relevant parameters that influence characteristic parameters such as permeability of a reservoir in a region around the well to be diagnosed, embodiments (e.g., embodiments 1-13) of the present invention creatively provide spatio-temporal evolution simulation equations that quantitatively simulate reservoir damage by relevant factors (factor 1—extraneous solid-phase particles, factor 2—clay swelling, factor 3—inorganic precipitation, factor 4—the migration of fine particle within a reservoir, factor 5—water lock effect, factor 6—stress sensitivity, factor 7—sand production, factor 8—wettability reversal, factor 9—emulsification, factor 10—organic scale, factor 11—Jamin effect, factor 12—bacteria, and factor 13—polymer), then the parameters such as the permeability of the reservoir damaged by the corresponding factors can be determined quantitatively by using the various spatio-temporal evolution simulation equations, and finally the total damage extent of the well to be diagnosed in different time and space and contributions of each relevant factor to the total damage extent can be determined in conjunction with the principle of superposition.

Figure 1A:
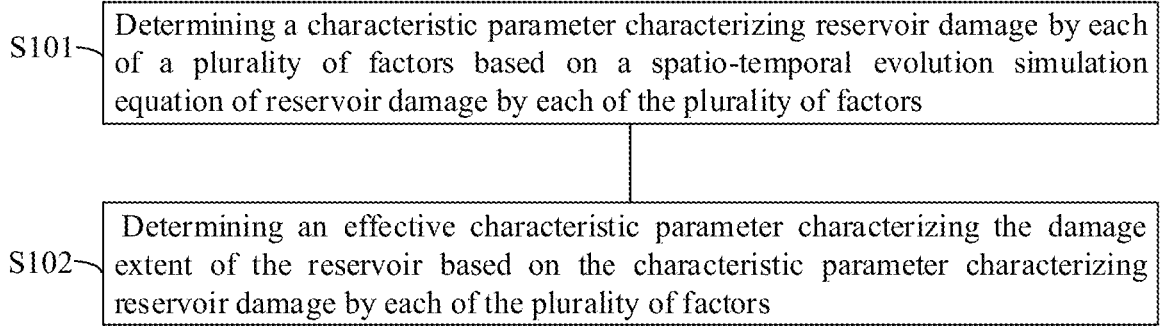
FIG. 1A is a flow diagram of a method for determining a damage extent of a reservoir provided in an embodiment of the present invention.

FIG. 1A is a flow diagram of a method for determining a damage extent of a reservoir provided in an embodiment of the present invention. As shown in FIG. 1A, the method may include: step S101, determining a characteristic parameter characterizing reservoir damage by each of a plurality of factors based on a spatio-temporal evolution simulation equation of reservoir damage by each of the plurality of factors, wherein the reservoir is located in a preset region of a well to be diagnosed; and step S102, determining an effective characteristic parameter characterizing the damage extent of the reservoir based on the characteristic parameter characterizing reservoir damage by each of the plurality of factors.

Specifically, for different types of wells to be diagnosed, factors that influence the permeability and other characteristic parameters of reservoirs in regions around the different types of wells to be diagnosed are obviously different, as shown in Table 1; and for the same type of wells to be diagnosed, relevant factors that influence the permeability and other characteristic parameters of reservoirs in regions around the same type of wells to be diagnosed in different development stages (e.g., a drilling stage, a water injection/a polymer injection stage, and an oil production stage) are also obviously different, as shown in Table 1. That is, the plurality of factors are different for different types of wells to be diagnosed; and the plurality of factors are also different for the same type of wells to be diagnosed in different development stages.

Table 1 relevant factors influencing the permeability of a reservoir in a region around a well to be diagnosed

| Type | Stage | | | |
|---|---|---|---|---|
| | Drilling stage (including well drilling, completion and repair) | Oil production stage | Water injection stage | Polymer injection stage |
| Production well | extraneous solid-phase particles clay swelling inorganic precipitation fine particle migration 5. water lock effect | fine particle migration stress sensitivity sand production wettability reversal emulsification organic scale 7. Jamin effect | / | / |
| Injection well | | / | extraneous solid-phase particles clay swelling inorganic precipitation fine particle migration water lock effect bacteria | extraneous solid-phase particles clay swelling inorganic precipitation fine particle migration polymer |

For the step S102, the determining an effective characteristic parameter characterizing a damage extent of the reservoir may include: determining an effective characteristic parameter $F(\vec{r}, t)$ characterizing the damage extent of the reservoir based on a characteristic parameter $F_i(\vec{r}, t)$ characterizing reservoir damage by an ith factor in the plurality of factors and the following formula, $$F(\vec{r}, t) = \sum_{i=1}^{n} L_i F_i(\vec{r}, t),$$

where $L_i$ is a weight of $F_i(\vec{r}, t)$ (which is reasonably set according to the actual situation; for example, it may be set to 1); $\vec{r}$ is any location in the reservoir; t is any time; and n is the number of the plurality of factors.

Furthermore, in the case where the characteristic parameter $F_i(\vec{r}, t)$ characterizing reservoir damage by the ith factor in the plurality of factors is obtained, based on the characteristic parameter $F_i(\vec{r}, t)$ characterizing reservoir damage by the ith factor in the plurality of factors and the following formula, the proportion $\delta_i(\vec{r}, t)$ or $F_i(\vec{r}, t)$ in the the effective characteristic parameter characterizing the damage extent of the reservoir may also be determined, $$\delta_i(\vec{r}, t) = F_i(\vec{r}, t) \bigg/ \sum_{i=1}^{n} L_i F_i(\vec{r}, t),$$

wherein the characteristic parameter may be permeability, skin factor and/or permeability damage rate, etc, which may be reasonably set according to actual needs in practical application, and some or all of the above three characteristic parameters may be calculated.

In the case where the well to be diagnosed is a water injection well, a polymer injection well or an oil production well and is in a drilling stage, the plurality of factors include at least two of: extraneous solid-phase particles, clay swelling, the migration of fine particle within the reservoir (which may be referred to as "fine particle migration"), inorganic precipitation, and water lock effect, which may be reasonable set according to actual needs in practical application.

In an embodiment, in the case where the well to be diagnosed is a water injection well, a polymer injection well or an oil production well and is in a drilling stage, the plurality of factors may include extraneous solid-phase particles, clay swelling, and fine particle migration.

For the step S102, the effective characteristic parameter $F(\vec{r}, t)$ characterizing the damage extent of the reservoir is determined based on characteristic parameters $F_1(\vec{r}, t)$, $F_2(\vec{r}, t)$ and $F_4(\vec{r}, t)$ (subscripts thereof correspond to the factor 1—extraneous solid-phase particles, the factor 2—clay swelling and the factor 4—fine particle migration in the drilling stage in Table 1, and the three characteristic parameters may be determined by spatio-temporal evolution simulation equations shown in the following Embodiments 1, 2 and 4, respectively) characterizing reservoir damage respectively by the extraneous solid-phase particles, the clay swelling, and the fine particle migration, and the following formula:

$$F(\vec{r},t)=F_1(\vec{r},t)+F_2(\vec{r},t)+F_4(\vec{r},t).$$

In another embodiment, the plurality of factors may further include at least one of:

inorganic precipitation and water lock effect. For example, the plurality of factors may further include both inorganic precipitation and water lock effect.

For the step S102, the effective characteristic parameter $F(\vec{r}, t)$ characterizing the damage extent of the reservoir is determined based on characteristic parameters $F_1(\vec{r}, t)$, $F_2(\vec{r}, t)$, $F_4(\vec{r}, t)$, $F_3(\vec{r}, t)$ and $F_5(\vec{r}, t)$ (which may be determined by spatio-temporal evolution simulation equations shown in the following Embodiments 1, 2, 4, 3 and 5 respectively) characterizing reservoir damage respectively by the extraneous solid-phase particles, the clay swelling, the fine particle migration, the inorganic precipitation, and the water lock effect, and the following formula:

$$F(\vec{r}, t)=\Sigma_{i=1}^{5} F_i(\vec{r}, t).$$

In the case where the well to be diagnosed is an oil production well and is in an oil production stage, the plurality of factors include at least two of: fine particle migration, sand production, emulsification, Jamin effect, stress sensitivity, wettability reversal, and organic scale, which may be reasonably set according to actual needs in practical application.

In an embodiment, in the case where the well to be diagnosed is an oil production well and is in an oil production stage, the plurality of factors may include fine particle migration, sand production, emulsification, and organic scale.

For the step S102, the effective characteristic parameter $F(\vec{r}, t)$ characterizing the damage extent of the reservoir is determined based on characteristic parameters $F_1(\vec{r}, t)$, $F_3(\vec{r}, t)$, $F_5(\vec{r}, t)$ and $F_6(\vec{r}, t)$ (subscripts thereof correspond to the factor 1—fine particle migration, the factor 3—sand production, the factor 5—emulsification, and the factor 6—Jamin effect in the oil production stage in Table 1, and the four characteristic parameters may be determined by spatio-temporal evolution simulation equations shown in the following Embodiments 4, 7, 9 and 10 respectively) characterizing reservoir damage respectively by the fine particle migration, the sand production, the emulsification, and the organic scale, and the following formula:

$$F(\vec{r}, t)=F_1(\vec{r}, t)+F_3(\vec{r}, t)+F_5(\vec{r}, t)+F_6(\vec{r}, t).$$

In another embodiment, the plurality of factors may further include at least one of: stress sensitivity, wettability reversal, and organic scale. For example, the plurality of factors may further include three of stress sensitivity, wettability reversal, and Jamin effect.

For the step S102, the effective characteristic parameter $F(\vec{r}, t)$ characterizing the damage extent of the reservoir is determined based on characteristic parameters $F_1(\vec{r}, t)$, $F_3(\vec{r}, t)$, $F_5(\vec{r}, t)$, $F_6(\vec{r}, t)$, $F_2(\vec{r}, t)$, $F_4(\vec{r}, t)$ and $F_7(\vec{r}, t)$ (which may be determined by spatio-temporal evolution simulation equations shown in the following Embodiments 4, 7, 9, 10, 6, 8 and 11 respectively) characterizing reservoir damage respectively by the fine particle migration, the sand production, the emulsification, the Jamin effect, the stress sensitivity, the wettability reversal, and the organic scale, and the following formula:

$$F(\vec{r}, t)=\Sigma_{i=1}^{7} F_i(\vec{r}, t).$$

In the case where the well to be diagnosed is a water injection well and is in a water injection stage, the plurality of factors include at least two of: clay swelling, bacteria, water lock effect, extraneous solid-phase particles, fine particle migration, and inorganic precipitation, which may be reasonably set according to actual needs in practical application.

In an embodiment, in the case where the well to be diagnosed is a water injection well and is in a water injection stage, the plurality of factors may include clay swelling, bacteria, and water lock effect.

For the step S102, the effective characteristic parameter $F(\vec{r}, t)$ characterizing the damage extent of the reservoir is determined based on characteristic parameters $F_2(\vec{r}, t)$, $F_5(\vec{r}, t)$ and $F_6(\vec{r}, t)$ (subscripts thereof correspond to the factor 2—clay swelling, the factor 5—water lock effect, and the factor 6—bacteria in the water injection stage in Table 1, and the three characteristic parameters may be determined by spatio-temporal evolution simulation equations shown in the following Embodiments 2, 12 and 5, respectively) characterizing reservoir damage respectively by the clay swelling, the bacteria, and the water lock effect, and the following formula:

$$F(\vec{r}, t)=F_2(\vec{r}, t)+F_5(\vec{r}, t)+F_6(\vec{r}, t).$$

In another embodiment, the plurality of factors may further include at least one of: extraneous solid-phase particles, fine particle migration, and inorganic precipitation. For example, the plurality of factors may further include three of extraneous solid-phase particles, fine particle migration, and inorganic precipitation.

For the step S102, the effective characteristic parameter $F(\vec{r}, t)$ characterizing the damage extent of the reservoir is determined based on characteristic parameters $F_2(\vec{r}, t)$, $F_5(\vec{r}, t)$, $F_6(\vec{r}, t)$, $F_1(\vec{r}, t)$, $F_4(\vec{r}, t)$ and $F_3(\vec{r}, t)$ (which may be determined by spatio-temporal evolution simulation equations shown in the following Embodiments 2, 12, 5, 1, 4 and 3 respectively) characterizing reservoir damage respectively by the clay swelling, the bacteria, the water lock effect, the extraneous solid-phase particles, the fine particle migration, and the inorganic precipitation, and the following formula:

$$F(\vec{r}, t)=\Sigma_{i=1}^{6}F_i(\vec{r}, t).$$

In the case where the well to be diagnosed is a polymer injection well and is in a polymer injection stage, the plurality of factors include at least two of: polymer, clay swelling, extraneous solid-phase particles, fine particle migration, and inorganic precipitation, which may be reasonably set according to actual needs in practical application.

In an embodiment, in the case where the well to be diagnosed is a polymer injection well and is in a polymer injection stage, the plurality of factors may include polymer and clay swelling.

For the step S102, the effective characteristic parameter $F(\vec{r}, t)$ characterizing the damage extent of the reservoir is determined based on characteristic parameters $F_2(\vec{r}, t)$ and $F_5(\vec{r}, t)$ (subscripts thereof correspond to the factor 2—clay swelling, and the factor 5—polymer in the polymer injection stage in Table 1, and the two characteristic parameters may be determined by spatio-temporal evolution simulation equations shown in the following Embodiments 13 and 2, respectively) characterizing reservoir damage respectively by the polymer, and the clay swelling, and the following formula:

$$F(\vec{r}, t)=F_2(\vec{r}, t)+F_5(\vec{r}, t).$$

In another embodiment, the plurality of factors may further include at least one of: extraneous solid-phase particles, fine particle migration, and inorganic precipitation. For example, the plurality of factors may further include three of extraneous solid-phase particles, fine particle migration, and inorganic precipitation.

For the step S102, the effective characteristic parameter $F(\vec{r}, t)$ characterizing the damage extent of the reservoir is determined based on characteristic parameters $F_2(\vec{r}, t)$, $F_5(\vec{r}, t)$, $F_1(\vec{r}, t)$, $F_4(\vec{r}, t)$, and $F_3(\vec{r}, t)$ (which may be determined by spatio-temporal evolution simulation equations shown in the following Embodiments 2, 13, 1, 4 and 3 respectively) characterizing reservoir damage respectively by the polymer, the clay swelling, the extraneous solid-phase particles, the fine particle migration, and the inorganic precipitation, and the following formula:

$$F(\vec{r}, t)=\Sigma_{i=1}^{5}F_i(\vec{r}, t).$$

In practical application, the plurality of factors may be reasonably set according to actual needs, i.e., not limited by the combinations of above embodiments.

Processes of establishing the spatio-temporal evolution simulation equation of reservoir damage by each of the 13 relevant factors in Table 1 described above and determining the related characteristic parameters by using the spatio-temporal evolution simulation equations is described below respectively (see Embodiments 1-13 for details, the 13 embodiments respectively corresponding to the 13 factors in Table 1). For the same factor involved in different stages, parameters such as permeability of the reservoir damaged by the same factor may be determined by referring to corresponding embodiments; specific values of some parameters in the corresponding embodiments described in different stages may be different.

It is to be noted that for the sake of simple description, for physical and chemical quantities that evolve with time and space in embodiments of the present invention, the variable $(\vec{r}, t)$ may be omitted, for example, $K(\vec{r}, t)$ may be shortened to K.

Embodiment 1—Extraneous Solid-Phase Particles

The essence of extraneous solid-phase particles invading a reservoir and causing clogging is migration and deposition after invasion of the exogenous solid-phase particles into a medium. Thus, the core of each embodiment of the present invention is to establish a kinetic model of migration and deposition of the solid-phase particles. Specifically, based on mass conservation, a diffusion relationship, and the like, a spatio-temporal evolution control phenomenological model (containing a concentration C of flowing particles and a concentration $C_d$ of deposited particles) for concentration distribution of the extraneous solid-phase particles in a reservoir around a well to be diagnosed is established, and in conjunction with a relationship between a deposition concentration and a characteristic parameter characterizing the damage extent of the reservoir such as permeability, spatio-temporal field distribution of the characteristic parameter such as permeability can be diagnosed.

Figure 1B:
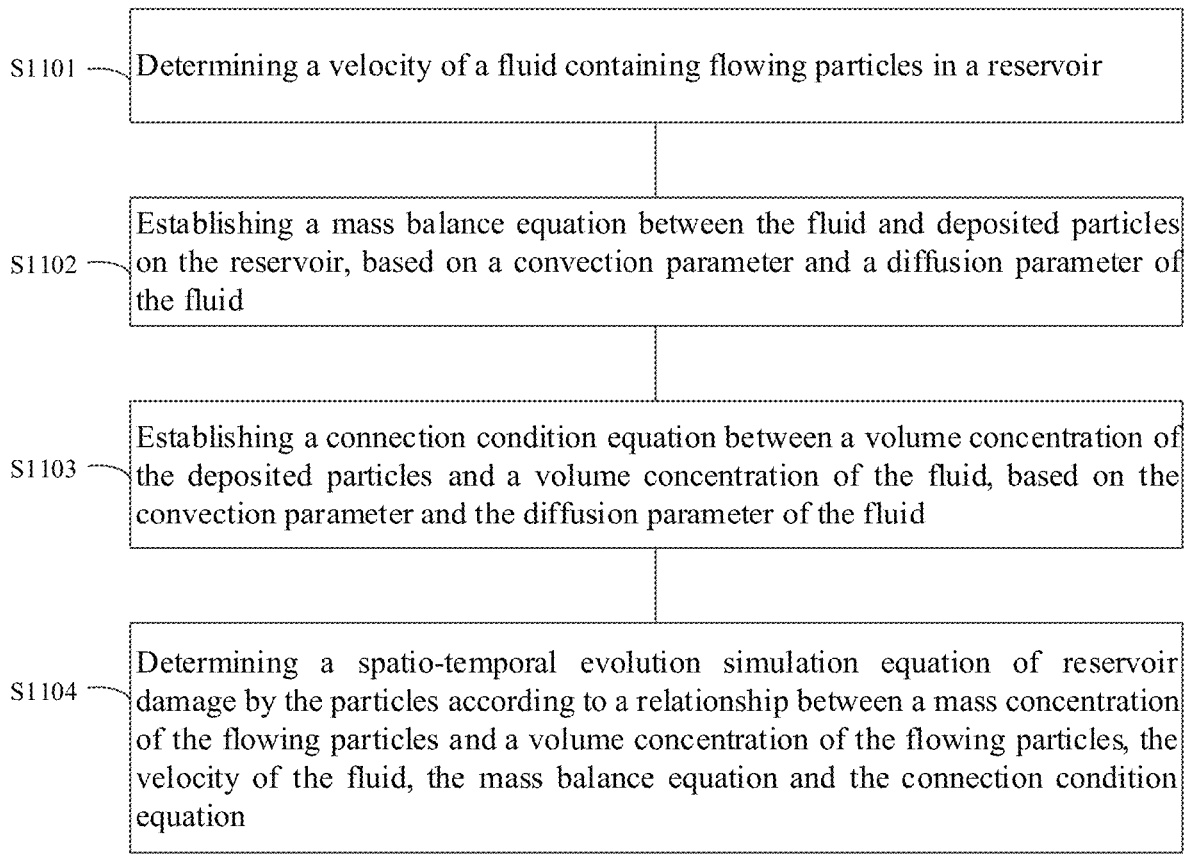
FIG. 1B is a flow diagram of a modeling method for reservoir damage by extraneous solid-phase particles provided in an embodiment of the present invention.

FIG. 1B is a flow diagram of a modeling method for reservoir damage by extraneous solid-phase particles provided in an embodiment of the present invention. The modeling method may include steps S1101-S1104.

Step S1101: determining a velocity of a fluid containing flowing particles in a reservoir.

The reservoir is located in a preset region of a well to be diagnosed (e.g., a water injection well, an oil production well, or the like).

For the step S1101, the determining a velocity of a fluid containing flowing particles in a reservoir may include: establishing a pressure conduction equation for the fluid entering the reservoir; and determining the velocity of the fluid according to the pressure conduction equation and a Darcy formula.

Specifically, a pressure is a force that drives a solid-liquid mixture (i.e., a fluid containing flowing particles) to continuously intrude from a wellbore of the water injection well into the reservoir around the well to be diagnosed, whereby the pressure conduction equation for the fluid entering the reservoir as expressed in formula (1-1) can be established:

$$\nabla^2 P(\vec{r}, t) = \frac{\phi \mu c_t}{K(\vec{r}, t)} \frac{\partial P(\vec{r}, t)}{\partial t}, \qquad (1\text{-}1)$$

and then the velocity of the fluid can be determined according to formula (1-1) and the Darcy formula (e.g., formula (1-2) below), $$v(\vec{r}, t) = -\frac{\tau K(\vec{r}, t)}{\mu \phi} \nabla P(\vec{r}, t), \qquad (1\text{-}2)$$

where $P(\vec{r}, t)$ is a pressure of the fluid; $\phi$ is a porosity of the reservoir; $\mu$ is fluid viscosity; $c_t$ is a fluid-rock integrated compression coefficient; $K(\vec{r}, t)$ is a permeability of the reservoir; and $\tau$ is a tortuosity of the reservoir.

Step S1102: establishing a mass balance equation between the fluid and deposited particles on the reservoir, based on a convection parameter and a diffusion parameter of the fluid.

According to conservation of mass, a change in the mass of the fluid is equal to a negative change in the mass of the deposited particles. For the step S1102, the establishing a mass balance equation between the fluid and deposited particles on the reservoir may include: establishing the mass balance equation expressed in the following formula (1-3), based on the convection parameter and the diffusion parameter of the fluid, $$\frac{\partial}{\partial t}(\rho \phi w(\vec{r}, t)) + \nabla(\rho u w(\vec{r}, t) + j(\vec{r}, t)) = -\dot{m}(\vec{r}, t), \qquad (1\text{-}3)$$

where $\rho$ is density of the fluid; $\phi$ is the porosity of the reservoir; $w(\vec{r}, t)$ is the mass fraction (which may also be called a mass concentration) of the flowing particles; u is a Darcy apparent velocity; $j(\vec{r}, t)$ is a diffusion flow rate, $j(\vec{r}, t) = -\phi \rho_L D(\vec{r}, t) \nabla w(\vec{r}, t)$, where $\rho_L$ is a density of the fluid, $D(\vec{r}, t)$ is a diffusion coefficient, $D(\vec{r}, t) = \alpha v(\vec{r}, t)$, $\alpha$ is a vertical diffusivity, and $v(\vec{r}, t)$ is a velocity of the fluid;

$$\dot{m}(\vec{r}, t) \equiv \frac{\partial m(\vec{r}, t)}{\partial t} = k(\vec{r}, t)(\rho u w(\vec{r}, t) + j(\vec{r}, t)),$$

where $\dot{m}(\vec{r}, t)$ is an accumulated mass of the deposited particles per unit time, and t is time.

Step S1103: establishing a connection condition equation between a volume concentration of the deposited particles and a volume concentration of the fluid, based on the convection parameter and the diffusion parameter of the fluid.

For the step S1103, the establishing a connection condition equation between a volume concentration of the deposited particles and to volume concentration of the fluid may include: establishing the connection condition equation expressed in the following formula (1-4), based on the convection parameter and the diffusion parameter of the fluid, $$\frac{\partial(\rho_p C_d(\vec{r}, t))}{\partial t} = k(\vec{r}, t)(\rho u w(\vec{r}, t) + j(\vec{r}, t)), \qquad (1\text{-}4)$$

where $\rho_P$ is particle density; $C_d(\vec{r}, t)$ is the volume concentration of the deposited particles; and $k(\vec{r}, t) = k_0(\vec{r}) G_1(C_d) F_1(T)$, where $k_0$ is an original fluid loss coefficient, $$G_1(C_d) = \left(1 - \frac{C_d}{C_{dmax}}\right)^{m_k}, \text{ and } F_1(T) = \exp\left(A_k\left(\frac{1}{T - T_{ik}} - \frac{1}{T_{ik} - T_{ck}}\right)\right).$$

Since the correlation between $F_1(T)$ and temperature is measured by exp(1/T), and in a common temperature range (e.g. 300 K to 400 K), the change of this function is actually very slow and actually close to an isothermal process, thus $$k(\vec{r}, t) = k_0(\vec{r}) \cdot \left(1 - \frac{C_d(\vec{r}, t)}{C_{dmax}}\right)^{m_k},$$

where $C_d(\vec{r}, t)$ is the volume concentration of the deposited particles, $C^{d\ max}$ is a maximum volume concentration of the deposited particles, and $m_k$ is a first empirical value. All of the above parameters can be either constants, or parameters that vary with space, i.e., in a non-homogeneous situation.

Step S1104: determining a spatio-temporal evolution simulation equation of reservoir damage by the particles according to a relationship between a mass fraction of the flowing particles and a volume concentration of the flowing particles, the velocity of the fluid, the mass balance equation and the connection condition equation.

Wherein the spatio-temporal evolution simulation equation is used to simulate a four-dimensional (4D) spatio-temporal evolution process of characteristics of reservoir damage caused by the extraneous solid-phase particles.

Wherein the relationship between the mass fraction of the flowing particles and the volume concentration of the flowing particles may be $$w(\vec{r}, t) = \frac{\rho_p}{\rho_L} C(\vec{r}, t),$$

where $\rho_P$ is the density of the deposited particles; $\rho_L$ is the density of the fluid; and $C(\vec{r}, t)$ is the volume concentration of the flowing particles. The spatio-temporal evolution simulation equation of reservoir damage by the particles may include: a spatio-temporal evolution simulation equation of reservoir damage by particle migration expressed by formula (1-5), and a spatio-temporal evolution simulation equation of reservoir damage by particle deposition expressed by formula (1-6).

For the step S1104, the determining a spatio-temporal evolution simulation equation of reservoir damage by the particles may include: determining the spatio-temporal evolution simulation equation of reservoir damage by particle migration expressed by formula (1-5) according to the relationship between the mass fraction of the flowing particles and the volume concentration of the flowing particles, the velocity of the fluid, and the mass balance equation expressed by formula (1-3):

$$\frac{\partial C(\vec{r}, t)}{\partial t} + \frac{v(\vec{r}, t)}{\tau}\left[1 - \left(1 - \frac{\rho_p}{\rho_L}C(\vec{r}, t)\right)k(\vec{r}, t)\alpha\tau\right]\nabla C(\vec{r}, t) + \frac{k(\vec{r}, t)v(\vec{r}, t)}{\tau}\left(1 - \frac{\rho_p}{\rho_L}C(\vec{r}, t)\right)C(\vec{r}, t_{i+1}) = \alpha v(\vec{r}, t)\nabla^2 C(\vec{r}, t), \quad (1-5)$$

and determining the spatio-temporal evolution simulation equation of reservoir damage by particle deposition expressed by formula (1-6) according to the relationship between the mass fraction of the flowing particles and the volume concentration of the flowing particles, the velocity of the fluid, and the connection condition equation expressed by formula (1-4):

$$\frac{\partial C_d(\vec{r}, t)}{\partial t} = \frac{v(\vec{r}, t)k(\vec{r}, t)\phi}{\tau}[C(\vec{r}, t) - \alpha\tau\nabla C(\vec{r}, t)], \quad (1-6)$$

where $C(\vec{r}, t)$ is the volume concentration of the flowing particles; $v(\vec{r}, t)$ is the velocity of the fluid; $\tau$ is the tortuosity of the reservoir; $\rho_P$ is the density of the deposited particles; $\rho_L$ is the density of the fluid;

$$k(\vec{r}, t) = k_0(\vec{r}) \cdot \left(1 - \frac{C_d(\vec{r}, t)}{C_{dmax}}\right)^{m_k},$$

where $k_0(\vec{r})$ is an initial value of the fluid loss coefficient of the reservoir; $C_d(\vec{r}, t_{i+1})$ is the volume concentration of the deposited particles; $C_{d\ max}$ is a maximum volume concentration of the deposited particles; $m_k$ is a first empirical value; $\alpha$ is a vertical diffusivity; and $\phi$ is the porosity of the reservoir. $k_0(\vec{r}) = f(N_R, N_{Pe}, N_A, N_{DL}, N_{E1}N_{E2}, N_G, N_{Lo}, N_{vdW}, \zeta_{p(g)})$, where $N_R, N_{Pe}, N_A, N_{DL}, N_{E1}, N_{E2}, N_G, N_{Lo}, N_{vdW}, \zeta_{p(g)}$ are a radius number, a Peclet number, an attraction number, an electrical double layer number, a first electric potential force number, a second electric potential force number, a gravity number, a London force number, a van der Waals force number, and potentials of flowing particles and matrix particles, respectively (for details of relevant expressions of the parameters, see Table 2).

TABLE 2

Table of dimensionless parameters containing a solid phase deposition driving factor and their expressions

| Parameter Name | Expression |
|---|---|
| $N_R$ (radius number) | i. $D_p/D_g$ |
| $N_{Pe}$ (Peclet number) | $uD_g/D_\infty$ |
| $N_A$ (attraction number) | $H/(12\pi\mu R_p^2 u)$ |
| $N_{DL}$ (electrical double layer number) | $\kappa_E R_p$ |
| $N_{E1}$ (first electric potential force number) | $v_0 R_p(\xi_p^2 + \xi_g^2)/(4k_B T)$ |
| $N_{E2}$ (second electric potential force number) | $2(\xi_p/\xi_g)(1 + (\xi_p/\xi_g)^2)$ |
| $N_G$ (Gravity number) | $2R_p^2(\rho_p - \rho_L)g/(9\ \mu u)$ |
| $N_{Lo}$ (London force number) | $H/(6k_B T)$ |
| $N_{vdW}$ (Van der Waals force number) | $H/(k_B T)$ |

Note:
$D_\infty$ is free diffusivity of the particles;
H is a Hamaker number;
$D_p$ and $D_g$ are diameters of the flowing particles and the matrix particles, respectively;
$\mu$ is a fluid viscosity;
$k_B$ is a Boltzmann constant;
and $\xi_p$ and $\xi_g$ are potentials of the flowing particles and the matrix particles, respectively.

In summary, according to the present invention, the mass balance equation between the fluid containing the flowing particles and the deposited particles on the reservoir is creatively established; the connection condition equation between the volume concentration of the deposited particles and the volume concentration of the fluid is established; and the spatio-temporal evolution simulation equation of reservoir damage by the particles is determined according to the relationship between the mass fraction of the flowing particles and the volume concentration of the flowing particles, the velocity of the fluid, the mass balance equation and the connection condition equation. Thus, by using the determined spatio-temporal evolution simulation equation, a four-dimensional spatio-temporal evolution process of characteristics of reservoir damage caused by extraneous solid-phase particles can be quantitatively simulated, which is of very great significance for optimal design of a declogging measure and improvement or restoration of oil well production and water well injection capacity for damaged wells, and improvement of numerical simulation precision of oil pools.

Figure 1C:
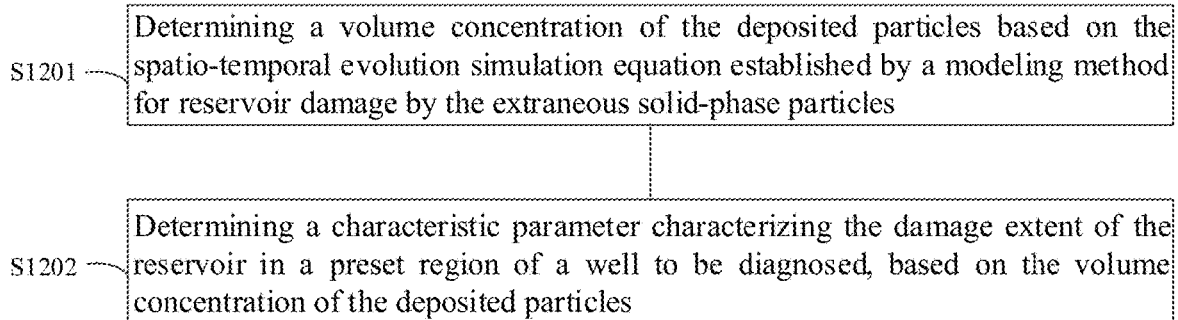
FIG. 1C is a flow diagram of a method for determining a damage extent of a reservoir provided in an embodiment of the present invention.

FIG. 1C is a flow diagram of a method for determining a damage extent of a reservoir provided in an embodiment of the present invention. As shown in FIG. 1C, the method for determining the damage extent of the reservoir may include steps S1201-S1202.

Step S1201: determining the volume concentration of the deposited particles based on the spatio-temporal evolution simulation equation established by the modeling method for reservoir damage by the extraneous solid-phase particles.

For the spatio-temporal evolution simulation equation of reservoir damage by particle migration expressed by formula (1-5) described above, in a one-dimensional situation, such an equation can be arranged into the following general form:

$$\frac{\partial f}{\partial t} + a_a \frac{\partial f}{\partial x} + b_b f = c_c \frac{\partial^2 f}{\partial x^2}, \quad (1-7)$$

where $a_a$, $b_b$, $c_c$ may be a constant (e.g., the diffusion coefficient) or a function (e.g., the velocity of the fluid); and $f$ may be a pressure, substance concentration, stress, or the like. A backward difference is used for time and a central difference is used for space. Then the above equation may use the following difference format:

$$\frac{f_i^n - f_i^{n-1}}{\Delta t} + a_i \frac{f_{i+1}^n - f_{i-1}^n}{2\Delta x} + b_i f_i^n = c_i \frac{f_{i+1}^n - 2f_i^n + f_{i-1}^n}{\Delta x^2}, \quad (1\text{-}8)$$

where $i=1, 2, 3 \ldots N_i$, $$N_i = \frac{x_{max}}{\Delta x},$$

$n=1, 2, 3, \ldots$, $t = n\Delta t$, $N_i$ being the number of discrete space points.

A solution interval is $x \in (0, x_{max})$, and $\Delta x$ and $\Delta t$ are space and time steps. Simultaneously, an initial condition $f_i^n|_{n=0} = f_i^0$, $i=1, 2, 3 \ldots, N_i$ and a boundary condition $(f_i^n|_{i=1} = f_0$, $n=1, 2, 3 \ldots$ (at a well wall) and $$\left. \frac{f_{i+1}^n - f_{i-1}^n}{2\Delta x} \right|_{i=N} = 0, n = 1, 2, 3 \ldots$$

(at a boundary of a preset range or several meters from the well wall, with a virtual grid i+1 being constructed) are considered.

First, for $i=2, 3, \ldots, N_i-1$, the above difference format is arranged as follows:

$$\left(\frac{1}{\Delta t} + b_i + \frac{2c_i}{\Delta x^2}\right) f_i^n + \left(\frac{a_i}{2\Delta x} - \frac{c_i}{\Delta x^2}\right) f_{i+1}^n - \left(\frac{a_i}{2\Delta x} + \frac{c_i}{\Delta x^2}\right) = \frac{1}{\Delta t} f_i^{n-1} \Rightarrow \quad (1\text{-}9)$$

$$f_i^n + \frac{\frac{a_i}{2\Delta x} - \frac{c_i}{\Delta x^2}}{\frac{1}{\Delta t} + b_i + \frac{2c_i}{\Delta x^2}} f_{i+1}^n - \frac{\frac{a_i}{2\Delta x} + \frac{c_i}{\Delta x^2}}{\frac{1}{\Delta t} + b_i + \frac{2c_i}{\Delta x^2}} f_{i-1}^n = \frac{\frac{1}{\Delta t}}{\frac{1}{\Delta t} + b_i + \frac{2c_i}{\Delta x^2}} f_i^{n-1} \Rightarrow$$

$$f_i^n + \frac{\frac{a_i}{2} - \frac{c_i}{\Delta x}}{\frac{\Delta x}{\Delta t} + b_i \Delta x + \frac{2c_i}{\Delta x}} f_{i+1}^n - \frac{\frac{a_i}{2} - \frac{c_i}{\Delta x}}{\frac{\Delta x}{\Delta t} + b_i \Delta x + \frac{2c_i}{\Delta x^2}} f_{i-1}^n =$$

$$\frac{\frac{\Delta x}{\Delta t}}{\frac{\Delta x}{\Delta t} + b_i \Delta x + \frac{2c_i}{\Delta x^2}} f_i^{n-1} \Rightarrow$$

$$f_i^n = A1_i f_{i-1}^n + A2_i f_{i+1}^n + A3_i f_i^{n-1} (i = 2, 3 \ldots, N_i - 1),$$

where $A1_i$, $A2_i$ and $A3_i$ are respectively:

$$\frac{\frac{a_i}{2} + \frac{c_i}{\Delta x}}{\frac{\Delta x}{\Delta t} + b_i \Delta x + \frac{2c_i}{\Delta x}}, \frac{\frac{c_i}{\Delta x} - \frac{a_i}{2}}{\frac{\Delta x}{\Delta t} + b_i \Delta x + \frac{2c_i}{\Delta x}} \text{ and } \frac{\frac{\Delta x}{\Delta t}}{\frac{\Delta x}{\Delta t} + b_i \Delta x + \frac{2c_i}{\Delta x}}. \quad (1\text{-}10)$$

Meanwhile, according to formula (1-5), we obtain:

$$a_i = \frac{v}{\tau}\left[1 - \left(1 - \frac{\rho_p}{\rho_L}\right)k_i \alpha \tau\right], b_i = \frac{k_i v}{\tau}\left(1 - \frac{\rho_p}{\rho_L} C_i\right), c_i = \alpha v. \quad (1\text{-}11)$$

Substituting formula (1-11) into formula (1-10) yields a specific expression of the iterative relational expression (1-9), which is not listed here as the specific expression of the iterative relational expression (1-9) is complicated. Then, iterative calculation is performed by using the initial condition and the boundary condition to obtain a value of the field $f$.

Next, a difference solution procedure for illustrating the boundary condition is described.

The above iterative relational expression (1-9) is applicable to a non-boundary grid. For i=1 (at the well wall), as a point-centered grid is used and it is a Dirichlet boundary condition, the following relational expression can be obtained directly:

$$f_1^n f_0 (\text{constant}), i=1. \quad (1\text{-}12)$$

For i=N (several meters from the well wall, at a boundary of a preset range), which is a Neumann or second-type (Neumann) boundary condition, a virtual grid $i=N_i+1$ is added, and $f_{i+1}^n = f_{i-1}^n$ is obtained from $$\left. \frac{f_{i+1}^n - f_{i-1}^n}{2\Delta x} \right|_{i=N} = 0, n = 1, 2, 3 \ldots,$$

and $f_{i+1}^n = f_{i-1}^n$ is substituted into formula (1-9) to yield:

$$f_i^n = (A1_i + A2_i) f_{i-1}^n + AQ3_i f_i^{n-1} (i=N). \quad (1\text{-}13)$$

The spatio-temporal variation of the field function $f$ can be solved according to the above process. Since the above numerical model is built for a reservoir near the wellbore of the well to be diagnosed, a cylindrical coordinate system needs to be used when the distribution of a physical quantity $f$ around the well is solved. Thus, formula $$\frac{\partial f}{\partial t} + a_a \frac{\partial f}{\partial x} + b_b f = c_c \frac{\partial^2 f}{\partial x^2}$$

needs to be transformed into $$\frac{\partial f}{\partial t} + a_3 \frac{\partial f}{\partial r} + b_3 f = c_3 \frac{1}{r} \frac{\partial}{\partial r}\left(r \frac{\partial}{\partial r} f\right).$$

This form is not conducive to an equally spaced difference, so that a coordinate transformation can be introduced: $r = r_w e^{x'}$, where $r_w$ is a radius of the wellbore, and x' is a dimensionless spatial coordinate. Substituting the transformation into a general equation yields an equation about x':

$$\frac{\partial f}{\partial t} + \frac{a}{r_w} \cdot e^{-x'} \frac{\partial f}{\partial x'} + bf = \frac{c}{r_w^2} e^{-x'^2} \frac{\partial^2 f}{\partial x'^2}, \quad (1\text{-}14)$$

and if $\frac{a}{r_w} \cdot e^{-x'}$ and $\frac{c}{r_w^2} e^{-x'^2}$ serve as new equation coefficients, the above formula is essentially same as $$\frac{\partial f}{\partial t} + a_a \frac{\partial f}{\partial x} + b_b f = c_c \frac{\partial^2 f}{\partial x^2}.$$

Thus, an equally spaced difference may be applied to the x' coordinate, and the iterative format described before is used. After the value of $f$ is calculated, the spatial coordinate may be mapped back from x' to r to obtain $f(r, t)$.

The spatio-temporal evolution simulation equation established by the above-mentioned modeling method for reservoir damage by the extraneous solid-phase particles comprehensively considers the influence of various physicochemical factors on the reservoir damage when the solid-phase particles invade the reservoir, and thus the volume concentration of the deposited particles obtained by the solution of this step S1201 is very precise.

Step S1202: determining a characteristic parameter characterizing the damage extent of the reservoir in a preset region of a well to be diagnosed, based on the volume concentration of the deposited particles.

Wherein the characteristic parameter may be permeability of the reservoir and/or a fluid loss coefficient of the reservoir.

In an embodiment, the characteristic parameter may be the permeability of the reservoir.

For the step S1202, the determining a characteristic parameter characterizing the damage extent of the reservoir in a preset region of a well to be diagnosed may include: determining the permeability $K(\vec{r}, t)$ the reservoir based on the volume concentration $C_d(\vec{r}, t)$ of the deposited particles and formula (1-15), $$K(\vec{r}, t)/K_0(\vec{r}) = \left(1 - \frac{C_d(\vec{r}, t)}{\phi_0}\right)^{m_K}, \quad (1\text{-}15)$$

In an embodiment, the characteristic parameter may be the fluid loss coefficient of the reservoir.

For the step S1202, the determining a characteristic parameter characterizing the damage extent of the reservoir in a preset region of a well to be diagnosed may include: determining the fluid loss coefficient $k(\vec{r}, t)$ of the reservoir based on the volume concentration $C_d(\vec{r}, t)$ of the deposited particles and formula (1-16), $$k(\vec{r}, t) = k_0(\vec{r}) \cdot \left(1 - \frac{C_d(\vec{r}, t)}{c_{dmax}}\right)^{m_k}, \quad (1\text{-}16)$$

where $\phi_0$ is an initial value of the porosity; $C_{d\,max}$ is a maximum volume concentration of the deposited particles; $m_k$ and $m_K$ are a first empirical value and a second empirical value, respectively; $K_0(\vec{r})$ is an initial value of the permeability of the reservoir; and $k_0(\vec{r})$ is an initial value of the fluid loss coefficient of the reservoir.

wherein the characteristic parameter may be a skin factor of the reservoir.

For the step S1202, the determining a characteristic parameter characterizing the damage extent of the reservoir in a preset region of a well to be diagnosed may include: determining the permeability $K(\vec{r}, t)$ of the reservoir based on the volume concentration $C_d(\vec{r}, t)$ of the deposited particles and formula $$K(\vec{r}, t)/K_0(\vec{r}) = \left(1 - \frac{C_d(\vec{r}, t)}{\phi_0}\right)^{m_K};$$

and determining the skin factor $s(\vec{r}, t)$ of the reservoir based on the permeability $K(\vec{r}, t)$ of the reservoir and formula (1-17), $$S(\vec{r}, t) = \left(\frac{1}{K_d(\vec{r}, t)} - 1\right)\ln\left(\frac{r_{sw}}{r_w}\right), \quad (1\text{-}17)$$

where $K_0(\vec{r})$ is the initial value of the permeability of the reservoir; and $K_d(\vec{r},t) = K(\vec{r}, t)/K_0(\vec{r})$.

The characteristic parameter obtained by the step S1202 (e.g., the permeability $K(\vec{r}, t)$ and the skin factor $S(\vec{r}, t)$ of the reservoir) is a result of 4D quantitative simulation of spatio-temporal evolution. Quantitative prediction of reservoir damage and spatio-temporal deduction of damage laws can be performed according to its evolution characteristics, which is of scientific guidance significance for preventing or avoiding reservoir damage, and formulating development plans for oil pools and subsequent well stimulation measures.

In summary, the volume concentration of the deposited particles can be determined by using the determined spatio-temporal evolution simulation equation, and then a characteristic parameter (e.g., the permeability and/or the skin factor of the reservoir) characterizing the damage extent of the reservoir in the preset region of the well to be diagnosed is determined based on the volume concentration of the deposited particles, whereby the four-dimensional spatio-temporal evolution process of the characteristics of reservoir damage caused by the extraneous solid-phase particles can be simulated quantitatively. Therefore, for a well with reservoir damage, quantitative simulation and spatial-temporal evolution of reservoir damage are achieved by using historical parameters, which is of great significance for optimal design of a declogging measure and improvement of numerical simulation precision of oil pools; and for a well without reservoir damage, quantitative prediction of reservoir damage and spatio-temporal deduction of damage laws can be performed according to physical property parameters and engineering parameters to be implemented, which is of scientific guidance significance for preventing or avoiding reservoir damage, and formulating development plans for oil pools and subsequent well stimulation measures.

Embodiment 2—Clay Swelling

Figure 2A:
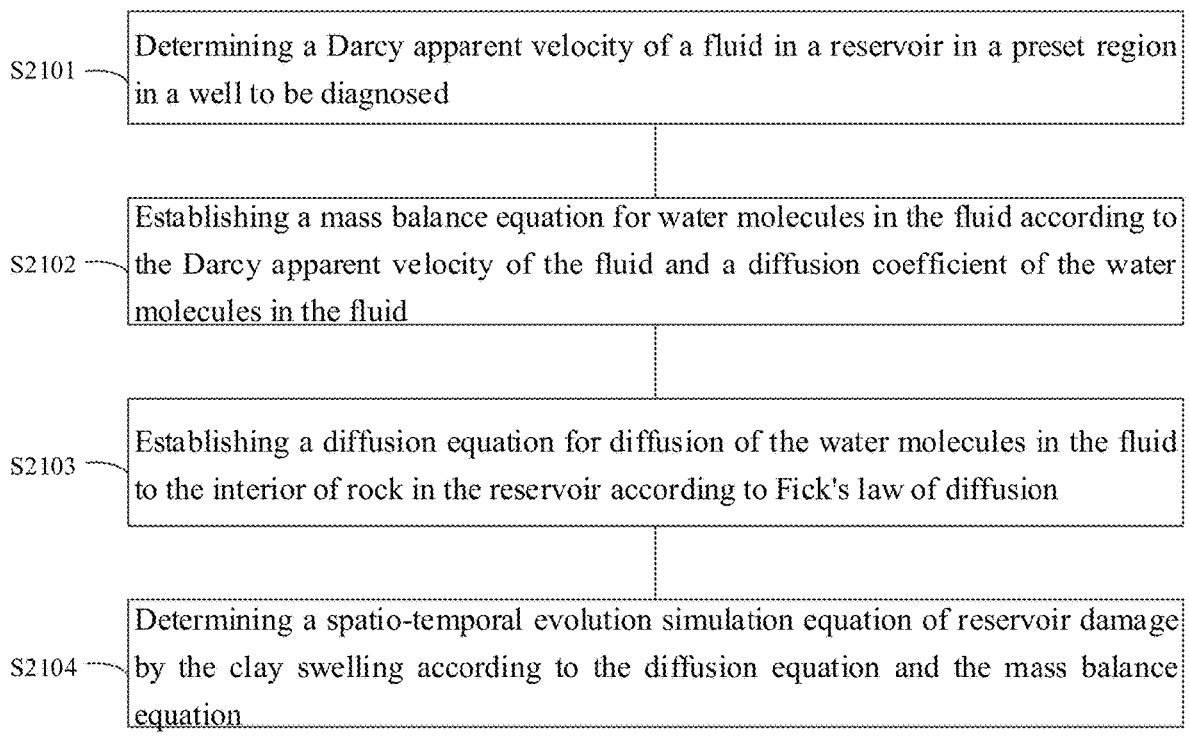
FIG. 2A is a flow diagram of a modeling method for reservoir damage by clay swelling provided in an embodiment of the present invention.
Figure 2B:
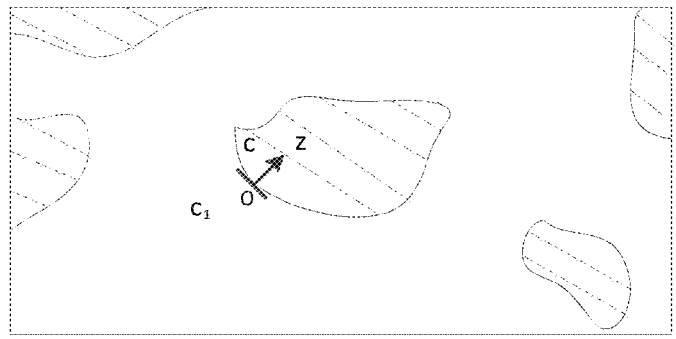
FIG. 2B is a flow diagram of diffusion of water molecules in pores in a reservoir toward the interior of rock provided in an embodiment of the present invention.

A process of diffusion of water molecules of an extraneous fluid (e.g., injected water) through a solid-liquid interface (between rock and the fluid in a reservoir) to the interior of a solid-phase medium (the rock in the reservoir) can be considered as a phenomenon in any local region of the solid-liquid interface, and for any sufficiently small-scale local region on the interface, a diffusion direction of the water molecules can be considered to be perpendicular to a tangential direction of a point (e.g., point O) in the region (i.e., the diffusion direction is perpendicular to a plane where the region is located), as shown in FIG. 2B (wherein shaded parts represent the rock, and the other blank part represents pores in the reservoir). The rock in the reservoir include clay, and during the diffusion of the water molecules into the rock, the clay swells, which in turn may lead to a reduction in the permeability (or even clogging) of the reservoir. Therefore, the core of embodiments of the present invention is to establish a kinetic model (i.e., a diffusion equation for the diffusion of the water molecules through the solid-liquid interface from a liquid phase in the pores to the interior of a solid phase and a convection diffusion equation for the fluid in the pores) of diffusion of the water molecules to the interior of the rock and water content variations within the pores in the reservoir. Specifically, based on Fick's law of diffusion, a convection diffusion relationship of the fluid in the pores in the reservoir, and the like, a spatio-temporal evolution control phenomenological model (containing a water volume fraction $c_1$ of the pores in the reservoir and an initial value $c_0$ of a water volume fraction of the rock in the reservoir) of porosity distribution in the reservoir around the well to be diagnosed, which is influenced by clay swelling is established, and in conjunction with a relationship between porosity of the reservoir and a characteristic parameter characterizing the damage extent of the reservoir such as permeability, spatio-temporal field distribution of the characteristic parameter such as permeability can be diagnosed.

FIG. 2A is a flow diagram of a modeling method for reservoir damage by clay swelling provided in an embodiment of the present invention. The modeling method may include steps S2101-S2104.

Step S2101: determining a Darcy apparent velocity of a fluid in a reservoir in a preset region of a well to be diagnosed.

wherein the well to be diagnosed may be, for example, a water injection well or oil production well.

For the step S2101, determining the velocity of the fluid in the reservoir may include: establishing a pressure conduction equation for the fluid entering the reservoir; and determining the Darcy apparent velocity of the fluid according to the pressure conduction equation and a Darcy formula.

Specifically, a pressure is a force that drives a solid-liquid mixture to continuously intrude from a wellbore of the water injection well into the reservoir around the well, whereby the pressure conduction equation for the fluid entering the reservoir as expressed in formula (2-1) can be established:

$$\nabla^2 P(\vec{r}, t) = \frac{\phi \mu c_t}{K(\vec{r}, t)} \frac{\partial P(\vec{r}, t)}{\partial t}, \quad (2\text{-}1)$$

and then the Darcy apparent velocity of the fluid can be determined according to formula (2-1) and the Darcy formula (e.g., formula (2-2) below), $$u(\vec{r}, t) = -\frac{K(\vec{r}, t)}{\mu} \nabla P(\vec{r}, t), \quad (2\text{-}2)$$

where $P(\vec{r}, t)$ is the pressure of the fluid; $\phi$ is the porosity of the reservoir; $\mu$ is fluid viscosity; $c_t$ is a fluid-rock integrated compression coefficient; and $K(\vec{r}, t)$ is the permeability of the reservoir.

Step S2102: establishing a mass balance equation for water molecules in the fluid according to the Darcy apparent velocity of the fluid and a diffusion coefficient of the water molecules in the fluid.

Under reservoir conditions, water contents at different locations within pores in the reservoir satisfy a mass conservation equation. The variation of the water contents within the reservoir is mainly determined by two processes: convection and diffusion. Specifically, for the step S2102, the establishing a mass balance equation for water molecules in the fluid may include: establishing the mass balance equation expressed in the following formula (2-3) according to the Darcy apparent velocity u of the fluid and the diffusion coefficient $D_w$ of the water molecules:

$$\phi_0 \frac{\partial c_1(\vec{r}, t)}{\partial t} = \nabla(D_w \nabla c_1(\vec{r}, t)) - \nabla((u c_1(\vec{r}, t)), \quad (2\text{-}3)$$

where $\phi_0$ is an initial value of the porosity of the reservoir; $c_1(\vec{r}, t)$ is a water volume fraction of the pores in the reservoir; and $\vec{r}$ is a spatial location of any point in the reservoir.

An initial condition for the mass balance equation for the water molecules in the fluid is $c_1(\vec{r}, t=0)=\phi_0 \cdot S_{wc}$, for the mass balance equation for the water molecules in the fluid is $c_1(|\vec{r}=r_w, t)=\phi_0$ (that is, the pores in the reservoir in a well wall of the water injection well is completely filled with water, i.e., the water saturation in the pores is 1), where $\phi_0$ is the initial value of the porosity of the reservoir; $r_w$ is a wellbore radius of the well to be diagnosed; and $S_{wc}$ is an irreducible water saturation in the reservoir.

Step S2103: establishing a diffusion equation for diffusion of the water molecules in the fluid to the interior of rock in the reservoir according to Fick's law of diffusion.

It should be noted that c(n, t) is a water volume fraction of rock in the reservoir at time t, at a coordinate n in a one-dimensional coordinate system (the direction of the coordinate axis is a normal direction of the solid-liquid interface at the location $\vec{r}$) established with a location $\vec{r}$ (e.g., point O in FIG. 2B) as the origin; and accordingly, a water volume fraction of pores in the reservoir at the location $\vec{r}$ is $c_1(\vec{r}, t)$.

A one-dimensional coordinate system n that is perpendicular to the solid-liquid interface and points to the interior of the solid phase can be established, wherein n=0 at the interface, and n>0 inside the solid phase, as shown in FIG. 2B. For the step S2103, the establishing a diffusion equation for diffusion of the water molecules in the fluid to the interior of rock in the reservoir may include: establishing a diffusion equation for diffusion of the water molecules in the fluid to the interior of the reservoir expressed by the following formula (2-4) according to Fick's law of diffusion:

$$\frac{\partial c(n, t)}{\partial t} = D_w \frac{\partial^2 c(n, t)}{\partial n^2}, \quad (2\text{-}4)$$

where n is a coordinate in the one-dimensional coordinate system established with the location $\vec{r}$ in the reservoir as the origin and with the normal direction of the interface between the fluid and the rock at the location $\vec{r}$ as the coordinate axis; t is time; $D_w$ is a diffusion coefficient of the water molecules; and c(n, t) is a water volume fraction of the rock in the reservoir.

Wherein an initial condition of the diffusion equation is c(n, t=0)=$c_0$; and a boundary condition of the diffusion equation is $$-D_w \frac{\partial c(n, t)}{\partial n}\bigg|_{n=0} = k_f(c_1 - c)\bigg|_{n=0} \text{ and } \lim_{n \to \infty} c(n, t) = c_0;$$

$D_w$ is the diffusion coefficient of the water molecules; c(n, t) is the water volume fraction of the rock in the reservoir; and $k_f$ is a membrane exchange coefficient.

Step S2104: determining a spatio-temporal evolution simulation equation of reservoir damage by the clay swelling according to the diffusion equation and the mass balance equation.

Figure 2C:
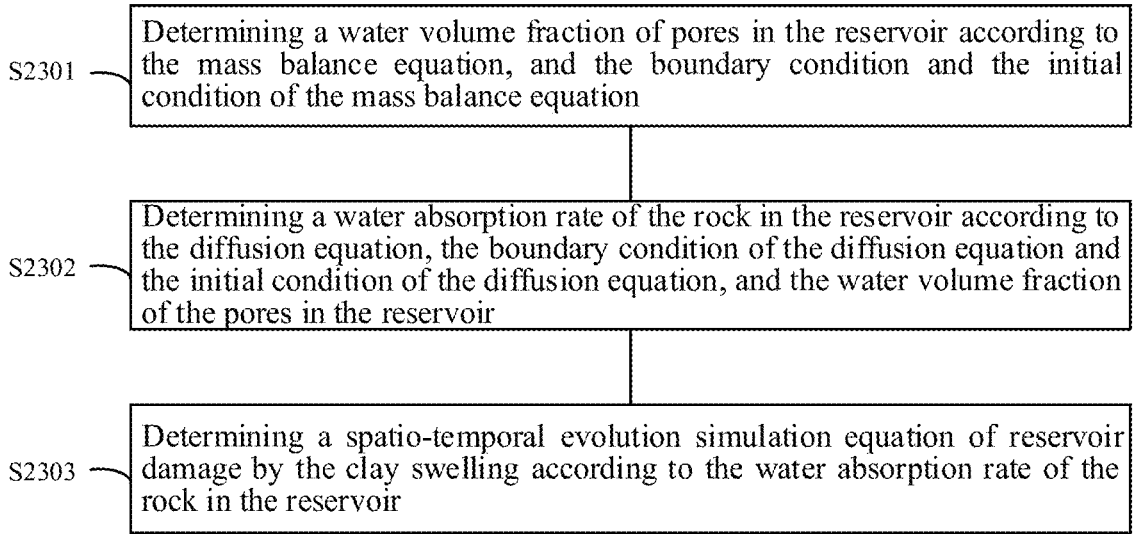
FIG. 2C is a flow diagram of determining a spatio-temporal evolution simulation equation for reservoir damage by clay swelling provided in an embodiment of the present invention.

For the step S2104, as shown in FIG. 2C, the determining a spatio-temporal evolution simulation equation of reservoir damage by the clay swelling may include steps S2301-S2303.

Step S2301: determining a water volume fraction of pores in the reservoir according to the mass balance equation, and the boundary condition and the initial condition of the mass balance equation.

The water volume fraction $c_1(\vec{r}, t)$ of the pores in the reservoir can be obtained according to the above formula (2-3) and the initial condition and the boundary condition of the mass balance equation for the water molecules in the fluid.

Step S2302: determining a water absorption rate of the rock in the reservoir according to the diffusion equation, the boundary condition of the diffusion equation and the initial condition of the diffusion equation, and the water volume fraction of the pores in the reservoir.

First, the water volume fraction $c(n, t)$ of the rock in the reservoir can be solved according to the above equations (2-4) and the boundary condition of the diffusion equation and the initial condition of the diffusion equation, $$c(n,t) = L^{-1}\left\{\frac{c_1-c_0}{\left(1+\sqrt{\frac{Dp}{k^2}}\right)p}e^{-\sqrt{\frac{p}{D}}n} + \frac{c_0}{p}\right\} =$$

$$(c_1-c_0)\left[\begin{array}{c}\mathrm{erfc}\left(\frac{n}{2\sqrt{Dt}}\right)\\-e^{\frac{k}{D}n+\frac{k^2}{D}t}\cdot\mathrm{erfc}\left(\frac{n}{2\sqrt{Dt}}+\sqrt{\frac{k^2}{D}t}\right)\end{array}\right] + c_0,$$

where $$\mathrm{erfc}(x) = \frac{2}{\sqrt{\pi}}\int_x^\infty e^{u^2}du$$

is a complementary error function, and $L^{-1}\{\cdot\}$ represents an inverse Laplace transform.

Then, $\dot{A}(\vec{r}, t)$ can be obtained according to $c_1(\vec{r}, t)$, $c(n, t)$ and the definition of the water absorption rate of the rock in the reservoir $$\dot{A}(\vec{r}, t) = -D_w \frac{\partial c(n,t)}{\partial n}\bigg|_{n=0},$$

$$\dot{A}(\vec{r}, t) = -D_w \frac{\partial c(n,t)}{\partial n}\bigg|_{n=0} = (c_1(\vec{r},t)-c_0)k_f\exp\left(\frac{k_f^2}{D_w}t\right)\mathrm{erfc}\left(\sqrt{\frac{k_f^2}{D_w}t}\right).$$

Specifically, the relative magnitudes of $C_1$ and $C_0$ determine whether $\dot{A}$ is positive or negative. If $c_1 > c_0$, then $\dot{A} > 0$, indicating that the water content in the pores is greater than the water content in the solid phase and water will diffuse into the solid phase; conversely, if $c_1 < c_0$, $\dot{A} < 0$ according to the two formulas, which means that the rock solid phase loses water. Finally, under reservoir conditions, the water content in the pores is always greater than or equal to the water content in the solid phase, and a limiting condition should be added for $\dot{A}$ such that it is equal to 0 when $c_1 < c_0$. Thus $\dot{A}$ is expressed as:

$$\dot{A}(\vec{r}, t) = \begin{cases}(c_1(\vec{r},t)-c_0)k_f\exp\left(\frac{k_f^2}{D_w}t\right)\mathrm{erfc}\left(\sqrt{\frac{k_f^2}{D_w}t}\right), & \text{if } c_1 > c_0 \\ 0, & \text{if } c_1 \le c_0\end{cases} \quad (2-5)$$

Step S2303: determining a spatio-temporal evolution simulation equation of reservoir damage by the clay swelling according to the water absorption rate of the rock in the reservoir.

For the step S2303, the determining a spatio-temporal evolution simulation equation of reservoir damage by the clay swelling may include: determining the spatio-temporal evolution simulation equation of reservoir damage by the clay swelling expressed by the following formula (2-6) according to the water absorption rate $\dot{A}(\vec{r}, t)$ of the reservoir:

$$-\frac{\partial}{\partial t}\phi(\vec{r}, t) = \lambda \cdot \dot{A}(\vec{r}, t), \quad (2-6)$$

where $\phi(\vec{r}, t)$ is the porosity of the reservoir; and $\lambda$ is a clay swelling coefficient.

Specifically, the clay expansion coefficient $$\lambda = \frac{k'PI^{2.44}Cc^{3.44}}{(Cc-10)^{2.44}},$$

where Cc is a mass percentage of clay in the rock; PI is a plasticity coefficient of the rock (dimensionless), where if PI<1~2, the rock is brittle rock; if 2<PI<6, the rock is plastic-brittle rock; and if PI>6, the rock is plastic rock; and k' is an empirical parameter.

$\dot{A}(\vec{r}, t)$ can be obtained according to the above formula (2-6). If $\dot{A} > 0$ (i.e., the water absorption rate is positive), the clay swells so that $$\frac{\partial \phi(\vec{r},t)}{\partial t} < 0, \text{ i.e.,}$$

the porosity decreases.

In summary, according to the present invention, the Darcy apparent velocity of the fluid in the reservoir in a preset region of a well to be diagnosed is creatively determined; the mass balance equation for water molecules in the fluid is established according to the Darcy apparent velocity of the fluid and the diffusion coefficient of the water molecules in the fluid; the diffusion equation for diffusion of the water molecules in the fluid to the interior of rock in the reservoir is established; and the spatio-temporal evolution simulation equation of reservoir damage by the clay swelling is determined according to the diffusion equation and the mass balance equation. Thus, using the determined spatio-temporal evolution simulation equation, a four-dimensional spatio-temporal evolution process of characteristics of reservoir damage caused by the clay swelling can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Figure 2D:
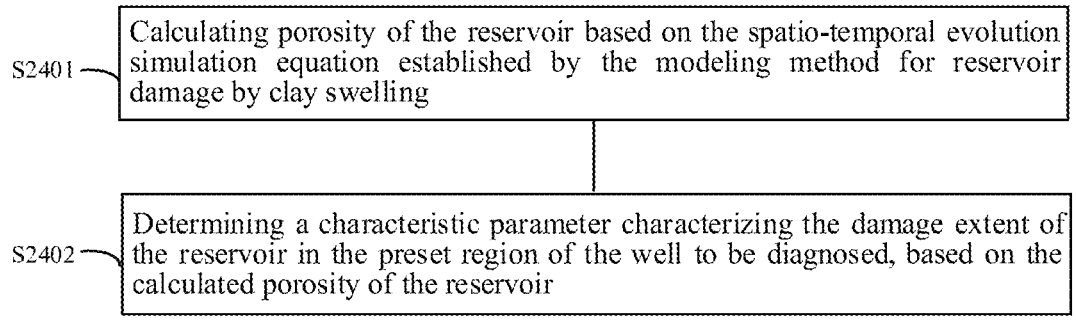
FIG. 2D is a flow diagram of a method for determining a damage extent of a reservoir provided in an embodiment of the present invention.

FIG. 2D is a flow diagram of a method for determining a damage extent of a reservoir provided in an embodiment of the present invention. As shown in FIG. 2D, the method for determining the damage extent of the reservoir may include steps S2401-S2402.

Step S2401: determining porosity of the reservoir based on the spatio-temporal evolution simulation equation established by the modeling method for reservoir damage by clay swelling.

For the solution of the spatio-temporal evolution simulation equation for reservoir damage by the clay swelling expressed by the above formula (2-6), $c_1(\vec{r}, t)$ needs to be calculated according to formula (2-3). For the specific solving process, reference can be made to the solving process of the volume concentration of the deposited particles in the above Embodiment 1, which will not be described here.

Figure 2E:
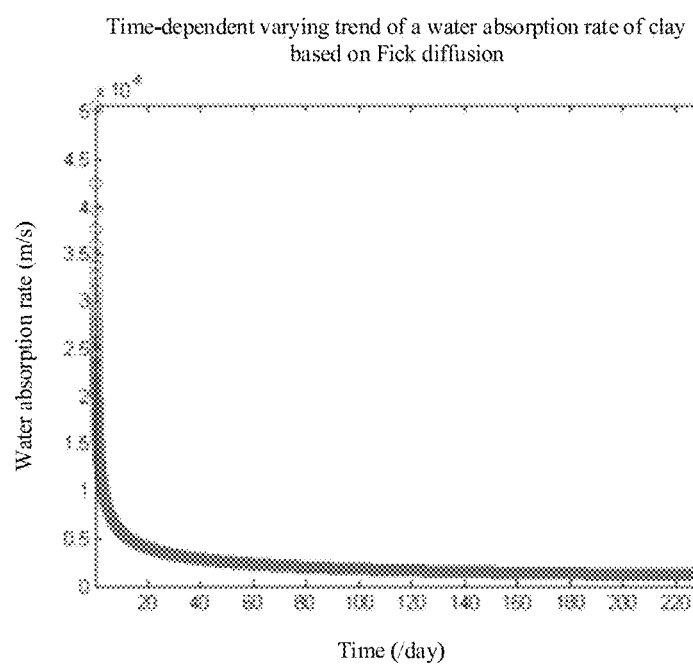
FIG. 2E is a schematic diagram of evolution of a water absorption rate over time provided in an embodiment of the present invention.

After the water volume fraction $c_1(r, t)$ of the pores in the reservoir is calculated by the above method, the water absorption rate Å of the reservoir can be calculated according to the above formula (2-5) (FIG. 2E illustrates variations of the water absorption rate Å at a particular location r in the reservoir with time), and thus the spatio-temporal evolution simulation equation established by the above modeling method of reservoir damage by the clay swelling comprehensively considers the influence of various physical and chemical factors on reservoir damage during the clay swelling, so the porosity of the reservoir obtained by this step S2401 is very precise.

Step S2402: determining a characteristic parameter characterizing the damage extent of the reservoir in a preset region of a well to be diagnosed, based on the determined porosity of the reservoir.

Wherein the characteristic parameter may be the permeability of the reservoir.

For the step S2402, the determining a characteristic parameter characterizing the damage extent of the reservoir in a preset region of a well to be diagnosed may include: determining the permeability $K(\vec{r}, t)$ of the reservoir based on the porosity $\phi(\vec{r}, t)$ of the reservoir and formula (2-7):

$$K(\vec{r}, t)/K_0(\vec{r}) = \left(\frac{\phi(\vec{r}, t)}{\phi_0}\right)^{m_K}, \qquad (2-7)$$

where $\phi_0$ is an initial value of the porosity of the reservoir; $m_K$ is a second empirical value; and $K_0(\vec{r})$ is an initial value of the permeability of the reservoir.

The characteristic parameter may be a fluid loss coefficient of the reservoir.

For the step S2402, the determining a characteristic parameter characterizing the damage extent of the reservoir in a preset region of a well to be diagnosed may include: determining the fluid loss coefficient $k(\vec{r}, t)$ of the reservoir based on the porosity $\phi(\vec{r}, t)$ of the reservoir and formula (2-8):

$$k(\vec{r}, t) = k_0(\vec{r}) \cdot \left(\frac{\phi(\vec{r}, t)}{\phi_{dmax}}\right)^{m_k}, \qquad (2-8)$$

where $\phi_0$ is the initial value of the porosity of the reservoir; $\phi_{d\ max}$ is maximum porosity of the reservoir, $m_k$ is a first empirical value; and $k_0(\vec{r})$ is an initial value of the fluid loss coefficient of the reservoir.

In the case where the characteristic parameter is the permeability of the reservoir and the fluid loss coefficient of the reservoir, the permeability of the reservoir can be determined by formula (2-7), and the fluid loss coefficient of the reservoir is determined by formula (2-8).

Wherein the characteristic parameter may be a skin factor of the reservoir.

For the step S2402, the determining a characteristic parameter characterizing the damage extent of the reservoir in a preset region of a well to be diagnosed may include: determining the permeability $K(\vec{r}, t)$ of the reservoir based on the porosity $\phi(r, t)$ of the reservoir and formula $$K(\vec{r}, t)/K_0(\vec{r}) = \left(\frac{\phi(\vec{r}, t)}{\phi_0}\right)^{m_K};$$

and determining the skin factor $S(\vec{r}, t)$ of the reservoir based on the permeability $K(\vec{r}, t)$ of the reservoir and formula (2-9):

$$S(\vec{r}, t) = \left(\frac{1}{K_d(\vec{r}, t)} - 1\right)\ln\left(\frac{r_{sw}}{r_w}\right), \qquad (2-9)$$

where $K_0(\vec{r})$ is the initial value of the permeability of the reservoir; and $K_d(\vec{r}, t) = K(\vec{r}, t)/K_0(\vec{r})$, $r_w$ is a wellbore radius of the well to be diagnosed, and $r_{sw}$ is a damage radius of the reservoir.

Figure 2F:
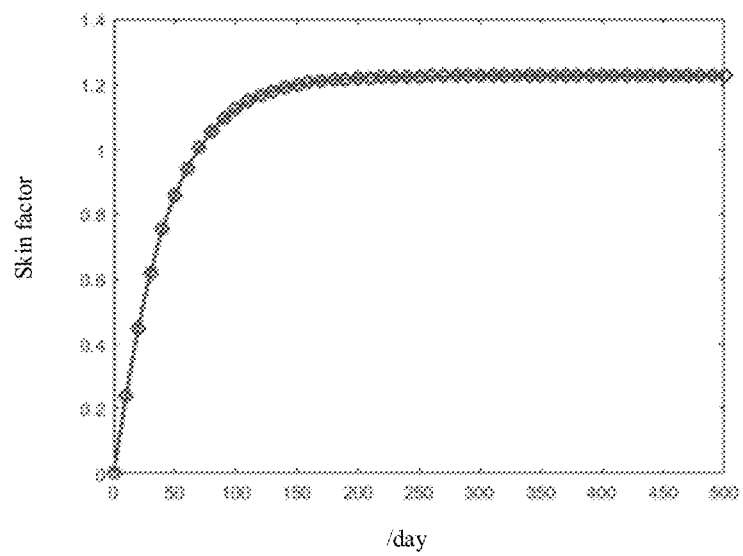
FIG. 2F is a schematic diagram of evolution of a skin factor over time provided in an embodiment of the present invention.
Figure 2G:
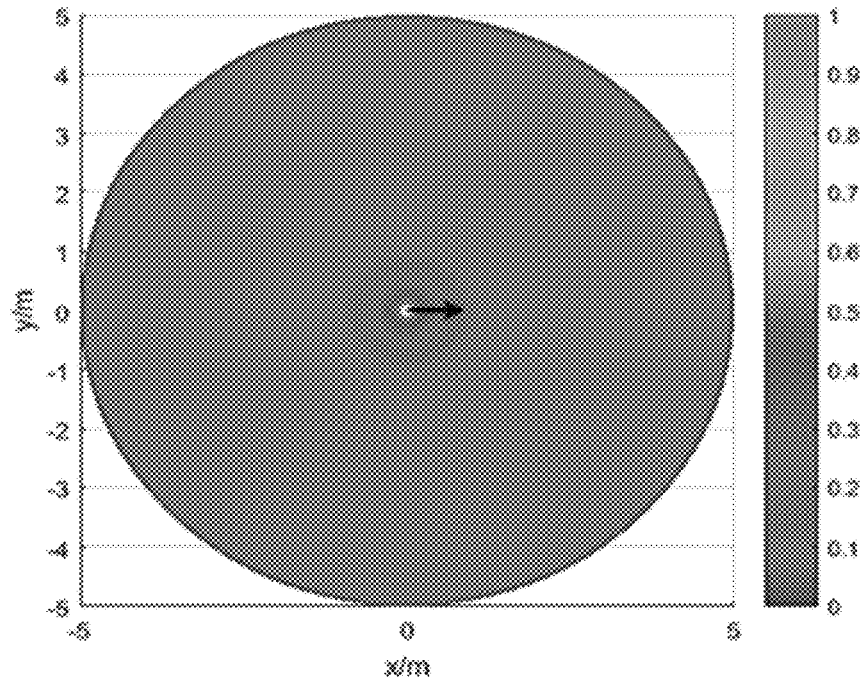
FIG. 2G is a flow diagram of a radius of reservoir damage by clay swelling at day 500 characterized by a permeability damage rate of a reservoir provided in an embodiment of the present invention.

The characteristic parameter obtained by the step S2402 (e.g., the permeability $K(\vec{r}, t)$ and the skin factor $S(\vec{r}, t)$ of the reservoir) is a result of 4D quantitative simulation of spatio-temporal evolution (as shown in FIG. 2F). More specifically, FIG. 2G shows a schematic diagram of a radius (a radius as indicated by an arrow) of reservoir damage by clay swelling at day 40 characterized by a permeability damage rate of the reservoir (the permeability damage rate $I(r_i, t)$ of the reservoir is determined based on the permeability $K(\vec{r}, t)$ of the reservoir and formula $$I(\vec{r}, t) = 1 - \frac{K(\vec{r}, t)}{K_{max}(\vec{r}, t)},$$

where $K_{max}(\vec{r}, t)$ is a maximum value of $K(\vec{r}, t)$), and a working person concerned can visually confirm the damage extent of the reservoir from FIG. 2G. Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

In summary, according to the present invention, the porosity of the reservoir can be creatively determined by using the determined spatio-temporal evolution simulation equation, then the characteristic parameter (e.g., the permeability and/or the skin factor of the reservoir) characterizing the damage extent of the reservoir in the preset region of the well to be diagnosed can be determined according to the porosity of the reservoir, and thus, a four-dimensional spatio-temporal evolution process of characteristics of reservoir damage caused by the clay swelling can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Embodiment 3—Inorganic Precipitation

Inorganic precipitation may occur when an extraneous fluid is incompatible with a fluid in a reservoir. The inorganic precipitation can clog fluid flow channels, thereby causing reservoir damage. General inorganic precipitation may include: calcium carbonate ($CaCO_3$), calcium sulfate ($CaSO_4$), strontium sulfate ($SrSO_4$), barium sulfate ($BaSO_4$) and other inorganic precipitates.

Figure 3A:
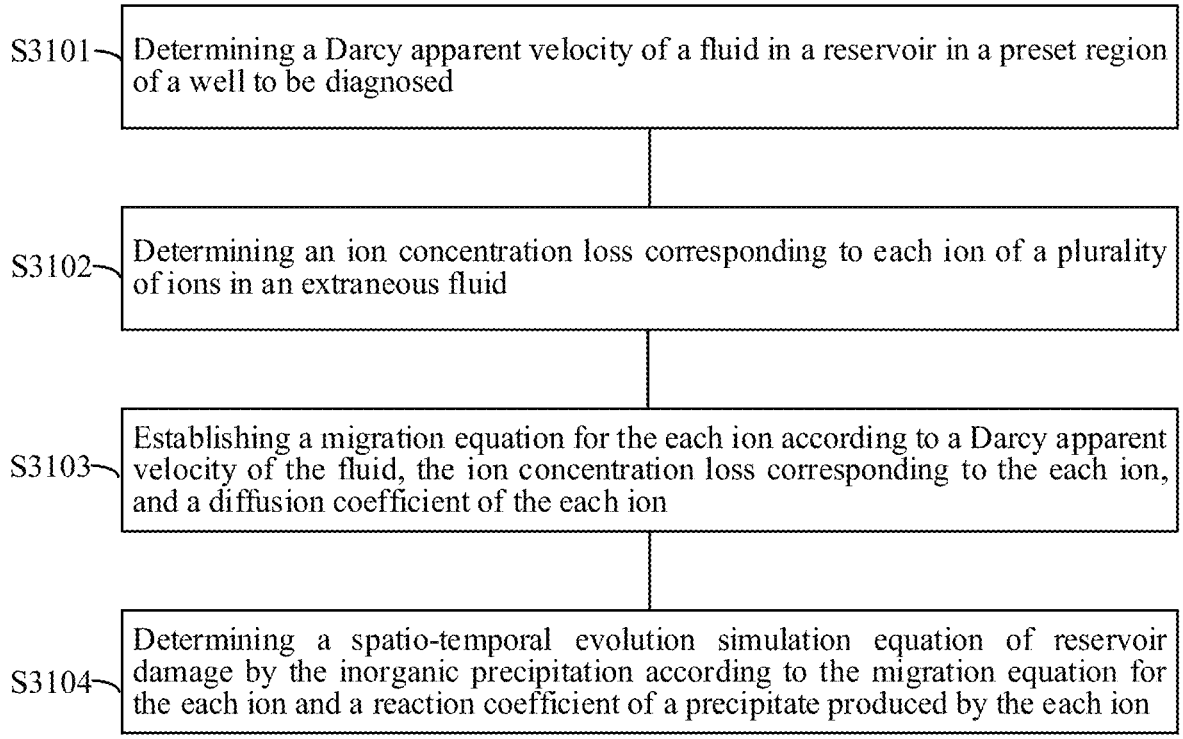
FIG. 3A is a flow diagram of a modeling method for reservoir damage by inorganic precipitation provided in an embodiment of the present invention.

FIG. 3A is a flow diagram of a modeling method for reservoir damage by inorganic precipitation provided in an embodiment of the present invention. As shown in FIG. 3A, the modeling method may include the following steps S3101-S3104.

Step S3101: determining a Darcy apparent velocity of a fluid in a reservoir in a preset region of a well to be diagnosed (e.g., a water injection well or an oil production well).

For the step S3101, determining the velocity of the fluid in the reservoir may include: establishing a pressure conduction equation for the fluid entering the reservoir; and determining the Darcy apparent velocity of the fluid according to the pressure conduction equation and a Darcy formula.

For the specific determination process, reference can be made to the process of determining a Darcy apparent velocity in the above Embodiment 2 (i.e., the above formulas (2-1) and (2-2) and related description thereof).

Step S3102: determining an ion concentration loss corresponding to each ion of a plurality of ions in an extraneous fluid.

Wherein the ion concentration loss is caused by a precipitation reaction between the each ion and a corresponding ion in the fluid in the reservoir.

For the step S3102, the determining an ion concentration loss corresponding to each ion of a plurality of ions in an extraneous fluid may include: determining the ion concentration loss $L_i(\vec{r}, t)$ corresponding to the each ion i according to a concentration $C_i(\vec{r}, t)$ of the each ion i, a concentration $C_j(\vec{r}, t)$ of an ion j of at least one ion that undergoes the precipitation reaction with the each ion i, and the following equation (3-1), $$L_i(\vec{r}, t) = \sum_{j=1}^{N_i} k_{ij} C_i^{\beta_i}(\vec{r}, t) C_j^{\beta_j}(\vec{r}, t), \quad (3-1)$$

where $k_{ij}$ is a reaction rate of the each ion i and the ion j; $N_i$ is the number of at least one ion that undergoes the precipitation reaction with the each ion i; and $\beta_i$ and $\beta_j$ are reaction coefficients of the ion i and the ion j, respectively.

Using $SO_4^{2-}$ in the extraneous fluid as an example, the $SO_4^{2-}$ can react with $Ca^{2+}$, $Ba^{2+}$ and $Sr^{2+}$ in the fluid in the reservoir to produce precipitates. At time t, at any spatial location $\vec{r}$ within the reservoir, an ion concentration loss resulting from the precipitation reaction between $SO_4^{2-}$ in the extraneous fluid and $Ca^{2+}$, $Ba^{2+}$ and $Sr^{2+}$ in the fluid in the reservoir is $$L_{[SO_4^{2-}]}(\vec{r}, t),$$

$$L_{[SO_4^{2-}]}(\vec{r}, t) = k_{[SO_4^{2-}][Ca^{2+}]} C_{[SO_4^{2-}]}^{\beta_{[SO_4^{2-}]}}(\vec{r}, t) C_{[Ca^{2+}]}^{\beta_{[Ca^{2+}]}}(\vec{r}, t) +$$
$$k_{[SO_4^{2-}][Ba^{2+}]} C_{[SO_4^{2-}]}^{\beta_{[SO_4^{2-}]}}(\vec{r}, t) C_{[Ba^{2+}]}^{\beta_{[Ba^{2+}]}}(\vec{r}, t) +$$
$$k_{[SO_4^{2-}][Sr^{2+}]} C_{[SO_4^{2-}]}^{\beta_{[SO_4^{2-}]}}(\vec{r}, t) C_{[Sr^{2+}]}^{\beta_{[Sr^{2+}]}}(\vec{r}, t),$$

where $$k_{[SO_4^{2-}][Ca^{2+}]}, k_{[SO_4^{2-}][Ba^{2+}]} \text{ and } k_{[SO_4^{2-}][Sr^{2+}]}$$

are reaction rates of the precipitation reactions between $SO_r^{2-}$ and $Ca^{2+}$, $Ba^{2+}$ and $Sr^{2+}$, respectively;

$$C_{[SO_4^{2-}]}(\vec{r}, t), C_{[Ca^{2+}]}(\vec{r}, t), C_{[Ba^{2+}]}(\vec{r}, t) \text{ and } C_{[Sr^{2+}]}(\vec{r}, t)$$

are concentrations of the ions $SO_4^{2-}$, $Ca^{2+}$, $Ba^{2+}$ and $Sr^{2+}$ at time t, at the reservoir space $\vec{r}$, respectively; and $$\beta_{[SO_4^{2-}][Ca^{2+}]}, \beta_{[SO_4^{2-}][Ba^{2+}]} \text{ and } \beta_{[SO_4^{2-}][Sr^{2+}]}$$

are a reaction coefficient of the ion $SO_4^{2-}$ and the ion $Ca^{2+}$, a reaction coefficient of the ion $SO_4^{2-}$ and the ion $Ba^{2+}$, and a reaction coefficient of the ion $SO_4^{2-}$ and the ion or $Sr^{2+}$, respectively. Similarly, an ion concentration loss in the reservoir resulting from a precipitation reaction between each of other ions in the extraneous fluid and a corresponding ion in the reservoir can be determined.

Specifically, the reaction rate $k_{ij}$ of the each ion i and the ion j is determined by a scaling index of a corresponding precipitate produced by the each ion i and the ion j. For example, the reaction rate $k_{ij}$ of the each ion i and the ion j may satisfy the following relational expression (3-2):

$$k_{ij} = \begin{cases} 0, & I_{Sij} \leq 0 \\ k_{ij0}, & I_{Sij} > 0 \end{cases} \quad (3\text{-}2)$$

where $k_{ij0}$ is a constant; and $I_{Sij}$ is the scaling index of the corresponding precipitate produced by the each ion i and the ion j. More specifically, the scaling index $I_{Sij}$ may be determined by the concentration of the each ion i, the ionic strength of the fluid, the concentration of the ion j, the temperature of the fluid and the pressure of the fluid.

Specifically, at a certain temperature T, pressure P and ion concentration ([Me] is a concentration of a (free) cation, wherein the cation may be a calcium ion, a strontium ion, a barium ion, or the like, and [An] is a concentration of a (free) anion, wherein the anion may be a bicarbonate ion, a sulfate ion, or the like), whether a precipitation reaction in a reservoir solution occurs is usually determined by the scaling index, which is expressed as:

$$I_s(P, T, S_i) = \log\left(\frac{[M_e][A_n]}{K_c(P, T, S_i)}\right) = \log([M_e][A_n] - \log K_c(P, T, S_i)), \quad (3\text{-}3)$$

where $S_i$ is the ionic strength of the fluid; and $K_C$ is a solubility product coefficient of the precipitation reaction.

If $I_S \leq 0$, the solution is in an undersaturated or saturated state, an inorganic precipitate is generated; if $I_S > 0$, the solution is in a supersaturated state, there is a tendency to generate an inorganic precipitate. $I_s$ varies with the reservoir location, ion concentration, temperature and pressure, and is a function related to time and space.

According to a Tomson-Oddo calculation method, scaling indices of four inorganic precipitates under reservoir conditions are respectively as follows:

(1) Calcium carbonate $CaCO_3$:

$I_s(P,T,S_i)=\log([Ca^{2+}][CO_3^-])+pH-2.42+0.02T-1.53\times 10^{-5}T^2-6.33\times 10^{31}\,^3P-2.02S_i^{1/2}+0.727S_i$ (2) Calcium sulfate $CaSO_4$:
a, when T<80° C., the precipitate formed is mainly $CaSO_4 \cdot 2H_2O$, and its scaling index is expressed as:

$I_S(P,T,S_i)[CaSO_4 \cdot 2H_2O]=\log([Ca^{2+}][SO_4^{2-}])+3.47+1.8\times 10^{31}\,^3T+2.5\times 10^{-6}T^2-5.9\times 10^{-5}P-1.13S_i^{1/2}+0.37S_i-2.0\times 10^{-3}S_i^{1/2}T,$ b, when 80° C.<T<121° C., the precipitate formed is mainly $CaSO_4 \cdot 1/2H_2O$, and its scaling index is expressed as:

$I_S(P,T,S_i)[CaSO_4 \cdot 1/2H_2O]=\log([Ca^{2+}][SO_4^{2-}])+4.04-1.9\times 10^{-3}T+11.9\times 10^{-6}T^2-6.9\times 10^{-5}P-1.66S_i^{1/2}+0.49S_i-0.66\times 10^{-3}S_i^{1/2}T,$ c, when T>121° C., the precipitate formed is mainly $CaSO_4$, and its scaling index is expressed as:

$I_S(P,T,S_i)[CaSO_4]=\log([Ca^{2+}][SO_4^{2-}])+2.52+9.98\times 10^{-3}T-0.97\times 10^{-6}T^2-3.07\times 10^{-5}P-1.09S_i^{1/2}+0.50S_i-3.3\times 10^{-3}S_i^{1/2}T,$ (3) Barium sulfate $BaSO_4$:

$I_S(P,T,S_i)[BaSO_4]=\log([Ba^{2+}][SO_4^{2-}])+10.03-4.8\times 10^{-3}T+11.4\times 10^{-6}T^2-4.8\times 10^{-5}P-2.62S_i^{1/2}+0.89S_i-2.0\times 10^{-3}S_i^{1/2}T,$ (4) Strontium sulfate $SrSO_4$:

$I_S(P,T,S_i)[SrSO_4]=\log([Sr^{2+}][SO_4^{2-}])+3.11+2.0\times 10^{-3}T+6.4\times 10^{-6}T^2-4.6\times 10^{-5}P-1.89S_i^{1/2}+0.67S_i-1.9\times 10^{-3}S_i^{1/2}T.$ The pH in the above formulas is a pH value of a liquid in the reservoir (a liquid formed by mixing an original liquid in the reservoir with an extraneous liquid).

Step S3103: establishing a migration equation for the each ion according to a Darcy apparent velocity of the fluid, the ion concentration loss corresponding to the each ion, and a diffusion coefficient of the each ion.

In an ion concentration control equation, a flow J of ion migration includes two parts: convection and diffusion, using the ion i as an example:

$$J_i = J_{id} + J_{ic} = -D_i \nabla C_i + u C_i,$$

where $J_i$ is a migration flow of the ion i; $J_{id}$ is a diffusion flow of the ion i; $J_{ic}$ is a convection flow of the ion i; u is the Darcy apparent velocity of the fluid; $C_i$ is the concentration of the each ion i; and $D_i$ is the diffusion coefficient of the each ion i.

For the step S3103, the precipitation reaction results in an ion concentration loss $L_i(\vec{r}, t)$ at a reservoir space $\vec{r}$ at time t, and a migration equation for the each ion i that can be established according to the law of mass conservation may include:

$$\phi(\vec{r}, t)\frac{\partial C_i(\vec{r}, t)}{\partial t} = \nabla \cdot (D_i \nabla C_i(\vec{r}, t)) - \nabla \cdot (u C_i(\vec{r}, t)) - \sum_{j=1}^{N_i} k_{ij} C_i^{\beta_i}(\vec{r}, t) C_j^{\beta_i}(\vec{r}, t), \quad (3\text{-}4)$$

where u is the Darcy apparent velocity of the fluid; $\phi(\vec{r}, t)$ is the porosity of the reservoir; and $D_i$ is the diffusion coefficient of the each ion i.

Step S3104: determining a spatio-temporal evolution simulation equation of reservoir damage by the inorganic precipitation according to the migration equation for the each ion and a reaction coefficient of a precipitate produced by the each ion.

Wherein the spatio-temporal evolution simulation equation is used to simulate a four-dimensional spatio-temporal evolution process of characteristics of reservoir damage caused by the corresponding precipitates produced by the plurality of ions.

For the step S3104, the determining a spatio-temporal evolution simulation equation of reservoir damage by the inorganic precipitation may include: determining the concentration $C_i(\vec{r}, t)$ of the each ion i according to the mass balance equation (3-4) of the each ion; and determining the spatio-temporal evolution simulation equation of reservoir damage by the inorganic precipitation expressed by the following formula (3-5) according to the concentration $C_i(\vec{r}, t)$ of the each ion i and a reaction coefficient $co_{ij}$ of a precipitate produced by the each ion:

$$d_{ij}(\vec{r}, t+dt) = d_{ij}(\vec{r}, t) + \frac{1}{\phi}CO_{ij}[C_i(\vec{r}, t+dt) - C_i(\vec{r}, t)], \quad (3\text{-}5)$$

where $d_{ij}(\vec{r}, t)$ is an accumulated concentration of the precipitate produced by the precipitation reaction between the ion i and the ion j at time t and at the reservoir space $\vec{r}$; and $d_{ij}(\vec{r}, t+dt)$ is an accumulated concentration of the precipitate produced by the precipitation reaction between the ion i and the ion j at time t+dt and at the reservoir space $\vec{r}$.

In summary, according to the present invention, the migration equation for the each ion of the plurality of ions in the extraneous fluid is creatively established according to the Darcy apparent velocity of the fluid in the reservoir in the preset region of the well to be diagnosed, the ion concentration loss corresponding to the each ion, and the diffusion coefficient of the each ion; and the spatio-temporal evolution simulation equation of reservoir damage by the inorganic precipitation is determined according to the migration equation for the each ion and the reaction coefficient of the precipitate produced by the each ion. Thus, by using the determined spatio-temporal evolution simulation equation, a four-dimensional spatio-temporal evolution process of characteristics of reservoir damage caused by the inorganic precipitation can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Figure 3B:
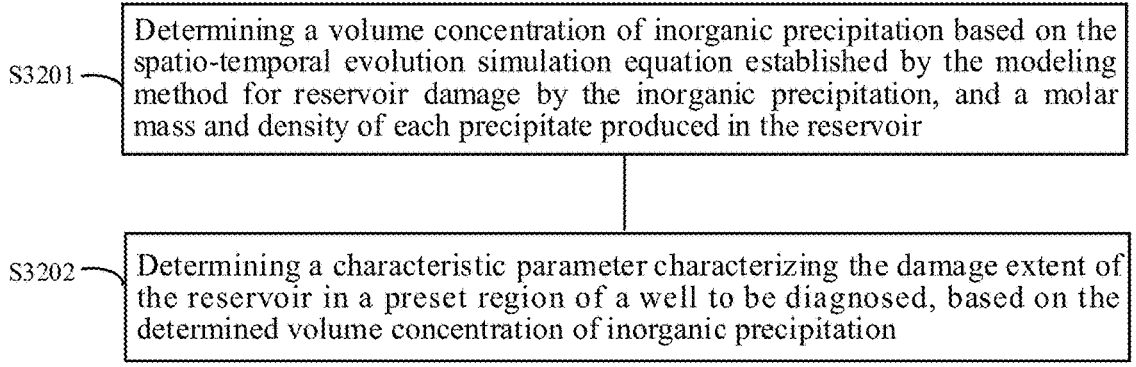
FIG. 3B is a flow diagram of a method for determining a damage extent of a reservoir provided in an embodiment of the present invention.

FIG. 3B is a flow diagram of a method for determining a damage extent of a reservoir provided in an embodiment of the present invention. As shown in FIG. 3B, the method may include steps S3201-S3202.

Step S3201: determining a volume concentration of inorganic precipitation based on the spatio-temporal evolution simulation equation established by the modeling method for reservoir damage by the inorganic precipitation, and a molar mass and density of each precipitate produced in the reservoir.

Wherein the each precipitate is produced by a precipitation reaction of an each ion of a plurality of ions in an extraneous fluid and a corresponding ion in a fluid in the reservoir, and the volume concentration of inorganic precipitation is a total volume concentration of the each precipitate.

For the migration equation of the each ion in reservoir damage by the inorganic precipitation expressed by the above formula (3-4), a water volume fraction $c_1(\vec{r}, t)$ of pores in the reservoir can be solved by referring to the process of solving a volume concentration of deposited particles in the above Embodiment 1, which will not be described here.

After the concentration $C_i(\vec{r}, t)$ of the each ion i is calculated by the above method, an accumulated concentration $d_{ij}(\vec{r}, t)$ of each precipitate can be calculated according to the above formula (3-5); and then a volume concentration $C_{d_{ij}}(\vec{r}, t)$ of the each precipitate can be determined according to the accumulated concentration $d_{ij}(\vec{r}, t)$, molar mass and density of the each precipitate, and finally a volume concentration $$C_d(\vec{r}, t) = \sum_{i=1}^{M} \sum_{j=1}^{N_i} C_{d_{ij}}(\vec{r}, t)$$

of all precipitates can be determined. where $N_i$ is the number of ions which are located in the reservoir and suffer from a precipitation reaction with the ion i; and M is the number of a plurality of ions in the extraneous fluid. The spatio-temporal evolution simulation equation established by the above modeling method for reservoir damage by the inorganic precipitation comprehensively considers the influence of various physicochemical factors on the reservoir damage when inorganic precipitation occurs in the reservoir, and thus the volume concentration of the inorganic precipitation obtained by the solution of the step S3201 is very precise.

Step S3202: determining a characteristic parameter characterizing the damage extent of the reservoir in a preset region of a well to be diagnosed, based on the determined volume concentration of inorganic precipitation.

Wherein the characteristic parameter may be permeability of the reservoir and/or a fluid loss coefficient of the reservoir.

In an embodiment, the characteristic parameter may be the permeability of the reservoir.

For the step S3202, the determining a characteristic parameter characterizing the damage extent of the reservoir in a preset region of a well to be diagnosed includes: determining the permeability $K(\vec{r}, t)$ of the reservoir based on the volume concentration $C_d(\vec{r}, t)$ of the inorganic precipitation and formula (3-6):

$$K(\vec{r}, t) / K_0(\vec{r}) = \left(1 - \frac{C_d(\vec{r}, t)}{\phi_0}\right)^{m_K}. \tag{3-6}$$

In an embodiment, the characteristic parameter may be the permeability of the reservoir.

For step S3202, the determining a characteristic parameter characterizing the damage extent of the reservoir in a preset region of a well to be diagnosed includes: determining the fluid loss coefficient $k(\vec{r}, t)$ of the reservoir based on the volume concentration $C_d(\vec{r}, t)$ of the inorganic precipitation and formula (3-7):

$$k(\vec{r}, t) / k_0(\vec{r}) \cdot \left(1 - \frac{C_d(\vec{r}, t)}{C_{dmax}}\right)^{m_k}, \tag{3-7}$$

where $\phi_0$ is an initial value of the porosity of the reservoir; $C_{d\,max}$ is a maximum volume concentration of the inorganic deposition; $m_k$ and $m_K$ are a first empirical value and a second empirical value, respectively; $K_o(\vec{r})$ is an initial value of the permeability of the reservoir; and $k_0(\vec{r})$ is an initial value of the fluid loss coefficient of the reservoir.

Wherein the characteristic parameter is a skin factor of the reservoir.

For the step S3202, the determining a characteristic parameter characterizing the damage extent of the reservoir in a preset region of a well to be diagnosed may include: determining the permeability $K(\vec{r}, t)$ of the reservoir based on the volume concentration $C_d(\vec{r}, t)$ of the inorganic precipitation and formula $$K(\vec{r}, t) / K_0(\vec{r}) = \left(1 - \frac{C_d(\vec{r}, t)}{\phi_0}\right)^{m_K};$$

and determining the skin factor $S(\vec{r}, t)$ of the reservoir based on the permeability $K(\vec{r}, t)$ of the reservoir and formula (3-8):

$$S(\vec{r}, t) = \left(\frac{1}{K_d(\vec{r}, t)} - 1\right)\ln\left(\frac{r_{sw}}{r_w}\right), \quad (3-8)$$

where $K_o(\vec{r})$ is the initial value of the permeability of the reservoir; and $\overline{K_d(\vec{r},t)} = K(\vec{r}, t)/K_o(\vec{r})$, $r_w$ is a wellbore radius of the well to be diagnosed, and $r_{sw}$ is a damage radius of the reservoir.

The characteristic parameter (e.g., the permeability $K(\vec{r}, t)$ and the skin factor $S(\vec{r}, t)$ of the reservoir) obtained by the step S3202 is a result of 4D quantitative simulation of spatio-temporal evolution (not shown). Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

In summary, the volume concentration of the inorganic precipitation can be determined by using the determined spatio-temporal evolution simulation equation, and then the characteristic parameter (e.g., the permeability and/or the skin factor of the reservoir) characterizing the damage extent of the reservoir in the preset region of the well to be diagnosed can be determined based on the determined volume concentration of the inorganic precipitation, whereby a four-dimensional spatio-temporal evolution process of the characteristics of reservoir damage caused by the inorganic precipitation can be simulated quantitatively. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Embodiment 4—Fine Particles Within a Reservoir

The essence of clogging by fine particles (i.e., solid-phase particles with particle sizes smaller than a preset size (e.g., 37 microns)) within a reservoir is migration and deposition of the fine particles within the reservoir. Thus, the core of embodiments of the present invention is to establish a kinetic model of migration and deposition of the fine particles within the reservoir. Specifically, based on mass conservation, a diffusion relationship, and the like, a spatio-temporal evolution control phenomenological model (containing a concentration C of migrating fine particles and a concentration $C_d$ of deposited fine particles) of concentration distribution of the fine particles within the reservoir around the well to be diagnosed is established, and in conjunction with a relationship between a deposition concentration and a characteristic parameter characterizing the damage extent of the reservoir such as permeability, spatio-temporal field distribution of the characteristic parameter such as permeability can be diagnosed.

It should be noted that for the sake of simple description, for physical and chemical quantities that evolve with time and space in embodiments of the present invention, a variable $(\vec{r}, t)$ may be omitted, for example, $\phi_w(\vec{r}, t)$ may be shortened to $\phi_w$; and $K(\vec{r}, t)$ may be shortened to K.

Figure 4A:
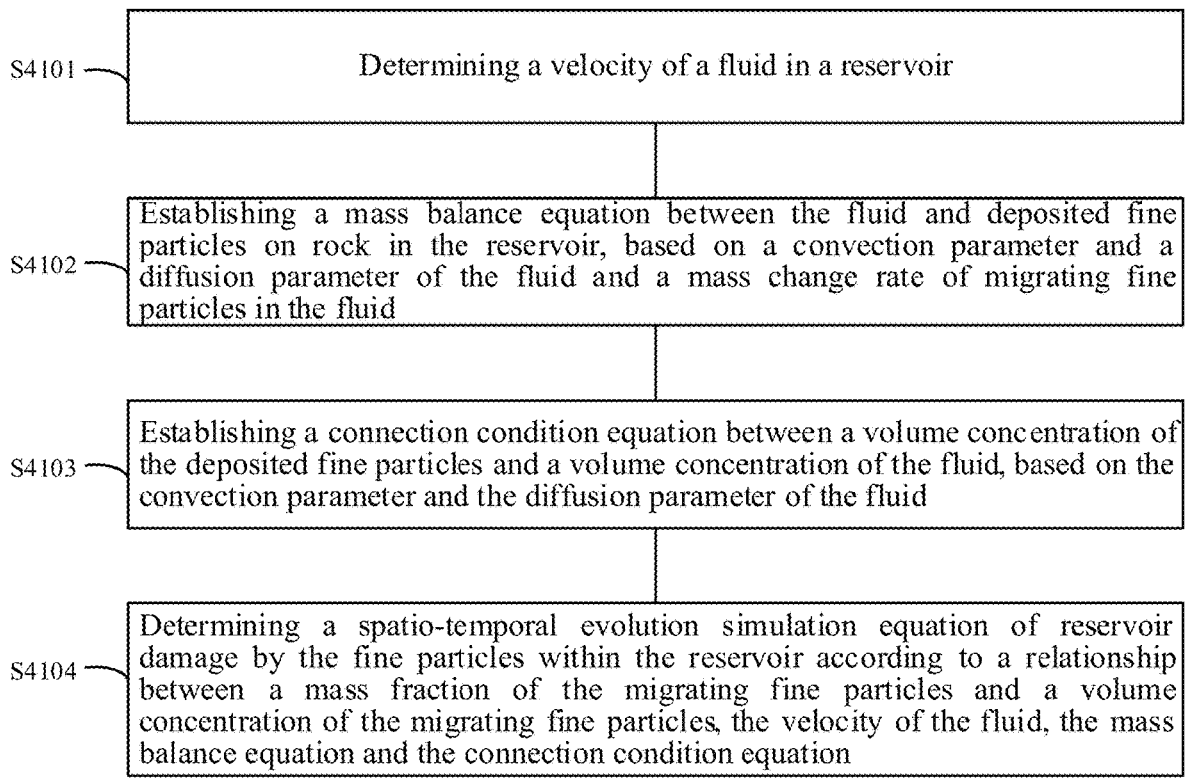
FIG. 4A is a flow diagram of a modeling method for reservoir damage by fine particles within a reservoir provided in an embodiment of the present invention.

FIG. 4A is a flow diagram of a modeling method for reservoir damage by fine particles within a reservoir provided in an embodiment of the present invention. The modeling method may include steps S4101-S4104.

Step S4101: determining a velocity of a fluid in a reservoir.

Wherein the reservoir is located in a preset region of a well to be diagnosed (e.g., a water injection well, or an oil production well).

For the step S4101, the determining a velocity of a fluid in a reservoir may include:
establishing a pressure conduction equation for the fluid entering the reservoir; and determining the velocity of the fluid according to the pressure conduction equation and a Darcy formula.

Specifically, a pressure is a force that drives a solid-liquid mixture (i.e., a fluid containing the migrating fine particles) to continuously intrude from a wellbore of the water injection well into the reservoir around the well, whereby the pressure conduction equation for the fluid entering the reservoir as expressed in formula (4-1) can be established:

$$\nabla^2 P(\vec{r}, t) = \frac{\phi \mu c_t}{K(\vec{r}, t)} \frac{\partial P(\vec{r}, t)}{\partial t}, \quad (4-1)$$

and then the velocity of the fluid can be determined according to formula (4-1) and the Darcy formula (e.g., formula (4-2) below):

$$v(\vec{r}, t) = -\frac{\tau K(\vec{r}, t)}{\mu \phi} \nabla P(\vec{r}, t), \quad (4-2)$$

where $P(\vec{r}, t)$ is the pressure of the fluid; $\phi$ is the porosity of the reservoir; $\mu$ is fluid viscosity; $c_t$ is a fluid-rock integrated compression coefficient; $K(\vec{r}, t)$ is the permeability of the reservoir; and $\tau$ is the tortuosity of the reservoir.

Step S4102: establishing a mass balance equation between the fluid and deposited fine particles on rock in the reservoir, based on a convection parameter and a diffusion parameter of the fluid and a mass change rate of the migrating fine particles in the fluid.

There is a correlation between the mass change rate of the migrating fine particles and the velocity of the fluid. A process of obtaining the mass change rate of the migrating fine particles is described in detail below.

In establishment of a fine particle migration damage model, first a critical velocity of the fluid when the deposited fine particles start to migrate is considered, and then how the migrating fine particles change a solid-liquid flow deposition equation is considered.

Figure 4B:
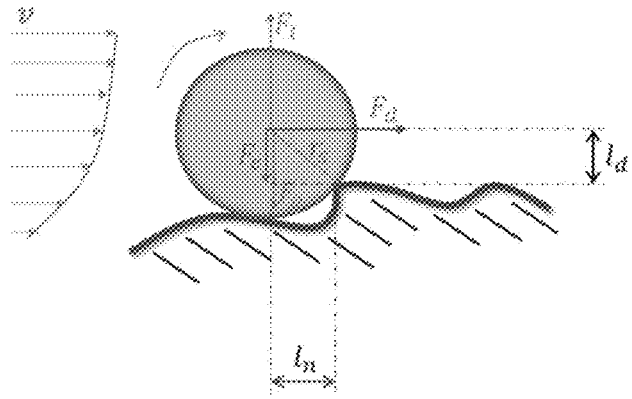
FIG. 4B shows a schematic diagram of forces on a fine particle on an inner surface of a rock pore when the fine particle start to move.

According to a fine particle starting model, forces on elastic solid fine particles with a radius $r_s$ on a rough inner surface of a rock pore is shown in FIG. 4B. The deposited fine particles are subjected to forces and moments due to fluid scouring and interaction with the rock surface, and the critical velocity is a corresponding fluid velocity when these forces and moments are just balanced. The critical velocity may be obtained by: establishing a moment balance equation for the deposited fine particles according to the forces on the deposited fine particles, wherein the forces on the deposited fine particles are related to the velocity of the fluid; and determining the critical velocity according to the moment balance equation for the deposited fine particles.

Specifically, the deposited fine particles are subjected to a dragging force $F_d$, a gravity $F_g$, an electrostatic force $F_e$, and a lifting force $F_l$ in the same direction as a flow velocity v. Since the magnitudes of both the dragging force $F_d$ and the lifting force $F_l$ are functions of the flow velocity v, the corresponding flow velocity when their moments are balanced is the critical velocity $v_{cr}$. According to the forces on the deposited fine particles, the moment balance equation for the deposited fine particles expressed by the following equation (4-3) is established:

$$F_d \cdot l_d = (F_e - F_l + F_g) \cdot l_n, \qquad (4\text{-}3)$$

The dragging force $F_d$ generated by a flow field near a rough inner surface of a rock pore, on the deposited fine particles attached to this surface can be obtained from an asymptotic solution of a Navier-Stokes equation, which is expressed as follows:

$$F_d = \omega \pi \mu r_s v_{cr}, \qquad (4\text{-}4)$$

where μ is the viscosity of the fluid, $r_s$ is the radius of the deposited fine particles, $v_{cr}$ is a flow velocity at a distance $r_s$ from the surface, and ω is a drag coefficient (e.g., ω=6×1.7 and in particular, if the value of ω is 6, the dragging force in this case corresponds to a dragging force on the solid-phase fine particle in free borderless flow).

The lifting force $F_l$ on the deposited fine particles by a shear flow field can be expressed as follows:

$$F_l = \chi [\rho \mu (r_s v_{cr})^3]^{1/2}, \qquad (4\text{-}5)$$

where ρ and μ are the density and viscosity of the fluid, respectively, and χ is a lift coefficient.

The gravity $F_g$ of the deposited fine particles can be expressed as follows:

$$F_g = \frac{4}{3}\pi(\rho_s - \rho)g r_s^3, \qquad (4\text{-}6)$$

where g is a gravitational acceleration, $\rho_s$ is the density of the deposited fine particle, and ρ is the density of the fluid.

Generally, the magnitude of the electrostatic force $F_e$ on the deposited fine particles is calculated from a derivative of an electrostatic potential with respect to space:

$$F_e = -\frac{\partial V(h)}{\partial h}, \qquad (4\text{-}7)$$

where V(h) is total electrostatic potential energy, which includes three parts: $V_{LVA}$ (London-Van der Waals potential), $V_{DLR}$ (electrical double layer potential) and $V_{BR}$ (Bonn potential). That is, V(h) can be expressed as:

$$V = V_{LVA} + V_{DLR} + V_{BR},$$

wherein $V_{LVA}$ and $V_{DLR}$ can be derived from the well-known DLVO theory:

$$V_{LVA} = -\frac{H}{6}\left[\frac{2(1+Z)}{Z(2+Z)} + \ln\left(\frac{Z}{2+Z}\right)\right],$$

$$V_{DLR} = \frac{\varepsilon_0 D_e r_s}{4}\left[2\psi_{01}\psi_{02}\ln\left(\frac{1+\exp(-\kappa h)}{1-\exp(-\kappa h)}\right) - (\psi_{01}^2 + \psi_{02}^2)\ln(1-\exp(-2\kappa h))\right],$$

wherein, $V_{BR}$ can be expressed as:

$$V_{BR} = \frac{H}{7560}\left(\frac{\sigma_{LJ}}{r_s}\right)^6\left[\frac{8+Z}{(2+Z)^7} + \frac{6-Z}{Z^7}\right], \text{ where } Z = \frac{h}{r_s}.$$

H is a Hamaker constant, h is a distance between the surface of the deposited fine particles and the surface of a medium (e.g., rock), $\varepsilon_0$ is a dielectric constant of the deposited fine particles, $D_e$ is e an electrical double layer constant of the deposited fine particles, $\psi_{01}$ and $\psi_{02}$ are surface potential energy of the deposited fine particles and rock framework fine particles, respectively, $\sigma_{LJ}$ is a Lennard-Jones potential constant of atomic or molecular interaction, and κ is an inverse Debye length (i.e., its magnitude is 1 divided by the length).

$v_{cr}$ and the flow velocity v of the fluid (the true Darcy velocity, v in the fine particle migration model) have a relationship as follows:

$$v_{cr} = \frac{3 r_s v}{r_c}, \qquad (4\text{-}8)$$

in the formula, $r_c$ is an average radius of reservoir pore throats (i.e., an average radius of pores); and a relationship between the flow velocity v of the fluid and a dragging force on the surface fine particles by the fluid can be determined by solving the equations (4-4) and (4-8) simultaneously.

A force arm $l_n$ (of a normal force $F_n$) is approximately a radius of a contact deformation surface of the deposited fine particle with a matrix (e.g., rock) under the action of the normal force $F_n$ ($F_n = F_e - F_l + F_g$):

$$l_n = \left(\frac{|F_e - F_l + F_g| r_s}{4K}\right)^{1/3}, \qquad (4\text{-}9)$$

where $r_s$ is a radius of a starting fine particle (under the scouring action of the fluid, part of the deposited fine particles start to migrate and enter the fluid to become migrating fine particles, and the part of the fine particles become starting fine particles), K is a complex Young's modulus, and $$K = \frac{4}{3\left(\frac{1-v_1^2}{E_1} + \frac{1-v_2^2}{E_2}\right)},$$

where $E_1$ and $E_2$ are Young's moduli of the starting fine particle and the matrix, respectively, and $v_1$ and $v_2$ are the Poisson's ratios of the starting fine particle and the matrix, respectively.

Once $l_n$ is obtained, $l_d$ can be determined from a simple geometric relationship:

$$l_d = \sqrt{r_s^2 - l_n^2}, \qquad (4\text{-}10)$$

and by solving simultaneous equations of the above formulas (4-3)-(4-10), the critical velocity $v_{cr}$ can be obtained, which is expressed as follows:

$$v_{cr} = \frac{r_c}{3\omega\pi\mu r_s^2} \cdot \frac{\frac{4}{3}\pi(\rho_s-\rho)r_s^2 - \chi\sqrt{27\rho\mu\left(\frac{r_s^2 v}{r_c}\right)^3} - \frac{\partial V(h)}{\partial h}}{\sqrt{\left[\frac{4Kr_s^2}{\frac{4}{3}\pi(\rho_s-\rho)r_s^2 - \chi\sqrt{27\rho\mu\left(\frac{r_s^2 v}{r_c}\right)^3} - \frac{\partial V(h)}{\partial h}}\right]^{\frac{2}{3}} - 1}} \quad (4\text{-}11)$$

According to formula (4-11), the critical velocity $v_{cr}$ is related to the mechanical, physical, and chemical properties of the deposited fine particles and the medium (e.g., rock). Only when the actual velocity of the fluid in the reservoir exceeds the critical velocity $v_{cr}$, can the deposited fine particles migrate under the action of the fluid to become migrating fine particles (or a migrating material source). In general, the flow velocity of the fluid closer to the center of the wellbore of the well to be diagnosed is higher, so a fine particle migration region should be an annular band near the wellbore.

According to a mass equation, assuming that the mass change rate of the migrating fine particles (i.e., the quantity of fine particles released) is $q_s$, $q_s$ has the following properties:

$$q_s : \begin{cases} > 0, & v \geq v_{cr} \\ = 0, & v < v_{cr} \end{cases}.$$

In other words, only when the velocity of the fluid (which can also be called fluid flow velocity) exceeds the critical velocity, can the fine particles incipiently move and enter the fluid to participate in migration, thereby increasing the mass of the fluid-solid mixture. Therefore, for the step S4102, the establishing a mass balance equation between the fluid and deposited fine particles on rock in the reservoir may include: establishing the mass balance equation expressed in the following formula, based on a convection parameter and a diffusion parameter of the fluid, $$\frac{\partial}{\partial t}\left(\rho\phi w(\vec{r}, t)\right) + \nabla\left(\rho u w(\vec{r}, t) + j(\vec{r}, t)\right) = -\dot{m} + q_s, \quad (4\text{-}12)$$

where $\rho$ is the density of the fluid; $\phi$ is the porosity of the reservoir; $w(\vec{r}, t)$ is the mass fraction (which may also be called a mass concentration) of the deposited fine particles; u is a Darcy apparent velocity; $j(\vec{r}, t)$ is a diffusion flow rate, $j(\vec{r}, t) = -\phi\rho_L D \nabla w(\vec{r}, t)$, where $\rho_L$ is the density of the fluid, $D(\vec{r}, t)$ is a diffusion coefficient of the migrating fine particles, $D(\vec{r}, t) = \alpha v(\vec{r}, t)$, $\alpha$ is a vertical diffusivity, and $v(\vec{r}, t)$ is the velocity of the fluid;

$$\dot{m}(\vec{r}, t) \equiv \frac{\partial(\vec{r}, t)}{\partial t} = k(\vec{r}, t)(\rho u w(\vec{r}, t) + j(\vec{r}, t)); \dot{m}(\vec{r}, t)$$

is an accumulated mass of the deposited fine particles per unit time; t is time; and $q_s$ is the mass change rate of the migrating fine particles.

Wherein the mass change rate $q_s$ of the migrating fine particles is obtained by: determining the intensity $Q(r)$ of a release field of the deposited fine particles; determining a decay function $Y(t)$ of the intensity of the release field; and determining the mass change rate $q_s = Q(r)Y(t)$ of the migrating fine particles according to the intensity $Q(r)$ of the release field and the decay function $Y(t)$ of the intensity of the release field. Specifically, the intensity $Q(r)$ of the release field may be a constant ($q^0$), and the decay function $Y(t)$ may be an exponential decay function that can vary with time (e.g., $e^{-\lambda t}$, where $\lambda$ is a decay constant).

Step S4103: establishing a connection condition equation between a volume concentration of the deposited fine particles and a volume concentration of the fluid, based on the convection parameter and the diffusion parameter of the fluid.

For the step S4103, the establishing a connection condition equation between a volume concentration of the deposited fine particles and a volume concentration of the fluid may include: establishing the connection condition equation expressed in the following formula (4-13), based on the convection parameter and the diffusion parameter of the fluid:

$$\frac{\partial(\rho_p C_d(\vec{r}, t))}{\partial t} = k(\vec{r}, t)(\rho u w(\vec{r}, t) + j(\vec{r}, t)), \quad (4\text{-}13)$$

where $\rho_p$ is the density of the deposited fine particles; $C_d(\vec{r}, t)$ is the volume concentration of the deposited fine particles; and $k(\vec{r}, t) = k_0(\vec{r}) G_l(C_d) F_1(T)$, where $k_0$ is an original fluid loss coefficient, $$G_1(C_d) = \left(1 - \frac{C_d}{C_{dmax}}\right)^{m_k}, \text{ and}$$

$$F_1(T) = \exp\left(A_k\left(\frac{1}{T - T_{ik}} - \frac{1}{T_{ik} - T_{ck}}\right)\right).$$

Since the correlation between $F_1(T)$ ($F_1(T)$ is an exponential function related to temperature) and temperature is measured by $\exp(1/T)$ and in a common temperature range (e.g. 300 K to 400 K), the change of this function is actually very slow and actually close to an isothermal process, thus $$k(\vec{r}, t) = k_0(\vec{r}) \cdot \left(1 - \frac{C_d(\vec{r}, t)}{C_{dmax}}\right)^{m_k},$$

where $C_d(\vec{r}, t)$ is the volume concentration of the deposited fine particles, $C_{d\,max}$ is a maximum volume concentration of the deposited fine particles, and $m_k$ is a first empirical value. All of the above parameters can be either constants, or parameters that vary with space, i.e., in a non-homogeneous situation.

Step S4104: determining a spatio-temporal evolution simulation equation of reservoir damage by the fine particles within the reservoir according to a relationship between a mass fraction of the migrating fine particles and a volume concentration of the migrating fine particles, the velocity of the fluid, the mass balance equation and the connection condition equation.

Wherein the spatio-temporal evolution simulation equation is used to simulate a four-dimensional spatio-temporal evolution process of characteristics of reservoir damage caused by the fine particles.

Wherein the relationship between the mass fraction of the migrating fine particles and the volume concentration of the migrating fine particles may be $$w(\vec{r}, t) = \frac{\rho_p}{\rho_L} C(\vec{r}, t),$$

where $\rho_p$ is the density of the deposited fine particles; $\rho_L$ is the density of the fluid; $w(\vec{r}, t)$ is the mass fraction of the migrating fine particles; and $C(\vec{r}, t)$ is the volume concentration of the migrating fine particles. The spatio-temporal evolution simulation equation of reservoir damage by the fine particles may include: a spatio-temporal evolution simulation equation of reservoir damage by fine particle migration expressed by formula (4-14), and a spatio-temporal evolution simulation equation of reservoir damage by fine particle deposition expressed by formula (4-15).

For the step S4104, the determining a spatio-temporal evolution simulation equation of reservoir damage by the fine particles may include: determining the spatio-temporal evolution simulation equation of reservoir damage by fine particle migration expressed by formula (4-14) according to the relationship between the mass fraction of the migrating fine particles and the volume concentration of the migrating fine particles, the velocity of the fluid, and the mass balance equation expressed by formula (4-12):

$$\frac{\partial C(\vec{r}, t)}{\partial t} + \frac{v(\vec{r}, t)}{\tau}\left[1 - \left(1 - \frac{\rho_p}{\rho_L}C(\vec{r}, t)\right)k(\vec{r}, t)\alpha\tau\right]\nabla C(\vec{r}, t) + \left(1 - \frac{\rho_p}{\rho_L}C(\vec{r}, t)\right)\left(\frac{k(\vec{r}, t)v(\vec{r}, t)}{\tau}C(\vec{r}, t) - \frac{q_s}{\rho_p\phi}\right) = \alpha v(\vec{r}, t)\nabla^2 C(\vec{r}, t), \quad (4\text{-}14)$$

and determining the spatio-temporal evolution simulation equation of reservoir damage by fine particle deposition expressed by formula (4-15) according to the relationship between the mass fraction of the migrating fine particles and the volume concentration of the migrating fine particles, the velocity of the fluid, and the connection condition equation expressed by formula (4-13):

$$\frac{\partial C_d(\vec{r}, t)}{\partial t} = \frac{v(\vec{r}, t)k(\vec{r}, t)\phi}{\tau}[C(\vec{r}, t) - \alpha\tau\nabla C(\vec{r}, t)], \quad (4\text{-}15)$$

where $C(\vec{r}, t)$ is the volume concentration of the migrating fine particles; $v(\vec{r}, t)$ is the velocity of the fluid; $\tau$ is the tortuosity of the reservoir; $\rho_p$ is the density of the deposited fine particles; $\rho_L$ is the density of the fluid;

$$k(\vec{r}, t) = k_0(\vec{r}) \cdot \left(1 - \frac{C_d(\vec{r}, t)}{C_{dmax}}\right)^{m_k},$$

and $k_0(\vec{r})$ is an initial value of the fluid loss coefficient of the reservoir; $C_d(\vec{r}, t)$ is the volume concentration of the deposited fine particles; $C_{d\,max}$ is the maximum volume concentration of the deposited fine particles; $m_k$ is the first empirical value; $\alpha$ is the vertical diffusivity; $\phi$ is the porosity of the reservoir; and $q_s$ is the mass change rate of the migrating fine particles. $k_0(\vec{r}) = f(N_R, N_{Pe}, N_A, N_{DL}, N_{E1}, N_{E2}, N_G, N_{Lo}, N_{vdW}, \zeta_{p(g)})$, where $N_R, N_{Pe}, N_A, N_{DL}, N_{E1}, N_{E2}, N_G, N_{Lo}, N_{vdW}, \zeta_{p(g)}$ are a radius number, a Peclet number, an attraction number, an electrical double layer number, a first electric potential force number, a second electric potential force number, a gravity number, a London force number, a van der Waals force number, and potentials of migrating fine particles and matrix particles (i.e., particles deposited on the rock), respectively (for details of relevant expressions of the parameters, see Table 2).

In summary, according to the present invention, the mass balance equation between the fluid and the deposited fine particles on rock in the reservoir is creatively established according to the convection parameter and the diffusion parameter of the fluid in the reservoir and the mass change rate of migrating fine particles; the connection condition equation between the volume concentration of the deposited fine particles and the volume concentration of the fluid is established according to the convection parameter and the diffusion parameter of the fluid; and the spatio-temporal evolution simulation equation of reservoir damage by the fine particles within the reservoir is determined according to the relationship between the mass fraction of the migrating fine particles and the volume concentration of the migrating fine particles, the velocity of the fluid, the mass balance equation and the connection condition equation. Thus, by using the determined spatio-temporal evolution simulation equation, a four-dimensional spatio-temporal evolution process of characteristics of reservoir damage caused by the fine particles within the reservoir can be quantitatively simulated. Therefore thereby, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Figure 4C:
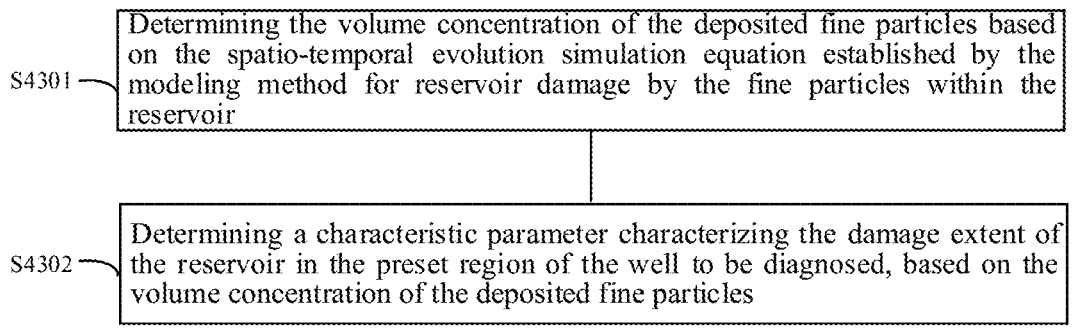
FIG. 4C is a flow diagram of a method for determining a damage extent of a reservoir provided in an embodiment of the present invention.

FIG. 4C is a flow diagram of a method for determining a damage extent of a reservoir provided in an embodiment of the present invention. As shown in FIG. 4C, the method for determining a damage extent of a reservoir may include steps S4301-S4302.

Step S4301: determining a volume concentration of the deposited fine particles based on the spatio-temporal evolution simulation equation established by the modeling method for reservoir damage by the fine particles within the reservoir.

For the spatio-temporal evolution simulation equation of reservoir damage by fine particle migration expressed by the above formula (4-14), the volume concentration $C(\vec{r}, t)$ of the deposited fine particles can be determined by referring to the process of solving a volume concentration of deposited particles in the above Embodiment 1, which will not be described here.

After the volume concentration $C(\vec{r}, t)$ of the migrating fine particles is calculated by the above method, the volume concentration $C_d(\vec{r}, t)$ of the deposited fine particles can be calculated according to the above formula (4-15), and thus the spatio-temporal evolution simulation equation established by the above modeling method for reservoir damage by the fine particles comprehensively considers the influence of various physical and chemical factors on reservoir damage during fine particle migration, so the volume concentration of the deposited fine particles obtained by the step S4301 is very precise.

Step S4302: determining a characteristic parameter characterizing the damage extent of the reservoir in a preset region of a well to be diagnosed, based on the volume concentration of the deposited fine particles.

Wherein the characteristic parameter may be permeability of the reservoir and/or a fluid loss coefficient of the reservoir.

In an embodiment, the characteristic parameter may be the permeability of the reservoir.

For the step S4302, the determining a characteristic parameter characterizing the damage extent of the reservoir in a preset region of a well to be diagnosed may include: determining the permeability $K(\vec{r}, t)$ of the reservoir based on the volume concentration $C_d(\vec{r}, t)$ of the deposited fine particles and formula (1-15).

In an embodiment, the characteristic parameter may be the fluid loss coefficient of the reservoir.

For the step S4302, the determining a characteristic parameter characterizing the damage extent of the reservoir in a preset region of a well to be diagnosed may include: determining the fluid loss coefficient $k(\vec{r}, t)$ of the reservoir based on the volume concentration $C_d(\vec{r}, t)$ of the deposited fine particles and formula (1-16), The characteristic parameter may be a skin factor of the reservoir.

Figure 4D:
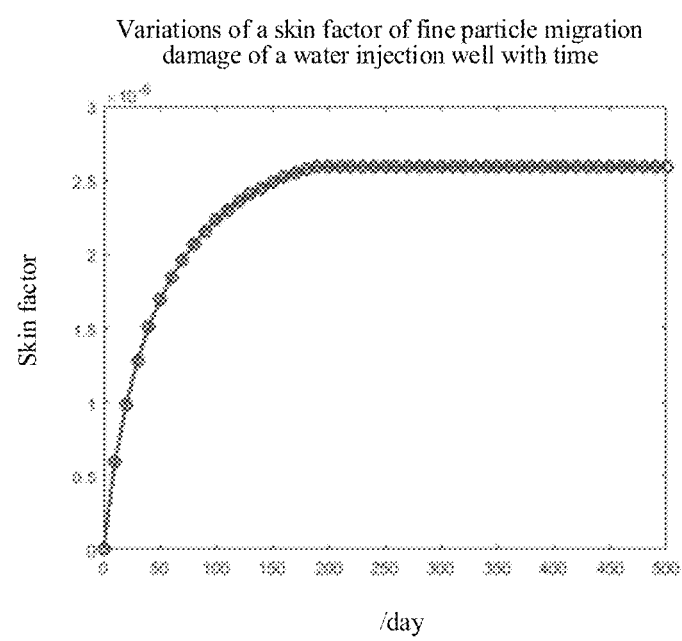
FIG. 4D is a schematic diagram of evolution of a skin factor over time provided in an embodiment of the present invention.
Figure 4E:
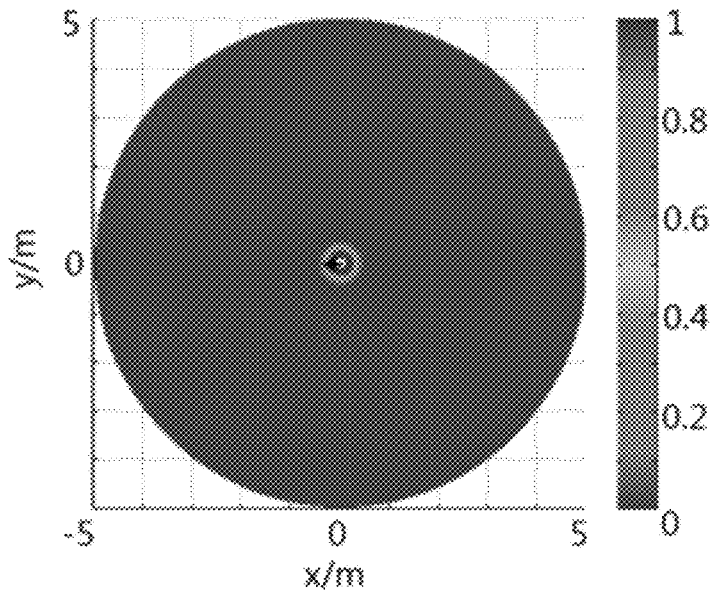
FIG. 4E is a flow diagram of a radius of reservoir damage by fine particle (within a reservoir migration) at day 40 characterized by a permeability damage rate of the reservoir provided in an embodiment of the present invention.

For the step S4302, determining the characteristic parameter characterizing the damage extent of the reservoir in the preset region of the well to be diagnosed may include: determining the permeability $K(\vec{r}, t)$ of the reservoir based on the volume concentration $C_d(\vec{r}, t)$ of the deposited fine particles and formula $$K(\vec{r}, t) = K_0(\vec{r}) \cdot \left(1 - \frac{C_d(\vec{r}, t)}{C_{dmax}}\right)^{m_K};$$

and determining the skin factor $S(\vec{r}, t)$ of the reservoir based on the permeability $K(\vec{r}, t)$ of the reservoir and formula (1-17), The characteristic parameter obtained by the step S4302 (e.g., the permeability $K(\vec{r}, t)$ and the skin factor $S(\vec{r}, t)$ of the reservoir) is a result of 4D quantitative simulation of spatio-temporal evolution (as shown in FIG. 4D). More specifically, FIG. 4E shows a schematic diagram of a radius (a radius as indicated by an arrow) of reservoir damage by fine particle migration at day 40 characterized by a permeability damage rate of the reservoir (the permeability damage rate $I(r_i, t)$ of the reservoir is determined based on the permeability $K(\vec{r}, t)$ of the reservoir and formula $$I(\vec{r}, t) = 1 - \frac{K(\vec{r}, t)}{K_{max}(\vec{r}, t)},$$

where $K_{max}(\vec{r}, t)$ is a maximum value of $K(\vec{r}, t)$), a working person concerned can visually confirm the damage extent of the reservoir from FIG. 4E. Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

In summary, the volume concentration of the deposited fine particles can be determined by using the determined spatio-temporal evolution simulation equation, and then the characteristic parameter (e.g., the permeability and/or the skin factor of the reservoir) characterizing the damage extent of the reservoir in the preset region of the well to be diagnosed can be determined according to the volume concentration of the deposited fine particles, whereby a four-dimensional spatio-temporal evolution process of characteristics of reservoir damage caused by the fine particles within the reservoir can be simulated quantitatively. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Embodiment 5—Water Lock Effect

A water lock effect mainly occurs in water-wettable reservoir rock. As water is a wetting phase, water always first occupies small pores and then medium and large pores to split oil gas into a dispersed phase, thus significantly reducing the permeation of oil gas in the reservoir (e.g., reducing the permeability of the reservoir). The water lock effect is controlled by a variety of factors such as reservoir lithology, physical properties, pore structures, and an invading fluid. Especially, geometrical characteristics of a reservoir medium have a great influence on reservoir damage by the water lock effect. Different pore throat structure distribution modes and complexity can lead to significant changes in the distribution mode of the water wetting phase in the rock, thus affecting the permeability of the reservoir.

Therefore, the core of the embodiments of the present invention is to establish a kinetic model (i.e., a diffusion equation for the diffusion of the water molecules through a solid-liquid interface from a liquid phase in the pores to the interior of a solid phase and a convection diffusion equation for the fluid in the pores) of diffusion of water molecules into the interior of the rock and water content variations within the pores in the reservoir. Specifically, based on Fick's law of diffusion, a convection diffusion relationship of the fluid in the pores in the reservoir, and the like, a spatio-temporal evolution control phenomenological model (containing a water volume fraction $c_1$ of the pores in the reservoir and an initial value $c_0$ of a water volume fraction of the rock in the reservoir) of porosity distribution in the reservoir around the well to be diagnosed influenced by the water lock effect is established, and in conjunction with a relationship between porosity of the reservoir and a characteristic parameter characterizing the damage extent of the reservoir such as permeability, spatio-temporal field distribution of the characteristic parameter such as permeability can be diagnosed.

Figure 5A:
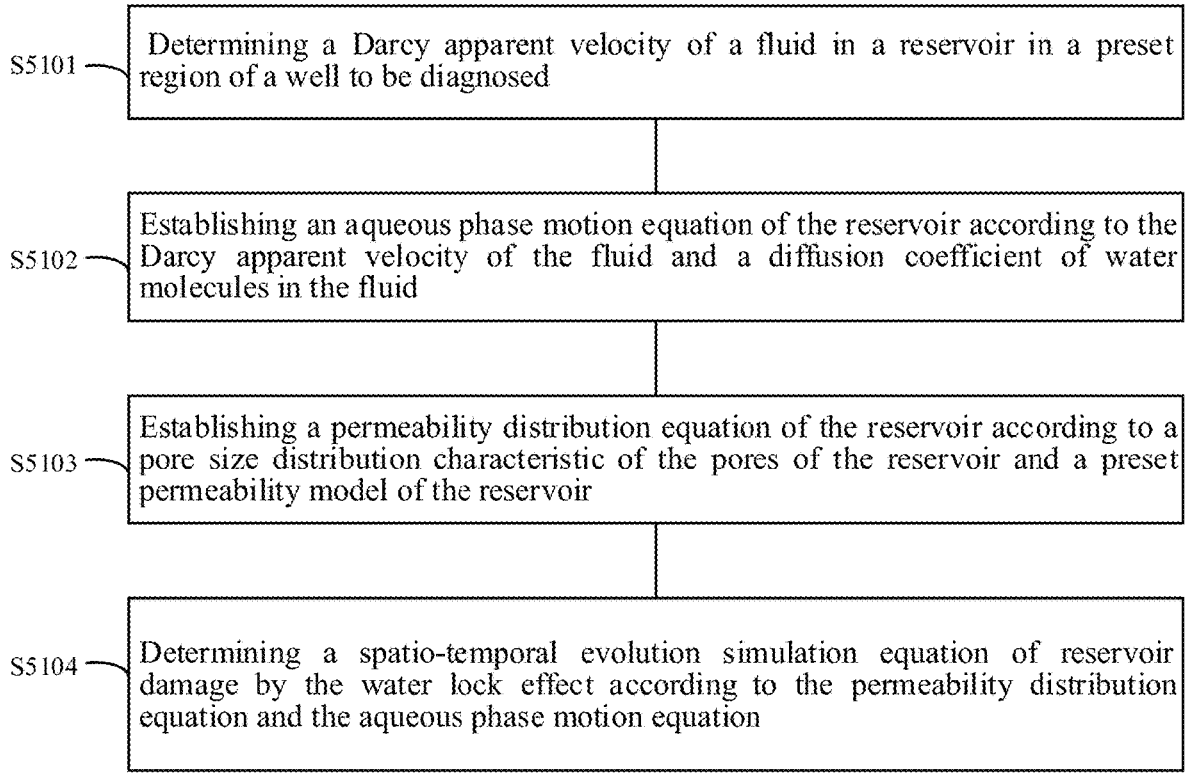
FIG. 5A is a flow diagram of a modeling method for reservoir damage by a water lock effect provided in an embodiment of the present invention.

FIG. 5A is a flow diagram of a modeling method for reservoir damage by a water lock effect provided in an embodiment of the present invention. The modeling method may include steps S5101-S5104.

Step S5101: determining a Darcy apparent velocity of a fluid in a reservoir in a preset region of a well to be diagnosed.

Wherein the well to be diagnosed may be, for example, a water injection well.

For the step S5101, determining a velocity of a fluid in a reservoir may include: establishing a pressure conduction equation for the fluid entering the reservoir; and determining the Darcy apparent velocity of the fluid according to the pressure conduction equation and a Darcy formula.

For the specific determination process, reference can be made to the process of determining the Darcy apparent velocity in the above Embodiment 2 (i.e., the above formulas (2-1) and (2-2) and related description thereof).

Step S5102: establishing an aqueous phase motion equation of the reservoir according to the Darcy apparent velocity of the fluid and a diffusion coefficient of water molecules in the fluid.

Under reservoir conditions, water contents at different locations within pores in the reservoir satisfy a mass conservation equation. Wherein the motion of an extraneous aqueous phase within the reservoir is mainly determined by two processes: convection and diffusion. Specifically, for the step S5102, the establishing an aqueous phase motion equation of the reservoir may include: establishing a mass balance equation expressed in the following formula according to the Darcy apparent velocity u of the fluid and the diffusion coefficient $D_w$ of the water molecules:

$$\phi_0 \frac{\partial \phi_w(\vec{r}, t)}{\partial t} = \nabla(D_w \nabla \phi_w(\vec{r}, t)) - \nabla(u\phi_w(\vec{r}, t)),$$

where $\phi_0$ is an initial value of porosity of the reservoir; $\phi_w(\vec{r}, t)$ is absolute porosity with pores in the reservoir being occupied by the aqueous phase; and $\vec{r}$ is a spatial location of any point in the reservoir (e.g., using the center of the well to be diagnosed as an origin).

The aqueous phase motion equation expressed by the following formula (5-1) is established according to the mass balance equation and a spatio-temporal distribution function $$S_w(\vec{r}, t) = \frac{\phi_w(\vec{r}, t)}{\phi_0}$$

of an aqueous phase saturation of the reservoir:

$$\phi_0 \frac{\partial S_w(\vec{r}, t)}{\partial t} = \nabla(D_w \nabla S_w(\vec{r}, t)) - \nabla(uS_w(\vec{r}, t)). \quad (5-1)$$

An initial condition for the aqueous phase motion equation is $S_w(\vec{r}, t=0)=S_{wc}$, and a boundary condition for the aqueous phase motion equation is $S_w(|\vec{r}|=r_w, t)=1$ (that is, reservoir pores at a well wall of the water injection well is completely filled with water, i.e., the aqueous phase saturation in the pores is 1), where $\phi_0$ is the initial value of the porosity of the reservoir; $r_w$ is a wellbore radius of the well to be diagnosed; and $S_{wc}$ is an irreducible water saturation in the reservoir.

Step S5103: establishing a permeability distribution equation of the reservoir according to a pore size distribution characteristic of the pores in the reservoir and a preset permeability model of the reservoir.

Figure 5B:
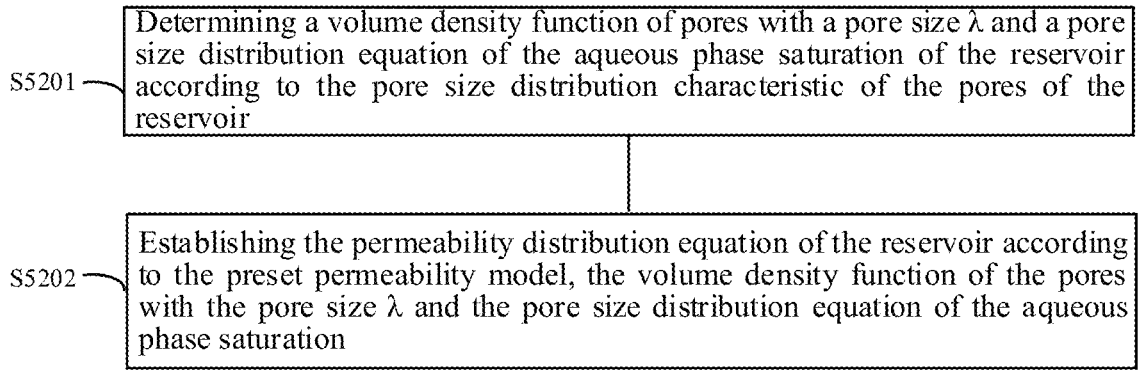
FIG. 5B is a flow diagram of establishing a permeability distribution equation of the reservoir provided in an embodiment of the present invention.

For the step S5103, as shown in FIG. 5B, the establishing a permeability distribution equation of the reservoir may include steps S5201-S5202.

Step S5201: determining a volume density function of pores with a pore size λ and a pore size distribution equation of the aqueous phase saturation of the reservoir according to the pore size distribution characteristic of the pores in the reservoir.

To quantitatively describe the pore structures of the reservoir, a fractal theory is used to study the water lock effect in the pore structures. According to the geometric principle of fractal, if pore size distribution of the reservoir has a fractal characteristic, the number N (>λ) of pores with a pore size larger than λ in the reservoir has the following power function relationship with λ:

$$N(>\lambda) = \left(\frac{\lambda_{max}}{\lambda}\right)^D, \quad (5-2)$$

where D is a fractal dimension of the pores (0<D<3).

Figure 5C:
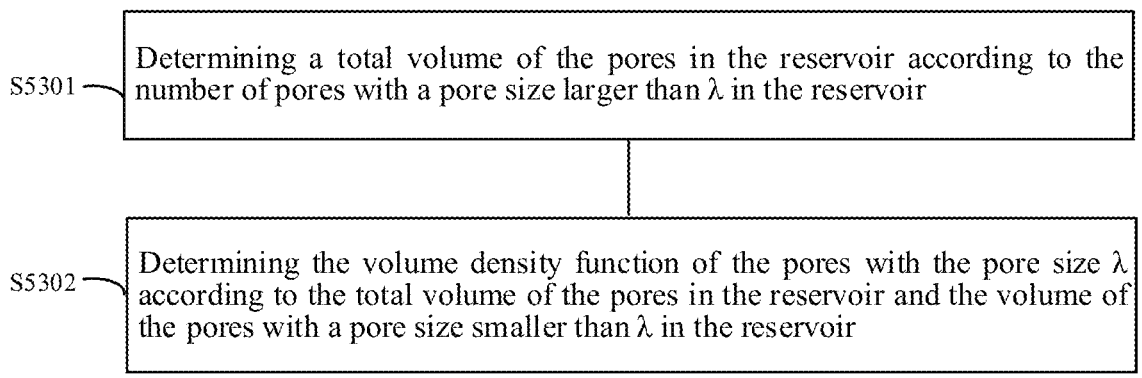
FIG. 5C is a flow diagram of determining a volume density function of pores with a pore size $\lambda$, provided in an embodiment of the present invention.

In the case where the pore size distribution characteristic of the pores in the reservoir is that the number N(>λ) of the pores with the pore size larger than λ in the reservoir satisfies the above formula (5-2), as shown in FIG. 5C, the determining a volume density function of pores with a pore size λ in the step S5201 may include steps S5301-S5302.

Step S5301: determining a total volume of the pores in the reservoir to be $\Phi_{max}=A(\lambda_{max}^{3-D}-\lambda_{min}^{3-D})$ according to the number N(>λ) of the pores with the pore size larger than λ in the reservoir.

Specifically, the total number $N(>\lambda_{min})$ of the pores in the reservoir can then be obtained according to the above formula (5-2):

$$N(>\lambda_{min}) = \left(\frac{\lambda_{max}}{\lambda_{min}}\right)^D, \quad (5-3)$$

the following formula (5-4) can be obtained according to formulas (5-2) and (5-3):

$$\frac{dN}{N(>\lambda_{min})} = -D\lambda_{min}^D \lambda^{D-1} d\lambda = f(\lambda)d\lambda, \quad (5-4)$$

then a relationship between the number N(>λ) of the pores with the pore size greater than λ and λ is a power function relationship expressed by the following formula (5-5):

$$N(>\lambda)=\int_\lambda^{\lambda_{max}} f(\lambda)d\lambda = a\lambda^{31\ D}, \quad (5-5)$$

λ, $\lambda_{min}$ and $\lambda_{max}$ in the formula (5-5) are a pore size, a minimum pore size and a maximum pore size of the pores, respectively ($\lambda_{min}$ and $\lambda_{max}$ can be obtained from an average pore size and a standard deviation of the pore size distribution; generally $$\frac{\lambda_{min}}{\lambda_{max}} \leq 0.01);$$

and a is a proportional constant.

Next, from formula (5-5), a pore size distribution density function $f(\lambda)$ of the reservoir can be obtained, which satisfies the following formula (5-6):

$$f(\lambda) = \frac{dN}{d\lambda} = a'\lambda^{-D-1}, \qquad (5\text{-}6)$$

in the formula, $a'=-Da$ is a proportional constant.

A fractal expression of the total volume of the pores in the reservoir can be obtained from the pore size distribution density function expressed by the above formula (5-6):

$$\Phi_{max} = \int_{\lambda_{min}}^{\lambda_{max}} f(\lambda)\alpha^3 d\lambda, \qquad (5\text{-}7)$$

where $\alpha$ is a constant related to the shape of the pores ($\alpha=1$ if the shape of the pores is cube, or $\alpha=\pi/6$ if the shape of the pores is sphere), and by integration, we can obtain:

$$\Phi_{max} = A(\lambda_{max}^{3-D} - \lambda_{min}^{3-D}), \qquad (5\text{-}8)$$

similarly, the volume of the pores with the pore size smaller than $\lambda$ in the reservoir is $\Phi_\lambda = \int_{\lambda_{min}}^{\lambda} f(\lambda)\alpha^3 d\lambda = A(\lambda^{3-D} - \lambda_{min}^{3-D})$.

Step S5302: according to the total volume $\Phi_{max}$ of the pores in the reservoir and the volume $\Phi_\lambda = A(\lambda^{3-D} - \lambda_{min}^{3-D})$ of the pores with the pore size smaller than $\lambda$ in the reservoir, determining the volume density function of the pores with the pore size $\lambda$ as:

$$d\xi = d\left(\frac{\Phi_\lambda}{\Phi_{max}}\right) = \frac{(3-D)\lambda^{2-D}}{\lambda_{max}^{3-D}\left(1-(\lambda_{min}/\lambda_{max})^{3-D}\right)} d\lambda, \qquad (5\text{-}9)$$

where D is the fractal dimension of the pores; and $\lambda$, $\lambda_{min}$ and $\lambda_{max}$ are the pore size, minimum pore size and maximum pore size of the pores, respectively; and $A=\alpha a'/(3-D)$ (a constant).

Step S5202: establishing the permeability distribution equation of the reservoir according to the preset permeability model, the volume density function of the pores with the pore size $\lambda$ and the pore size distribution equation of the aqueous phase saturation.

Figure 5D:
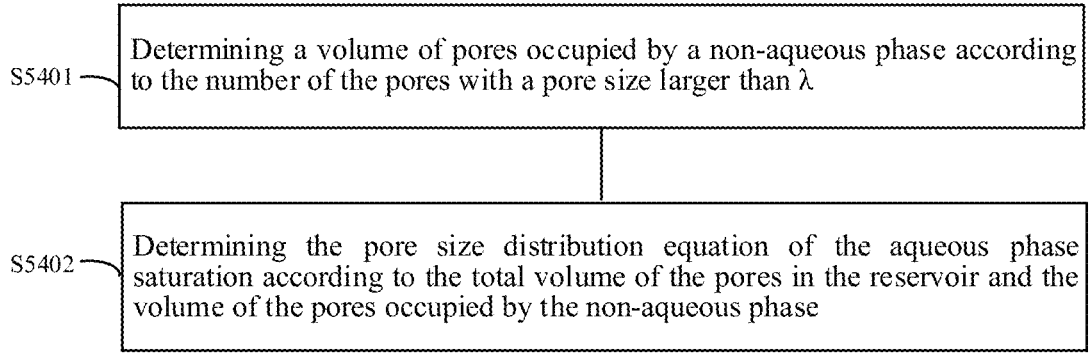
FIG. 5D is a flow diagram of determining a pore size distribution equation of an aqueous phase saturation of the reservoir provided in an embodiment of the present invention.

As shown in FIG. 5D, determining a pore size distribution equation of the aqueous phase saturation of the reservoir in step S5201 may include steps S5401-S5402.

Step S5401: determining a volume of pores occupied by a non-aqueous phase to be $\Phi_{nw}(\lambda) = A(\lambda_{max}^{3-D} - \lambda^{3-D})$ according to the number $N(>\lambda)$ of the pores with the pore size larger than $\lambda$.

Assuming that the pores with the pore size smaller than $\lambda$ are completely occupied by the aqueous phase, and the pores with the pore size larger than $\lambda$ are completely occupied by the non-aqueous phase (i.e., the rock in the reservoir is water-wettable (i.e., hydrophilic)), the volume $\Phi_{nw}(\lambda)$ of the pores occupied by the non-aqueous phase can be obtained in conjunction with the above formula (5-8), $$\Phi_{nw}(\lambda) = A(\lambda_{max}^{3-D} - \lambda^{3-D}). \qquad (5\text{-}10)$$

Step S5402: determining the pore size distribution equation $$S_w(\lambda) = \frac{(\lambda/\lambda_{max})^{3-D} - (\lambda_{min}/\lambda_{max})^{3-D}}{1 - (\lambda_{min}/\lambda_{max})^{3-D}}$$

of the aqueous phase saturation expressed by the following formula according to the total volume $\Phi_{max}$ of the pores in the reservoir and the volume $\Phi_{nw}(\lambda)$ of the pores occupied by the non-aqueous phase.

Wherein D is the fractal dimension of the pores; and $\lambda$, $\lambda_{min}$ and $\lambda_{max}$ are the pore size, minimum pore size and maximum pore size of the pores, respectively; and $A=\alpha a'/(3-D)$.

Specifically, a pore size distribution equation of a non-aqueous phase saturation can be determined according to formula (5-8) and formula (5-10) to be $$S_{nw}(\lambda) = \frac{\Phi_{nw}(\lambda)}{\Phi_{max}} = \frac{1 - (\lambda_{min}/\lambda_{max})^{3-D}}{1 - (\lambda_{min}/\lambda_{max})^{3-D}},$$

and then the pore size distribution equation of the aqueous phase saturation can be determined from the pore size distribution equation $S_{nw}(\lambda)$ of the non-aqueous phase saturation, $$S_w(\lambda) = 1 - S_{nw}(\lambda) = \frac{(\lambda/\lambda_{max})^{3-D} - (\lambda_{min}/\lambda_{max})^{3-D}}{1 - (\lambda_{min}/\lambda_{max})^{3-D}}. \qquad (5\text{-}11)$$

According to a linear Hagen-Poiseuille viscous flow, permeability of a capillary bundle model can be expressed as $$K = \frac{\phi}{8\tau^2} \sum_i \xi_i \lambda_i^2.$$

In the embodiments of the present invention, a permeable channel of the reservoir can be regarded as an accumulation of multiple capillary bundles. Due to the continuity of the pore size distribution, the expression of the permeability of the capillary bundle model can be written in integral form as:

$$K = \frac{\phi_0}{8\tau^2} \int \lambda^2 d\xi. \qquad (5\text{-}12)$$

In the case where the preset permeability model of the reservoir satisfies $$K = \frac{\phi_0}{8\tau^2} \int \lambda^2 d\xi,$$

establishing the permeability distribution equation of the reservoir may include: establishing a permeability distribution equation (not shown) of the reservoir according to the preset permeability model $$K = \frac{\phi_0}{8\tau^2} \int \lambda^2 d\xi$$

of the reservoir, the volume density function $d\xi$ of the pores with the pore size $\lambda$ and the pore size distribution equation of the aqueous phase saturation.

According to the established permeability distribution equation, a distribution equation of a permeability damage rate expressed by the following formula can be further established, $$K_d(S_w) = 1 - \frac{K}{K_{max}} = \qquad (5-13)$$

$$\left(\frac{1 - \left(\frac{\lambda_{min}}{\lambda_{max}}\right)^{5-D}}{1 - \left(\frac{\lambda_{min}}{\lambda_{max}}\right)^{3-D}}\right) \cdot \frac{1 - \left(1 - \left(\frac{\lambda_{min}}{\lambda_{max}}\right)^{3-D}\right) \cdot S_w - \left(\frac{\lambda_{min}}{\lambda_{max}}\right)^{3-D}}{1 - \left(\left(1 - \left(\frac{\lambda_{min}}{\lambda_{max}}\right)^{3-D}\right) \cdot S_w + \left(\frac{\lambda_{min}}{\lambda_{max}}\right)^{3-D}\right)^{\left(\frac{5-D}{3-D}\right)}}.$$

Specifically, first, substituting formula (5-9) into formula (5-12) can yield a pore size distribution function of the permeability of the reservoir:

$$K(\lambda) = \frac{\phi}{8\tau^2} \int_\lambda^{\lambda_{max}} \frac{(3-D)\lambda^{4-D}}{\lambda_{max}^{3-D}(1-(\lambda/\lambda_{max})^{3-D})} d\lambda = \frac{\phi\lambda_{max}^2}{8\tau^2}\left(\frac{3-D}{5-D}\right)\left(\frac{1-(\lambda/\lambda_{max})^{5-D}}{1-(\lambda/\lambda_{max})^{3-D}}\right)$$

and then, replacing a variable λ in the above pore size distribution function K(λ) of the permeability by $S_w$ according to a relational expression between λ and the water saturation $S_w(\lambda)$ in formula (5-11) can yield formula (5-13).

Step S5104: determining the spatio-temporal evolution simulation equation of reservoir damage by the water lock effect according to the permeability distribution equation and the aqueous phase motion equation, wherein the spatio-temporal evolution simulation equation is used to simulate a four-dimensional spatio-temporal evolution process of characteristics of reservoir damage caused by the water lock effect.

Specifically, the spatio-temporal distribution function $S_w(\vec{r}, t)$ of the aqueous phase saturation of the reservoir can be obtained according to formula (5-1), and $S_w(\vec{r}, t)$ is substituted into a four-dimensional spatio-temporal distribution form of the permeability of the reservoir, i.e., the spatio-temporal evolution simulation equation of reservoir damage by the water lock effect is obtained.

In summary, according to the present invention, the Darcy apparent velocity of the fluid in the reservoir in the preset region of the well to be diagnosed is creatively determined; the aqueous phase motion equation of the reservoir is established according to the Darcy apparent velocity of the fluid and the diffusion coefficient of the water molecules in the fluid; the permeability distribution equation of the reservoir is established; and the spatio-temporal evolution simulation equation of reservoir damage by the water lock effect is determined according to the permeability distribution equation and the aqueous phase motion equation. Thus, by using the determined spatio-temporal evolution simulation equation, a four-dimensional spatio-temporal evolution process of characteristics of reservoir damage caused by the water lock effect can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Correspondingly, another embodiment of the present invention further provides a method for determining a damage extent of a reservoir. The method may include: determining a characteristic parameter characterizing the damage extent of the reservoir in a preset region of a well to be diagnosed, based on the spatio-temporal evolution simulation equation established by the modeling method for reservoir damage by the water lock effect.

For the solution of the spatio-temporal evolution simulation equation for reservoir damage by the water lock effect described above, $S_w(\vec{r}, t)$ needs to be calculated according to formula (5-1). For the specific solving process, reference can be made to the solving process of the volume concentration of the deposited particles in the above Embodiment 1, which will not be described here.

Figure 5E:
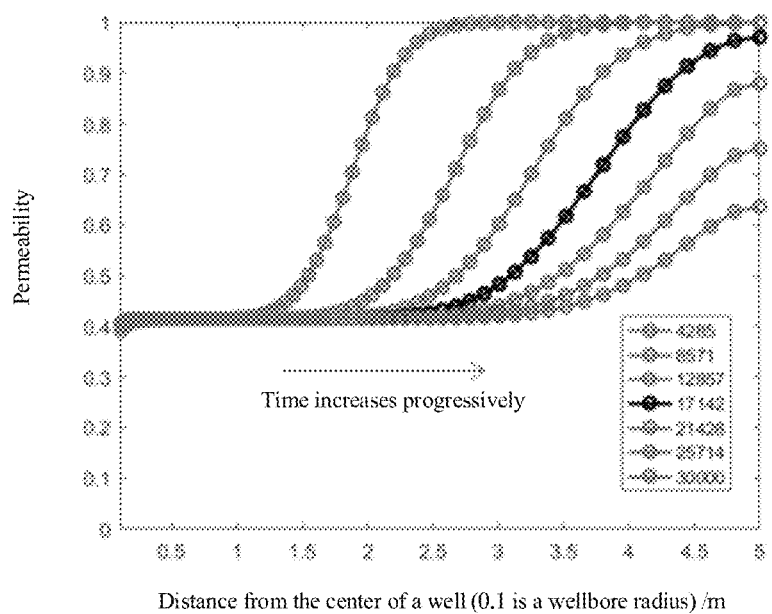
FIG. 5E is a schematic diagram of evolution of permeability over time provided in an embodiment of the present invention.

After the aqueous phase saturation $S_w(\vec{r}, t)$ of the reservoir is calculated by the above method, the permeability K($\vec{r}$, t) of the reservoir can be calculated according to the above formula (5-13) (of course, variations of the permeability K($\vec{r}$, t) at a particular location r in the reservoir with time may also be obtained, as shown in FIG. 5E), and thus the spatio-temporal evolution simulation equation established by the above modeling method for reservoir damage by the water lock effect comprehensively considers the influence of various physical and chemical factors on reservoir damage during damage by the water lock, so the permeability of the reservoir obtained by the embodiment is very precise.

The characteristic parameter characterizing the damage extent of the reservoir in the preset region of the well to be diagnosed can be calculated based on the permeability of the reservoir.

In an embodiment, the characteristic parameter may be a permeability damage rate of the reservoir.

Correspondingly, the determining a characteristic parameter characterizing the damage extent of the reservoir in a preset region of a well to be diagnosed may include: determining the permeability K($\vec{r}$, t) of the reservoir based on the spatio-temporal evolution simulation equation; and determining the permeability damage rate I($\vec{r}$, t) of the reservoir based on the permeability K($\vec{r}$, t) of the reservoir and formula (5-14):

$$I(\vec{r}, t) = 1 - \frac{K(\vec{r}, t)}{K_{max}(\vec{r}, t)}, \qquad (5-14)$$

where $K_{max}(\vec{r}, t)$ is a maximum value of K ($\vec{r}$, t).

In another embodiment, the characteristic parameter may be a skin factor of the reservoir.

The determining a characteristic parameter characterizing the damage extent of the reservoir in a preset region of a well to be diagnosed may include: determining the permeability K($\vec{r}$, t) of the reservoir based on the spatio-temporal evolution simulation equation; and determining the skin factor S($\vec{r}$, t) of the reservoir based on the permeability K($\vec{r}$,t) of the reservoir and formula (5-15):

$$S(\vec{r}, t) = \left(\frac{1}{K_d(\vec{r}, t)} - 1\right)\ln\left(\frac{r_{sw}}{r_w}\right), \qquad (5-15)$$

where $K_o(\vec{r})$ is an initial value of the permeability of the reservoir; and $\overline{K_d(\vec{r},t)} = K(\vec{r}, t)/\overline{K_o(\vec{r})}$, $r_w$ is a wellbore radius of the well to be diagnosed, and $r_{sw}$ is a damage radius of the reservoir.

Figure 5F:
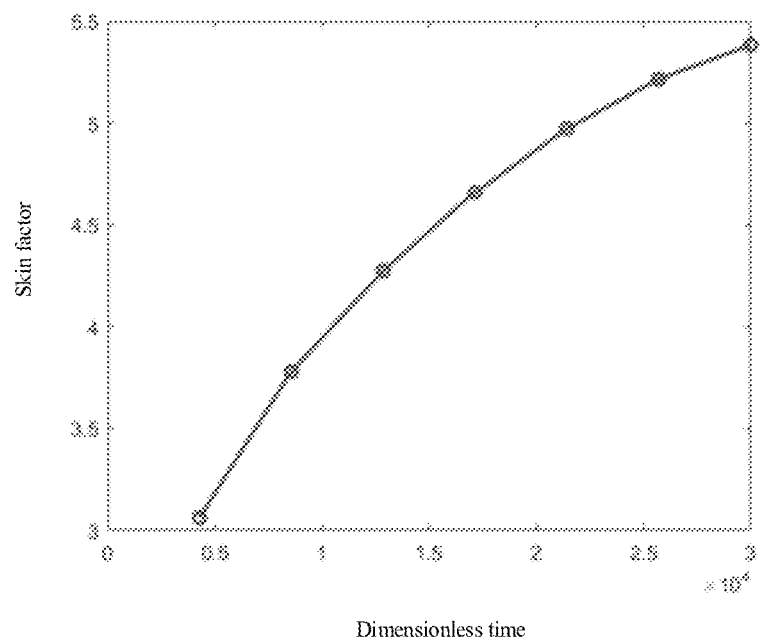
FIG. 5F is a schematic diagram of evolution of a skin factor over time provided in an embodiment of the present invention.

The characteristic parameters obtained by the above embodiments (e.g., the permeability $K(\vec{r}, t)$ and the skin factor $S(\vec{r}, t)$ of the reservoir) are a result of 4D quantitative simulation of spatio-temporal evolution (FIG. 5F shows variations of the skin factor at a location $\vec{r}$ with time). Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

Embodiment 6—Stress Sensitivity

Figure 6A:
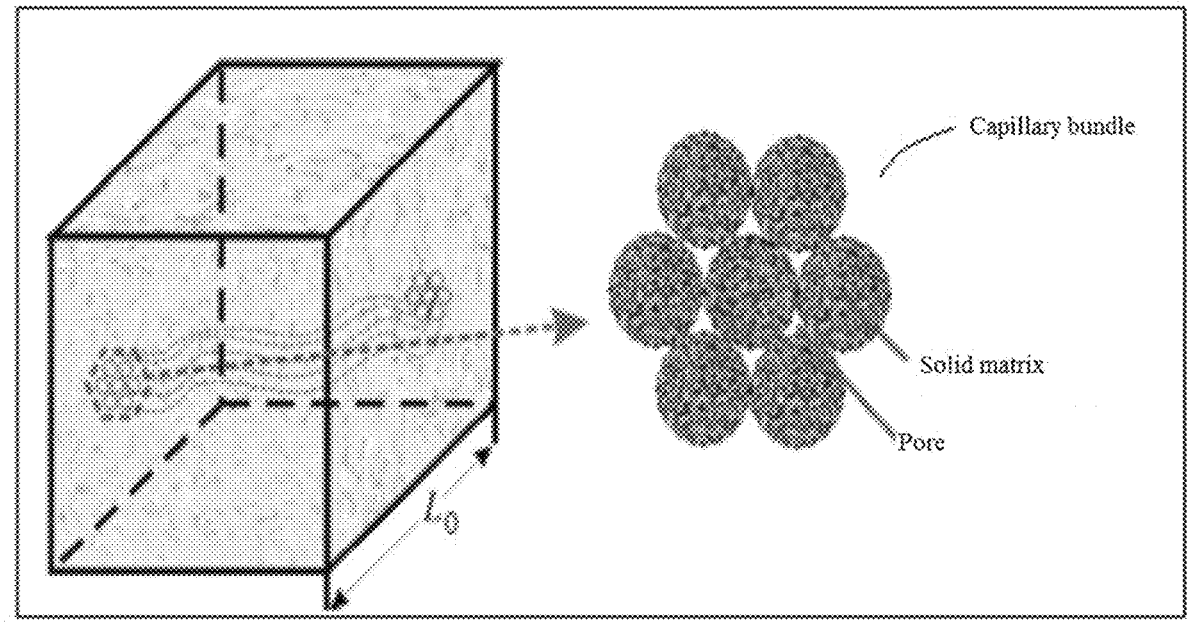
FIG. 6A is a model diagram of a porous medium formed by capillary bundle provided in an embodiment of the present invention.

The distribution of pore structures and solid matrices (i.e., rock matrix or framework particles) within a reservoir is very complex. A microscopic solid matrix (i.e., a cluster) forms a seepage channel, and multiple pores (equivalent to hydraulic bundles) are formed between multiple solid matrices (i.e., clusters), and the multiple solid matrices and the multiple pores form a bundle of capillary tubes (also called a capillary bundle) as shown in FIG. 6A. These pores have particular tortuosity such that an actual length $L_{c0}$ of the solid matrices and the pores is greater than a length $L_0$ of a porous medium formed by the capillary bundle (i.e., an apparent length of the capillary bundle), as shown in FIG. 6A.

Figure 6B:
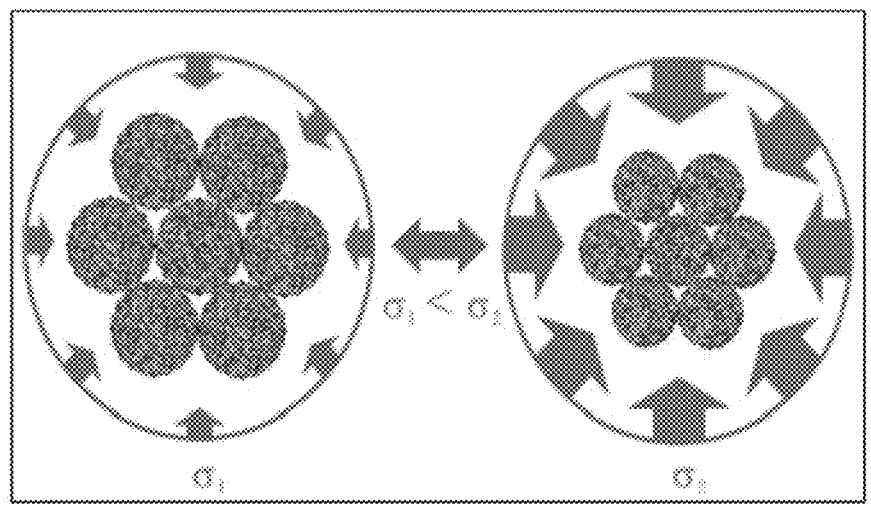
FIG. 6B is a cross-sectional diagram of the capillary bundle shown in FIG. 6A under effective stress provided in an embodiment of the present invention.
Figure 6C:
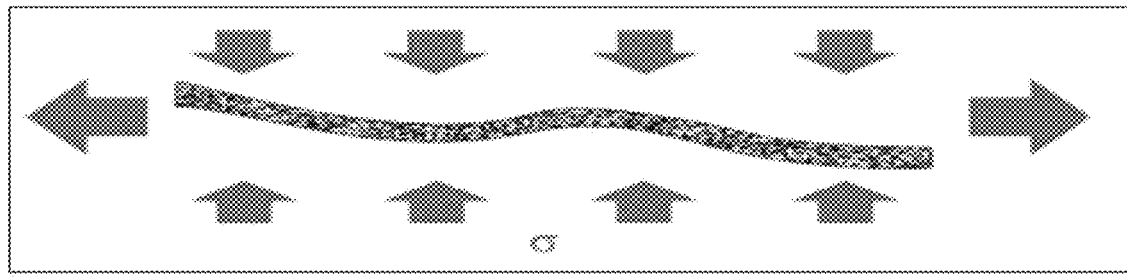
FIG. 6C is a longitudinal schematic diagram of a solid matrix shown in FIG. 6A under effective stress provided in an embodiment of the present invention.

Moreover, the reservoir is subjected to a downward pressure due to the action of an overlying rock layer of the reservoir on the one hand, and the reservoir is subjected to an upward pressure due to the support of a fluid within the reservoir on the other hand. As a result, under the action of the two pressures (i.e., effective stress) on the reservoir, the capillary bundle shrinks (as shown in FIG. 6B) and the capillary bundle extends (as shown in FIG. 6C), which in turn influences the permeability of the fluid in the reservoir (i.e., the permeability of the reservoir for short). Stress sensitivity is influenced by various factors such as pore structures, lithology, physical properties and an invading fluid of the reservoir. Thus, the core of the embodiments of the present invention is to establish a distribution equation of a flow rate and permeability of the fluid in the reservoir under the action of the effective stress. Specifically, the flow rate of the fluid in the reservoir is determined according to pore size distribution characteristics of the pores in the reservoir, a diameter and length of each capillary bundle of the reservoir under the effective stress, and a fluid flow formula, and spatio-temporal field distribution of the characteristic parameter of reservoir damage (such as the permeability) can be diagnosed in conjunction with a permeability model.

Figure 6D:
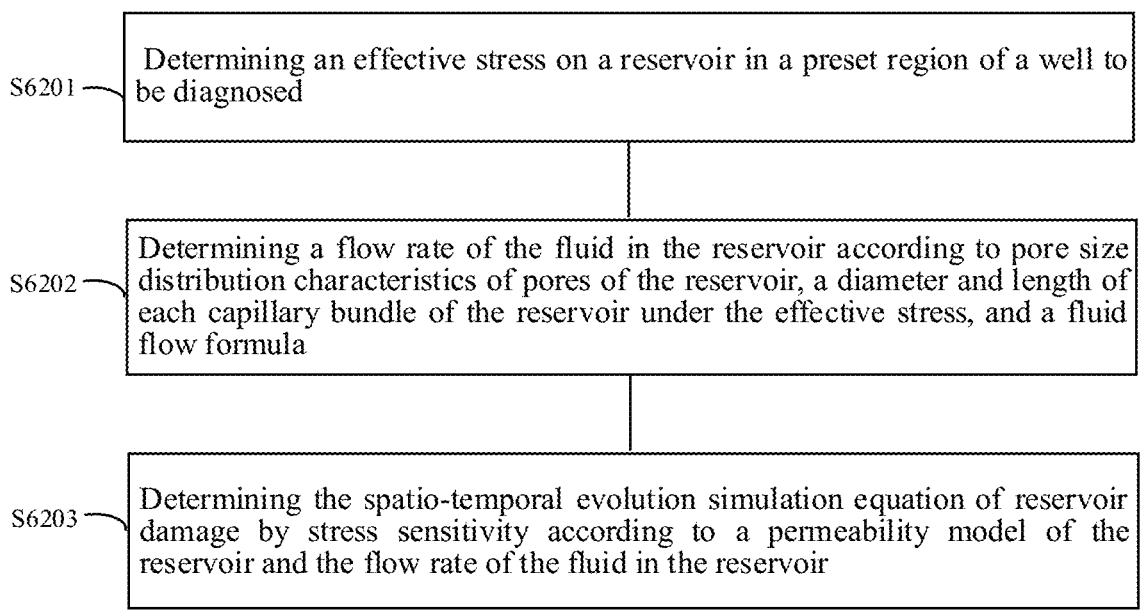
FIG. 6D is a flow diagram of a modeling method for reservoir damage by stress sensitivity provided in an embodiment of the present invention.

FIG. 6D is a flow diagram of a modeling method for reservoir damage by stress sensitivity provided in an embodiment of the present invention. As shown in FIG. 6D, the modeling method may include steps S6201-S6203.

Step S6201: determining an effective stress on a reservoir in a preset region of a well to be diagnosed.

For the step S6201, the determining an effective stress on a reservoir in a preset region of a well to be diagnosed may include: establishing a pressure conduction equation for a fluid entering the reservoir; and determining the effective stress on the reservoir according to the pressure conduction equation and a pressure from an overlying rock layer of the reservoir.

Specifically, a pressure is a force that drives a solid-liquid mixture to continuously intrude from a wellbore of a water injection well into the reservoir around the well to be diagnosed, whereby the pressure conduction equation for the fluid entering the reservoir as expressed in formula (6-1) can be established:

$$\nabla^2 P(\vec{r}, t) = \frac{\phi_0 \mu c_t}{K(\vec{r}, t)} \frac{\partial P(\vec{r}, t)}{\partial t}, \quad (6\text{-}1)$$

An initial condition for the pressure conduction equation is $P(\vec{r}, t=0) = P_0$, and a boundary condition for the pressure conduction equation is $P(|\vec{r}|=r_w, t) = P_w$ (that is, the pressure at a well wall of the water injection well is $P_w$).

Then, a pressure $P(\vec{r}, t)$ (i.e., a pore pressure) generated by the fluid on the reservoir can be obtained according to formula (6-1), and an effective stress $\sigma(\vec{r}, t)$ on the reservoir can then be determined according to $P(\vec{r}, t)$ and a pressure $P_A(\vec{r}, t)$ from the overlying rock layer:

$$\sigma(\vec{r}, t) = P_A(\vec{r}, t) - P(\vec{r}, t) \quad (6\text{-}2)$$

Step S6202: determining a flow rate of the fluid in the reservoir according to pore size distribution characteristics of pores in the reservoir, a diameter and length of each capillary bundle of the reservoir under the effective stress, and a fluid flow formula.

Wherein the capillary bundle is composed of a plurality of solid matrices and pores between the plurality of solid matrices.

Figure 6E:
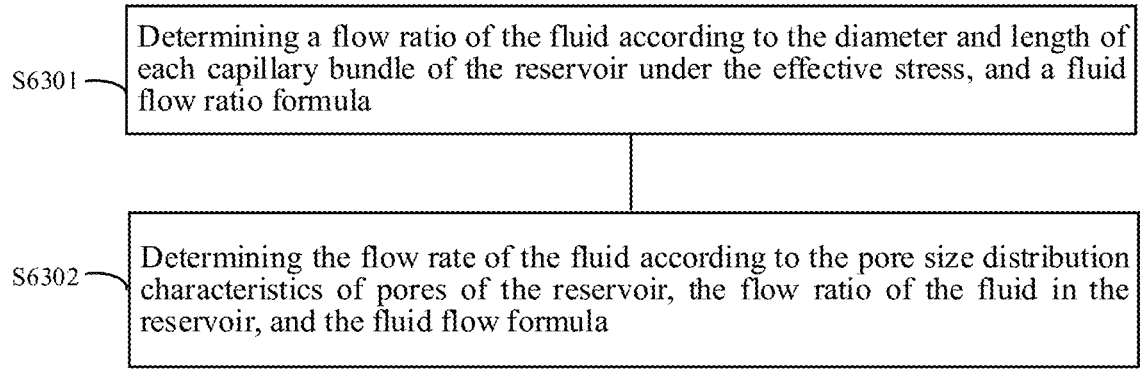
FIG. 6E is a flow diagram of determining a flow rate of a fluid in a reservoir provided in an embodiment of the present invention.

For the step S6202, as shown in FIG. 6E, the determining a flow rate of the fluid in the reservoir may include steps S6301-S6302.

Before performing step S6301, the determining a flow rate of the fluid in the reservoir may further include: determining the diameter of each capillary bundle of the reservoir under the effective stress according to an elastic modulus of the reservoir; and determining the length of each capillary bundle of the reservoir under the effective stress according to the elastic modulus and a Poisson's ratio of the reservoir.

Processes of determining the diameter and length of each capillary bundle of the reservoir under the effective stress are described below respectively.

A transverse wave velocity of the well to be diagnosed is a key feature for determining important data such as the Poisson's ratio and elastic modulus of the reservoir. During field logging, shear wave logging is generally not performed for the well to be diagnosed, but rather the Poisson's ratio is determined from a silt content and a linear formula about the silt content. Wherein the linear formula is fitted by particular rock samples, so the precision of the Poisson's ratio determined by the linear formula is very low for different reservoirs. In the embodiment, the transverse wave velocity of the well to be diagnosed can be indirectly calculated according to acquired transverse wave velocities and longitudinal wave velocities of a plurality of adjacent wells around the well to be diagnosed, and a longitudinal wave velocity acquired by field logging of the well to be diagnosed.

Before performing the step of determining the length of each capillary bundle of the reservoir under the effective stress, the determining a flow rate of the fluid in the reservoir may further include: determining a transverse wave velocity of the reservoir according to a transverse wave velocity and a longitudinal wave velocity of each of a plurality of particular adjacent wells located in the preset region; and determining the elastic modulus and the Poisson's ratio of the reservoir according to the transverse wave velocity of the reservoir.

Wherein the particular adjacent wells may be wells for which transverse and longitudinal wave velocities have been acquired by means of logging.

Specifically, the transverse wave velocity $v_t$ of the well to be diagnosed may be determined by a longitudinal wave velocity $v_l$ and a relational expression $v_t = \alpha v_l - b$. The coefficients a and b in the relational expression may be calculated based on the transverse and longitudinal wave velocities of the adjacent wells. For example, the coefficients a and b are obtained by linear regression using a least square method:

$$a = \frac{\sum_{i=1}^{n} v_{li} v_{ti} - n\overline{v_t}\,\overline{v_l}}{\sum_{i=1}^{n} v_{li}^2 - n(\overline{v_l})^2}, \quad b = \overline{v_t} - a\overline{v_l},$$

where n is the number of adjacent wells in the preset area for which the transverse and wave velocities are obtained by logging; $v_{ti}$ is a transverse wave velocity of an ith adjacent well; $v_{li}$ is a longitudinal wave velocity of the ith adjacent well; $\overline{v_t}$ is an average value of the transverse wave velocities of the n adjacent wells; and $\overline{v_l}$ is an average value of the longitudinal wave velocities of the n adjacent wells.

Compared with an existing method of obtaining a Poisson's ratio described above, the result of the transverse wave velocity of the well to be diagnosed obtained from logging data such as the transverse and longitudinal wave velocities of the adjacent wells in the embodiment is very precise because the logging data is very precise, and thus the Poisson's ratio and other data obtained subsequently are also very accurate. Next, how to acquire the Poisson's ratio and the elastic modulus of the reservoir by using the transverse wave velocity of the well to be diagnosed will be introduced below.

Specifically, the Poisson's ratio v and the elastic modulus E of the reservoir can be obtained from the following formula (6-3) and the transverse wave velocity of the well to be diagnosed:

$$\begin{cases} E = \dfrac{\rho}{\Delta t_t^2} \dfrac{3\Delta t_t^2 - 4\Delta t^2}{\Delta t_t^2 - \Delta t^2} \\ v = \dfrac{0.5\Delta t_t^2 - \Delta t^2}{\Delta t_t^2} \\ \Delta t_t = \dfrac{1}{v_t} \end{cases} \quad (6\text{-}3)$$

where $\rho$ is a volume density of the reservoir; $\Delta t_t$ is a transverse wave time difference (which can be measured by a single-transmitter dual-receiver sound velocity measurement device, i.e., a time difference between reception, of transverse waves of glide waves formed by sound waves, by two receivers spaced by a distance L in a vertical direction); and $\Delta t$ is a sound wave time difference (which can be measured by a single-transmitter dual-receiver sound velocity measurement device, i.e., a time difference between reception, of glide waves formed by sound waves, by two receivers spaced by a distance L in the vertical direction).

Based on the acquired elastic modulus and Poisson's ratio, the diameter and length of any one capillary bundle in the reservoir under a certain stress are determined below.

First, the determining the diameter of each capillary bundle of the reservoir under the effective stress may include: determining the diameter $\lambda_p$ of the particular capillary bundle of the reservoir under the effective stress $\sigma(\vec{r}, t)$ according to the elastic modulus E of the reservoir and the following equation:

$$\lambda_p = F(1+\sigma(\vec{r}, t)/E)\lambda_{c0},$$

where F is a shape factor of the particular capillary bundle; and $\lambda_{c0}$ is an initial diameter of the particular capillary bundle of the reservoir under no effective stress.

Second, the determining the length of each capillary bundle of the reservoir under the effective stress may include: determining an initial length $L_{c0}$ of the particular capillary bundle of the reservoir under no effective stress according to an apparent length of the particular capillary bundle of the reservoir under no effective stress, the initial diameter of the particular capillary bundle of the reservoir under no effective stress, and a fractal scale law; and determining a length $L_p$ of the particular capillary bundle of the reservoir under the effective stress $\sigma(\vec{r}, t)$ according to the elastic modulus E of the reservoir, the Poisson's ratio v of the reservoir, the initial length $L_{c0}$ of the particular capillary bundle of the reservoir under no effective stress, and the following formula: $L_p = [1 - \sigma(\vec{r}, t)/(vE)]L_{c0}$.

Wherein the determining the initial length $L_{c0}$ of the particular capillary bundle of the reservoir under no effective stress may include: determining the initial length $L_{c0}$ of the particular capillary bundle of the reservoir under no effective stress according to the apparent length $L_0$ of the particular capillary bundle of the reservoir under no effective stress, the initial diameter $\lambda_{c0}$ of the particular capillary bundle of the reservoir under no effective stress, and the fractal scale law $L_{c0} = \lambda_{c0}^{1-D_{cT}} L_0^{D_{cT}}$, where $D_{cT}$ is a tortuous fractal dimension of the particular capillary bundle.

Step S6301: determining a flow ratio of the fluid according to the diameter and length of each capillary bundle of the reservoir under the effective stress, and a fluid flow ratio formula.

The flow ratio $q(\lambda_{c0}, \sigma(\vec{r}, t))$ of the fluid is determined according to the obtained diameter $\lambda_p$ and length $L_p$ of the particular capillary bundle of the reservoir under the effective stress $\sigma(\vec{r}, t)$ described above, and the fluid flow ratio formula $$q = \frac{\pi G \lambda_p^4 \Delta p}{128 \mu L_p}, \quad q\left(\lambda_{c0}, \sigma(\vec{r}, t)\right) = \frac{\pi G \Delta p F^4 \lambda_{c0}^{3+D_{cT}} (1+\sigma/E)^4}{128 \mu L_0^{D_{cT}} [1-\sigma/(vE)]}, \quad (6\text{-}4)$$

wherein G is a geometric factor of a transverse section of the particular capillary bundle; $\Delta p$ is a displacement pressure at both ends of the transverse section of the reservoir; and F is a shape factor of the particular capillary bundle.

Step S6302: determining a flow rate of the fluid according to the pore size distribution characteristics of pores of the reservoir, the flow ratio of the fluid in the reservoir, and the fluid flow formula.

For the step S6302, the determining a flow rate of the fluid includes: determining the flow rate $Q(\sigma(\vec{r}, t))$ of the fluid according to the pore size distribution characteristics $$N_c(\lambda_{c0} \leq L_0) = \left(\frac{\lambda_{c0max}}{\lambda_{c0}}\right)^{D_{cf}}$$

of pores of the reservoir, the flow ratio $q(\lambda_{c0}, \sigma(\vec{r}, t))$ of the fluid in the reservoir, and the fluid flow formula $Q = \int_{\lambda_{c0min}}^{\lambda_{c0max}} q(\lambda_{c0}, \sigma(\vec{r}, t))dN_c$, where $\lambda_{c0}$ is the initial diameter of the particular capillary bundle of the reservoir; $\lambda_{c0max}$, $\lambda_{c0min}$ is an initial diameter of a maximum capillary bundle and a minimum capillary bundle of the reservoir; $D_{cf}$ a fractal dimension of the pores; and $\sigma(\vec{r}, t)$ is the effective stress.

Specifically, based on the theory of rock fractal geometry, number density $N_c$ of pores of a solid matrix of with a diameter $\lambda_{c0}$ (i.e., number cumulative distribution of solid matrices of a certain diameter per unit volume, or pore size distribution characteristics of the pores) satisfies the relation:

$$N_c(\lambda_{c0} \leq L_0) = \left(\frac{\lambda_{c0max}}{\lambda_{c0}}\right)^{D_{cf}}.$$

For a two-dimensional (reservoir) model, $0 < D_{cf} < 2$; and for a three-dimensional (reservoir) model, $0 < D_{cf} < 3$.

According to the pore size distribution characteristics of the pores in the reservoir described above, $dN_c = D_{cf}\lambda_{c0max}^{D_{cf}}\lambda_{c0}^{-(D_{cf}+1)}d\lambda_{c0}$ can be obtained, and then $dN_c$ and formula (6-4) are substituted into the fluid flow formula to obtain the flow rate $Q(\sigma(\vec{r}, t))$ of the fluid expressed by the following formula (6-5):

$$Q(\sigma(\vec{r}, t)) = \frac{\pi G \Delta p F^4 \lambda_{c0max}^{3+D_{cT}}(1+\sigma/E)^4}{128 \mu L_0^{D_{cT}}(3+D_{cT}-D_{cf})[1-\sigma/(vE)]}\left[1-\left(\frac{\lambda_{c0min}}{\lambda_{c0max}}\right)^{3+D_{cT}-D_{cf}}\right]. \quad (6-5)$$

Step S6203: determining a spatio-temporal evolution simulation equation of reservoir damage by stress sensitivity according to a permeability model of the reservoir and the flow rate of the fluid in the reservoir.

Wherein the spatio-temporal evolution simulation equation is used to simulate a four-dimensional spatio-temporal evolution process of characteristics of reservoir damage caused by stress sensitivity.

For the step S6203, the determining a spatio-temporal evolution simulation equation of reservoir damage by stress sensitivity may include: determining the spatio-temporal evolution simulation equation of reservoir damage by the stress sensitivity according to the permeability model $$K(\sigma(\vec{r}, t)) = \frac{Q(\sigma(\vec{r}, t))\mu L_0}{A \Delta p}$$

of the reservoir and the flow rate $Q(\sigma(\vec{r}, t))$ of the fluid in the reservoir of the reservoir. Where $\mu$ is the viscosity of the fluid; $L_0$ is the apparent length of the particular capillary bundle of the reservoir under no effective stress; A is an area of a transverse section of the reservoir; and $\Delta p$ is the displacement pressure at both ends of the transverse section of the reservoir. Specifically, $A = L_0^2 = \int_{\lambda_{c0min}}^{\lambda_{c0max}} \sqrt{3}[(1+\sigma(\vec{r}, t)/E)\lambda_{c0}]^2 \, dN_c$, and then the above $dN_c$ is substituted to obtain A.

Specifically, the spatio-temporal evolution simulation equation of reservoir damage by the stress sensitivity expressed by the following formula (6-6) can be obtained according to the permeability model $$K(\sigma(\vec{r}, t)) = \frac{Q(\sigma(\vec{r}, t))\mu L_0}{A \Delta p}$$

of the reservoir and the flow rate $Q(\sigma(\vec{r}, t))$ expressed by the above formula (6-5), $$K(\sigma(\vec{r}, t)) = \frac{(2 - D_{cf})\pi G F^4 L_0^{1-D_{cT}} \lambda_{cmax0}^{1+D_{cT}} (1+\sigma(\vec{r}, t)/E)^2}{32\sqrt{3}(3+D_{cT}-D_{cf}) [1-\sigma(\vec{r}, t)/(vE)][1-(\lambda_{cmin0}/\lambda_{cmax0})^{2-D_{cf}}]}. \quad (6-6)$$

In summary, according to the present invention, the effective stress on the reservoir in the preset region of the well to be diagnosed is creatively determined; the flow rate of the fluid in the reservoir is determined according to the pore size distribution characteristics of the pores of the reservoir, the diameter and length of each capillary bundle of the reservoir under the effective stress, and the fluid flow formula; and the spatio-temporal evolution simulation equation of reservoir damage by the stress sensitivity is determined according to the permeability model of the reservoir and the flow rate of the fluid in the reservoir. Thus, by using the determined spatio-temporal evolution simulation equation, a four-dimensional spatio-temporal evolution process of the characteristics of reservoir damage caused by the stress sensitivity can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Correspondingly, another embodiment of the present invention further provides a method for determining a damage extent of a reservoir. The method includes: determining a characteristic parameter characterizing the damage extent of the reservoir in a preset region of a well to be diagnosed, based on the spatio-temporal evolution simulation equation by the modeling method for reservoir damage by stress sensitivity.

For the solution of the spatio-temporal evolution simulation equation for reservoir damage by pressure sensitivity expressed by the above formula (6-6), $P(\vec{r}, t)$ needs to be calculated according to formula (6-1). For the specific solving process, reference can be made to the solving process of the volume concentration of the deposited particles in the above Embodiment 1, which will not be described here. Then an aqueous phase saturation $S_w(\vec{r}, t)$ of the reservoir is determined according to the $P(\vec{r}, t)$ obtained by calculation.

After $P(\vec{r}, t)$ and the aqueous phase saturation $S_w(\vec{r}, t)$ of the reservoir are calculated by the above method, the permeability $K(\vec{r}, t)$ of the reservoir can be calculated according to the above formula (6-6), and thus the spatio-temporal evolution simulation equation established by the above modeling method for reservoir damage by pressure sensitivity comprehensively considers the influence of various physical and chemical factors on reservoir damage during damage by pressure sensitivity, so the permeability of the reservoir obtained by the embodiment is very precise.

A characteristic parameter characterizing the damage extent of the reservoir in the preset region of the well to be diagnosed can be calculated based on the permeability of the reservoir.

In an embodiment, the characteristic parameter may be a fluid loss coefficient of the reservoir.

Correspondingly, the determining a characteristic parameter characterizing the damage extent of the reservoir in a preset region of a well to be diagnosed may include: determining permeability $K(\vec{r}, t)$ of the reservoir based on the spatio-temporal evolution simulation equation; and determining a permeability damage rate $I(\vec{r}, t)$ of the reservoir based on the permeability $K(\vec{r}, t)$ of the reservoir and formula (5-14).

In another embodiment, the characteristic parameter may be a skin factor of the reservoir.

The determining a characteristic parameter characterizing the damage extent of the reservoir in a preset region of a well to be diagnosed may include: determining the permeability $K(\vec{r}, t)$ of the reservoir based on the spatio-temporal evolution simulation equation; and determining the skin factor S of the reservoir based on the permeability $K(\vec{r}, t)$ of the reservoir and formula (5-15).

Figure 6F:
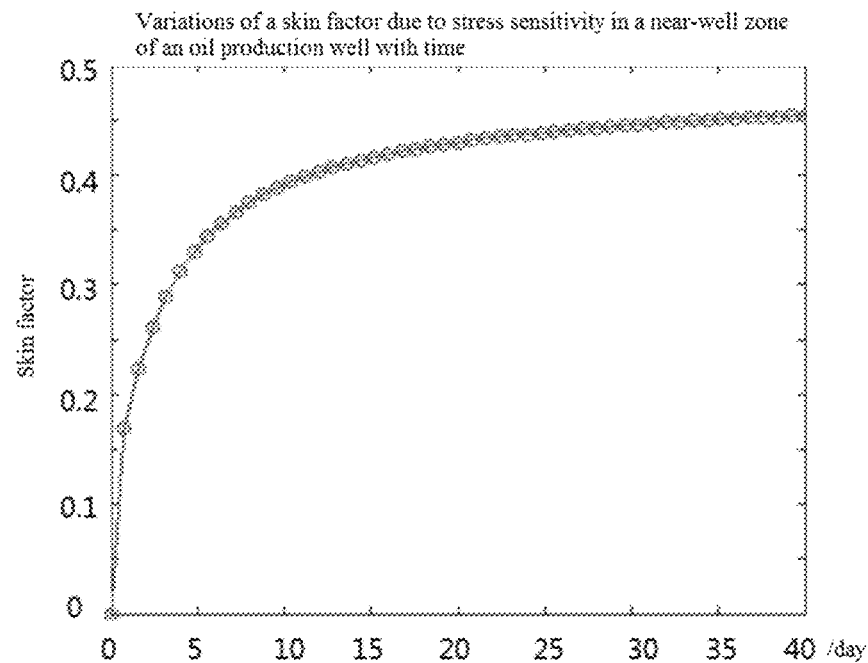
FIG. 6F is a schematic diagram of evolution of a skin factor over time provided in an embodiment of the present invention.
Figure 6G:
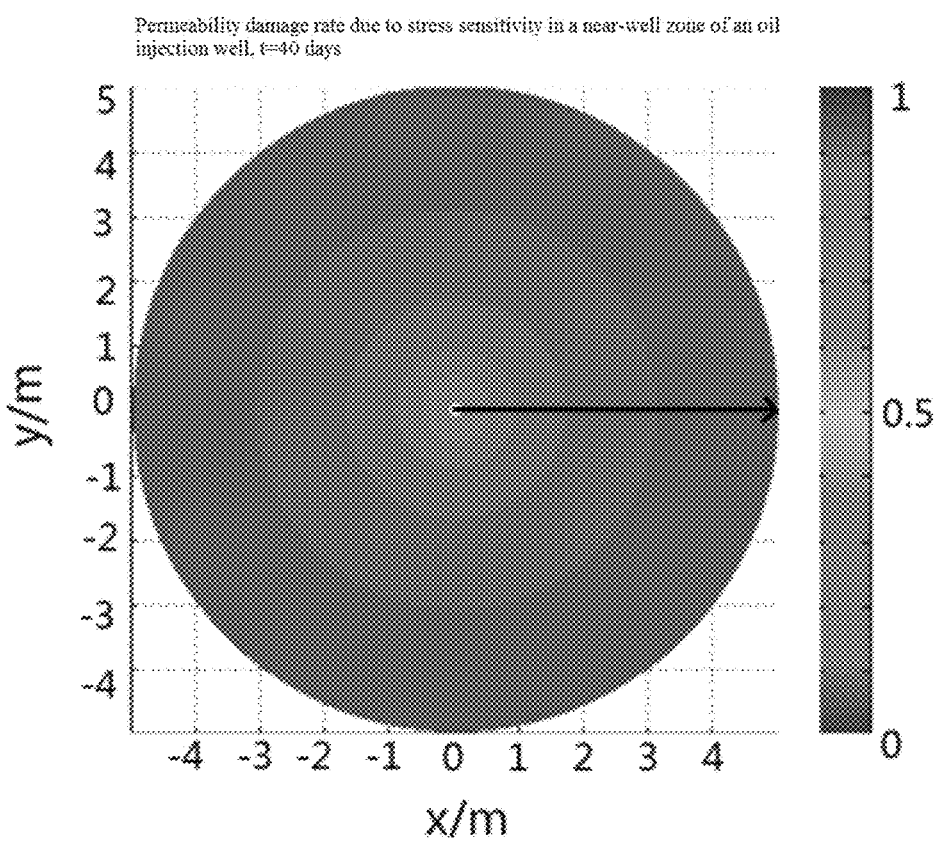
FIG. 6G is a flow diagram of a radius of reservoir damage by stress sensitivity at day 40 characterized by a permeability damage rate of a reservoir provided in an embodiment of the present invention.

The characteristic parameters (e.g., the permeability $K(\vec{r}, t)$ the skin factor $S(\vec{r}, t)$ and the permeability damage rate of the reservoir) obtained by the above embodiments are a result of 4D quantitative simulation of spatio-temporal evolution (as shown in FIG. 6F). More specifically, FIG. 6G shows a schematic diagram of a radius (a radius as indicated by an arrow) of reservoir damage by stress sensitivity at day 40 characterized by the permeability damage rate of the reservoir, and a working person concerned can visually confirm the damage extent of the reservoir from FIG. 6G. Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

Embodiment 7—Sand Production

According to a sand production mechanism, key parameters of reservoir damage by sand production are a threshold flow velocity and a critical flow velocity, so the core of quantitative simulation of spatio-temporal evolution of reservoir damage by sand production is to solve the threshold flow velocity and the critical flow velocity. The threshold flow velocity is a flow velocity for incipient motion of sand grains. When a fluid flow velocity is greater than the threshold flow velocity, part of the sand grains start to move, and sand produced at the moment is attached sand; and if the fluid flow velocity exceeds the critical flow velocity, shear failure occurs on a rock framework, a large amount of sand starts to be produced, and the sand produced at the moment includes attached sand and framework sand. When the fluid flow velocity exceeds the threshold flow velocity and is lower than the critical flow velocity, the reservoir starts to produce sand partly, which has almost no influence on the reservoir (e.g., permeability), and proper sand production is helpful to the permeability instead; and when the fluid flow velocity is greater than the critical flow velocity such that the reservoir produces a large amount of sand, relatively great damage is caused to the reservoir (e.g., permeability), so only the situation where the fluid flow velocity is greater than the critical flow velocity such that the reservoir is influenced is considered in the embodiments of the present invention. The critical flow velocity is related to a critical production differential pressure (or critical production), so a specific process of determining the critical production differential pressure (or critical production) is involved herein. On this basis, based on mass conservation, a diffusion relationship, and the like, a spatio-temporal evolution control phenomenological model (containing a concentration C of sand grains and a concentration Cd of deposited sand grains) of concentration distribution of the sand grains in a reservoir around a well to be diagnosed is established, and in conjunction with a relationship between a deposition concentration and a characteristic parameter characterizing the damage extent of the reservoir such as permeability, spatio-temporal field distribution of the characteristic parameter such as permeability can be diagnosed.

Figure 7A:
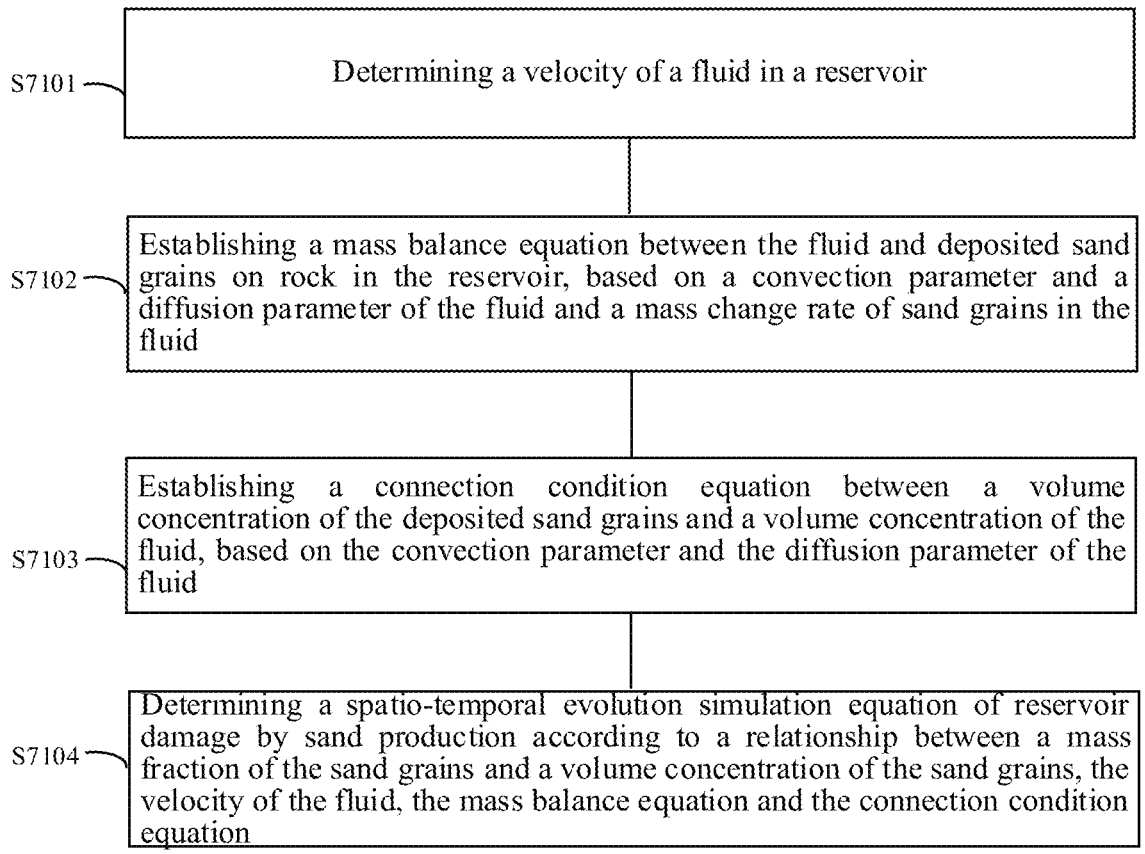
FIG. 7A is a flow diagram of a modeling method for reservoir damage by sand production provided in an embodiment of the present invention.

FIG. 7A is a flow diagram of a modeling method for reservoir damage by sand production provided in an embodiment of the present invention. The modeling method may include steps S7101-S7104.

Step S7101: determining a velocity of a fluid in a reservoir.

Wherein the reservoir is located in a preset region of a well to be diagnosed (e.g., a water injection well).

For the step S7101, the determining a velocity of a fluid in a reservoir may include: establishing a pressure conduction equation for the fluid entering the reservoir; and determining the velocity of the fluid according to the pressure conduction equation and a Darcy formula.

For the specific determination process, reference can be made to the process of determining a velocity of a fluid in the above Embodiment 1 (i.e., the above formulas (1-1) and (1-2) and related description thereof).

Step S7102: establishing a mass balance equation between the fluid and deposited sand grains on rock in the reservoir, based on a convection parameter and a diffusion parameter of the fluid and a mass change rate of sand grains in the fluid.

There is a correlation between the mass change rate of the sand grains and a crude oil production of the reservoir. Specifically, the correlation between the mass change rate of the sand grains and the crude oil production of the reservoir includes: the mass change rate of the sand grains is greater than 0 in the case where the crude oil production of the reservoir is greater than critical production.

In an embodiment, the critical production is obtained by: determining a pressure of the fluid according to the pressure conduction equation; determining a critical flowing bottom hole pressure of the fluid at the time the reservoir starts to produce sand according to an effective radial stress and an effective circumferential stress of the reservoir and a Mohr-Coulomb criterion; and determining the critical production according to the critical flowing bottom hole pressure of the fluid, the pressure of the fluid and a Dupuit formula.

In establishment of a sand production damage model, first a critical velocity of the fluid when the sand grains incipiently move and migrate is considered, and then how the sand grains change a solid-liquid flow deposition equation is considered.

When a stratum is drilled, stress distribution around the well changes and stress concentration occurs at a well wall.

Under the combined effect of a downhole liquid column pressure (a first term on the right side of the following formula), a crustal stress (second and third terms on the right side of the following formula) and fluid seepage (a fourth term on the right side of the following formula), a radial stress $\sigma_r(\vec{r}, t)$ and a circumferential stress $\sigma_\theta(\vec{r}, t)$ of the reservoir (e.g., the rock of the reservoir is an isotropic uniform elastomer) are respectively:

$$\sigma_r(\vec{r}, t) =$$

$$\frac{r_w^2}{r^2}P(\vec{r}, t) + \frac{(\sigma_H + \sigma_h)}{2}\left(1 - \frac{r_w^2}{r^2}\right) + \frac{(\sigma_H - \sigma_h)}{2}\left(1 + \frac{3r_w^4}{r^4} - 4\frac{r_w^2}{r^2}\right)\cos 2\theta +$$

$$\delta\left[\frac{\beta(1 - 2v(\vec{r}, t))}{2(1 - v(\vec{r}, t))}\left(1 - \frac{r_w^2}{r^2}\right) - \phi\right](P(\vec{r}, t) - P(\vec{r}, 0));$$

$$\sigma_\theta(\vec{r}, t) = -\frac{r_w^2}{r^2}P(\vec{r}, t) + \frac{(\sigma_H + \sigma_h)}{2}\left(1 + \frac{r_w^2}{r^2}\right) - \frac{(\sigma_H - \sigma_h)}{2}\left(1 + \frac{3r_w^4}{r^4}\right)\cos 2\theta +$$

$$\delta\left[\frac{\beta(1 - 2v(\vec{r}, t))}{2(1 - v(\vec{r}, t))}\left(1 + \frac{r_w^2}{r^2}\right) - \phi\right](P(\vec{r}, t) - P(\vec{r}, 0)),$$

where $r_w$ is a wellbore radius of the well to be diagnosed; P($\vec{r}$, t) is the pressure of the fluid; $\sigma_H$ and $\sigma_h$ are a maximum horizontal crustal stress and a minimum horizontal crustal stress, respectively; $v(\vec{r}, t)$ is a flow velocity of the fluid; $\phi$ is porosity of the reservoir; $\beta$ is a pore Biot coefficient $$\beta = 1 - \frac{C_r}{C_b},$$

where $C_r$ is a rock basement compression coefficient; and $C_b$ is a rock volume compression coefficient); $\theta$ is an included angle between radial and horizontal maximum crustal stress directions at $\vec{r}$ in the reservoir; and $\delta$ is 1 when permeation occurs at the well wall, and $\delta$ is 0 when permeation does not occur at the well wall. A situation where permeation occurs at the well wall (i.e., $\delta$ is 1) is considered here.

$$\sigma_r(\vec{r}, t)P(\vec{r}, 0) = \frac{r_w^2}{r^2}P(\vec{r}, t) + \qquad (7\text{-}1)$$

$$\frac{(\sigma_H + \sigma_h)}{2}\left(1 - \frac{r_w^2}{r^2}\right) + \frac{(\sigma_H - \sigma_h)}{2}\left(1 + \frac{3r_w^4}{r^4} - 4\frac{r_w^2}{r^2}\right)\cos 2\theta +$$

$$\left[\frac{\beta(1 - 2v(\vec{r}, t))}{2(1 - v(\vec{r}, t))}\left(1 - \frac{r_w^2}{r^2}\right) - \phi\right](P(\vec{r}, t) - P(\vec{r}, 0));$$

$$\sigma_\theta(\vec{r}, t) = \qquad (7\text{-}2)$$

$$-\frac{r_w^2}{r^2}P(\vec{r}, t) + \frac{(\sigma_H + \sigma_h)}{2}\left(1 + \frac{r_w^2}{r^2}\right) - \frac{(\sigma_H - \sigma_h)}{2}\left(1 + \frac{3r_w^4}{r^4}\right)\cos 2\theta +$$

$$\left[\frac{\beta(1 - 2v(\vec{r}, t))}{2(1 - v(\vec{r}, t))}\left(1 + \frac{r_w^2}{r^2}\right) - \phi\right](P(\vec{r}, t) - P(\vec{r}, 0)),$$

For a porous permeable reservoir, a relationship between the radial stress and an effective radial stress $\sigma'_r$ of the reservoir satisfies the following formula (7-3), and a relationship between the circumferential stress and an effective circumferential stress $\sigma'_\theta$ of the reservoir satisfies the following formula (7-4):

$$\sigma_\theta = \sigma'_\theta + \beta P(\vec{r}, t); \qquad (7\text{-}3)$$

$$\sigma_r = \sigma'_r + \beta P(\vec{r}, t). \qquad (7\text{-}4)$$

A tectonic stress is neglected, and according to an Anderson uniaxial strain model ($\sigma_H = \sigma_h$), an oilfield crustal stress is:

$$\sigma_H - \beta P(\vec{r}, 0) = \sigma_h - \beta P(\vec{r}, 0) = \frac{v(\vec{r}, t)}{1 - v(\vec{r}, t)}(\sigma_v - \beta P(\vec{r}, 0)), \qquad (7\text{-}5)$$

where $\sigma^v$ is a pressure from an overlying rock layer of the reservoir. According to density logging data, the overlying rock layer pressure $\sigma_v$ can be obtained by the following formula:

$$\sigma_v = \frac{\int_0^H \rho_b(h)g\,dh}{1000}.$$

If a theoretical value of an overlying rock layer gradient is adopted, $\sigma_v = 22.7$ H, where H is a depth; and if the overlying rock layer pressure is assumed to increase uniformly with the depth, $\sigma_v = [\rho_S(1-\phi) + \rho_L\phi]gH$, where $\rho_s$ is the average density of the rock framework; $\rho_L$ is the density of the fluid; and H is the depth.

According to the above formulas (7-1)-(7-5), it can be determined that the effective radial stress and an effective axial stress of the reservoir satisfy the following equations, respectively:

$$\sigma'_r = \frac{r_w^2}{r^2}P(\vec{r}, t) + \left[\frac{v(\vec{r}, t)}{1 - v(\vec{r}, t)}(\sigma_v - \beta P(\vec{r}, 0)) + \beta P(\vec{r}, 0)\right]\left(1 - \frac{r_w^2}{r^2}\right) + \qquad (7\text{-}6)$$

$$\left[\frac{\beta(1 - 2v(\vec{r}, t))}{2(1 - v(\vec{r}, t))}\left(1 - \frac{r_w^3}{r^2}\right) - \phi\right](P(\vec{r}, t) - P(\vec{r}, 0)) - \beta P(\vec{r}, t),$$

$$\sigma'_\theta = -\frac{r_w^2}{r^2}P(\vec{r}, t) + \left[\frac{v(\vec{r}, t)}{1 - v(\vec{r}, t)}(\sigma_v - \beta P(\vec{r}, 0)) + 2\beta P_p\right]\left(1 + \frac{r_w^2}{r^2}\right) + \qquad (7\text{-}7)$$

$$\left[\frac{\beta(1 - 2v(\vec{r}, t))}{2(1 - v(\vec{r}, t))}\left(1 + \frac{r_w^2}{r^2}\right) - \phi\right](P(\vec{r}, t) - P(\vec{r}, 0)) - \beta P(\vec{r}, t).$$

When $r = r_w$ and the depth is the depth where a bottom hole is located, $P(\vec{r}, t) = P_{wf}$. As a differential pressure is the largest at the well wall, only after the reservoir at the well wall produces sand, can other locations produce sand. In the embodiment, the effective radial stress and the effective circumferential stress on the surface of the well wall are considered as:

$$\sigma'_r = (1 - \beta - \phi)P_{wf} + \phi P(\vec{r}, 0); \quad (7\text{-}8)$$

$$\sigma'_\theta = \quad (7\text{-}9)$$

$$\frac{2v(\vec{r}, t)}{1 - v(\vec{r}, t)}\sigma_v - \left(\beta\frac{v(\vec{r}, t)}{1 - v(\vec{r}, t)} + \phi + 1\right)P_{wf} + \left(\beta\frac{s - 4v(\vec{r}, t)}{1 - v(\vec{r}, t)} + \phi\right)P(\vec{r}, 0).$$

Under the combined effect of the crustal stress, pore pressures in the stratum and friction during fluid seepage on stratum rock, the effective radial stress increases and exceeds a yield condition in an unconsolidated sandstone reservoir, which will cause instability and plastic flow of the reservoir rock to produce sand, and reservoir rock failure follows the Mohr-Coulomb criterion. Specifically, when a maximum principal stress $\sigma_{max}$ and a minimum principal stress $\sigma_{min}$ are used, fluid pressures in the pores of the reservoir are considered, the Mohr-Coulomb criterion can be expressed as:

$$\sigma_{max} - \beta P(\vec{r}, 0) = 2C\frac{\cos\varphi}{1 - \sin\varphi} + (\sigma_{min} - \beta P(\vec{r}, 0))\frac{1 + \sin\varphi}{1 - \sin\varphi}, \quad (7\text{-}10)$$

where C is a sand-mudstone cohesive force; $\varphi$ is a stratum internal frictional angle; $v_{po}$ is a Poisson's ratio of the rock; $v_p$ is a longitudinal wave velocity; and $v_{cl}$ is a shale content (%).

For the sand-mudstone cohesive force C, the sand-mudstone cohesive force $CS_o$ and a sound wave propagation velocity $v_p$ satisfy the following relationship:

$$C = 5.44 \times 10^{-15}\rho_b^2(1 - 2v_{po})\left(\frac{1 + v_{po}}{1 - v_{po}}\right)^2 v_p^4(1 + 0.78v_{mcl}),$$

where $\rho_b(H)\rho_b(H)$ is rock volume density in the reservoir at the depth H. The shale content $V_{mcl}$ can be calculated according to spontaneous potential logging data and using an empirical formula:

$$v_{mcl} = 1 - \frac{PSP}{SSP},$$

where PSP is a spontaneous potential of argillaceous sandstone; and SSP is a static spontaneous potential of water-bearing clean sandstone in the preset region. The stratum internal frictional angle $\varphi$ can be calculated by the following equation:

$$\varphi = 2.564 \log_{10}[M + (M^2 + 1)^{1/2}] + 20, \text{ where } M = 58.93 - 1.785C.$$

$$\sigma_{max} = \sigma'_\theta, \sigma_{min} = \sigma'_r, \text{ and,}$$

and equations (7-8)-(7-9) are substituted into the above formula (7-10) to obtain the critical flowing bottom hole pressure at the time when the well to be diagnosed starts to produce sand:

$$P_{cr} = P_{wf} = \frac{\frac{2v(\vec{r}, t)}{1 - v(\vec{r}, t)}\sigma_v - 2C\frac{\cos\varphi}{1 - \sin\varphi} + \left[\beta\frac{2 - 3v(\vec{r}, t)}{1 - v(\vec{r}, t)} + \phi + (\phi - \beta)\frac{1 + \sin\varphi}{1 - \sin\varphi}\right]P(\vec{r}, 0)}{(1 - \beta - \phi)\frac{1 + \sin\varphi}{1 - \sin\varphi} + \beta\frac{v(\vec{r}, t)}{1 - v(\vec{r}, t)} + \phi + 1}, \quad (7\text{-}11)$$

and hence, according to the above formula (7-11), a critical production differential pressure $\Delta P_{cr}$ can be obtained:

$$\Delta P_{cr} = P(\vec{r}, 0) - P_{cr}. \quad (7\text{-}12)$$

After the critical production differential pressure $\Delta P_{cr}$ is obtained, the critical production $Q_{cr}$ can be determined from the Dupuit formula (7-13):

$$Q_{cr} = \frac{2\pi KH\Delta P_{cr}}{\mu_o B_o\left(\ln\frac{r_e}{r_w}\right)}, \quad (7\text{-}13)$$

where $B_o$ is an oil phase volume factor; $r_e$ an oil pool radius; $r_w$ is the wellbore radius of the well to be diagnosed; $\mu_o$ is crude oil viscosity; and K is the permeability of the reservoir.

According to formula (7-13), it can be known that the critical production $Q_{cr}$ is closely related to the velocity of the fluid. Only when the actual velocity of the fluid in the reservoir exceeds the critical velocity (or the actual production of crude oil exceeds the critical production), can the reservoir produce sand under the action of the fluid.

According to a mass equation, assuming that the mass change rate of the sand grains (i.e., the amount of sand grains released) is $q_s$, $q_s$ has the following properties:

$$q_s: \begin{cases} > 0, & Q \geq Q_{cr} \\ = 0, & Q < Q_{cr} \end{cases}.$$

In other words, only when the production of crude oil exceeds the critical production, can the reservoir produce sand and the sand grains formed by sand production enter the fluid to participate in migration, thereby increasing the mass of the fluid-solid mixture. Therefore, for step S7102, establishing a mass balance equation between the fluid and the deposited sand grains on rock in the reservoir may include: establishing the mass balance equation expressed in the following formula, based on a convection parameter and a diffusion parameter of the fluid, $$\frac{\partial}{\partial t}(\rho\phi w(\vec{r}, t)) + \nabla(\rho uw(\vec{r}, t) + j(\vec{r}, t)) = -\dot{m}(\vec{r}, t) + q_s, \quad (7\text{-}14)$$

where $\rho$ is the density of the fluid; $\phi$ is the porosity of the reservoir; w ($\vec{r}$, t) is the mass fraction (which may also be called a mass concentration) of the deposited sand grains; u is a Darcy apparent velocity; j ($\vec{r}$, t) is a diffusion flow rate, j($\vec{r}$, t) = $-\phi\rho_L D\nabla w(\vec{r}, t)$, where $\rho_L$ is the density of the fluid (i.e. $\rho_L = \rho$), D($\vec{r}$, t) is a diffusion coefficient of the sand grains, D($\vec{r}$, t) = $\alpha v(\vec{r}, t)$, $\alpha$ is a vertical diffusivity, and v($\vec{r}$, t) is the velocity of the fluid;

$$\dot{m}(\vec{r}, t) \equiv \frac{\partial m(\vec{r}, t)}{\partial t} = k(\vec{r}, t)(\rho u w(\vec{r}, t) + j(\vec{r}, t));$$

$\dot{m}(\vec{r}, t)$ is an accumulated mass of the deposited sand grains per unit time; t is time; and $q_s$ is the mass change rate of the sand grains.

The mass change rate $q_s$ of the sand grains is obtained by: determining the intensity Q(r) of a release field of the deposited sand grains; determining a decay function Y(t) of the intensity of the release field; and determining the mass change rate $q_s=Q(r)Y(t)$ of the sand grains according to the intensity Q(r) of the release field and the decay function Y(t) of the intensity of the release field. Specifically, the intensity Q(r) of the release field may be a constant ($q_0$), and the decay function Y(t) may be an exponential decay function (e.g. $e^{-\lambda t}$, where $\lambda$ is a decay constant) that can vary with time.

Step S7103: establishing a connection condition equation between a volume concentration of the deposited sand grains and a volume concentration of the fluid, based on the convection parameter and the diffusion parameter of the fluid.

For the step S7103, the establishing a connection condition equation between a volume concentration of the deposited sand grains and a volume concentration of the fluid may include: establishing the connection condition equation expressed in the following formula (7-15), based on the convection parameter and the diffusion parameter of the fluid, $$\frac{\partial (\rho_p C_d(\vec{r}, t))}{\partial t} = k(\vec{r}, t)(\rho u w(\vec{r}, t) + j(\vec{r}, t)), \qquad (7\text{-}15)$$

where $\rho_p$ is the density of the deposited sand grains; $C_d$ is the volume concentration of the deposited sand grains; and $k(\vec{r}, t) = k_0(\vec{r})G_1(C_d)F_1(T)$, where $k_0$ is an original fluid loss coefficient, $$G_1(C_d) = \left(1 - \frac{C_d}{C_{dmax}}\right)^{m_k}, \text{ and } F_1(T) = \exp\left(A_k\left(\frac{1}{T - T_{ik}} - \frac{1}{T_{ik} - T_{ck}}\right)\right).$$

Since the correlation between $F_1(T)$ and temperature is measured by $\exp(1/T)$ and in a common temperature range (e.g., 300 K to 400 K), the change of this function is actually very slow and actually close to an isothermal process, thus $$k(\vec{r}, t) = k_0(\vec{r}) \cdot \left(1 - \frac{C_d(\vec{r}, t)}{C_{dmax}}\right)^{m_k},$$

where $C_d(\vec{r}, t)$ is the volume concentration of the deposited sand grains, $C_{d\ max}$ is a maximum volume concentration of the deposited sand grains, and $m_k$ is a first empirical value. All of the above parameters can be either constants, or parameters that vary with space, i.e., in a non-homogeneous situation.

Step S7104: determining a spatio-temporal evolution simulation equation of reservoir damage by the sand production according to a relationship between the mass fraction of the sand grains and the volume concentration of the sand grains, the velocity of the fluid, the mass balance equation and the connection condition equation.

Wherein the relationship between the mass fraction of the migrating sand grains and the volume concentration of the migrating sand grains may be $$w(\vec{r}, t) = \frac{\rho_p}{\rho_L} C(\vec{r}, t),$$

where $\rho_p$ is the density of the deposited sand grains; $\rho_L$ is the density of the fluid; $w(\vec{r}, t)$ is the mass fraction of the sand grains; and $C(\vec{r}, t)$ is the volume concentration of the sand grains. The spatio-temporal evolution simulation equation of reservoir damage by the sand production may include: a spatio-temporal evolution simulation equation of reservoir damage by the sand production expressed by formula (7-16), and a spatio-temporal evolution simulation equation of reservoir damage by the sand grain deposition expressed by formula (7-17).

For the step S7104, the determining a spatio-temporal evolution simulation equation of reservoir damage by the sand production may include: determining the spatio-temporal evolution simulation equation of reservoir damage by the sand production expressed by formula (7-16) according to the relationship between the mass fraction of the sand grains and the volume concentration of the sand grains, the velocity of the fluid, and the mass balance equation expressed by formula (7-14):

$$\frac{\partial C(\vec{r}, t)}{\partial t} + \frac{v(\vec{r}, t)}{\tau}\left[1 - \left(1 - \frac{\rho_p}{\rho_L}C(\vec{r}, t)\right)k(\vec{r}, t)\alpha\tau\right]\nabla C(\vec{r}, t) + \qquad (7\text{-}16)$$

$$\left(1 - \frac{\rho_p}{\rho_L}C(\vec{r}, t)\right)\left(\frac{k(\vec{r}, t)v(\vec{r}, t)}{\tau}C(\vec{r}, t) - \frac{q_s}{\rho_p \phi}\right) = \alpha v(\vec{r}, t)\nabla^2 C(\vec{r}, t);$$

and determining the spatio-temporal evolution simulation equation of reservoir damage by the sand grain deposition expressed by formula (7-17) according to the relationship between the mass fraction of the sand grains and the volume concentration of the sand grains, the velocity of the fluid, and the connection condition equation expressed by formula (7-15):

$$\frac{\partial C_d(\vec{r}, t)}{\partial t} = \frac{v(\vec{r}, t)k(\vec{r}, t)\phi}{\tau}[C(\vec{r}, t) - \alpha\tau\nabla C(\vec{r}, t)], \qquad (7\text{-}17)$$

where $C(\vec{r}, t)$ where the volume concentration of the sand grains; $v(\vec{r}, t)$ is the velocity of the fluid; $\tau$ is the tortuosity of the reservoir; $\rho_p$ is the density of the deposited sand grains; $\rho_L$ is the density of the fluid;

$$k(\vec{r}, t) = k_0(\vec{r}) \cdot \left(1 - \frac{C_d(\vec{r}, t)}{C_{dmax}}\right)^{m_k},$$

and $k_0(\vec{r})$ is an initial value of the fluid loss coefficient of the reservoir; $C_d(\vec{r}, t)$ is the volume concentration of the deposited sand grains; $C_{d\ max}$ is the maximum volume concentration of the deposited sand grains; $m_k$ is a first empirical value; α is vertical diffusivity; ϕ is porosity of the reservoir; and $q_s$ is a mass change rate of the sand grains.

$k_0(\vec{r})=f(N_R, N_{Pe}, N_A, N_{DL}, N_{E1}, N_{E2}, N_G, N_{Lo}, N_{vdW}, \zeta_{p(g)})$, where $N_R, N_{Pe}, N_A, N_{DL}, N_{E1}, N_{E2}, N_G, N_{Lo}, N_{vdW}, \zeta_{p(g)}$ are a radius number, a Peclet number, an attraction number, an electrical double layer number, a first electric potential force number, a second electric potential force number, a gravity number, a London force number, a van der Waals force number, and potentials of sand grains and matrix particles (i.e., particles deposited on the rock), respectively (for details of relevant expressions of the parameters, see Table 2).

In summary, according to the present invention, the mass balance equation between the fluid and the deposited sand grains on the rock in the reservoir is creatively established based on the convection parameter and the diffusion parameter of the fluid and the mass change rate of sand grains in the fluid, wherein there is a correlation between the mass change rate of the sand grains and a crude oil production of the reservoir; the connection condition equation between the volume concentration of the deposited sand grains and the volume concentration of the fluid is established based on the convection parameter and the diffusion parameter of the fluid; and the spatio-temporal evolution simulation equation of reservoir damage by the sand production is determined according to the relationship between the mass fraction of the sand grains and the volume concentration of the sand grains, the velocity of the fluid, the mass balance equation and the connection condition equation. Thus, by using the determined spatio-temporal evolution simulation equation, a four-dimensional spatio-temporal evolution process of characteristics of reservoir damage caused by the sand production can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Figure 7B:
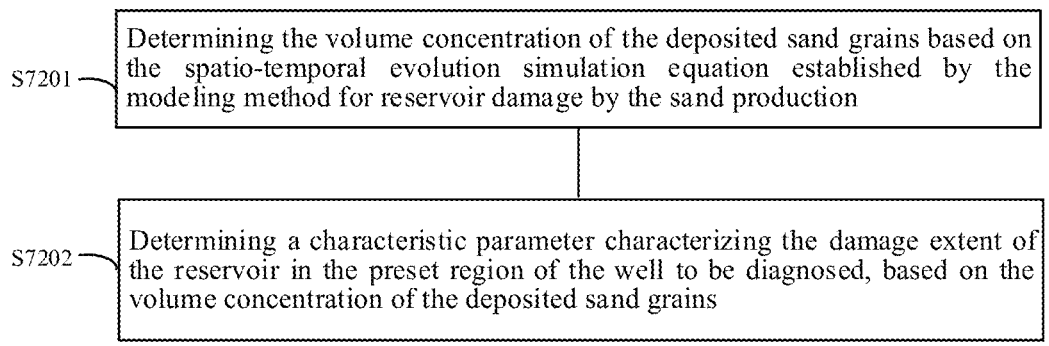
FIG. 7B is a flow diagram of a method for determining a damage extent of a reservoir provided in an embodiment of the present invention.

FIG. 7B is a flow diagram of a method for determining a damage extent of a reservoir provided in an embodiment of the present invention. As shown in FIG. 7B, the method for determining the damage extent of the reservoir may include steps S7201-S7202.

Step S7201: determining the volume concentration of the deposited sand grains based on the spatio-temporal evolution simulation equation established by the modeling method for reservoir damage by the sand production.

For the spatio-temporal evolution simulation equation of reservoir damage by the sand production expressed by the above formula (7-16), the volume concentration $C(\vec{r}, t)$ of the sand grains can be calculated by referring to the process of solving a volume concentration of deposited particles in the above Embodiment 1.

After the volume concentration $C(\vec{r}, t)$ of the sand grains is calculated by the above method, the volume concentration $C_d(\vec{r}, t)$ of the deposited sand grains can be calculated according to the above formula (7-17), and thus the spatio-temporal evolution simulation equation established by the above modeling method of reservoir damage by the sand grains comprehensively considers the influence of various physical and chemical factors on reservoir damage during sand production, so the volume concentration of the deposited sand grains obtained by the step S7201 is very precise.

Step S7202: determining a characteristic parameter characterizing the damage extent of the reservoir in a preset region of a well to be diagnosed, based on the volume concentration of the deposited sand grains.

In an embodiment, the characteristic parameter may be permeability of the reservoir.

For the step S7202, the determining a characteristic parameter characterizing the damage extent of the reservoir in a preset region of a well to be diagnosed may include: determining the permeability $K(\vec{r}, t)$ of the reservoir based on the volume concentration $C_d(\vec{r}, t)$ of the deposited sand grains and formula (1-15).

In an embodiment, the characteristic parameter may be a fluid loss coefficient of the reservoir.

For the step S7202, the determining a characteristic parameter characterizing the damage extent of the reservoir in a preset region of a well to be diagnosed may include: determining the permeability $K(\vec{r}, t)$ of the reservoir based on the volume concentration $C_d(\vec{r}, t)$ of the deposited sand grains and formula (1-15); and determining the fluid loss coefficient $k(\vec{r}, t)$ of the reservoir based on the volume concentration $C_d(\vec{r}, t)$ of the deposited sand grains and formula (1-16).

Wherein the characteristic parameter may be a skin factor of the reservoir.

For the step S7202, the determining a characteristic parameter characterizing the damage extent of the reservoir in a preset region of a well to be diagnosed may include: determining the permeability $K(\vec{r}, t)$ of the reservoir based on the volume concentration of the deposited sand grains and formula $$K(\vec{r}, t)/K_0(\vec{r}) = \left(1 - \frac{C_d(\vec{r}, t)}{\phi_0}\right)^{m_k};$$

and determining the skin factor $S(\vec{r}, t)$ of the reservoir based on the permeability $K(\vec{r}, t)$ of the reservoir and formula (1-17).

Figure 7C:
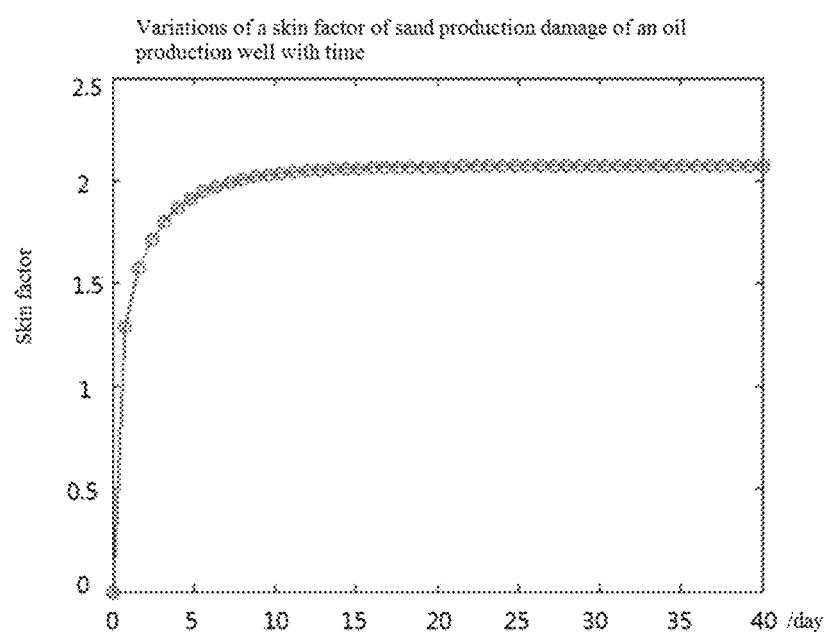
FIG. 7C is a schematic diagram of evolution of a skin factor over time provided in an embodiment of the present invention.
Figure 7D:
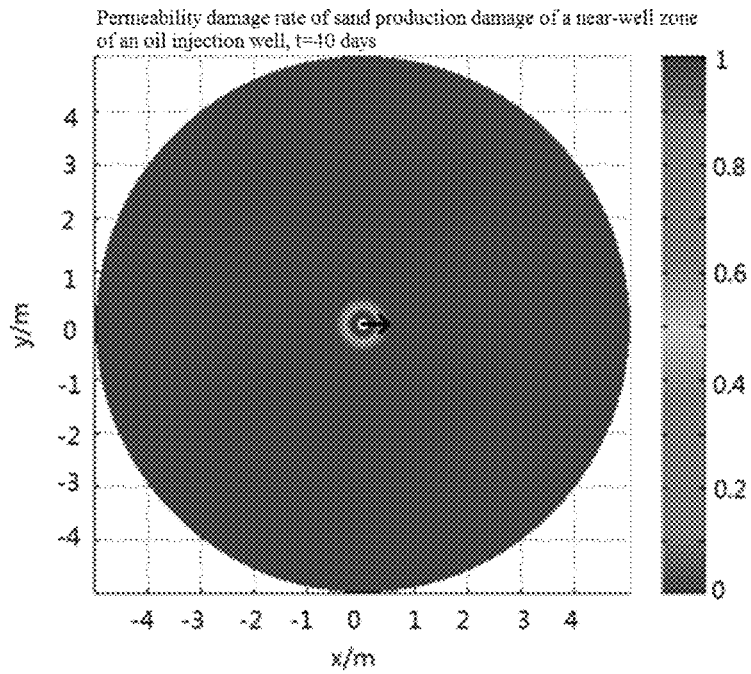
FIG. 7D is a flow diagram of a radius of reservoir damage by sand production at day 40 characterized by a permeability damage rate of a reservoir provided in an embodiment of the present invention.

The characteristic parameter (e.g., the permeability $K(\vec{r}, t)$ and the skin factor $S(\vec{r}, t)$ of the reservoir) obtained by the step S7202 is a result of 4D quantitative simulation of spatio-temporal evolution (as shown in FIG. 7C). More specifically, FIG. 7D shows a schematic diagram of a radius (a radius as indicated by an arrow) of reservoir damage by sand production at day 40 characterized by a permeability damage rate of the reservoir (the permeability damage rate $I(r_i, t)$ of the reservoir is determined based on the permeability $K(\vec{r}, t)$ of the reservoir and formula $$I(\vec{r}, t) = 1 - \frac{K(\vec{r}, t)}{K_{max}(\vec{r}, t)},$$

where $K_{max}(\vec{r}, t)$ is a maximum value of $K(\vec{r}, t)$), and a working person concerned can visually confirm the damage extent of the reservoir from FIG. 7D. Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

In summary, the volume concentration of the deposited sand grains can be determined by using the determined spatio-temporal evolution simulation equation, and then the characteristic parameter (e.g., the permeability and/or the skin factor of the reservoir) characterizing the damage extent of the reservoir in the preset region of the well to be diagnosed can be determined according to the volume concentration of the deposited sand grains, whereby a four-dimensional spatio-temporal evolution process of the characteristics of reservoir damage caused by the sand production can be simulated quantitatively. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Embodiment 8—Wettability Reversal

Wettability reversal is a phenomenon in which surfaces of pores in a reservoir change from hydrophilic to lipophilic, which weakens circulation of an oil phase in the pores, resulting in poor permeability of the reservoir. When an oil-phase saturation is high, the oil phase occupies large pores and is good in connectivity, and its flow has characteristics similar to a capillary flow, and the permeability is in a linear relation with the square of the saturation; and when the oil-phase saturation is low, the oil phase is mainly dispersed and attached to wall surfaces of small pores, and is poor in connectivity, and as the saturation decreases, the permeability of the oil phase decreases at a faster rate (e.g., changing based on the 4th power law).

On the one hand, a wettability damage extent of the reservoir is determined by a relationship between relative permeability of the oil phase and the oil (or water) saturation; on the other hand, pressure distribution in the reservoir also influences a fluid flow velocity and permeability in the pores. Therefore, the core of the embodiments of the present invention is to establish a pressure distribution field of the oil phase (considering pressure distribution of the oil phase and an aqueous phase in the fluid, respectively) and a convection diffusion law of the oil phase. Specifically, the pressure distribution field of the oil phase is determined according to a pressure distribution equation of the reservoir in a preset region around a well to be diagnosed and a force balance condition of capillaries; and spatio-temporal field distribution of a characteristic parameter characterizing the damage extent of the reservoir such as permeability can be diagnosed in conjunction with a Darcy formula and the convection diffusion law of the oil phase.

Figure 8A:
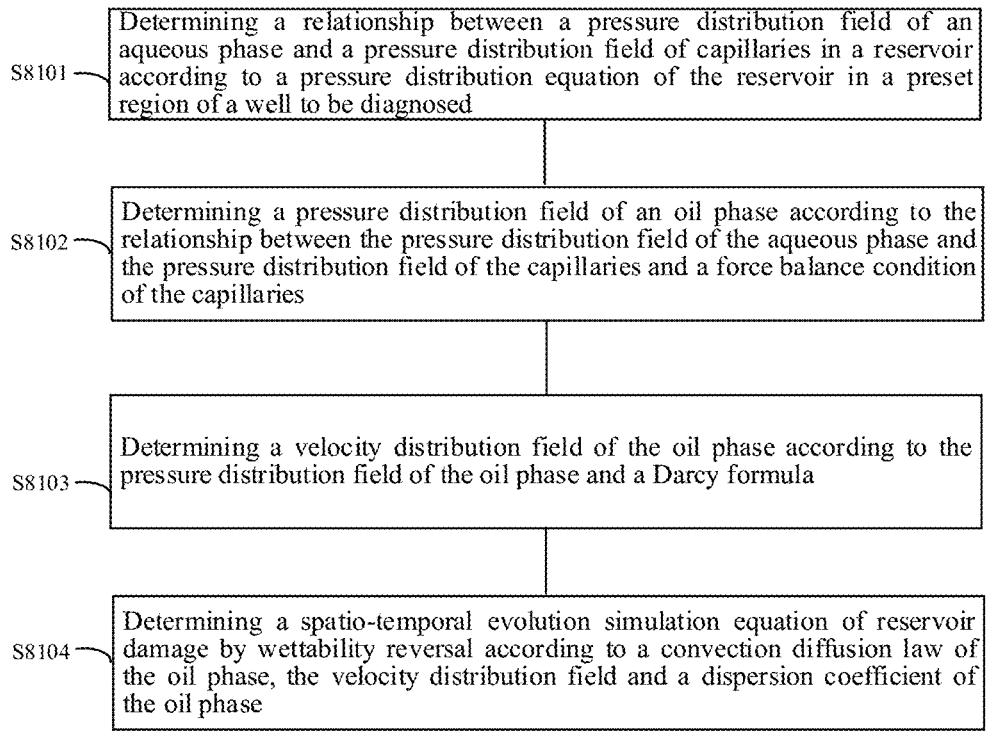
FIG. 8A is a flow diagram of a modeling method for reservoir damage by wettability reversal provided in an embodiment of the present invention.

FIG. 8A is a flow diagram of a modeling method for reservoir damage by wettability reversal provided in an embodiment of the present invention. As shown in FIG. 8A, the modeling method may include steps S8101-S8104.

Step S8101: determining a relationship between a pressure distribution field of an aqueous phase and a pressure distribution field of capillaries in a reservoir according to a pressure distribution equation of the reservoir in a preset region of a well to be diagnosed.

Wherein the capillaries are formed by the wettability reversal of a contact surface between the aqueous phase and an oil phase in the reservoir.

Usually, a pressure field of a liquid (mixture of an oil phase and an aqueous phase) is used to describe a pressure distribution field of the reservoir as a whole, but in the embodiment, the oil phase is separated from the aqueous phase, and pressure distribution of the reservoir is considered by using pressure distribution of the oil phase and pressure distribution of the aqueous phase, respectively, so that the pressure distribution of the reservoir can be simulated more closely to the actual situation in the reservoir, and thus a spatio-temporal evolution simulation equation of reservoir damage by wettability reversal can be simulated more precisely (i.e., a very precise reservoir permeability result is obtained) by means of the pressure distribution field of the oil phase.

For the step S8101, the relationship between the pressure distribution field $P_w(\vec{r}, t)$ of the aqueous phase and the pressure distribution field $P_c(\vec{r}, t)$ of the capillaries in the reservoir is determined according to the pressure distribution equation of the reservoir in the preset region of the well to be diagnosed expressed in the following formula (8-1):

$$\phi c_t \left( \frac{\partial P_w(\vec{r}, t)}{\partial t} \right) = \nabla \cdot \left[ \frac{kk_{rw}}{\mu_w} \nabla \cdot P_w(\vec{r}, t) \right] + \nabla \cdot \left[ \frac{kk_{ro}}{\mu_o} \nabla \cdot P_w(\vec{r}, t) \right] - \nabla \cdot \left[ \frac{kk_{ro}}{\mu_o} \nabla \cdot P_c(\vec{r}, t) \right], \quad (8\text{-}1)$$

where $\phi$ is porosity (a constant) of the reservoir; $c_t$ is an integrated compression coefficient (a constant) of the reservoir; $k$, $k_{rw}$ and $k_{ro}$ are permeability of the reservoir, relative permeability of the oil phase and relative permeability of the aqueous phase of the reservoir; and $\mu_w$ and $\mu_o$ are the viscosity of the aqueous phase and the viscosity of the oil phase of the reservoir.

Step S8102: determining a pressure distribution field of the oil phase according to the relationship between the pressure distribution field of the aqueous phase and the pressure distribution field of the capillaries and a force balance condition of the capillaries.

The force balance condition of the capillaries may be a three-force balance condition expressed by the following formula (8-2), $$P_c(\vec{r}, t) = P_o(\vec{r}, t) - P_w(\vec{r}, t), \quad (8\text{-}2)$$

where $P_c(\vec{r}, t)$ is a pressure of the capillaries and $P_c(\vec{r}, t)$ is determined by an effective water saturation in the capillaries; $P_o(\vec{r}, t)$ is the pressure distribution field of the oil phase; and $P_w(\vec{r}, t)$ is the pressure distribution field of the aqueous phase.

Determining $P_c(\vec{r}, t)$ by an effective water saturation in the capillaries may include: determining $P_c(\vec{r}, t)$ according to the effective water saturation and the following formula (8-3):

$$P_c(\vec{r}, t) = P_{ce}(S_w^*(\vec{r}, t))^{-\frac{1}{m}}, \qquad (8\text{-}3)$$

where $S^*_w$ is the effective water saturation in the capillaries; m is a Corey constant; and $P_{ce}$ is a pressure threshold of the capillaries.

Specifically, the effective water saturation $S^*_w$ may be determined by: determining, according to a saturation of the oil phase and a saturation of the aqueous phase, the effective water saturation expressed by the following formula (8-4):

$$S^*_w(\vec{r}, t) = [(S_w(\vec{r}, t) - S_{wir})/(1 - S_o(\vec{r}, t) - S_{wir})], \qquad (8\text{-}4)$$

wherein $S_o(\vec{r}, t)$ is the saturation of the oil phase; $S_w(\vec{r}, t)$ is the saturation of the aqueous phase, and $S_o(\vec{r}, t) + S_w(\vec{r}, t) = 1$; and $S_{wir}$ is an irreducible water saturation in the capillaries.

In other words, the pressure distribution field $P_o(\vec{r}, t)$ of the oil phase can be obtained according to the above formulas (8-1)-(8-4).

Step S8103: determining a velocity distribution field of the oil phase according to the pressure distribution field of the oil phase and a Darcy formula.

Specifically, the velocity distribution field of the oil phase can be determined by substituting the pressure distribution field $P_o(\vec{r}, t)$ of the oil phase into the Darcy formula expressed by the following formula (8-5):

$$u_o(\vec{r}, t) = -\frac{K(\vec{r}, t)}{\mu_0} \nabla P_o(\vec{r}, t), \qquad (8\text{-}5)$$

where $\mu_o$ is viscosity of the oil phase; and $K(\vec{r}, t)$ is permeability of the reservoir.

Step S8104: determining a spatio-temporal evolution simulation equation of reservoir damage by wettability reversal according to a convection diffusion law of the oil phase, the velocity distribution field and a dispersion coefficient of the oil phase.

Wherein the spatio-temporal evolution simulation equation is used to simulate a four-dimensional spatio-temporal evolution process of characteristics of reservoir damage caused by wettability reversal.

For the step S8104, the determining a spatio-temporal evolution simulation equation of reservoir damage by wettability reversal may include: determining, according to the convection diffusion law of the oil phase, the velocity distribution field $u_o(\vec{r}, t)$ and the dispersion coefficient $D_o$ of the oil phase, the spatio-temporal evolution simulation equation of reservoir damage by the wettability reversal expressed by the following formula:

$$\phi(\vec{r}, t) \frac{\partial S_o(\vec{r}, t)}{\partial t} = \nabla \cdot (D_o \nabla S_o(\vec{r}, t)) - \nabla \cdot (u_o(\vec{r}, t) S_o(\vec{r}, t)), \qquad (8\text{-}6)$$

where $\phi(\vec{r}, t)$ is the porosity of the reservoir; and $S_o(\vec{r}, t)$ is the saturation of the oil phase.

That is, the saturation $S_o(\vec{r}, t)$ of the oil phase (i.e., the spatio-temporal evolution simulation equation of reservoir damage by the wettability reversal) can be determined according to formulas (8-1)-(8-6).

In summary, according to the present invention, the relationship between the pressure distribution field of the aqueous phase and the pressure distribution field of the capillaries in the reservoir is creatively determined according to a pressure distribution equation of the reservoir in the preset region around the well to be diagnosed; then the pressure distribution field of the oil phase is determined according to the relationship between the pressure distribution field of the aqueous phase and the pressure distribution field of the capillaries and the force balance condition of the capillaries; subsequently the velocity distribution field of the oil phase is determined according to the pressure distribution field of the oil phase and the Darcy formula; and finally the spatio-temporal evolution simulation equation of reservoir damage by wettability reversal is determined according to the convection diffusion law of the oil phase, the velocity distribution field and the dispersion coefficient of the oil phase. Thus, by using the determined spatio-temporal evolution simulation equation, a four-dimensional spatio-temporal evolution process of characteristics of reservoir damage caused by wettability reversal can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Figure 8B:
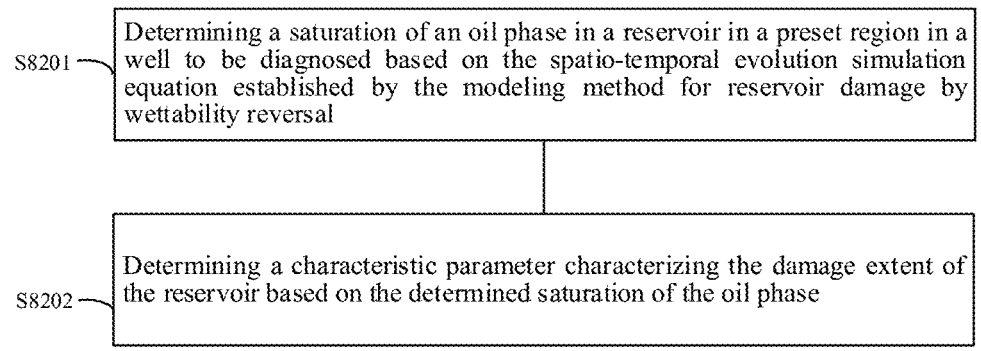
FIG. 8B is a flow diagram of a method for determining a damage extent of a reservoir provided in an embodiment of the present invention.

FIG. 8B is a flow diagram of a method for determining a damage extent of a reservoir provided in an embodiment of the present invention. As shown in FIG. 8B, the method may include steps S8201-S8202.

Step S8201: determining a saturation of an oil phase in a reservoir in a preset region of a well to be diagnosed based on the spatio-temporal evolution simulation equation established by the modeling method for reservoir damage by wettability reversal.

For the solution of the spatio-temporal evolution simulation equation of reservoir damage by wettability reversal expressed by the above formula (8-6), reference can be made to the process of solving the volume concentration of the deposited particles in the above Embodiment 1, so that the saturation $S_o(\vec{r}, t)$ of the oil phase can be calculated.

The saturation $S_o(\vec{r}, t)$ of the oil phase can be calculated by the above method. As the spatio-temporal evolution simulation equation established by the above modeling method for reservoir damage by wettability reversal comprehensively considers the influence of various physical and chemical factors on reservoir damage during wettability reversal, the saturation of the oil phase obtained by the step S8201 is very precise.

Step S8202: determining a characteristic parameter characterizing the damage extent of the reservoir based on the determined saturation of the oil phase.

For the step S8202, the characteristic parameter may be relative permeability of the oil phase. Correspondingly, the determining a characteristic parameter characterizing the damage extent of the reservoir may include: determining the relative permeability $K_{ro}(\vec{r}, t)$ of the oil phase based on the saturation $S_o(\vec{r}, t)$ of the oil phase and a relationship between the relative permeability and the saturation of the oil phase expressed by the following formula (8-7):

$$K_{ro}(\vec{r}, t) = \alpha_0 \alpha_1 S_o(\vec{r}, t) + \alpha_5 S_o^2(\vec{r}, t) + \alpha_3 S_o^3(\vec{r}, t) + \alpha_4 S_o^4(\vec{r}, t), \tag{8-7}$$

where $\alpha_1$, $\alpha_2$, $\alpha_3$, $\alpha_4$, $\alpha_5$ are constants, and $0 \leq K_{ro}(\vec{r}, t) \leq 1$.

Further, the permeability $K(\vec{r}, t)$ of the oil phase can be determined according to the relative permeability $K_{ro}(\vec{r}, t)$.

In an embodiment, the characteristic parameter may be a permeability damage rate of the reservoir.

Correspondingly, the determining a characteristic parameter characterizing the damage extent of the reservoir may include: calculating the permeability damage rate $I(\vec{r}, t)$ of the reservoir based on the permeability $K(\vec{r}, t)$ of the reservoir and formula (8-8), $$I(\vec{r}, t) = 1 - \frac{K(\vec{r}, t)}{K_{max}(\vec{r}, t)}, \tag{8-8}$$

where $K_{max}(\vec{r}, t)$ is a maximum value of $K(\vec{r}, t)$.

In another embodiment, the characteristic parameter may be a skin factor of the reservoir. Correspondingly, the determining a characteristic parameter characterizing the damage extent of the reservoir may include: calculating the skin factor $S(\vec{r}, t)$ of the reservoir based on the permeability $K(\vec{r}, t)$ of the reservoir and formula (8-9):

$$S(\vec{r}, t) = \left( \frac{1}{K_d(\vec{r}, t)} - 1 \right) \ln\left( \frac{r_{sw}}{r_w} \right), \tag{8-9}$$

where $K_o(\vec{r})$ is an initial value of the permeability of the reservoir; and $\overline{K_d(\vec{r}, t)} = K(\vec{r}, t)/(K_o(\vec{r})$, $r_w$ is a wellbore radius of the well to be diagnosed, and $r_{sw}$ is a damage radius of the reservoir.

Figure 8C:
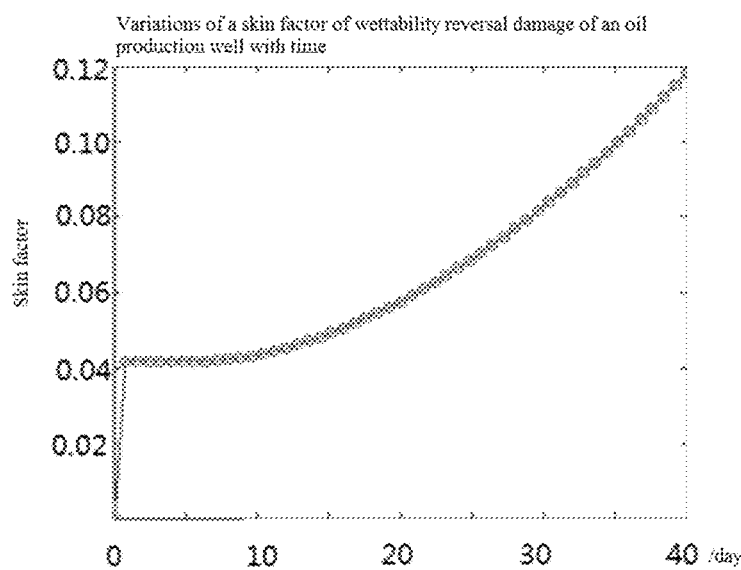
FIG. 8C is a schematic diagram of evolution of a skin factor over time provided in an embodiment of the present invention.
Figure 8D:
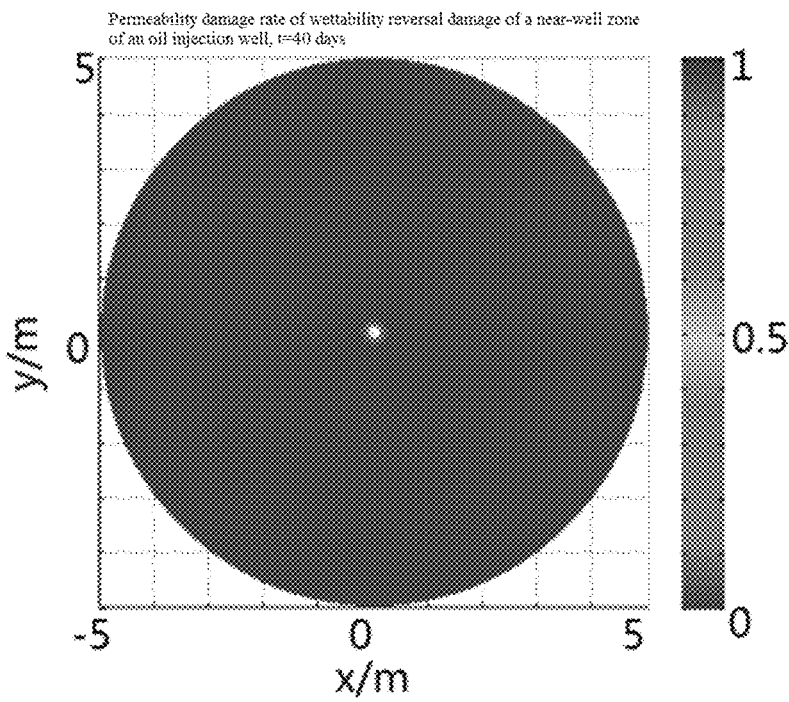
FIG. 8D is a flow diagram of a radius of reservoir damage by wettability reversal at day 365 characterized by a permeability damage rate of a reservoir provided in an embodiment of the present invention.

The characteristic parameter (e.g., the permeability $K(\vec{r}, t)$ and the skin factor $S(\vec{r}, t)$ of the reservoir) obtained by the step S8202 is a result of 4D quantitative simulation of spatio-temporal evolution (as shown in FIG. 8C). More specifically, FIG. 8D shows a schematic diagram of a radius (a radius as indicated by an arrow) of reservoir damage by wettability reversal at day 365 characterized by the permeability damage rate of the reservoir, and a working person concerned can visually confirm the damage extent of the reservoir from FIG. 8D. Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

In summary, according to the present invention, the saturation of the oil phase can be creatively calculated by using the determined spatio-temporal evolution simulation equation, then the characteristic parameter (e.g., the permeability and/or the skin factor of the reservoir) characterizing the damage extent of the reservoir in the preset region of the well to be diagnosed can be determined based on the determined saturation of the oil phase, and thus, a four-dimensional spatio-temporal evolution process of characteristics of reservoir damage caused by wettability reversal can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Embodiment 9—Emulsification

In a porous medium in a reservoir, a low interfacial tension and a high mechanical shear between an oil phase and an aqueous phase are main factors that cause emulsion formation. Therefore, a radius of emulsified droplets formed is determined based on the influence of a temperature field of the reservoir on the viscosity of the oil phase and an emulsification condition of a fluid; then, a spatio-temporal evolution control phenomenological model of a clogging probability is determined based on a pore size distribution function of the reservoir and the radius of the emulsified droplets; and subsequently, in conjunction with a relationship between the clogging probability and a characteristic parameter characterizing the damage extent of the reservoir such as permeability, spatio-temporal field distribution of the characteristic parameter such as permeability can be diagnosed.

Figure 9A:
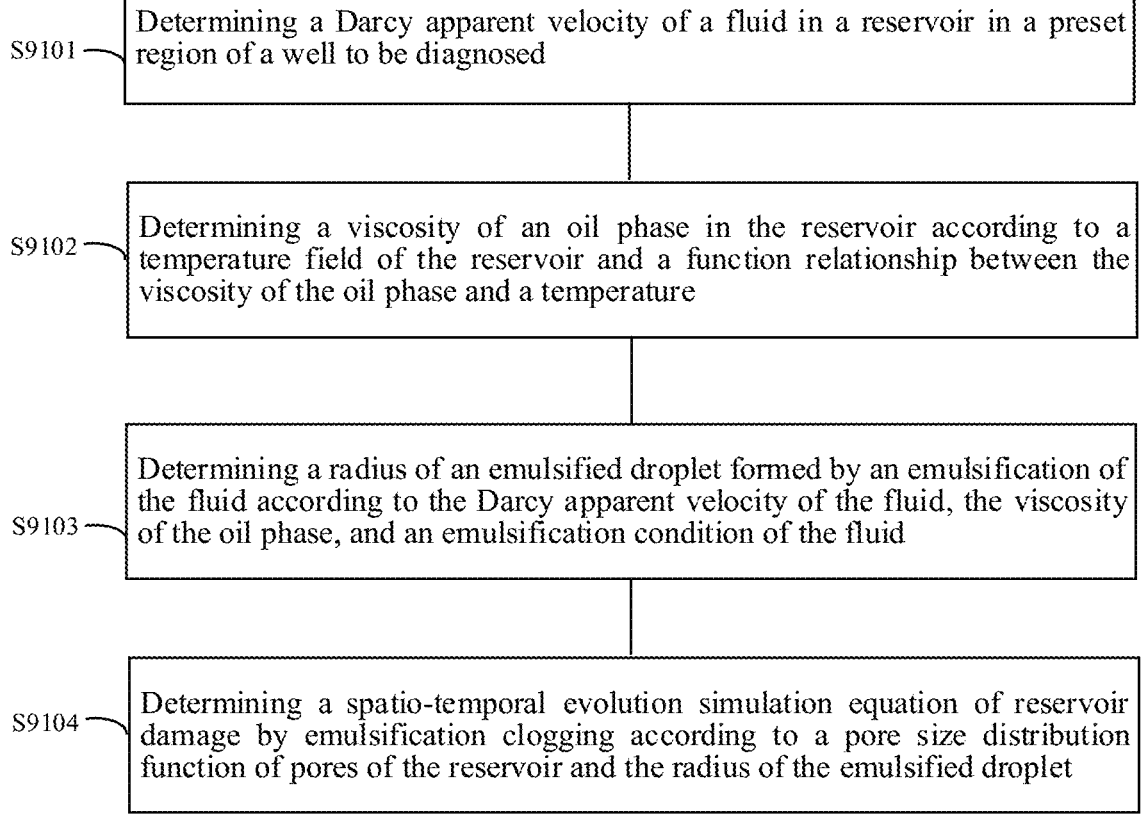
FIG. 9A is a flow diagram of a modeling method for reservoir damage by emulsification clogging provided in an embodiment of the present invention.

FIG. 9A is a flow diagram of a modeling method for reservoir damage by emulsification clogging provided in an embodiment of the present invention. The modeling method may include steps S9101-S9104.

Step S9101: determining a Darcy apparent velocity of a fluid in a reservoir in a preset region of a well to be diagnosed.

Wherein the well to be diagnosed may be, for example, an oil production well.

For the step S9101, determining the velocity of the fluid in the reservoir may include:

establishing a pressure conduction equation for the fluid entering the reservoir; and determining the Darcy apparent velocity of the fluid according to the pressure conduction equation and a Darcy formula.

For the specific determination process, reference can be made to the process of determining the Darcy apparent velocity in the above Embodiment 2 (i.e., the above formulas (2-1) and (2-2) and related description thereof).

Step S9102: determining a viscosity of an oil phase in the reservoir according to a temperature field of the reservoir and a function relationship between the viscosity of the oil phase and a temperature.

Before performing the step S9102, the modeling method may further include: determining the temperature field of the reservoir according to a thermal conductivity coefficient of the fluid, a thermal diffusion coefficient of the reservoir, an average flow velocity of an extraneous fluid, and a heat balance equation of the reservoir.

Specifically, the temperature field $T(\vec{r}, t)$ of the reservoir is determined according to the thermal conductivity coefficient $D_f$ of the fluid, the thermal diffusion coefficient $D_l$ of the reservoir, the average flow velocity $u_m$ of the extraneous fluid, and the heat balance equation of the reservoir expressed by the following formula (9-1):

$$\frac{\partial T(\vec{r}, t)}{\partial t} = (D_f + D_l) \nabla^2 T(\vec{r}, t) - u_m \nabla T(\vec{r}, t). \quad (9\text{-}1)$$

In conjunction with an initial condition and a boundary condition, temperature distribution (i.e., the temperature field) of the reservoir under different spatio-temporal conditions can be calculated by this formula (9-1). See the following description for details of the specific calculation procedure.

For the step S9102, the viscosity $\mu_0(\vec{r}, t)$ of the oil phase is determined according to the temperature field $T(\vec{r}, t)$ of the reservoir and the function relationship between the viscosity and the temperature of the oil phase expressed by the following formula (9-2):

$$\log[\log(\mu_0(\vec{r}, t)+1)] = a - b\gamma_{API} - c \log(T(\vec{r}, t)), \quad (9\text{-}2)$$

where $\gamma_{API}$ is a gravitational parameter of the oil phase; a and b are both constants; and $\vec{r}$ is a spatial location of any point in the reservoir. Viscosity distribution of the oil phase under different spatio-temporal conditions of the reservoir can be calculated according to formulas (9-1) and (9-2). Since the viscosity distribution of the oil phase is greatly influenced by the temperature distribution of the reservoir, a calculation result of the viscosity of the oil phase obtained by considering the temperature field of the reservoir is more accurate, and reservoir damage by the emulsification clogging can be simulated more precisely according to the viscosity of the oil phase.

Step S9103: determining a radius of an emulsified droplet formed by an emulsification of the fluid according to the Darcy apparent velocity of the fluid, the viscosity of the oil phase, and an emulsification condition of the fluid.

Wherein the emulsification condition of the fluid may be a critical condition expressed by the following formula (9-3):

$$\left(\frac{\mu_w}{K_w} - \frac{\mu_0(\vec{r}, t)}{K_o}\right) u(\vec{r}, t) + (\rho_w - \rho_o)g < 0, \quad (9\text{-}3)$$

wherein $\mu_w$ is viscosity of the aqueous phase in the fluid; $\mu_o$ is viscosity of the oil phase; $K_w$ is permeability of the aqueous phase; $K_o$ is permeability of the oil phase; $\rho_w$ is density of the aqueous phase; $\rho_o$ is density of the oil phase; g is a gravitational acceleration; $\mu_0(\vec{r}, t)$ is viscosity of the oil phase; $u(\vec{r}, t)$ is a Darcy apparent velocity of the fluid; and r is a spatial location of any point in the reservoir.

That is, if inequality (9-3) is satisfied, it indicates that oil-water emulsification occurs in the reservoir.

For the step S9103, the determining a radius of an emulsified droplet formed by an emulsification of the fluid may include: determining, according to the Darcy apparent velocity $u(\vec{r}, i\Delta t)$ of the fluid, $\mu_0(\vec{r}, i\Delta t)$ the viscosity of the oil phase, and the emulsification condition of the fluid, the radius of the emulsified droplet expressed by the following formula (9-4):

$$\lambda_o = (\vec{r}, i\Delta t) =$$

-continued $$\begin{cases} \left(\frac{9\pi\sigma\bar{\lambda}}{2\left(\frac{\phi\mu_o(\vec{r}, i\Delta t)}{K}u(\vec{r}, i\Delta t) + \rho g\right)}\right)^{\frac{1}{3}}, & \text{if } \left(\frac{9\pi\sigma\bar{\lambda}}{2\left(\frac{\phi\mu_o(\vec{r}, i\Delta t)}{K}u(\vec{r}, i\Delta t) + \rho g\right)}\right)^{\frac{1}{3}} < \bar{\lambda} \\ 0, & \text{if } \left(\frac{9\pi\sigma\bar{\lambda}}{2\left(\frac{\phi\mu_o(\vec{r}, i\Delta t)}{K}u(\vec{r}, i\Delta t) + \rho g\right)}\right)^{\frac{1}{3}} \geq \bar{\lambda} \end{cases}$$

(9-4) where $\sigma$ is an oil-water interfacial tension; $\bar{\lambda}$ is an average value of pore sizes of the reservoir; $\phi$ is porosity of the reservoir; K is permeability of the reservoir; $\rho$ is the density of the oil phase; and $i\Delta t$ is an ith time increment, i being a non-negative integer.

Step S9104: determining a spatio-temporal evolution simulation equation of reservoir damage by emulsification clogging according to a pore size distribution function of pores of the reservoir and the radius of the emulsified droplet.

Wherein the spatio-temporal evolution simulation equation is used to simulate a four-dimensional spatio-temporal evolution process of reservoir damage characteristics caused by the emulsification clogging.

For the step S9104, the determining a spatio-temporal evolution simulation equation of reservoir damage by emulsification clogging may include: determining, according to the pore size distribution function $N(\lambda, \mu_s, \sigma_s)$ of the pores of the reservoir and the radius $\lambda_o(\vec{r}, i\Delta t)$ of the emulsified droplet, the spatio-temporal evolution simulation equation of reservoir damage by emulsification clogging expressed by the following formula (9-5):

$$\beta(\lambda_o(\vec{r}, i\Delta t)) = \int_0^{\lambda_o(\vec{r}, i\Delta t)} N(\lambda, \mu_s, \sigma_s) dr,$$

(9-5) where $\beta(\lambda_o(\vec{r}, i\Delta t))$ is a clogging probability of the reservoir; $\mu_s$ and $\sigma_s$ are a first pore size distribution characteristic parameter and a second pore size distribution characteristic parameter, respectively; $i\Delta t$ is the ith time increment, i being a non-negative integer; and $\vec{r}$ is a spatial location of any point in the reservoir.

In an embodiment, the pore size distribution function $N(\lambda)$ of the pores in the reservoir may be approximated as a log-normal function expressed by the following formula (9-6):

$$N(\lambda, \mu_s, \sigma_s) = \frac{1}{\sigma_s \sqrt{2\pi}} \exp\left[-\frac{(\ln\lambda - \mu_s)^2}{2\sigma_s^2}\right].$$

$\mu_s$ and $\sigma_s$ in the above formula can be calculated by the following process: a pore size average value and standard deviation can be calculated as $$E(\lambda) = e^{\mu_s + \frac{\sigma_s^2}{2}}$$

(i.e., $\bar{\lambda}$) and $$SD(\lambda) = e^{\mu_s + \frac{\sigma_s^2}{2}} \sqrt{e^{\sigma_s^2} - 1} = E(\lambda)\sqrt{e^{\sigma_s^2} - 1}$$

according to field data, and then expressions of $\mu_s$ and $\sigma_s$ shown in the following formula (9-7) can be obtained according to the pore size average value and standard deviation:

$$\mu_s = \ln\left[\frac{\bar{\lambda}}{\sqrt{1 + (SD(\lambda)/\bar{\lambda})^2}}\right], \sigma_s = \sqrt{\ln\left[1 + \left(\frac{SD(\lambda)}{\bar{\lambda}}\right)^2\right]}. \quad (9\text{-}7)$$

Since the pore size average value and standard deviation are known quantities, the corresponding $\mu_s$ and $\sigma_s$, can be obtained, and then $\mu_s$ and $\sigma_s$ are substituted into the above formula (9-6) to obtain a specific form of the pore size distribution function.

For an emulsified droplet with a radius $\lambda_o$, only part of the pores smaller than $\lambda_o$ in the distribution function is clogged by the emulsified droplet, so the clogging probability β (i.e., the cumulative distribution from 0 to $\lambda_o$) in the above formula (9-5) can be specifically expressed as the following formula (9-8):

$$\beta(\lambda_o(\vec{r}, i\Delta t)) = \int_0^{\lambda_o(\vec{r}, i\Delta t)} N(\lambda, \mu_s, \sigma_s) dr = \frac{1}{2}\text{erfc}\left(-\frac{\ln\lambda_o(\vec{r}, i\Delta t) - \mu_s}{\sigma_s\sqrt{2}}\right), \quad (9\text{-}8)$$

where erfc( ) is a complementary error function:

$$\text{erfc}(x) = \frac{2}{\sqrt{\pi}} \int_x^\infty e^{z^2} dz.$$

In summary, according to the present invention, the Darcy apparent velocity of the fluid in the reservoir in the preset region of the well to be diagnosed is creatively determined; the viscosity of the oil phase in the reservoir is determined according to the temperature field of the reservoir and the function relationship between the viscosity of the oil phase and the temperature; the radius of the emulsified droplet formed by an emulsification of the fluid is determined according to the emulsification condition of the fluid; and the spatio-temporal evolution simulation equation of reservoir damage by emulsification clogging is determined according to the pore size distribution function of the pores of the reservoir and the radius of the emulsified droplet. Thus, by using the determined spatio-temporal evolution simulation equation, a four-dimensional spatio-temporal evolution process of characteristics of reservoir damage caused by emulsification clogging can be quantitatively simulated. Therefore performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Figure 9B:
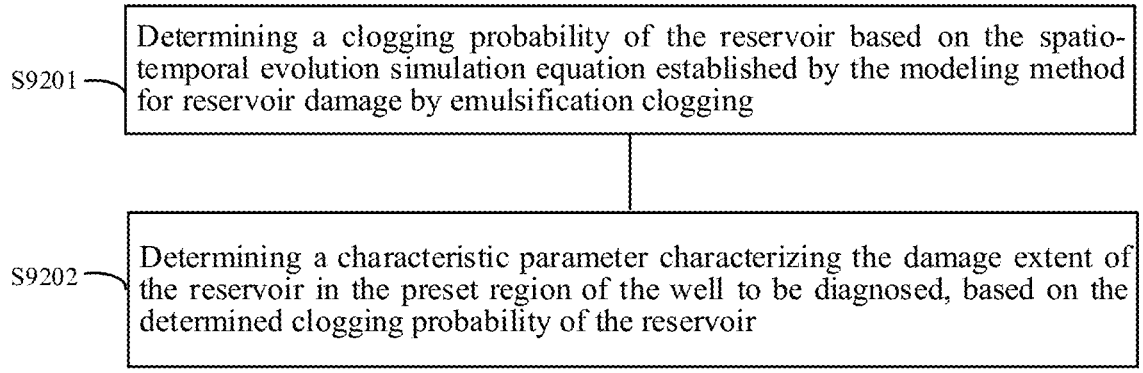
FIG. 9B is a flow diagram of a method for determining a damage extent of a reservoir provided in an embodiment of the present invention.

FIG. 9B is a flow diagram of a method for determining a damage extent of a reservoir provided in an embodiment of the present invention. As shown in FIG. 9B, the method for determining a damage extent of a reservoir may include steps S9201-S9202.

Step S9201: determining a clogging probability of the reservoir based on the spatio-temporal evolution simulation equation established by the modeling method for reservoir damage by emulsification clogging.

For the solution of the spatio-temporal evolution simulation equation for reservoir damage by emulsification clogging expressed by the above formula (9-8), $T(\vec{r}, t)$ needs to be calculated according to formula (9-1). For the specific solving process, reference can be made to the solving process of the volume concentration of the deposited particles in the above Embodiment 1, which will not be described here.

After the temperature field $T(\vec{r}, t)$ of the reservoir is calculated by the above method, the clogging probability of the reservoir can be calculated according to the above formulas (9-2), (9-4) and (9-8), and thus the spatio-temporal evolution simulation equation established by the above modeling method for reservoir damage by emulsification clogging comprehensively considers the influence of various physical and chemical factors on reservoir damage during emulsification clogging, so the clogging probability of the reservoir obtained by the step S9201 is very precise.

Step S9202: determining a characteristic parameter characterizing the damage extent of the reservoir in a preset region of a well to be diagnosed, based on the determined clogging probability of the reservoir.

Wherein the characteristic parameter may be permeability of the reservoir.

For the step S9202, the determining a characteristic parameter characterizing the damage extent of the reservoir in a preset region of a well to be diagnosed may include: determining the permeability $K_d(\vec{r}, t)$ of the reservoir based on the determined clogging probability $\beta(\lambda_o(\vec{r}, i\Delta t))$ of the reservoir and the following formula (9-9):

$$K_d\left(\vec{r}, t = n\Delta t\right) = \left(1 - \frac{\sum_{i=0}^{n} \beta(\lambda_o(\vec{r}, i\Delta t))\lambda_o(\vec{r}, i\Delta t)}{\mu_s}\right)^{m_K}, \quad (9\text{-}9)$$

where $\mu_s$ is a first pore size distribution characteristic parameter; $\lambda_o(\vec{r}, i\Delta t)$ is a radius of an emulsified droplet; $m_K$ is a second empirical value; and n is a total number of time increments $\Delta t$.

Wherein the characteristic parameter may be a skin factor of the reservoir.

For the step S9202, the determining a characteristic parameter characterizing the damage extent of the reservoir in a preset region of a well to be diagnosed may include: determining the permeability $K_d(\vec{r}, t)$ of the reservoir based on the determined clogging probability) $\beta(\lambda_o(\vec{r}, i\Delta t))$ of the reservoir and the following formula:

$$K_d\left(\vec{r}, t = n\Delta t\right) = \left(1 - \frac{\sum_{i=0}^{n} \beta(\lambda_o(\vec{r}, i\Delta t))\lambda_o(\vec{r}, i\Delta t)}{\mu_s}\right)^{m_k};$$

and determining the skin factor $S(\vec{r}, t)$ of the reservoir based on the permeability $K_d(\vec{r}, t)$ of the reservoir and formula (9-10):

$$S(\vec{r}, t) = \left(\frac{1}{K_d(\vec{r}, t)} - 1\right) \ln\left(\frac{r_{sw}}{r_w}\right), \qquad (9\text{-}10)$$

where $\mu_s$ is the first pore size distribution characteristic parameter; $\lambda_o(\vec{r}, i\Delta t)$ is the radius of the emulsified droplet; $m_K$ is the second empirical value; n is the total number of time increments $\Delta t$; $r_w$ is a wellbore radius of the well to be diagnosed, and $r_{sw}$ is a damage radius of the reservoir.

Figure 9C:
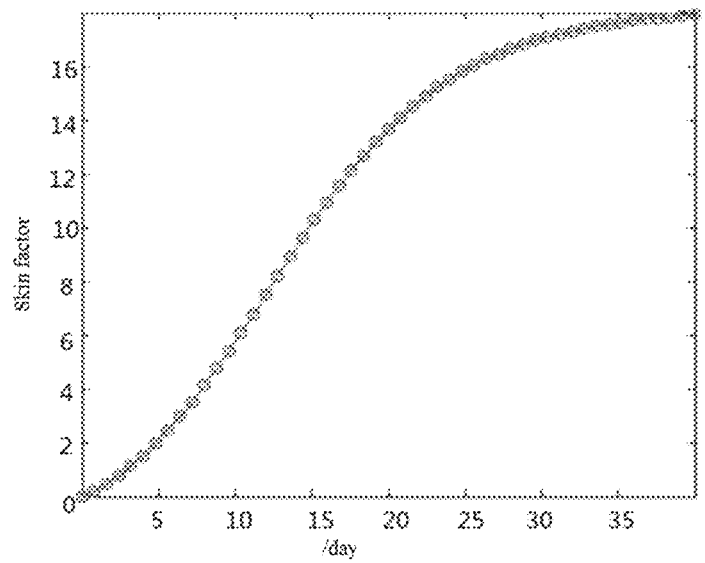
FIG. 9C is a schematic diagram of evolution of a skin factor over time provided in an embodiment of the present invention.
Figure 9D:
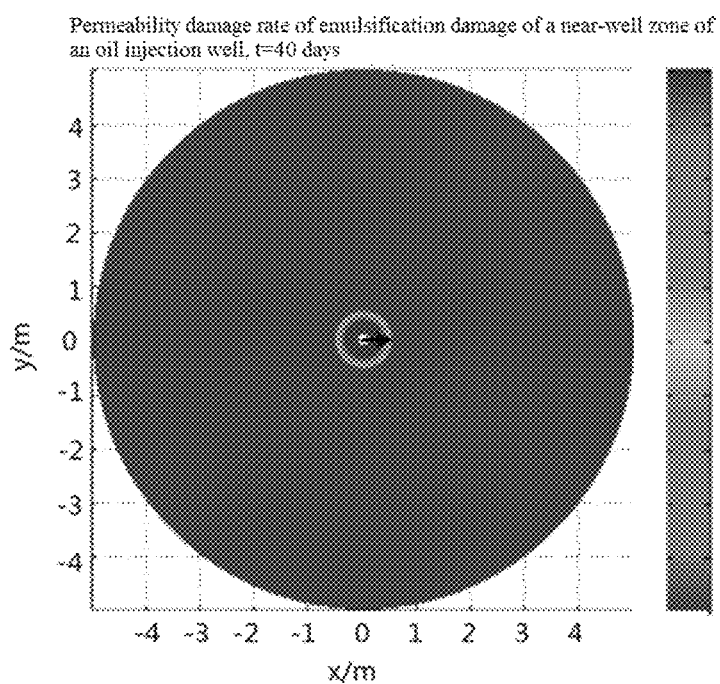
FIG. 9D is a flow diagram of a radius of reservoir damage by emulsification clogging at day 40 characterized by a permeability damage rate of a reservoir provided in an embodiment of the present invention.

The characteristic parameter (e.g., the permeability $K_d(\vec{r}, t)$ and the skin factor $S(\vec{r}, t)$ of the reservoir) obtained by the step S9202 is a result of 4D quantitative simulation of spatio-temporal evolution (as shown in FIG. 9C). More specifically, FIG. 9D shows a schematic diagram of a radius (a radius as indicated by an arrow) of reservoir damage by emulsification clogging at day 40 characterized by a permeability damage rate of the reservoir (the permeability damage rate $I(r_i, t)$ of the reservoir is determined based on the permeability $K(\vec{r}, t)$ of the reservoir and formula $$I(\vec{r}, t) = 1 - \frac{K(\vec{r}, t)}{\lambda_{max}(\vec{r}, t)},$$

where $K_{max}(\vec{r}, t)$ is a maximum value of $K(\vec{r}, t)$), and a working person concerned can visually confirm the damage extent of the reservoir from FIG. 9D. Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

In summary, according to the present invention, the clogging probability of the reservoir can be creatively calculated by using the determined spatio-temporal evolution simulation equation, then the characteristic parameter (e.g., the permeability and/or the skin factor of the reservoir) characterizing the damage extent of the reservoir in the preset region of the well to be diagnosed can be determined based on the determined clogging probability, and thus, a four-dimensional spatio-temporal evolution process of characteristics of reservoir damage caused by emulsification clogging can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Embodiment 10—Organic Scale

During oilfield development, a pressure equilibrium state in an oil reservoir is destroyed, resulting in overflow of some light components and precipitation of some heavy components in crude oil, and the precipitation forms organic scale, which clogs oil gas flow channels to cause serious damage to the reservoir. Generally speaking, the organic scale such as asphaltene is partially dissolved and partially suspended as a colloid in the crude oil, and the colloidal precipitation of the organic scale such as asphaltene is related to its dissolving capacity. Thus, the core of the embodiments of the present invention is to establish a kinetic model of variations of the dissolving capacity of the organic scale with a reservoir pressure. Specifically, based on the influence of the pressure on the dissolving capacity of the organic scale, and the like, a spatio-temporal evolution control phenomenological model of organic scale particle distribution in a reservoir around a well to be diagnosed influenced by the organic scale is established, and in conjunction with a relationship between organic scale particle distribution and both the porosity of the reservoir and a characteristic parameter characterizing the damage extent of the reservoir (such as permeability), spatio-temporal field distribution of the characteristic parameter such as permeability can be diagnosed.

Figure 10A:
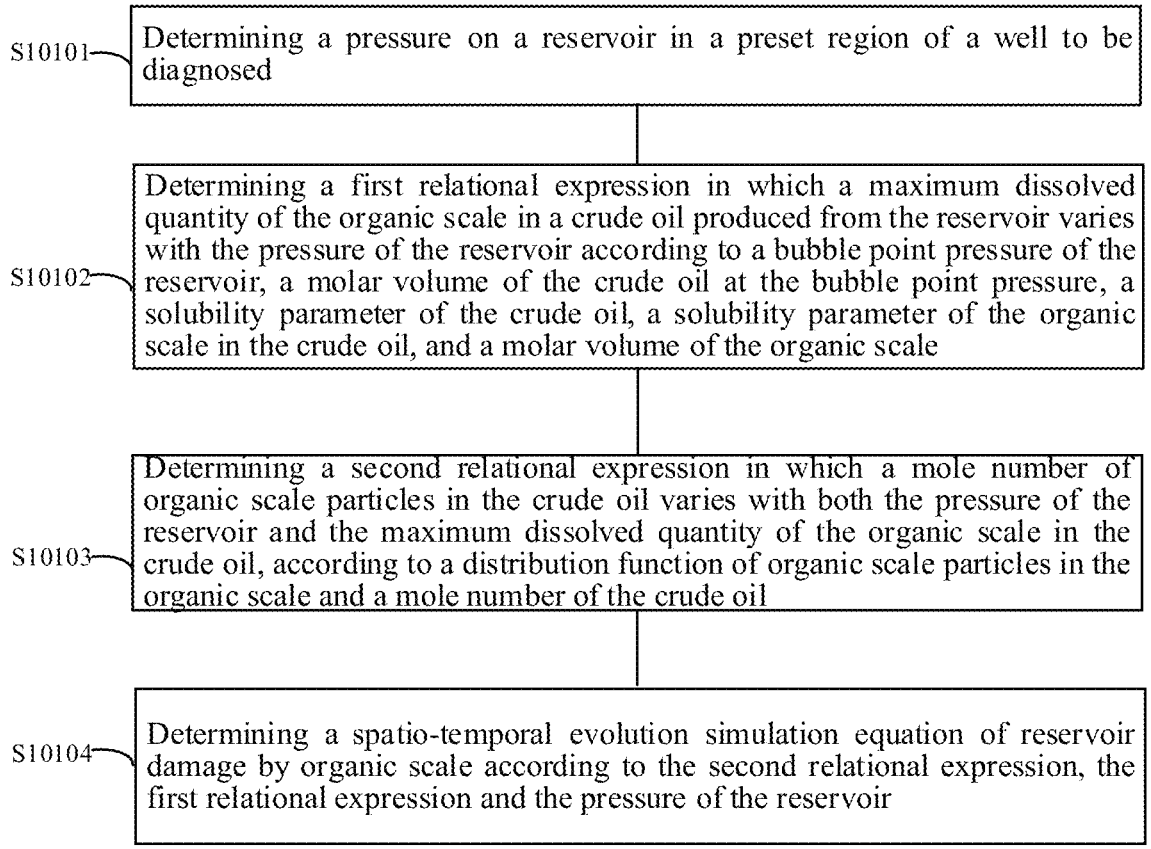
FIG. 10A is a flow diagram of a modeling method for reservoir damage by organic scale provided in an embodiment of the present invention.

FIG. 10A is a flow diagram of a modeling method for reservoir damage by organic scale provided in an embodiment of the present invention. As shown in FIG. 10A, the modeling method includes the following steps S10101-S10104.

Step S10101: determining a pressure of a reservoir in a preset region of a well to be diagnosed.

Figure 10B:
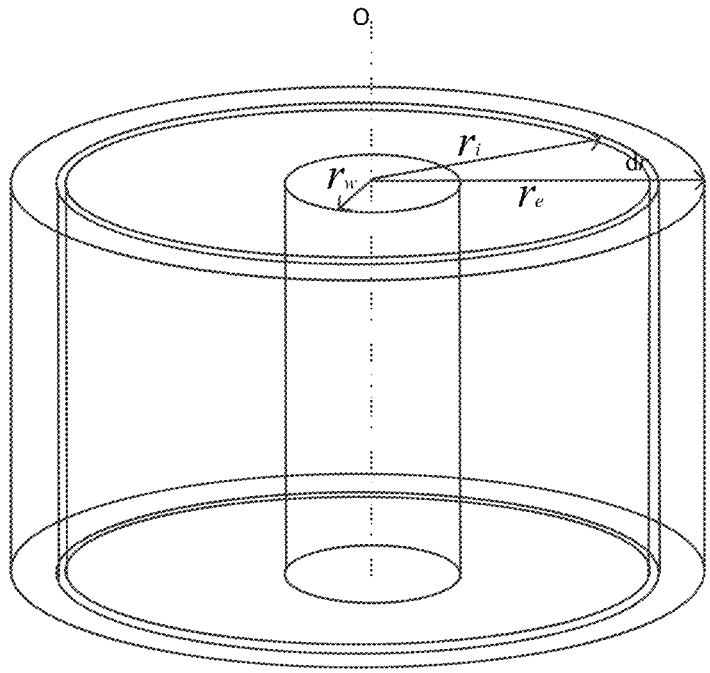
FIG. 10B is a flow diagram of a reservoir modeling provided in an embodiment of the present invention.

First, a cylindrical model of the reservoir (or an oil pool) as shown in FIG. 10B can be established i.e., with a central axis O of the well to be diagnosed (e.g., an oil production well) as a reference central axis, the reservoir is divided into a plurality of cylindrical shells, and a thickness of each cylindrical shell is a preset thickness dr (e.g., a value of the thickness is very small).

Due to flow symmetry of a fluid, the pressure inside each cylindrical shell has equal magnitude (e.g., the pressure inside an ith cylindrical shell is $P(r_i)$). According to a continuity equation of the pressure of the reservoir expressed by the following formula (10-1), an inner boundary condition $P(r_w) = P_w$, (i.e., a horizontal distance from a wall of the well to be diagnosed to the reference central axis is $r_w$, and the pressure at the wall of the well to be diagnosed is $P_w$) and an outer boundary condition $P(r_e) = P_e$ (i.e., a horizontal distance from the cylindrical shell where the outermost part of the reservoir is located to the reference central axis is $r_e$, and the pressure at the cylindrical shell where the outermost part of the reservoir is located is $P_e$), expression (10-2) of $P(r_i)$ can be obtained, $$\frac{d^2 P(r_i, t)}{dr_i^2} + \frac{dP(r_i, t)}{r_i} = 0, \qquad (10\text{-}1)$$

$$P(r_i, t) = P_e - \frac{P_e - P_w}{\ln\frac{r_e}{r_w}} \ln\frac{r_e}{r_i}. \qquad (10\text{-}2)$$

In conjunction with the above formula (10-2) and a Dupuit formula expressed in the following formula (10-3), a reservoir pressure $P(r_i, t)$ at the ith cylindrical shell expressed by the following (10-4) can be obtained:

$$Q_0 = \frac{P_e - P_w}{\frac{\mu}{2\pi KH} \ln\frac{r_e}{r_w}}, \qquad (10\text{-}3)$$

where $Q_o(t)$ is crude oil production of the well to be diagnosed; K is permeability of the reservoir; H is the thickness of the reservoir; and μ is viscosity of the fluid within the reservoir.

For the step S10101, the determining a pressure of a reservoir in a preset region of a well to be diagnosed may include: in the case where the reservoir is divided into a plurality of cylindrical shells with a central axis of the well to be diagnosed as a reference central axis and having a preset thickness, determining, according to the continuity equation of the pressure of the reservoir and the Dupuit formula, the pressure $P(r_i)$ of the reservoir expressed by the following formula (10-4):

$$P(r_i, t) = P(r_e) - \frac{Q_o(t)\mu}{2\pi KH} \ln\left(\frac{r_e}{r_i}\right), \qquad (10\text{-}4)$$

where $r_i$ is an average horizontal distance from the ith cylindrical shell of the plurality of cylindrical shells to the reference central axis; $r_e$ is an oil pool radius of the reservoir; $Q_o(t)$ is the crude oil production of the well to be diagnosed; K is permeability of the reservoir; H is the thickness of the reservoir; and μ is the viscosity of the fluid within the reservoir.

Step S10102: determining a first relational expression in which a maximum dissolved quantity of the organic scale in a crude oil produced from the reservoir varies with the pressure of the reservoir according to a bubble point pressure of the reservoir, a molar volume of the crude oil at the bubble point pressure, a solubility parameter of the crude oil, a solubility parameter of the organic scale in the crude oil, and a molar volume of the organic scale.

Wherein the solubility parameter of the crude oil is acquired by: determining solubility parameters of a plurality of preset components according to boiling point temperatures, critical temperatures and molar volumes of the plurality of preset components and the temperature of the reservoir, wherein the plurality of preset components are asphaltenes (e.g. C7, C8, and other C7+ asphaltenes) with a plurality of preset carbon contents; and determining the solubility parameter of the crude oil according to the solubility parameters and volume fractions of the plurality of preset components in the crude oil.

Specifically, the behavior of cohesive energy of crude oil molecules per unit volume (i.e., the solubility parameter $S_L$ of the crude oil) is the most complex, and the solubility parameters $\delta_i(P)$ of the components (e.g., asphaltenes with a plurality of preset carbon contents (e.g., C7, C8, and other C7+ asphaltenes)) need to be solved separately first. For the component i, $$\delta_i(P) = \left(\frac{\Delta H'_{i|T} - R \cdot T}{V_i(P)}\right)^{0.5}, \text{ wherein} \qquad (10\text{-}5)$$

$$\Delta H'_{i|T} = \Delta H'_{i|T_{bi}} \times \left(\frac{T_{ci} - T}{T_{ci} - T_{bi}}\right)^{0.38},$$

$$\Delta H'_{i|T_{bi}} = 1.014 \times T_{bi} \times (8.75 + 4.571 \ln(T_{bi})),$$

where $T_{ci}$ and $T_{bi}$ are a critical temperature and a boiling point temperature of the component i, respectively; $V_i$ is a molar volume of the component i ($V_i(P) = x_i V(P)$, where $x_i$ is a molar fraction of the component i; V(P) can be calculated from $$P = \frac{RT}{Vb} - \frac{a}{V(V+b) + b(V-b)},$$

where a and b are a first empirical coefficient and a second empirical coefficient, respectively); T is the temperature of the reservoir; and R is a gas constant.

Then, in conjunction with the above formula (10-5) and by using $\delta_L = \Sigma_i^n \phi_i \delta_i(P)$, $\delta_L$ is calculated, where $\phi_i$ is the volume fraction (which can be obtained from analytical data of oil physical properties) of the component i; and n is the number of the components.

Figure 10C:
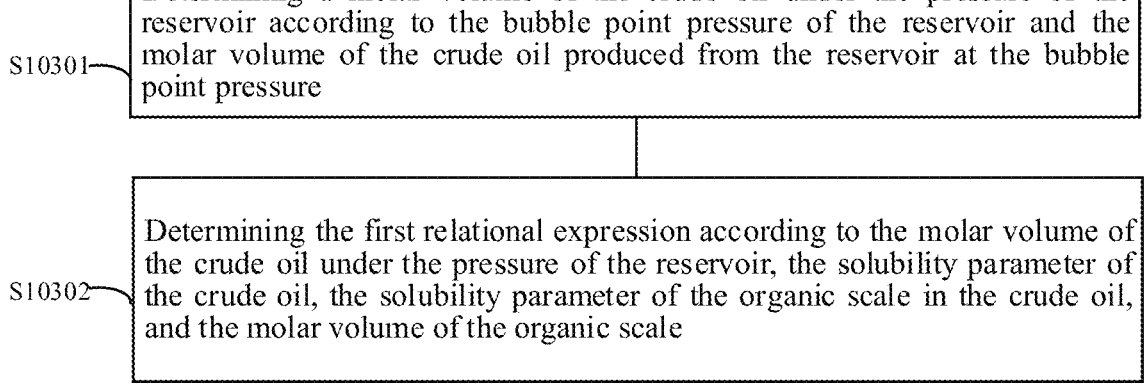
FIG. 10C is a flow diagram of determining a relational expression in which a maximum dissolved quantity of organic scale varies with a pressure provided in an embodiment of the present invention.

For the step S10102, the determining a first relational expression in which a maximum dissolved quantity of the organic scale in a crude oil produced from the reservoir varies with the pressure of the reservoir includes the following steps S10301-S10302, as shown in FIG. 10C.

Step S10301: determining a molar volume of the crude oil under the pressure of the reservoir according to the bubble point pressure of the reservoir and the molar volume of the crude oil produced from the reservoir at the bubble point pressure.

For the step S10301, the determining a molar volume of the crude oil under the pressure of the reservoir may include: determining, according to the bubble point pressure $P_b$ of the reservoir and the molar volume $V_{Lb}$ of the crude oil produced from the reservoir at the bubble point pressure, the molar volume $V_L(P(r_i, t))$ of the crude oil under the pressure $P(r_i, t)$ of the reservoir expressed by the following formula (10-6):

$$\begin{cases} V_L(P(r_i,t)) = V_{Lb} e^{-C_f(P(r_i,t)-P_b)}, & \text{if } P(r_i,t) \geq P_b \\ V_L(P(r_i,t)) = \dfrac{V_{Lb}\left[-\dfrac{P_b - P(r_i,t)}{P_b}\right]}{\left(1 - \dfrac{1}{B_o}\right) + e^{C_f(P_b - P(r_i,t))}}, & \text{if } P(r_i,t) < P_b \end{cases} \qquad (10\text{-}6)$$

where $C_f$ is a compression coefficient (e.g., (10~440)×10$^{-4}$ MPa$^{-1}$) of the crude oil; and $B_o$ is a compression coefficient (usually 1.0-1.2) of the crude oil.

When the pressure P is higher than the bubble point pressure, a pure compression process occurs, and the volume decreases as the pressure increases; and when the pressure P is lower than the bubble point pressure, on the one hand, the volume increases as the pressure decreases, and on the other hand, the crude oil decomposes into a gas phase and the volume decreases, forming an extreme value at a certain pressure point.

Step S10302: determining the first relational expression according to the molar volume of the crude oil under the pressure of the reservoir, the solubility parameter of the crude oil, the solubility parameter of the organic scale in the crude oil, and the molar volume of the organic scale.

For the step S10302, the determining the first relational expression may include: determining, according to the molar volume $V_L(P(r_i, t))$ of the crude oil under the pressure of the reservoir, the solubility parameter $\delta_L(P(r_i, t))$ of the crude oil, the solubility parameter $\delta_a$ of the organic scale in the crude oil, and the molar volume $V_a$ of the organic scale, the first relational expression expressed by the following formula (10-7):

$$(\phi_a)_{max}(P(r_i, t)) = \exp \qquad (10\text{-}7)$$

-continued $$\left\{\frac{V_a}{V_L(P(r_i,t))}\left[1-\frac{V_L(P(r_i,t))}{V_a}-\frac{V_L(P(r_i,t))}{RT}(\delta_a-\delta_L(P(r_i,t)))^2\right]\right\},$$

where exp{ } is an exponential function with a natural constant e as its base, T is the temperature of the reservoir; R is the gas constant; and $(\phi_a)_{max}$ may be in %. In an embodiment, the value of the parameter may be calculated by: $\delta_a = 9.99 \times (1 - 5.94 \times 10^{-4} T)$.

Step S10103: determining a second relational expression in which a mole number of organic scale particles in the crude oil varies with both the pressure of the reservoir and the maximum dissolved quantity of the organic scale in the crude oil, according to a distribution function of organic scale particles in the organic scale and a mole number of the crude oil.

Wherein the distribution function is a proportional function of a mole number of organic scale particles with a particle size greater than a preset particle size to a total mole number of the organic scale particles.

For the step S10103, determining the second relational expression may include:

determining, according to the distribution function $f_{trap}(R_p)$ of organic scale particles in the organic scale and the mole number $\eta_o$ of the crude oil, the second relational expression in which the mole number $\eta(P(r_i, t), (\phi_a)_{max}(P(r_i, t)))$ of organic scale particles in the crude oil varies with both the pressure $P(r_i, t)$ of the reservoir and the maximum dissolved quantity $(\phi_a)_{max}(P(r_i, t))$ of the organic scale in the crude oil, which is expressed by the following formula (10-8):

$$\eta(P(r_i,t),(\phi_a)_{max}(P(r_i,t)))=\int_0^t \eta_o[\phi_a-(\phi_a)_{max}(P(r_i,t))]f_{trap}(R_p)dt, \quad (10\text{-}8)$$

where $\eta_o$ is the mole number of the crude oil; $\phi_a$ is the total content of the organic scale in the crude oil; and $R_p$ is the preset particle size.

The parameters in the above formula are explained and described below. For the mole number $$\eta_o = \frac{\rho_o Q_{o0}(t)}{MW_o}$$

of the crude oil, $\rho_o$ is density of the crude oil; $Q_o(t)$ is the crude oil production of the well to be diagnosed; and $MW_o$ is an average molar mass of the crude oil. $\eta_o[\phi_a-(\phi_a)_{max}(P(r_i, t))]$ represents a mole number change rate of organic scale particles in the ith cylindrical shell at time t; and for the distribution function $f_{trap}(R_p)$, $f_{trap}(R_p) = \int_{R_p}^{\infty} f(r)dr$, where $f(r)$ is a density distribution function (which can be a normal distribution function) of organic scale particles (e.g., asphaltene particles) in the organic scale (e.g., asphaltene). As $f_{trap}(R_p)$ represents a mole number proportion of the organic scale particles with a particle size greater than the preset particle size (e.g., an average pore size of pores of the reservoir), the above formula (10-8) represents the mole number of the organic scale particles with the particle size in the ith cylindrical shell greater than the preset particle size.

Step S10104: determining a spatio-temporal evolution simulation equation of reservoir damage by organic scale according to the first relational expression, the second relational expression and the pressure of the reservoir.

Wherein the spatio-temporal evolution simulation equation is used to simulate a four-dimensional spatio-temporal evolution process of reservoir damage characteristics caused by organic scale.

Specifically, formulas (10-4) and (10-8) are substituted into formula (10-7) to determine the spatio-temporal evolution simulation equation of reservoir damage by organic scale. As a result, the specific form of the spatio-temporal evolution simulation equation is very complex and is not illustrated here. That is, the spatio-temporal evolution simulation equation of reservoir damage by organic scale is equivalent to an equation set composed of formulas (10-4), and (10-7)-(10-8).

The embodiments of the present application mainly discuss the specific case of asphaltene, that is, the two concepts of organic scale and asphaltene are interchangeable.

In summary, according to the present invention, the first relational expression in which the maximum dissolved quantity of the organic scale in the crude oil varies with the pressure of the reservoir is determined creatively according to the bubble point pressure of the reservoir, the molar volume of crude oil produced from the reservoir at the bubble point pressure, the solubility parameter of the crude oil, the solubility parameter of the organic scale in the crude oil, and the molar volume of the organic scale; the second relational expression in which the mole number of the organic scale particles in the crude oil varies with both the pressure of the reservoir and the maximum dissolved quantity of the organic scale in the crude oil is determined according to the distribution function of organic scale particles in the organic scale and the mole number of the crude oil; and the spatio-temporal evolution simulation equation of reservoir damage by organic scale is determined according to the first relational expression, the second relational expression and the pressure of the reservoir. Thus, by using the determined spatio-temporal evolution simulation equation, a four-dimensional spatio-temporal evolution process of reservoir damage characteristics caused by organic scale can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Figure 10D:
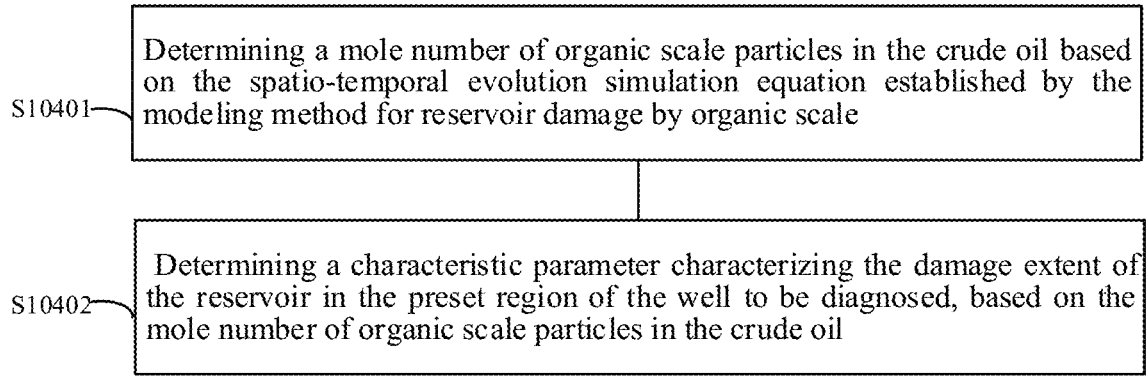
FIG. 10D is a flow diagram of a method for determining a damage extent of a reservoir provided in an embodiment of the present invention.

FIG. 10D is a flow diagram of a method for determining a damage extent of a reservoir provided in an embodiment of the present invention. As shown in FIG. 10D, the method may include steps S10401-S10402.

Step S10401: determining a mole number of organic scale particles in the crude oil based on the spatio-temporal evolution simulation equation established by the modeling method for reservoir damage by organic scale.

For the pressure equation expressed by the above formula (10-1), the pressure $P(r_i, t)$ of the reservoir and the mole number $\eta(P(r_i, t), (\phi_a)_{max}(P(r_i, t)))$ of the organic scale particles in the crude oil can be calculated by referring to the process of solving the volume concentration of the deposited particles in the above Embodiment 1.

The pressure $P(r_i, t)$ of the reservoir and the mole number $\eta(P(r_i, t), (\phi_a)_{max}(P(r_i, t)))$ of the organic scale particles in the crude oil may be calculated by the above method, as the spatio-temporal evolution simulation equation established by the above modeling method for reservoir damage by organic scale comprehensively considers the influence of various physical and chemical factors on reservoir damage when the reservoir is clogged by organic scale particles, the mole number of the organic scale particles in the crude oil obtained by the step S10401 is very precise.

Step S10402: determining a characteristic parameter characterizing the damage extent of the reservoir in the preset region of the well to be diagnosed, based on the mole number of the organic scale particles in the crude oil.

In an embodiment, the characteristic parameter is a permeability of the reservoir.

For the step S10402, the determining a characteristic parameter characterizing the damage extent of the reservoir in the preset region of the well to be diagnosed may include: determining porosity $\phi(r_i, t)$ of the reservoir based on the mole number $\eta(P(r_i, t), (\phi_a)_{max}(P(r_i, t)))$ of the organic scale particles in the crude oil and a formula)

Where $\phi_0$ is an initial value of the porosity; $m_K$ is a second empirical value; and $K_0(r_i)$ is an initial value of the permeability of the reservoir.

In an embodiment, the characteristic parameter is a fluid loss coefficient of the reservoir.

For the step S10402, the determining a characteristic parameter characterizing the damage extent of the reservoir in the preset region of the well to be diagnosed d may include: determining the porosity $\phi(r_i, t)$ of the reservoir based on the mole number $\eta(P(r_i, t), (\phi_a)_{max}(P(r_i, t)))$ of the organic scale particles in the crude oil and the formula $$\phi(r_i, t) = \phi_0 + \frac{\eta(P(r_i, t), (\phi_a)_{max}(P(r_i, t)))V_a \times 10^{-6}}{2\pi H \phi_0 r_i dr},$$

where dr is the preset thickness of the cylindrical shell; and determining the fluid loss coefficient $k(r_i, t)$ of the reservoir based on the porosity $\phi(r_i, t)$ of the reservoir and the formula $$k(r_i, t) = k_0(r_i) \cdot \left(\frac{\phi(r_i, t)}{\phi_0}\right)^{m_k}.$$

Where $\phi_0$ is the initial value of the porosity; $m_k$ is a first empirical value; and $k_0(r_i)$ is an initial value of the fluid loss coefficient of the reservoir.

In an embodiment, the characteristic parameter is a skin factor of the reservoir.

For the step S10402, the determining a characteristic parameter characterizing the damage extent of the reservoir in the preset region of the well to be diagnosed may include: determining the porosity $\phi(r_i, t)$ of the reservoir based on the mole number $\eta(P(r_i, t), (\phi_a)_{max}(P(r_i, t)))$ of the organic scale particles in the crude oil and the formula $$\phi(r_i, t) = \phi_0 + \frac{\eta(P(r_i, t), (\phi_a)_{max}(P(r_i, t)))V_a \times 10^{-6}}{2\pi H \phi_0 r_i dr};$$

determining the permeability $K(r_i, t)$ reservoir based on the porosity $\phi(r_i, t)$ of the reservoir and the formula $$K(r_i, t)/K_0(r_i) = \left(\frac{\phi(r_i, t)}{\phi_0}\right)^{m_k};$$

and determining the skin factor $S(r_i, t)$ of the reservoir based on the permeability $K(r_i, t)$ of the reservoir and the formula $$S(r_i, t) = \left(\frac{1}{\overline{K_d(r_i, t)}} - 1\right)\ln\left(\frac{r_{sw}}{r_w}\right).$$

Where $\phi_0$ is the initial value of the porosity; $m_K$ is the second empirical value; $K_0(r_i)$ is the initial value of the permeability of the reservoir; $\overline{K_d(r_i, t)} = K(r_i, t)/K_0(r_i)$; $r_w$ is a wellbore radius of the well to be diagnosed, and $r_{sw}$ is a damage radius of the reservoir.

Figure 10E:
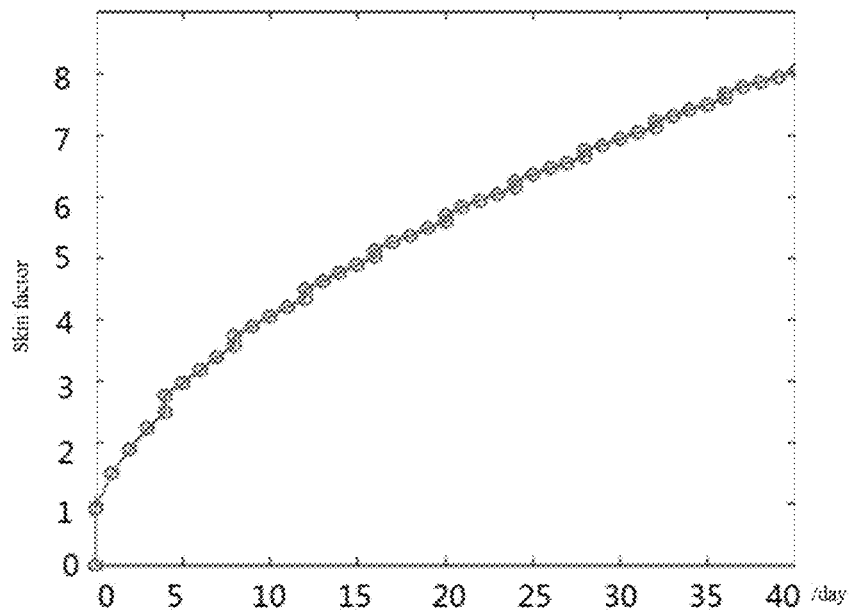
FIG. 10E is a schematic diagram of evolution of a skin factor over time provided in an embodiment of the present invention.
Figure 10F:
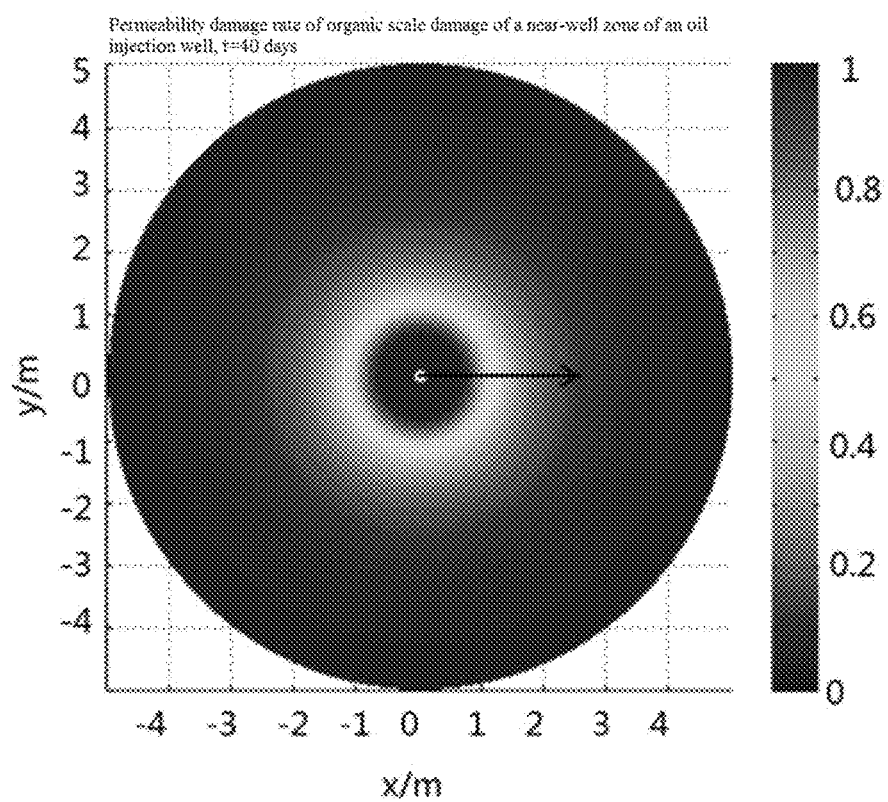
FIG. 10F is a flow diagram of a radius of reservoir damage by organic scale at day 40 characterized by a permeability damage rate of a reservoir provided in an embodiment of the present invention.

The characteristic parameter (e.g., the permeability $K(r_i, t)$ and the skin factor $S(r_i, t)$ of the reservoir) obtained by the step S10402 is a result of 4D quantitative simulation of spatio-temporal evolution (as shown in FIG. 10E). More specifically, FIG. 10F shows a schematic diagram of a radius (a radius as indicated by an arrow) of reservoir damage by organic scale at day 40 characterized by a permeability damage rate of the reservoir (the permeability damage rate $I(r_i, t)$, of the reservoir is determined based on the permeability $K(r_i, t)$ of the reservoir and a formula $$I(r_i, t) = 1 - \frac{K(r_i, t)}{K_{max}(r_i, t)},$$

where $K_{max}(r_i, t)$ is a maximum value of $K(r_i, t)$), and a working person concerned can visually confirm the damage extent of the reservoir from FIG. 10F. Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

In summary, according to the present invention, the mole number of the organic scale particles in the crude oil is creatively determined based on the spatio-temporal evolution simulation equation established by the modeling method for reservoir damage by organic scale; and the characteristic parameter characterizing the damage extent of the reservoir in the preset region of the well to be diagnosed is determined based on the mole number of organic scale particles in the crude oil. Thus, a four-dimensional spatio-temporal evolution process of characteristics of reservoir damage caused by organic scale can be quantitatively simulated. Therefore, performing quantitative prediction of reservoir damage and spatio-temporal deduction of damage laws, which is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Embodiment 11—Jamin Effect

During flowing of an oil phase and an aqueous phase within a low-permeability reservoir, there are usually a large quantity of dispersed oil droplets and air bubbles. When these individuals move to narrow pore throats (for example, pores with a pore size of 2.5 µm) in the reservoir, as the diameters of these individuals are larger than the diameters of the pore throats, the flowing of these individuals is obstructed, forcing the oil droplets, air bubbles or the like to deform. Therefore, the phenomenon of additional capillary resistance on the oil droplets, bubbles or the like during movement in the reservoir with uneven diameter distribution is called a Jamin effect. Compared with the water lock effect, it is the oil droplets, air bubbles and the like that are forced to deform by the resistance in the small pore throats, and a wetting phase is water and a non-wetting phase is the oil droplets or bubbles in this case.

Usually, the Jamin effect occurs when the following conditions are satisfied at the same time: firstly, crude oil should be in a dispersed state and cannot move in the form of a continuous oil flow; secondly, diameters of channels of the geological reservoir should be relatively small. When a dispersed oil droplet moves into a narrow channel of the reservoir, as its diameter is larger than the diameter of the channel, the oil droplet cannot continue to move due to resistance, or when an oil droplet flows in a variable diameter channel, a capillary effect occurs, which leads to Jamin damage (a situation where permeability of the reservoir decreases due to the Jamin effect).

Specifically, the droplet moves from left to right under the action of a displacement pressure P on the left and right sides of the reservoir. When the oil droplet moves to a pore 1, due to the obstruction of the pore 1, a front end of the oil droplet ($2R_1=\lambda$, where $R_1$ is a radius of curvature of a liquid surface at the front end, and $\lambda$ is a pore size of the pore 1) is subjected to a pre-bubble pressure $P_1$; a rear end of the oil droplet (its diameter $2R_2=\overline{\lambda}$, where $R_2$ is a radius of curvature of a liquid surface at the rear end, and $\overline{\lambda}$ is an average pore size of pores) is subjected to $P_3$; and the interior of the oil droplet is subjected to an intra-bubble pressure $P_2$; and $P_1$, $P_2$, and $P_3$ satisfy the following two equations:

$$P_2 - P_1 = \frac{2\sigma}{R_1},$$

$$P_2 - P_3 = \frac{2\sigma}{R_2}.$$

As a result, the additional resistance on the oil droplet due to the Jamin effect is:

$$P_c = 2\sigma\left(\frac{1}{R_1} - \frac{1}{R_2}\right),$$

and due to the front end $$R_1 = \frac{\lambda}{2}$$

of the droplet, the back end $$R_2 = \frac{\overline{\lambda}}{2}$$

of the droplet, and $\overline{\lambda} > \lambda$, $$P_c = 4\sigma\left(\frac{1}{\lambda} - \frac{1}{\overline{\lambda}}\right).$$

where $\sigma$ is a surface tension of the liquid droplet. When the displacement pressure (i.e., a pressure difference outside the orifice throat) reaches at least $P_c$, the air bubble or droplet can pass through the pore throat. Otherwise, it is clogged.

The Jamin effect is influenced by various factors such as pore structures, lithology, physical properties and an invading fluid of the reservoir. Jiamin damage is closely related to geometric properties of a pore medium of rock. Different pore throat structure distribution modes and complexity can lead to significant changes in the distribution pattern of a water wetting phase in the rock, thus affecting the permeability of the reservoir. Therefore, the core of the embodiments of the present invention is to establish a kinetic model (i.e., an aqueous phase motion equation and a permeability distribution equation in the reservoir) of aqueous phase saturation variations within the pores in the reservoir. Specifically, the aqueous phase motion equation in the reservoir is established based on a convection diffusion relation (i.e. mass balance equation) for a fluid within the pores in the reservoir, and the like; the permeability distribution equation is established based on pore size distribution characteristics of the pores and a preset permeability model; then a spatio-temporal evolution control phenomenological model of permeability distribution in the reservoir around a well to be diagnosed influenced by the Jamin effect is determined according to the aqueous phase motion equation and the permeability distribution equation, and thus spatio-temporal field distribution of characteristic parameter characterizing the damage extent of the reservoirs such as permeability can be diagnosed.

Figure 11A:
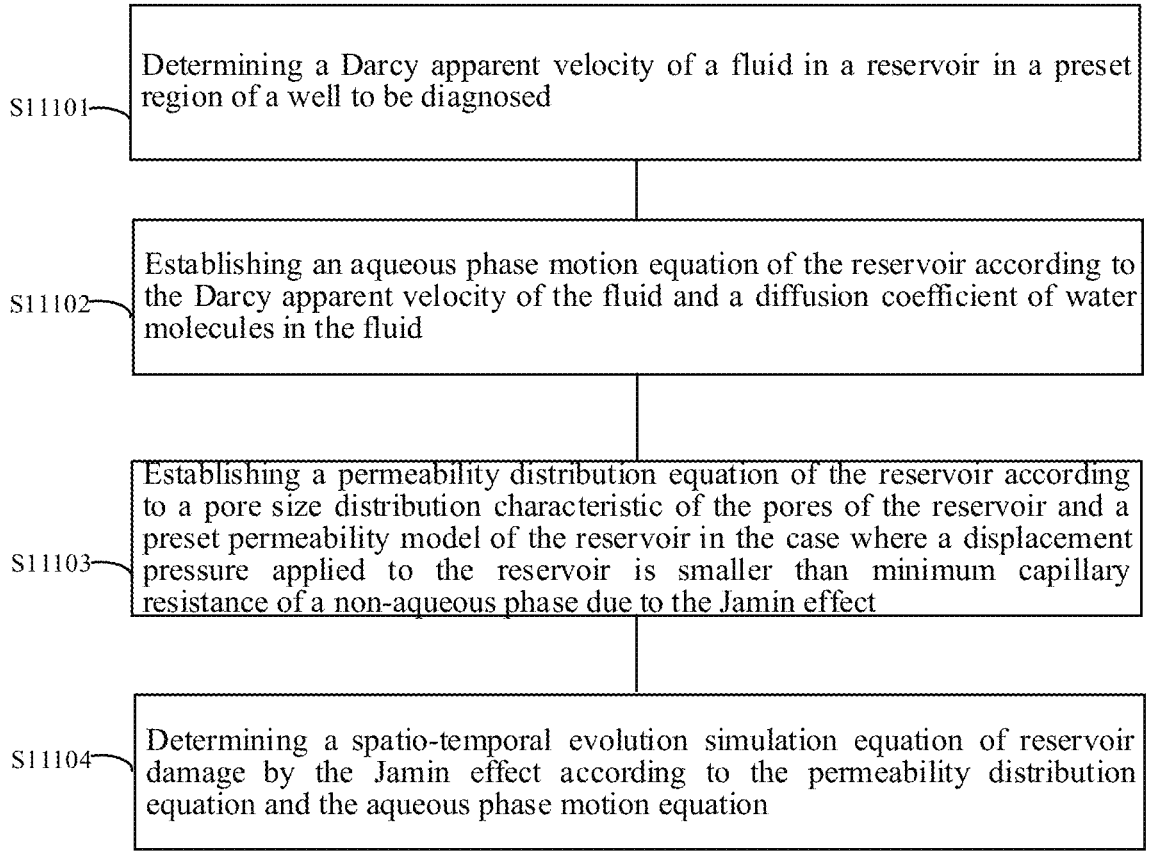
FIG. 11A is a flow diagram of a modeling method for reservoir damage by a Jamin effect provided in an embodiment of the present invention.
Figure 11B:
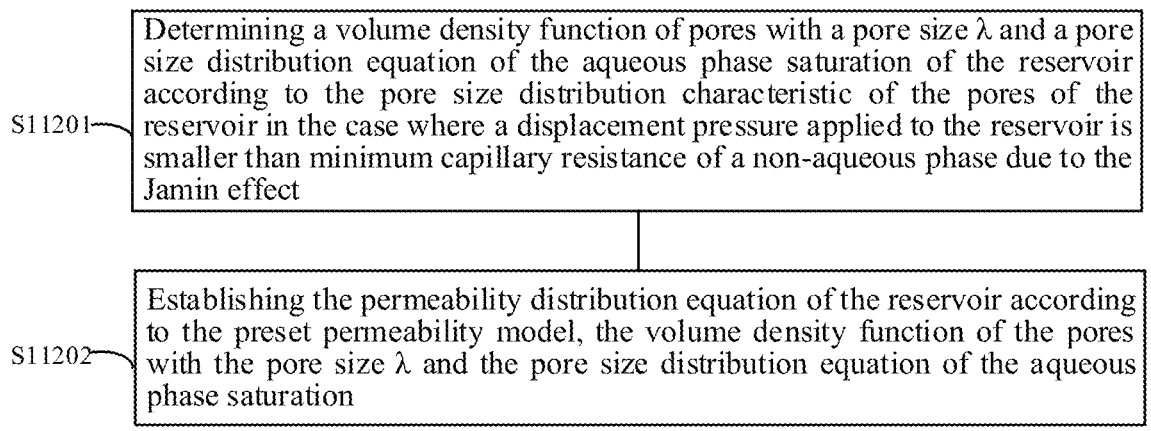
FIG. 11B is a flow diagram of establishing a permeability distribution equation of a reservoir provided in an embodiment of the present invention.

FIG. 11A is a flow diagram of a modeling method for reservoir damage by a Jamin effect provided in an embodiment of the present invention. The modeling method may include steps S11101-S11104.

Step S11101: determining a Darcy apparent velocity of a fluid in a reservoir in a preset region of a well to be diagnosed.

Wherein the permeability of the reservoir is lower than preset permeability; and the well to be diagnosed may be, for example, an oil production well.

For the step S11101, determining the velocity of the fluid in the reservoir may include: establishing a pressure conduction equation for the fluid entering the reservoir; and determining the Darcy apparent velocity of the fluid according to the pressure conduction equation and a Darcy formula.

For the specific determination process, reference can be made to the process of determining the Darcy apparent velocity in the above Embodiment 2 (i.e., the above formulas (2-1) and (2-2) and related description thereof).

Step S11102: establishing an aqueous phase motion equation of the reservoir according to the Darcy apparent velocity of the fluid and a diffusion coefficient of water molecules in the fluid.

Under reservoir conditions, water contents at different locations within pores in the reservoir satisfy a mass conservation equation. Motion of an extraneous aqueous phase within the reservoir is mainly determined by two processes: convection and diffusion. Specifically, for the step S11102, the establishing an aqueous phase motion equation of the reservoir may include: establishing, according to the Darcy apparent velocity $u$ of the fluid and the diffusion coefficient $D_w$ of the water molecules, a mass balance equation expressed in the following formula:

$$\phi_0 \frac{\partial \phi_w(\vec{r}, t)}{\partial t} = \nabla(D_w \nabla \phi_w(\vec{r}, t)) - \nabla(u \phi_w(\vec{r}, t)),$$

where $\phi_0$ is an initial value of porosity of the reservoir; $\phi_w(\vec{r}, t)$ is absolute porosity with the pores in the reservoir being occupied by the aqueous phase; and $\vec{r}$ is a spatial location of any point in the reservoir (e.g., using the center of the well to be diagnosed as an origin).

The aqueous phase motion equation expressed by the following formula (11-1) is established according to the mass balance equation and a spatio-temporal distribution function $$S_w(\vec{r}, t) = \frac{\phi_w(\vec{r}, t)}{\phi_0}$$

of an aqueous phase saturation of the reservoir:

$$\phi_0 \frac{\partial S_w(\vec{r}, t)}{\partial t} = \nabla(D_w \nabla S_w(\vec{r}, t)) - \nabla(u S_w(\vec{r}, t)). \quad (11\text{-}1)$$

An initial condition for the aqueous phase motion equation is $S_w(\vec{r}, t=0) = S_{wc}$, and a boundary condition for the aqueous phase motion equation is $S_w(|\vec{r}|=r_w, t)=1$ (that is, reservoir pores in a well wall of the water injection well are completely filled with water, i.e., the aqueous phase saturation in the pores is 1), where $\phi_0$ is an initial value of the porosity of the reservoir; $r_w$ is a wellbore radius of the well to be diagnosed; and $S_{wc}$ is an irreducible water saturation in the reservoir.

Step S11103: establishing a permeability distribution equation of the reservoir according to a pore size distribution characteristic of the pores of the reservoir and a preset permeability model of the reservoir.

For the step S11103, as shown in FIG. 2, the establishing a permeability distribution equation of the reservoir may include steps S11201-S11202.

Step S11201: determining a volume density function of pores with a pore size λ and a pore size distribution equation of the aqueous phase saturation of the reservoir according to the pore size distribution characteristic of the pores of the reservoir.

Pore structures of the rock of reservoir are strongly irregular and controlled by a variety of factors, such that pores in a pore structure model based on classical geometry are greatly different from real pores. To quantitatively describe the pore structures of the reservoir, a fractal theory is used to study the Jamin effect of two-phase flow in the pore structures, and a wetting film effect of the aqueous phase on the inner surfaces of pore channels is ignored. According to the geometric principle of fractal, if pore size distribution of the reservoir has a fractal characteristic, a number N (>λ) of pores with a pore size larger than λ in the reservoir has the following power function relationship with λ:

$$N(>\lambda) = \left(\frac{\lambda_{max}}{\lambda}\right)^D,$$

where D is a fractal dimension (2<D<3) of the pores.

Figure 11C:
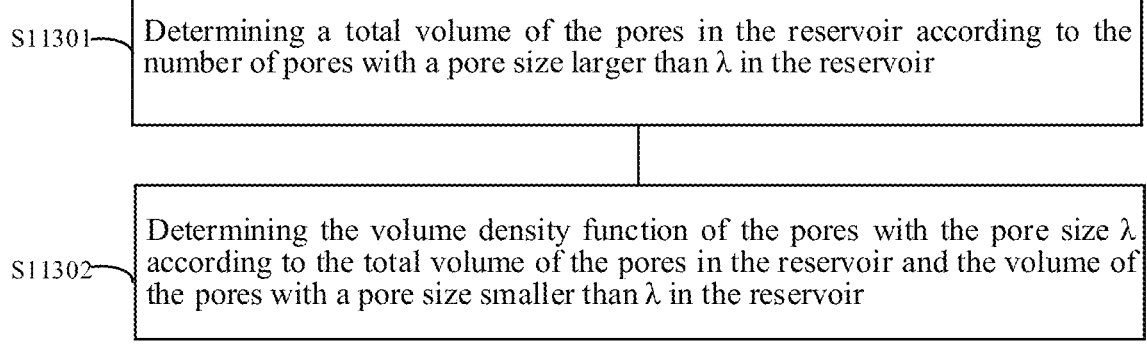
FIG. 11C is a flow diagram of determining a volume density function of pores with a pore size $\lambda$, provided in an embodiment of the present invention.

In the case where the pore size distribution characteristic of the pores of the reservoir is that the number N(>λ) of the pores with the pore size larger than λ in the reservoir satisfies the above formula $$N(>\lambda) = \left(\frac{\lambda_{max}}{\lambda}\right)^D,$$

as shown in FIG. 11C, determining the volume density function of the pores with the pore size λ in the step S11201 may include steps S11301-S11302.

Step S11301: determining a total volume of the pores in the reservoir to be $\Phi_{max} = A(\lambda_{max}^{3-D} - \lambda_{min}^{3-D})$ according to the number N(>λ) of the pores with the pore size larger than λ in the reservoir.

Specifically, the total number $N(>\lambda_{min})$ of the pores in the reservoir and the number λ of pores with the pore size larger than λ can be obtained according to the above formula $$N(>\lambda) = \left(\frac{\lambda_{max}}{\lambda}\right)^D; N(>\lambda_{min}) = \left(\frac{\lambda_{max}}{\lambda_{min}}\right)^D, \quad (11\text{-}2)$$

$$N(<\lambda) = \left(\frac{\lambda_{max}}{\lambda_{min}}\right)^D - \left(\frac{\lambda_{max}}{\lambda}\right)^D, \quad (11\text{-}3)$$

according to formulas (11-2) and (11-3), the following formula (11-4) can be obtained:

$$\frac{dN}{N(>\lambda_{min})} = D\lambda_{min}^D \lambda^{-D-1} d\lambda = f(\lambda) d\lambda, \quad (11\text{-}4)$$

$f(\lambda)$ in the above formula (11-4) is a pore size distribution density function of the reservoir, and a relationship between the number $N(<\lambda_{pc})$ of the pores with the pore size smaller than $\lambda_{pc}$ and λ is a power function relationship expressed by the following formula (11-5):

$$N(<\lambda_{pc}) = \int_\lambda^{\lambda_{pc}} f(\lambda) d\lambda = a\lambda^{-D}, \quad (11\text{-}5)$$

λ, $\lambda_{min}$, $\lambda_{max}$ and $\lambda_{pc}$ in the above related formula are a pore size, a minimum pore size, a maximum pore size of the pores ($\lambda_{min}$ and $\lambda_{max}$ can be obtained from an average pore size and a standard deviation of the pore size distribution; generally $$\left.\frac{\lambda_{min}}{\lambda_{max}} \leq 0.01\right)$$

and a maximum diameter with the Jamin effect, respectively (i.e., a particular pore size of a pore where a non-aqueous phase is subjected to minimum capillary resistance); and α is a proportional constant.

Next, from formula (11-5), the pore size distribution density function $f(\lambda)$ of the reservoir can be obtained, which satisfies the following formula (11-6):

$$f(\lambda) = \frac{dN}{d\lambda} = a'\lambda^{-D-1}, \quad (11\text{-}6)$$

in the formula, $\alpha'=-Da$ is a proportional constant.

A fractal expression of the total volume of the pores in the reservoir can be obtained from the pore size distribution density function expressed by the above formula (11-6):

$$\Phi_{max} = \int_{\lambda_{min}}^{\lambda_{max}} f(\lambda)\alpha^3 d\lambda, \tag{11-7}$$

where $\alpha$ is a constant related to the shape of the pores ($\alpha=1$ if the shape of the pores is a cube, or $\alpha=\pi/6$ if the shape of the pores is a sphere), and by integration, we can obtain:

$$\Phi_{max} A(\lambda_{max}^{3-D} - \lambda_{min}^{3-D}), \tag{11-8}$$

similarly, the volume of the pores with the pore size smaller than $\lambda$ in the reservoir is $\Phi_\lambda = \int_{\lambda_{min}}^{\lambda} f(\lambda)\alpha^3 d\lambda = A(\lambda^{3-D} - \lambda_{min}^{3-D})$.

Step S11302: according to the total volume $\Phi_{max}$ of the pores in the reservoir and the volume $\Phi_\lambda = A(\lambda^{3-D} - \lambda_{min}^{3-D})$ of the pores with the pore size smaller than $\lambda$ in the reservoir, determining the volume density function of the pores with the pore size $\lambda$ as:

$$d\xi = \frac{(3-D)\lambda^{2-D}}{\lambda_{max}^{3-D}\left(1-(\lambda_{min}/\lambda_{max})^{3-D}\right)} d\lambda, \tag{11-9}$$

wherein D is the fractal dimension of the pores; and $\lambda$, $\lambda_{min}$ and $\lambda_{max}$ are the pore size, minimum pore size and maximum pore size of the pores, respectively; and $A=\alpha\alpha'/(3-D)$ (a constant).

Step S11202: establishing a permeability distribution equation of the reservoir according to the preset permeability model, the volume density function of the pores with the pore size $\lambda$ and the pore size distribution equation of the aqueous phase saturation.

Figure 11D:
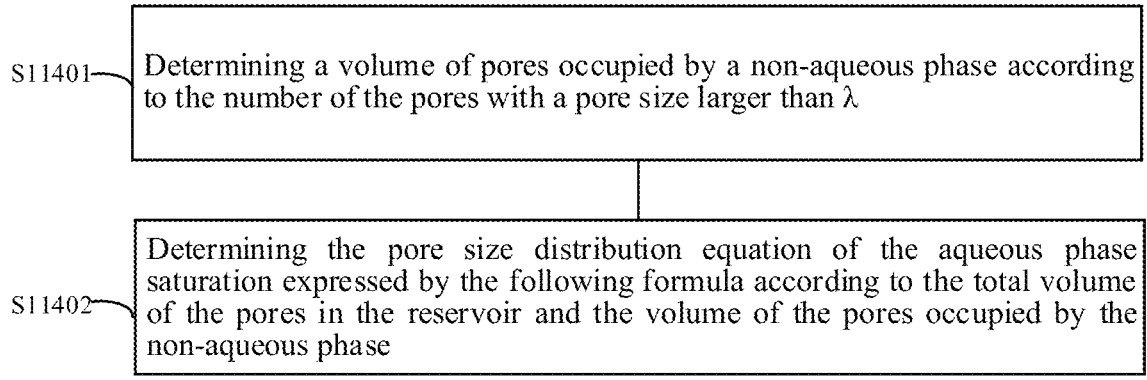
FIG. 11D is a flow diagram of determining a pore size distribution equation of an aqueous phase saturation of a reservoir provided in an embodiment of the present invention.

As shown in FIG. 11D, determining the pore size distribution equation of the aqueous phase saturation of the reservoir in the step S11202 may include steps S11401-S11402.

Step S11401: determining a volume of pores occupied by a non-aqueous phase to be $\Phi_{nw}(\lambda)=A(\lambda_{pc}^{3-D} - \lambda^{3-D})$ according to the number $N(>\lambda)$ of the pores with the pore size larger than $\lambda$.

Wherein $\lambda_{pc}$ is a particular pore size of a pore where the non-aqueous phase is subjected to minimum capillary resistance (i.e., a maximum pore throat diameter with the Jamin effect).

In the case where the reservoir is water-wettable (i.e., hydrophilic), a displacement pressure P (gradually increasing from zero to P) is applied to both sides of the reservoir, and oil droplets or air bubbles can smoothly pass through pores with a pore size in the range of $\lambda_{max}$ to $\lambda_{pc}$ (i.e., communicating pores are opened successively from the maximum pore size $\lambda_{max}$ to $\lambda_{pc}$) according to the conditions for producing the Jamin effect. When the pressure P does not reach $P_c$, pore throats with $\lambda$ larger than $\lambda_{pc}$ are completely occupied by water, while pore throats with $\lambda$ smaller than $\lambda_{pc}$ are still clogged by the oil droplets or air bubbles.

Since the pore size distribution density function $f(\lambda)$ determined by the above formula (11-6) can be determined according to the number $N(>\lambda)$ of pores with a pore size greater than $\lambda$ in the reservoir, thus a volume $\Phi_{nw}(\lambda)$ of pores occupied by the non-aqueous phase when the pressure P does not reach $P_c$ can be obtained according to $f(\lambda)$, $$\Phi_{nw}(\lambda) = A(\lambda_{pc}^{3-D} - \lambda^{3-D}). \tag{11-10}$$

Step S11402: determining, according to the total volume $\Phi_{max}$ of the pores in the reservoir and the volume $\Phi_{nw}(\lambda)$ of the pores occupied by the non-aqueous phase, the pore size distribution equation $$S_w(\lambda) = 1 - \left(\frac{\lambda_{pc}}{\lambda_{max}}\right)^{3-D} + \left(\frac{\lambda}{\lambda_{max}}\right)^{3-D}$$

of the aqueous phase saturation expressed by the following formula, where D is the fractal dimension of the pores; and $\lambda$, $\lambda_{min}$ and $\lambda_{max}$ are the pore size, minimum pore size and maximum pore size of the pores, respectively; and $A=\alpha\alpha'/(3-D)$.

Specifically, the volume of the pores occupied by the aqueous phase can be determined according to formulas (11-8) and (11-10) to be $\Phi_w(\lambda) = \Phi_{max} - \Phi_{nw}(\lambda) = A(\lambda_{max}^{3-D} - \lambda_{min}^{3-D} - \lambda_{pc}^{3-D} + \lambda^{3-D})$; and the following formula can be obtained in conjunction with formula (11-8):

$$S_w(\lambda) = \frac{\Phi_w}{\Phi_{max}} = 1 - \frac{\left(\frac{\lambda}{\lambda_{max}}\right)^{3-D} - \left(\frac{\lambda_{pc}}{\lambda_{max}}\right)^{3-D}}{1 - \left(\frac{\lambda_{min}}{\lambda_{max}}\right)^{3-D}}.$$

Since $\lambda_{min} \ll \lambda_{max}$, and $$\frac{\lambda_{min}}{\lambda_{max}} \approx 0,$$

the above equation can be written as the following formula (11-11), i.e., the pore size distribution equation (11-11) of the aqueous phase saturation can be determined:

$$S_w(\lambda) = 1 - \left(\frac{\lambda_{pc}}{\lambda_{max}}\right)^{3-D} + \left(\frac{\lambda}{\lambda_{max}}\right)^{3-D}. \tag{11-11}$$

According to the theory of fluid mechanics, under the effect of a differential pressure $\Delta P$, a total flow rate of the fluid with viscosity $\mu$ passing through a capillary bundle can be described by a Hagen-poiseuille equation:

$$Q = \sum_i Q_i = \frac{\Delta P}{128\,\mu L_c^2} \sum_i V_i \lambda_i^2,$$

in the above formula, $\lambda_i$ is a diameter of a pore channel i (i.e., a pore size of a pore i), $V_i$ is a volume of the pore channel i, $V_i = \Phi_0 M L_m \xi_i$, $\Phi_0$ is the porosity of the reservoir, $\xi_i$ is a pore volume fraction of the pore channel i, $L_c$ is a bending length of the pore channel i, $L_m$ is a straight length of the pore channel i, M is an average pore throat cross-sectional area, $$\tau = \frac{L_c}{L_m}$$

is tortuosity of the pore channel i (it may also be calculated by empirical formula $$\tau = \Phi_0^{-\frac{3}{4}} -$$

0.35). Substituting the above quantities into the above formula yields:

$$q = \frac{\Delta P \Phi_0 M}{128 \mu \tau L_c} \sum_k \xi_i \lambda_i^2,$$

and according to a Darcy's law, permeability of a capillary bundle model can be expressed as $$K = \frac{\phi_0}{128\tau} \sum_i \xi_i \lambda_i^2.$$

In the embodiments of the invention, a permeable channel of the reservoir can be regarded as an accumulation of multiple capillary bundles. Due to the continuity of the size distribution of the pores, the expression of the permeability of the capillary bundle model can be written in an integral form as:

$$K = \frac{\phi_0}{128\tau} \int \lambda^2 d\xi. \quad (11\text{-}12)$$

Figure 11E:
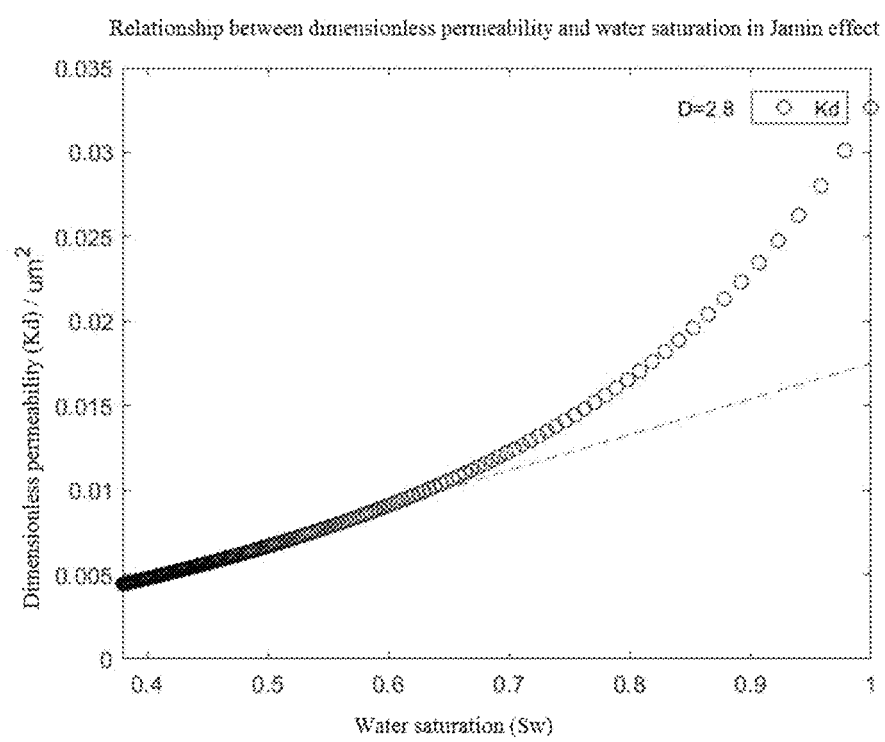
FIG. 11E is a schematic diagram of evolution of permeability with a water saturation provided in an embodiment of the present invention.

In the case where the preset permeability model of the reservoir satisfies $$K = \frac{\phi_0}{128\tau} \int \lambda^2 d\xi,$$

the establishing apermeability distribution equation of the reservoir may include: establishing, according to the preset permeability model $$K = \frac{\phi_0}{128\tau} \int \lambda^2 d\xi$$

of the reservoir, the volume density function $d\xi$ of the pores with the pore size $\lambda$ and the pore size distribution equation of the aqueous phase, the permeability distribution equation of the reservoir:

$$K(S_w) = \left(\frac{\phi_0 S_w}{128\tau}\right)\left(\frac{3-D}{5-D}\right) \frac{\lambda_{max}^{5-D} - [\lambda_{max}^{3-D}(S_w - 1) + \lambda_{pc}^{3-D}]^{\frac{5-D}{3-D}}}{\lambda_{max}^{3-D}(2-S_w) - \lambda_{pc}^{3-D}}. \quad (11\text{-}13)$$

Wherein an initial condition for the pressure conduction equation is $K(t=0)=1$. $K(S_w)$ is a function of permeability with respect to water saturation (as shown in FIG. 11E, the function may be called dimensionless permeability); $\phi_0$ is initial porosity of the reservoir; $S_w$ is a water saturation; D is the fractal dimension of the pores, which can be calculated from $$D = 3 - \frac{\ln \phi_0}{\ln \frac{\lambda_{min}}{\lambda_{max}}}$$

(a larger D indicates a larger proportion of small pore throats; for a conventional reservoir $\lambda_{max}>20$ μm, D<2.6; and for a low permeability reservoir $\lambda_{max}<0.2$ μm, D>2.8), τ is the tortuosity, $\lambda_{max}$ is the maximum pore throat diameter, and $\lambda_{min}$ is a minimum pore throat diameter).

Specifically, first, the displacement pressure is gradually increased until P is achieved, at the moment, pore throats with a diameter larger than λ are completely occupied by water, wherein the absolute porosity with pores being occupied by the aqueous phase is $\phi_w$, and formula (11-9) is substituted into formula (11-12) to obtain the pore size distribution function of the permeability of the reservoir:

$$K(\lambda) = \frac{\phi_w \lambda_{max}^2}{128\tau}\left(\frac{3-D}{5-D}\right)\left(\frac{1-(\lambda/\lambda_{max})^{5-D}}{1-(\lambda/\lambda_{max})^{3-D}}\right);$$

and then, the variable λ in the above pore size distribution function $K(\lambda)$ of the permeability is replaced by $S_w$ according to the relational expression between λ and the water saturation $S_w(\lambda)$ in formula (11-11), and in conjunction with $\phi_w=\phi_0 S_w$, to obtain formula (11-13) (i.e., obtaining an expression of the dimensionless permeability, which is a function of the water saturation).

Step S11104: determining a spatio-temporal evolution simulation equation of reservoir damage by the Jamin effect according to the permeability distribution equation and the aqueous phase motion equation, wherein the spatio-temporal evolution simulation equation is used to simulate a four-dimensional spatio-temporal evolution process of characteristics of reservoir damage caused by the Jamin effect.

Figure 11F:
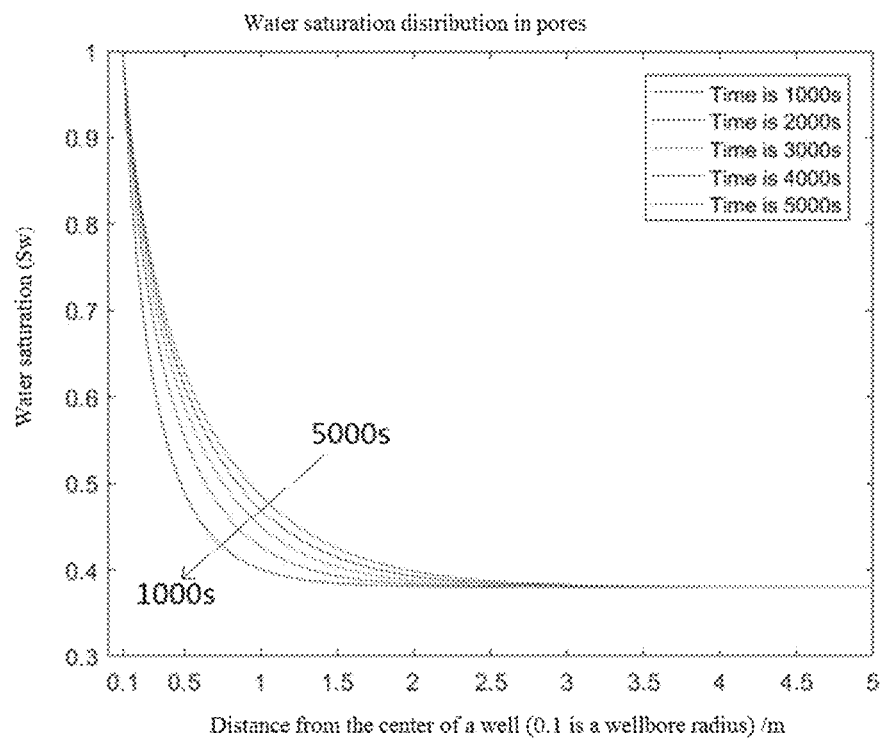
FIG. 11F is a schematic diagram of evolution of a water saturation over space provided in an embodiment of the present invention.

Specifically, the spatio-temporal distribution function $S_w(\vec{r}, t)$ of the aqueous phase saturation of the reservoir (as shown in FIG. 11F) can be obtained according to formula (11-1), and $S_w(\vec{r}, t)$ is substituted into formula (11-13) to obtain a four-dimensional spatio-temporal distribution form of the permeability of the reservoir, i.e., the spatio-temporal evolution simulation equation of reservoir damage by the Jamin effect.

In summary, according to the present invention, the Darcy apparent velocity of the fluid in the reservoir in the preset region in the well to be diagnosed is creatively determined, wherein the permeability of the reservoir is lower than preset permeability; the aqueous phase motion equation of the reservoir is established according to the Darcy apparent velocity of the fluid and the diffusion coefficient of water molecules in the fluid; the permeability distribution equation of the reservoir is established; and the spatio-temporal evolution simulation equation of reservoir damage by the Jamin effect is determined according to the permeability distribution equation and the aqueous phase motion equation. Thus, by using the determined spatio-temporal evolution simulation equation, a four-dimensional spatio-temporal evolution process of reservoir damage characteristics caused by the Jamin effect can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Correspondingly, another embodiment of the present invention further provides a method for determining a damage extent of a reservoir. The method may include: determining a characteristic parameter characterizing the damage extent of the reservoir in the preset region of the well to be diagnosed, based on the spatio-temporal evolution simulation equation by the modeling method for reservoir damage by the Jamin effect.

For the solution of the spatio-temporal evolution simulation equation for reservoir damage by the Jamin effect expressed by the above formula (11-13), $S_w(\vec{r}, t)$ needs to be calculated according to formula (11-1). For the specific solving process, reference can be made to the solving process of the volume concentration of the deposited particles in the above Embodiment 1, which will not be described here.

After the aqueous phase saturation $S_w(\vec{r}, t)$ of the reservoir is calculated by the above method, the permeability $K(\vec{r}, t)$ of the reservoir can be calculated according to the above formula (11-13), and thus the spatio-temporal evolution simulation equation established by the above modeling method of reservoir damage by the Jamin effect comprehensively considers the influence of various physical and chemical factors on reservoir damage during damage by the Jamin effect, so the permeability of the reservoir obtained by the embodiment is very precise.

A characteristic parameter characterizing the damage extent of the reservoir in the preset region of the well to be diagnosed is calculated based on the permeability of the reservoir.

In an embodiment, the characteristic parameter may be a permeability damage rate of the reservoir.

Correspondingly, the determining a characteristic parameter characterizing the damage extent of the reservoir in the preset region of the well to be diagnosed may include: determining the permeability $K(\vec{r}, t)$ of the reservoir based on the spatio-temporal evolution simulation equation; and determining the permeability damage rate $I(\vec{r}, t)$ of the reservoir based on the permeability $K(\vec{r}, t)$ of the reservoir and formula (5-14).

In another embodiment, the characteristic parameter may be a skin factor of the reservoir.

The determining a characteristic parameter characterizing the damage extent of the reservoir in the preset region of the well to be diagnosed may include: determining the permeability $K(\vec{e}, t)$ of the reservoir based on the spatio-temporal evolution simulation equation; and determining the skin factor $S(\vec{r}, t)$ of the reservoir based on the permeability $K(\vec{r}, t)$ of the reservoir and formula (5-15).

Figure 11G:
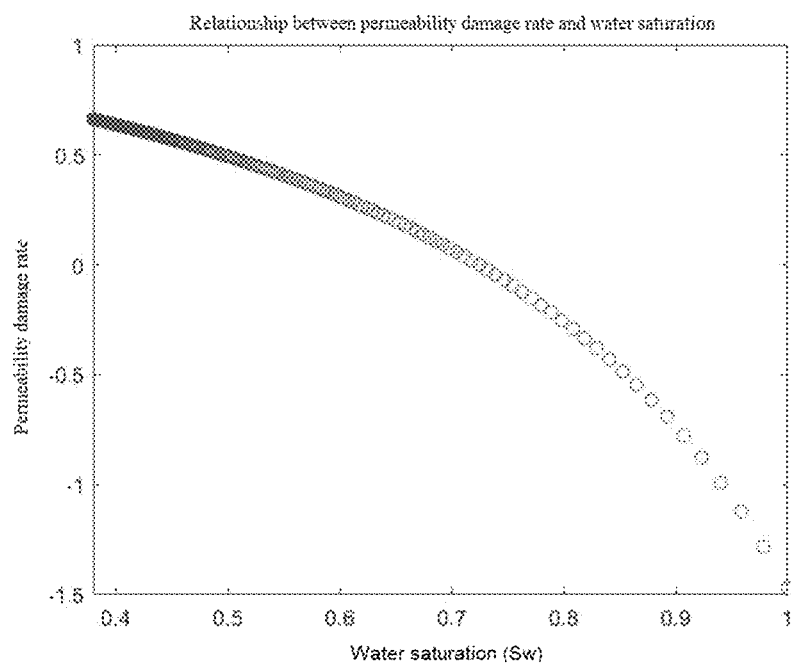
FIG. 11G is a schematic diagram of variations of a permeability damage rate with a water saturation provided in an embodiment of the present invention.

The characteristic parameters (e.g., the permeability damage rate $I(S_w)$ of the reservoir) obtained by the above embodiments are a result of 4D quantitative simulation of spatio-temporal evolution (as shown in FIG. 11G respectively). Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

Embodiment 12—Bacteria

The metabolism of bacteria is controlled by catalysis of various enzymes in their cells, and the activity of the enzymes is extremely sensitive to temperature; for example, a too high or too low temperature can inactivate the enzymes in the cells. During water injection, a temperature change interval is formed between the interior of a well and a reservoir, and seriously affects the rate of bacterial metabolism, such that bacteria are attached to rock surfaces and form biofilms, thereby reducing the porosity of the reservoir. Thus, the core of the embodiments of the present invention is to establish a variation relationship between an apparent concentration distribution equation of nutrients in a fluid within the reservoir and a temperature and a variation relationship between an apparent concentration distribution equation of bacteria in the fluid and a temperature. Specifically, based on energy conservation, mass conservation, a diffusion relationship, and the like, a spatio-temporal evolution control phenomenological model of concentration distribution of the nutrients and the bacteria in the fluid within the reservoir around a well to be diagnosed is established, and in conjunction with a relationship between concentration distribution and a characteristic parameter characterizing the damage extent of the reservoir such as permeability, spatio-temporal field distribution of the characteristic parameter such as permeability can be diagnosed.

Figure 12A:
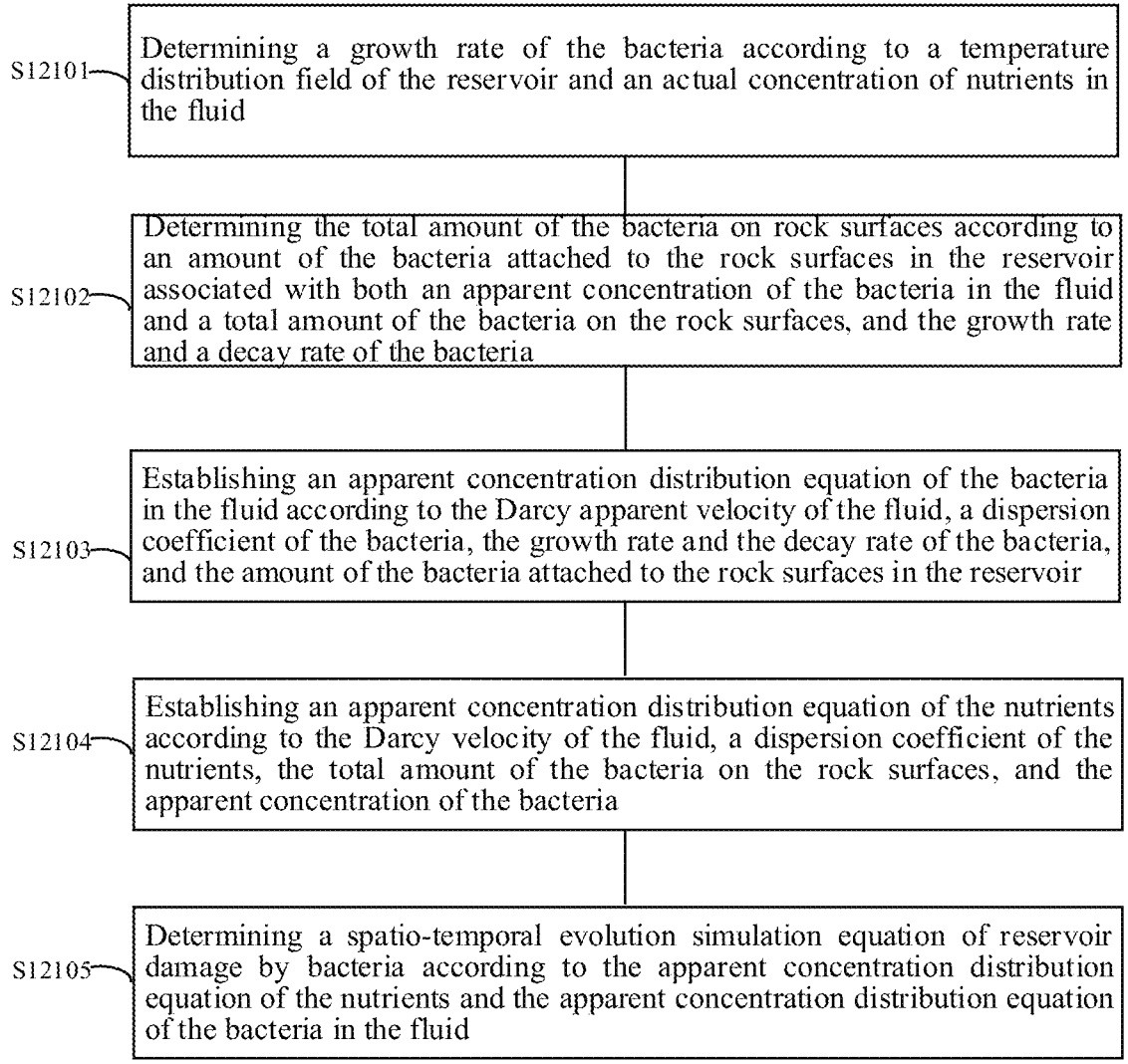
FIG. 12A is a flow diagram of a modeling method for reservoir damage by bacteria provided in an embodiment of the present invention.

FIG. 12A is a flow diagram of a modeling method for reservoir damage by bacteria provided in an embodiment of the present invention. The modeling method may include steps S12101-S12105.

Before performing step S12101, the modeling method further includes: determining a Darcy apparent velocity of a fluid in a reservoir in a preset region of a well to be diagnosed.

Determining the velocity of the fluid in the reservoir may include: establishing a pressure conduction equation for the fluid entering the reservoir; and determining the Darcy apparent velocity of the fluid according to the pressure conduction equation and a Darcy formula.

For the specific determination process, reference can be made to the process of determining the Darcy apparent velocity in the above Embodiment 2 (i.e., the above formulas (2-1) and (2-2) and related description thereof).

Before performing step S12101, the modeling method further includes: determining a temperature distribution field of the reservoir according to the Darcy apparent velocity of the fluid, a thermal conductivity coefficient and thermal diffusivity of the fluid, and an energy conservation law.

During water injection, energy is transferred between reservoir rock and the fluid by means of temperature changes due to a temperature difference between the temperature of the injected water and the temperature of the reservoir. In this case, a mathematical model of field-scale reservoir temperature distribution can be established according to the Darcy apparent velocity $u(\vec{r}, t)$ of the fluid in the reservoir in the preset region of the well to be diagnosed, the thermal conductivity coefficient $D_{con}$ and the thermal diffusivity $D_{dis}$ of the fluid, and the energy conservation law, to obtain an expression of a reservoir temperature distribution control equation.

$$\frac{\partial T}{\partial t} = (D_{con} + D_{dis})\nabla^2 T - u\nabla T, \quad (12\text{-}1)$$

where $T(\vec{r}, t)$ is the reservoir temperature distribution; and the thermal diffusivity may be expressed by thermal conductivity.

Step S12101: determining a growth rate of the bacteria according to the temperature distribution field of the reservoir and an actual concentration of nutrients in the fluid.

Figure 12B:
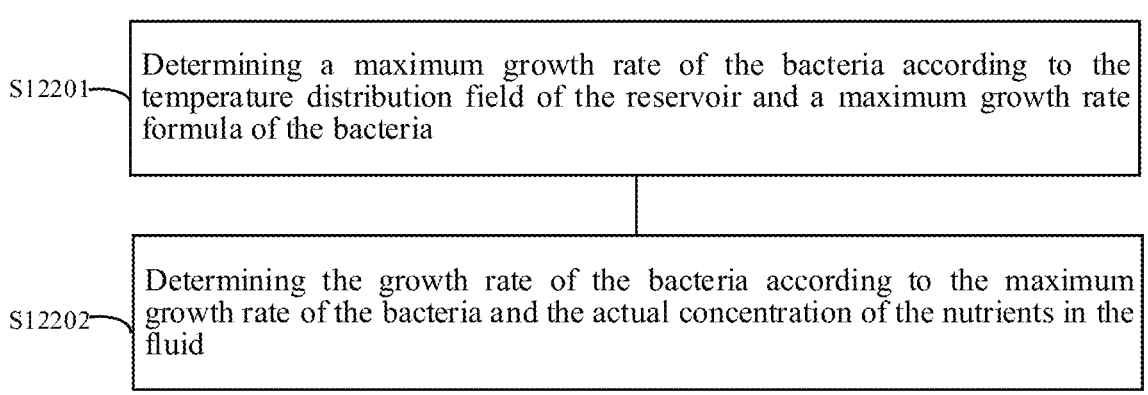
FIG. 12B is a flow diagram of determining a growth rate of bacteria provided in an embodiment of the present invention.

For the step S12101, determining the growth rate of the bacteria (including bacteria attached to rock surfaces and bacteria in the fluid) may include the following steps S12201-S12202, as shown in FIG. 12B.

Step S12201: determining a maximum growth rate of the bacteria according to the temperature distribution field of the reservoir and a maximum growth rate formula of the bacteria.

Currently, a square root model containing parameters such as activation energy and frequency factor is usually used to describe the maximum growth rate of the bacteria, but the field applicability of this model is poor (mainly embodied in inaccurate prediction results). However, after continuous research, the inventor found that the temperature of the reservoir is a main factor that influences the maximum growth rate of the bacteria and the distribution of the bacteria in the reservoir. Therefore, under the condition of a sufficient injected water source and bacterial nutrient source, the embodiment uses the maximum growth rate formula of the bacteria (including bacteria attached to rock surfaces and bacteria in the fluid) with the temperature as a main variable to simulate the spatial distribution of the maximum growth rate of the bacteria in the reservoir.

For the step S12201, the determining a maximum growth rate of the bacteria includes:

determining the maximum growth rate $g_{max}(\vec{r}, t)$ of the bacteria according to the temperature distribution field $T(\vec{r}, t)$ of the reservoir and the maximum growth rate formula of the bacteria expressed by the following formula (12-2):

$$g_{max}(\vec{r}, t) = [b_1(T(\vec{r}, t) - T_{min})]^2 * \{1 - \exp[c_1(T(\vec{r}, t) - T_{max})]\}, \quad (12\text{-}2)$$

where $b_1$ and $c_1$ are a first bacterial growth empirical parameter and a second bacterial growth empirical parameter, respectively; $T_{max}$ and $T_{min}$ are a maximum temperature and a minimum temperature for bacterial growth, respectively.

Step S12202: determining the growth rate of the bacteria according to the maximum growth rate of the bacteria and the actual concentration of the nutrients in the fluid.

Considering that bacterial growth is an irreversible first-order reaction or that bacterial metabolism consumes the nutrients, for the step S12202, the determining the growth rate of the bacteria includes: determining the growth rate $g_{actual}$ bacteria according to the maximum growth rate $g_{max}(\vec{r}, t)$ of the bacteria, the actual concentration $c_{nu}$ of the nutrients in the fluid, a Monod half growth coefficient ks, and the following formula (12-3):

$$g_{actual} = \frac{g_{max} C_{nu}}{k_s + C_{nu}}. \quad (12\text{-}3)$$

Step S12102: determining the total amount of the bacteria on rock surfaces according to an amount of the bacteria attached to the rock surfaces in the reservoir associated with both an apparent concentration of the bacteria in the fluid and a total amount of the bacteria on the rock surfaces, and the growth rate and a decay rate of the bacteria.

Specifically, main factors that influence the amount of the bacteria attached to the rock surfaces in the reservoir are bacterial adsorption and desorption rates, and the bacteria attached to the rock surfaces of the reservoir form biofilms, so the amount $C_{deposition}$ of the bacteria attached to the rock surfaces in the reservoir can be determined according to a clogging rate $k_{clogging}$ (a constant which may be in 1/day), a declogging rate $k_{declogging}$ (a constant which may be in 1/day), the apparent concentration $C_{bacteriantran}$ of the bacteria in the fluid, the total amount $V_{bacteriatran}$ of the bacteria on the rock surfaces, and the following formula (12-4):

$$C_{deposition} = k_{clogging} C_{bacterian} - k_{declogging} V_{bacteriatran}. \quad (12\text{-}4)$$

The bacteria attached to the rock surfaces form biofilms, thereby reducing the porosity of the reservoir. In the embodiment, the amount of the bacteria on the rock surfaces is determined mainly by two factors: a net value added by bacterial growth and decay, and the attached amount.

For the step S12102: the determining the total amount of the bacteria on the rock surfaces may include: determining the total amount $V_{bacteriatran}$ of the bacteria on the rock surfaces according to the amount $C_{deposition}$ of the bacteria attached to the rock surfaces in the reservoir, and the growth rate $g_{actual}$ and the decay rate $k_{decay}$ of the bacteria, and the following formula:

$$\frac{\partial bacteriatran}{\partial t} = (g_{actual} - k_{decay}) V_{bacteriatran} + C_{depositon}. \quad (12\text{-}5)$$

In the above formula (12-5), the variation of the total amount of the bacteria on the rock with time is illustrated on the left side, and a total growth value of metabolic decay of the bacteria on the rock surfaces and a quantity of deposited bacteria are illustrated on the right side respectively.

Step S12103: establishing an apparent concentration distribution equation of the bacteria in the fluid according to the Darcy apparent velocity of the fluid, a dispersion coefficient of the bacteria, the growth rate and the decay rate of the bacteria, and the amount of the bacteria attached to the rock surfaces in the reservoir.

In the embodiment, main considerations are diffusion of the bacteria due to a concentration gradient, convection migration of the bacteria due to water injection, and growth and decay of the bacteria, and the first four factors cause changes in bacterial concentration (including a decrease in concentration due to the formation of biofilms by the bacteria attached to rock of the reservoir). Since the macroscopic effect of irregular motion of bacterial flagellar oscillation in the reservoir is not obvious, the irregular motion effect generated by flagellar oscillation is merged into a convection term in the model; and the effect of bacterial Brownian motion is covered by the effect of bacterial diffusion. In addition, since bacterial chemotaxis has a small effect on distribution rules of the bacteria in the reservoir, this effect is covered by the convective effect, and is combined with the convection term into one term.

For the step S12103, the establishing the apparent concentration distribution equation of the bacteria in the fluid may include: establishing, according to the Darcy apparent velocity u of the fluid, the dispersion coefficient $D_{sum}$ of the bacteria, the growth rate $g_{actual}$ and the decay rate $k_{decay}$ of the bacteria, and the amount $C_{deposition}$ of the bacteria attached to the rock surfaces in the reservoir, the apparent concentration distribution equation of the bacteria in the fluid expressed by the following formula (12-6):

$$D_{sum}\nabla^2 C_{bacteriatran} - u\nabla C_{bacteriatran} + (g_{actual} - k_{decay})C_{bacteriatran} = \frac{\partial bacteriatran}{\partial t} + C_{depositon}, \quad (12\text{-}6)$$

where $c_{nufrol}$ is apparent concentration distribution of the bacteria in the fluid.

Step S12104: establishing an apparent concentration distribution equation of the nutrients according to the Darcy velocity of the fluid, the dispersion coefficient of the nutrients, the total amount of the bacteria on the rock surfaces, and the apparent concentration of the bacteria.

In the embodiment, main considerations are diffusion of the nutrients due to a concentration gradient, and convection migration of the nutrients due to water injection, and the two factors cause changes in nutrient concentration.

For the step S12104, the establishing the apparent concentration distribution equation of the nutrients may include: establishing, according to the Darcy velocity $u(\vec{r}, t)$ of the fluid, the dispersion coefficient $D^{nusum}$ of the nutrients, the total amount $V_{bacteriatran}$ of the bacteria on the rock surfaces in the reservoir, and the apparent concentration $C_{bacteriatran}$ of the bacteria, the apparent concentration distribution equation of the nutrients expressed by the following formula (12-7):

$$D_{nusum}\nabla^2 C_{nutran} - u\nabla C_{nutran} - \frac{g_{actual}}{Y}(C_{bacteriatran} - V_{bacteriatran}) = \frac{\partial nutran}{\partial t}. \quad (12\text{-}7)$$

where $g_{actual}$ is the growth rate of the bacteria; Y is a yield coefficient of the bacteria; and $C_{nutran}$ is apparent concentration distribution of the nutrients. A one-dimensional form of the above formula (12-7) may be written as $$D_{nusum}\frac{\partial^2 C_{nutran}}{\partial x^2} - u\frac{\partial C_{nutran}}{\partial x} - \frac{g_{actual}}{Y}(C_{bacteriatran} - V_{bacteriatran}) = \frac{\partial nutran}{\partial t}.$$

Step S12105: determining a spatio-temporal evolution simulation equation of reservoir damage by bacteria according to the apparent concentration distribution equation of the nutrients and the apparent concentration distribution equation of the bacteria in the fluid.

Wherein the spatio-temporal evolution simulation equation is used to simulate a four-dimensional spatio-temporal evolution process of characteristics of reservoir damage caused by the bacteria.

Specifically, the spatio-temporal evolution simulation equation of reservoir damage by bacteria can be obtained according to the apparent concentration distribution equation of the nutrients expressed by the above formula (12-7) and the apparent concentration distribution equation of the bacteria in the fluid expressed by the above formula (12-6), and in conjunction with other equations (12-1)-(12-5). That is, the spatio-temporal evolution simulation equation of reservoir damage by bacteria is equivalent to an equation set composed of formulas (12-1)-(12-7).

In summary, according to the present invention, the growth rate of the bacteria is creatively determined according to the temperature distribution field of the reservoir and the actual concentration of the nutrients in the fluid; the total amount of the bacteria on rock surfaces is determined according to the amount of the bacteria attached to the rock surfaces in the reservoir, and the growth rate and the decay rate of the bacteria; the apparent concentration distribution equation of the bacteria in the fluid is established according to the Darcy apparent velocity of the fluid, the dispersion coefficient of the bacteria, the growth rate and the decay rate of the bacteria, and the amount of the bacteria attached to the rock surfaces in the reservoir; the apparent concentration distribution equation of the nutrients is established according to the Darcy velocity of the fluid, the dispersion coefficient of the nutrients, the total amount of the bacteria on the rock surfaces, and the apparent concentration of the bacteria; and the spatio-temporal evolution simulation equation of reservoir damage by bacteria is determined according to the apparent concentration distribution equation of the nutrients and the apparent concentration distribution equation of the bacteria in the fluid. Thus, by using the determined spatio-temporal evolution simulation equation, a four-dimensional spatio-temporal evolution process of characteristics of reservoir damage caused by bacteria can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Figure 12C:
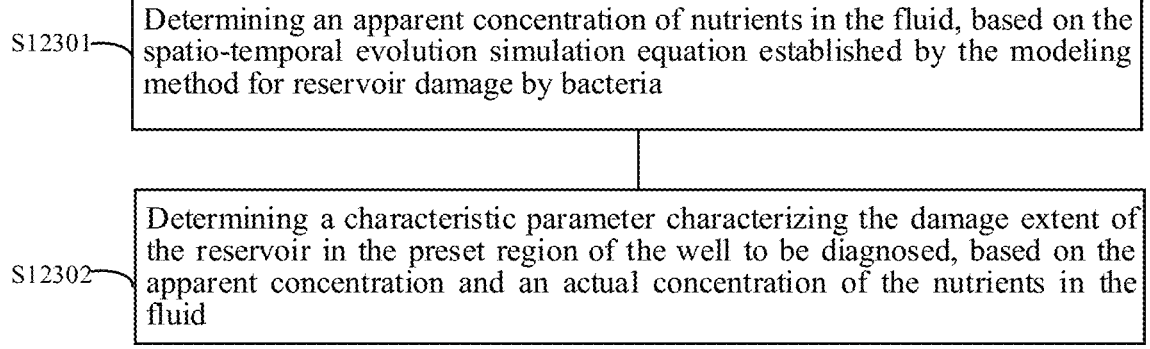
FIG. 12C is a flow diagram of a method for determining a damage extent of a reservoir provided in an embodiment of the present invention.

FIG. 12C is a flow diagram of a method for determining a damage extent of a reservoir provided in an embodiment of the present invention. As shown in FIG. 12C, the method may include steps S12301-S12302.

Step S12301: determining an amount of bacteria attached to rock surfaces, based on the spatio-temporal evolution simulation equation established by the modeling method for reservoir damage by bacteria.

For the spatio-temporal evolution simulation equation of reservoir damage by bacteria expressed by the above formulas (12-6)-(12-7), the amount of the attached bacteriadeposition can be solved by referring to the process of solving the volume concentration of deposited particles in the above Embodiment 1.

The amount of the attached bacteria $C_{deposition}$ is calculated by the above method. As the spatio-temporal evolution simulation equation established by the above modeling method for reservoir damage by bacteria comprehensively considers the influence of various physical and chemical factors on reservoir damage during migration of the bacteria and nutrients in the fluid, the amount of the attached (deposited) bacteria obtained by the step S12301 is very precise.

Step S12302: determining a characteristic parameter characterizing the damage extent of the reservoir in the preset region of the well to be diagnosed, based on the amount of the bacteria attached to the rock surfaces.

Wherein the characteristic parameter is permeability of the reservoir.

For the step S12302, the determining a characteristic parameter characterizing the damage extent of the reservoir in the preset region of the well to be diagnosed may include: determining the permeability $K(\vec{r}, t)$ of the reservoir based on the amount $C_{deposition}$ of the bacteria attached to the rock surfaces and the density ρ of the bacteria and the following formula (12-8), $$K(\vec{r}, t)/K_0(\vec{r}) = \left(\frac{\phi_0 - C_{deposition}(\vec{r}, t)/\rho}{\phi_0}\right)^3, \quad (12\text{-}8)$$

where $\phi_0$ is an initial value of porosity of the reservoir; and $K_o(\vec{r})$ is an initial value of the permeability of the reservoir. Wherein the characteristic parameter is a skin factor of the reservoir.

For the step S12302, the determining a characteristic parameter characterizing the damage extent of the reservoir in the preset region of the well to be diagnosed includes: determining the permeability $K(\vec{r}, t)$ of the reservoir based on the apparent concentration $C_{nutran}(\vec{r}, t)$ and the actual concentration $c_{nu}(\vec{r}, t)$ of the nutrients in the fluid and formula $$K(\vec{r}, t)/K_0(\vec{r}) = \left(\frac{C_{nutran}(\vec{r}, t)}{C_{nu}(\vec{r}, t)\phi_0}\right)^3;$$

and determining the skin factor $S(\vec{r}, t)$ of the reservoir based on the permeability $K(\vec{r}, t)$ of the reservoir and the following formula (12-9):

$$S(\vec{r}, t) = \left(\frac{1}{K_d(\vec{r}, t)} - 1\right)\ln\left(\frac{r_{sw}}{r_w}\right), \quad (12\text{-}9)$$

where $K_o(\vec{r})$ is an initial value of the permeability of the reservoir; and $\overline{K_d(\vec{r}, t)} = K(\vec{r}, t)/K_o(\vec{r})$, $r_w$ is a wellbore radius of the well to be diagnosed, and $r_{sw}$ is a damage radius of the reservoir.

The characteristic parameter (e.g., the permeability $K(\vec{r}, t)$ and the skin factor $S(\vec{r}, t)$ of the reservoir) obtained by the step S12302 is a result of 4D quantitative simulation of spatio-temporal evolution (not shown). Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

In summary, the apparent concentration of the nutrients in the fluid can be determined by using the determined spatio-temporal evolution simulation equation, and then the characteristic parameter (e.g., the permeability and/or the skin factor of the reservoir) characterizing the damage extent of the reservoir in the preset region of the well to be diagnosed can be determined based on the apparent concentration and the actual concentration of the nutrients in the fluid, whereby a four-dimensional spatio-temporal evolution process of the reservoir damage characteristic caused by bacteria can be simulated quantitatively. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Embodiment 13—Polymer

Figures 13A, 13B:
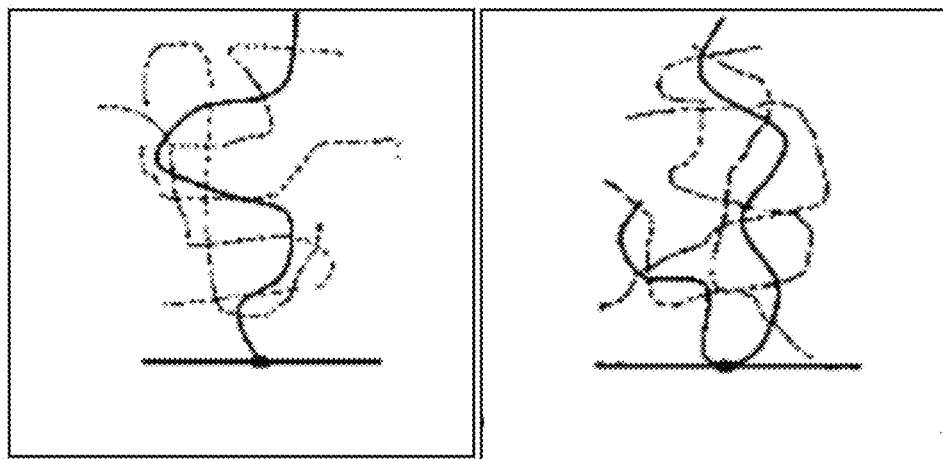
FIGS. 13A to 13C are schematic diagrams of a layer adsorption mode of a polymer provided in an embodiment of the present invention.
Figure 13C:
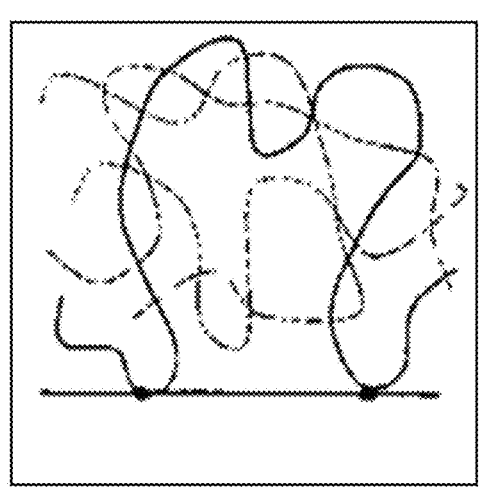
Figure 13D:
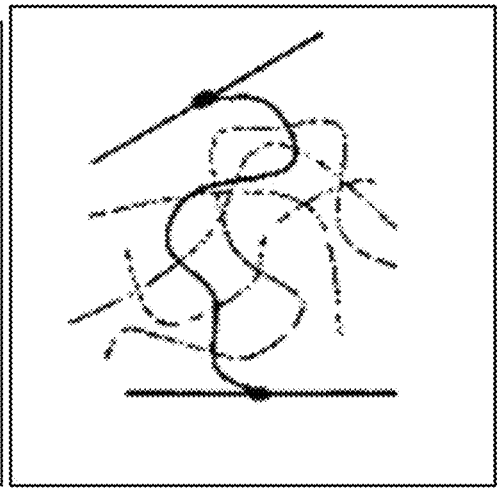
FIG. 13D is a schematic diagram of a bridging adsorption mode of a polymer provided in an embodiment of the present invention.

According to the adsorption mechanism of polymers on the surfaces of porous media, adsorption of polymers on a reservoir includes layer adsorption (as shown in FIG. 13A)-FIG. (13C) for example) and bridging adsorption (as shown in FIG. 13D). There is very rich physicochemical interaction between a polymer and a medium wall, and the adsorption behavior is very complex. At the beginning of polymer adsorption, the polymer is subjected to layer adsorption such that more and more molecular chains of the polymer are adsorbed together to form an adsorbed polymer (i.e., precipitated polymer); when more and more molecular chains of the polymer are adsorbed at the same location in the reservoir, the mass of the adsorbed polymer here becomes larger and larger, and when the mass of the adsorbed polymer at that location is greater than a critical mass (m>$m_c$), the polymer is subjected to bridging adsorption such that more molecular chains are adsorbed together to form an adsorbed polymer (i.e., precipitated polymer) with a larger mass or a larger quantity of molecular chains. In practical application, the mass of the adsorbed polymer can easily reach the critical mass, so the following embodiments are described and explained with a scenario in which bridging adsorption occurs.

The essence of clogging by polymer adsorption is migration and adsorption of polymers in a fluid within the reservoir. Thus, the core of the embodiments of the present invention is to establish a kinetic model of migration and adsorption of a polymer according to the law of mass conservation. Specifically, based on mass conservation, a diffusion relationship, and the like, a spatio-temporal evolution control phenomenological model (containing a concentration C of the polymer in a fluid) of concentration distribution of the polymer in a reservoir around a well to be diagnosed is established, and in conjunction with a relationship between the concentration C and a characteristic parameter characterizing the damage extent of the reservoir such as permeability, spatio-temporal field distribution of the characteristic parameter such as permeability can be diagnosed.

Figure 13E:
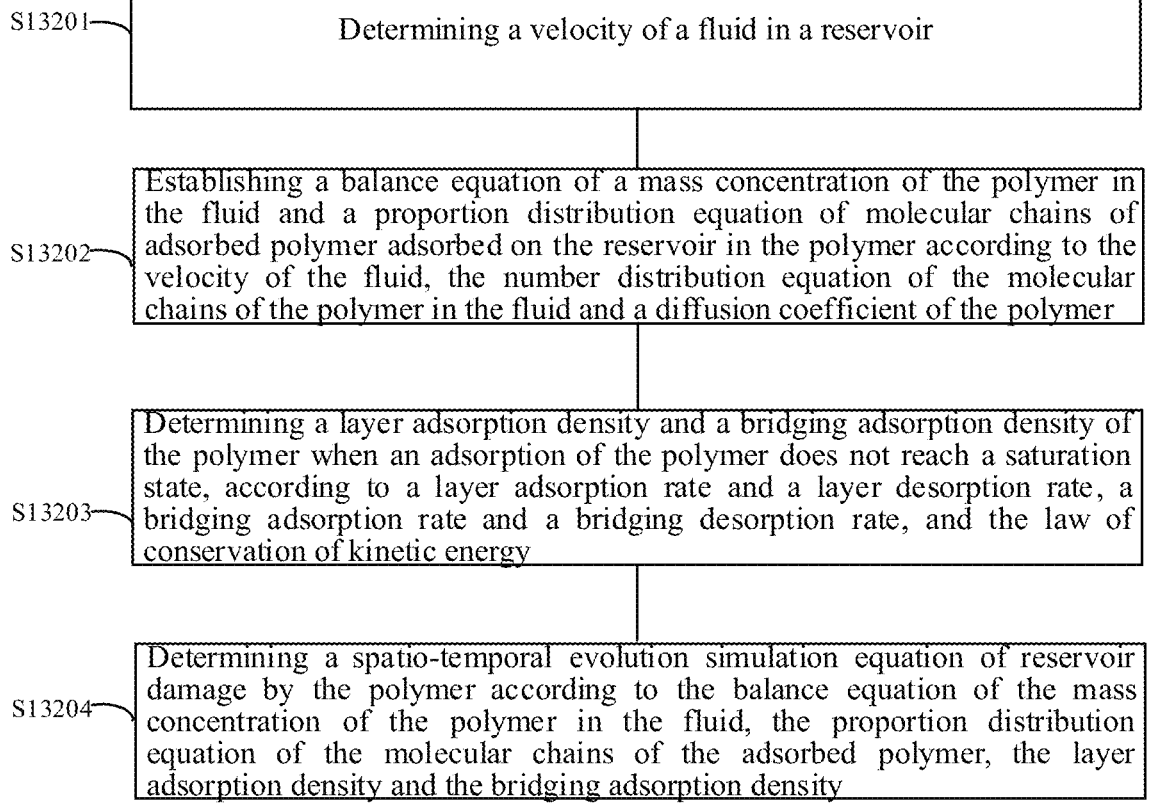
FIG. 13E is a flow diagram of a modeling method for reservoir damage by a polymer provided in an embodiment of the present invention.

FIG. 13E is a flow diagram of a modeling method for reservoir damage by a polymer provided in an embodiment of the present invention. As shown in FIG. 13E, the modeling method may include the following steps S13201-S13204.

Step S13201: determining a velocity of a fluid in a reservoir.

Wherein the reservoir is located in a preset region of a well to be diagnosed (e.g., a polymer injection well).

For the step S13201, determining the velocity of the fluid containing the polymer in the reservoir includes: establishing a pressure conduction equation for the fluid entering the reservoir; and determining the velocity of the fluid according to the pressure conduction equation and a Darcy formula.

For the specific determination process, reference can be made to the process of determining the velocity of the fluid in the above Embodiment 1 (i.e., the above formulas (1-1) and (1-2) and related description thereof).

At the time t, a total number of of molecular chains of the polymer contained in a unit control volume of the fluid at a location $\vec{r}$ in a porous medium of the reservoir is N ($\vec{r}$, t), and the unit control volume flows at a velocity v in a pore for time $\Delta t$ with a displacement r. Layer adsorption and bridging adsorption cause the number of molecular chains of the polymer adsorbed on the reservoir to change, so the number of molecular chains of the polymer contained in the unit control volume becomes N ($\vec{r}+\Delta\vec{r}$, t+$\Delta t$). During the above adsorption process, the total number of polymer molecular chains in the entire reservoir remains unchanged.

Before performing step S13202, the modeling method may further include: establishing, based on the number of molecular chains of the polymer subjected to layer adsorption on the reservoir and the number of molecular chains of the polymer subject to bridging adsorption on the reservoir, a number distribution equation of molecular chains of the polymer in the fluid expressed by the following formula (13-1):

$$N(\vec{r}+\Delta\vec{r}, t+\Delta t) - N(\vec{r}, t) = \int_{t}^{t+\Delta t}\left(\chi\frac{\partial A_l}{\partial t} + \frac{\partial A_b}{\partial t}\right)dt, \quad (13-1)$$

where $\chi$ is a mass proportion of the polymer subjected to layer adsorption at any location $\vec{r}$ of the reservoir at time t (i.e., the proportion of the mass of the polymer subject to layer adsorption at any location $\vec{r}$ in the reservoir in a total mass of all adsorbed polymer at that location at time t);

$$\frac{\partial A_l}{\partial t} = \rho_s A_s^l \frac{1-\phi_0}{\phi_0 m}\frac{\partial \Gamma_l}{\partial t}, \frac{\partial A_b}{\partial t} = \rho_s A_s^b \frac{1-\phi_0}{\phi_0 m}\frac{\partial \Gamma_b}{\partial t},$$

where m is an average mass of molecular chains of the adsorbed polymer; $\rho_s$ is density of the adsorbed polymer; $A_s^l$ and $A_s^b$ are a specific surface area of the reservoir where layer adsorption occurs and a specific surface area of the reservoir where bridging adsorption occurs, respectively; $\phi_0$ is porosity of the reservoir (the porosity of the reservoir can be considered to be unchanged in various embodiments of the present invention); $\Gamma_l$, $\Gamma_b$ are layer adsorption density and bridging adsorption density, respectively; and N ($\vec{r}$, t) is the number of molecular chains of the polymer in the fluid at any location $\vec{r}$ in the reservoir at time t, Step S13202: establishing a balance equation of a mass concentration of the polymer in the fluid and a proportion distribution equation of molecular chains of adsorbed polymer adsorbed on the reservoir in the polymer according to the velocity of the fluid, the number distribution equation of the molecular chains of the polymer in the fluid and a diffusion coefficient of the polymer.

Wherein the proportion of the molecular chains of the adsorbed polymer is the proportion of a number of the molecular chains of the adsorbed polymer in an initial number of molecular chains of the polymer in the fluid.

Figure 13F:
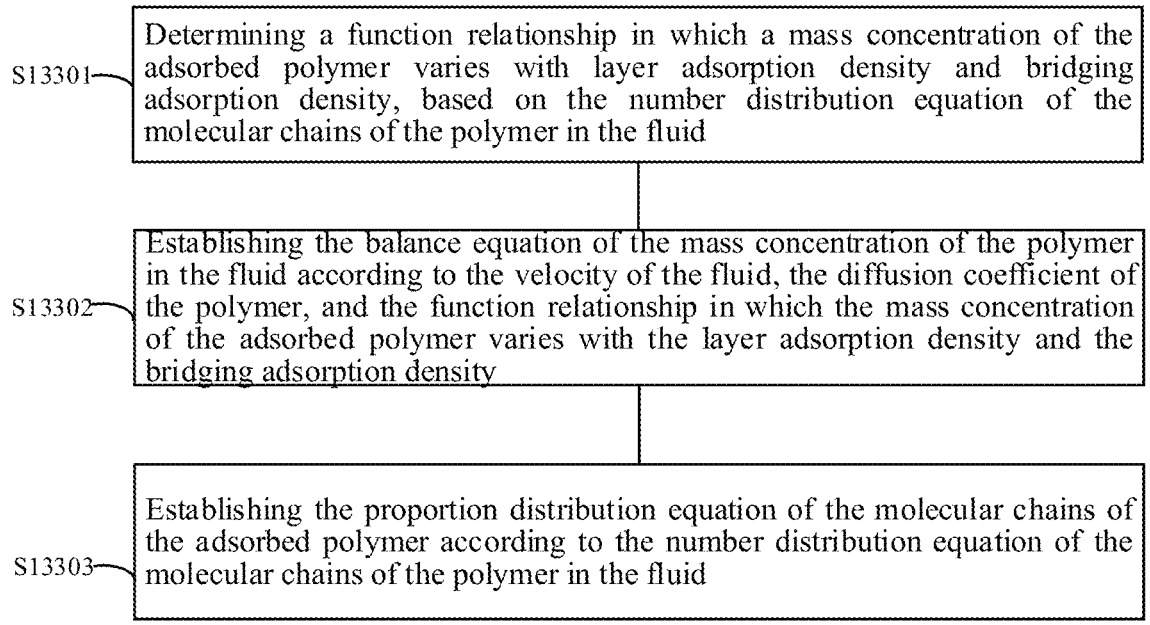
FIG. 13F illustrates establishment of a proportion distribution equation of molecular chains of an adsorbed polymer provided in an embodiment of the present invention.

For the step S13202, the establishing a balance equation of a mass concentration of the polymer in the fluid and a proportion distribution equation of molecular chains of adsorbed polymer adsorbed on the reservoir in the polymer may include the following steps S13301-S13303, as shown in FIG. 13F.

Step S13301: determining a function relationship in which a mass concentration of the adsorbed polymer varies with layer adsorption density and bridging adsorption density, based on the number distribution equation of the molecular chains of the polymer in the fluid.

Both the left and right sides of the above formula (13-1) represent the number of molecular chains subjected to polymer adsorption per unit control volume. Multiplying the two sides of formula (13-1) by m (the mass of the polymer subject to adsorption) and taking a limit value $\Delta t\to 0$ yields a formula with two sides that can represent a molecular mass (i.e., mass concentration $C_d(\Gamma_l, \Gamma_b)$) of the polymer subject to polymer adsorption per unit control volume, $$C_d(\Gamma_l, \Gamma_b) = \chi\rho_s A_s^l\frac{1-\phi_0}{\phi_0}\frac{\partial \Gamma_l}{\partial t} + \rho_s A_s^b\frac{1-\phi_0}{\phi_0}\frac{\partial \Gamma_b}{\partial t}, \quad (13-2)$$

where $\chi\rho_s A_s^l\frac{1-\phi_0}{\phi_0}\frac{\partial \Gamma_l}{\partial t}$ represents a mass concentration of the polymer subjected to layer adsorption; and $$\rho_s A_s^b\frac{1-\phi_0}{\phi_0}\frac{\partial \Gamma_b}{\partial t}$$

represents a mass concentration of the polymer subject to bridging adsorption.

Step S13302: establishing the balance equation of the mass concentration of the polymer in the fluid according to the velocity of the fluid, the diffusion coefficient of the polymer, and the function relationship in which the mass concentration of the adsorbed polymer varies with the layer adsorption density and the bridging adsorption density.

For the adsorption process of the polymer, the polymer molecular chains follow the law of mass conservation, i.e., the change in the mass of flowing polymer molecules is equal to the negative change in the mass of polymer molecules adsorbed on surfaces of the porous medium of the reservoir:

$$\frac{\partial \phi_0\rho w(\vec{r}, t)}{\partial t} + \frac{\partial}{\partial \vec{r}}\left(\phi_0 v(\vec{r}, t)\rho w(\vec{r}, t) + j(\vec{r}, t)\right) = -m_d,$$

where j ($\vec{r}$, t) is a diffusion flow rate of the polymer, and $$j(\vec{r}, t) = -\phi_0 D\frac{\partial \rho w(\vec{r}, t)}{\partial x},$$

where D represents the diffusion coefficient of the polymer; $m_d$ ($\vec{r}$, t) represents the mass of the polymer subjected to adsorption; u ($\vec{r}$, t) is the velocity of the fluid; $\rho$ is density of the fluid; w ($\vec{r}$, t) is a mass fraction of the flowing polymer molecules in the fluid; and $\phi_0$ is an initial value of the porosity of the reservoir. If the change in the mass per unit control volume (i.e., the change in the mass concentration) is considered, due to microscopic changes within the pores (not considering the porosity $\phi_0$), the above formula can be changed to the mass concentration shown in following formula (13-3).

For the step S13302, the establishing the balance equation of the mass concentration of the polymer in the fluid may include: establishing, according to the velocity $v(\vec{r}, t)$ of the fluid, the diffusion coefficient D of the polymer, and the function relationship $C_d(\Gamma_l, \Gamma_b)$ in which the mass concentration of the adsorbed polymer varies with the layer adsorption density and the bridging adsorption density, the balance equation of the mass concentration of the polymer in the fluid expressed by the following formula (13-3):

$$\frac{\partial C(\vec{r}, t)}{\partial t} + \nabla(v(\vec{r}, t)C(\vec{r}, t) - D\nabla C(\vec{r}, t)) = -C_d(\Gamma_l, \Gamma_b), \quad (13-3)$$

where $C(\vec{r}, t)$ is the mass concentration of the polymer in the fluid ($C=\rho w(\vec{r}, t)$); and $\Gamma_l$ and $\Gamma_b$ are the layer adsorption density and the bridging adsorption density, respectively.

Step S13303: establishing the proportion distribution equation of the molecular chains of the adsorbed polymer according to the number distribution equation of the molecular chains of the polymer in the fluid.

For the step S13303, the establishing the proportion distribution equation of the molecular chains of the adsorbed polymer may include: establishing, according to the number distribution equation of the molecular chains of the polymer in the fluid and $$P_{poly} = \frac{N}{N_0},$$

the proportion distribution equation of the molecular chains of the adsorbed polymer expressed by the following formula (13-4):

$$\frac{\partial P_{poly}(\vec{r}, t)}{\partial t} + v(\vec{r}, t)\nabla P_{poly}(\vec{r}, t) = \quad (13-4)$$

$$-\chi\rho_s A_s^l \frac{1-\phi}{\phi C_0} \frac{\partial \Gamma_l}{\partial t} - \rho_s A_s^b \frac{1-\phi}{\phi C_0} \frac{\partial \Gamma_b}{\partial t},$$

where $C_0$ is an initial mass concentration of the polymer in the fluid; $N_0$ is an initial number of the molecular chains of the polymer in the fluid; $P_{poly}$ is the proportion of the number of the molecular chains of the adsorbed polymer in the initial number of the molecular chains of the polymer in the fluid; and $v(\vec{r}, t)$ is the velocity of the fluid.

Specifically, Taylor first-order expansion (ignoring the second-order term) is carried out for the first term at the left side of the number distribution equation of the molecular chains of the polymer in the fluid expressed by the equation (13-1), and then both sides of the equation are simultaneously divided by $\Delta t$, where $$\frac{\Delta \vec{r}}{\Delta t} = v(\vec{r}, t),$$

and when $\Delta t \rightarrow 0$, the above formula (13-1) becomes:

$$\frac{\partial N(\vec{r}, t)}{\partial t} + v(\vec{r}, t)\frac{\partial N(\vec{r}, t)}{\partial \vec{r}} = -\chi\frac{\partial A_l}{\partial t} - \frac{\partial A_b}{\partial t}, \text{ where } \frac{\partial A_l}{\partial t} \text{ and } \frac{\partial A_b}{\partial t} \quad (13-5)$$

represent an adsorption rate for layer adsorption and an adsorption rate for bridging adsorption (i.e., the number of polymer molecular chains adsorbed per unit time), respectively:

$$\frac{\partial A_l}{\partial t} = \rho_s A_s^l \frac{1-\phi_0}{\phi_0 m} \frac{\partial \Gamma_l}{\partial t},$$

$$\frac{\partial A_b}{\partial t} = \rho_s A_s^b \frac{1-\phi_0}{\phi_0 m} \frac{\partial \Gamma_b}{\partial t},$$

where $\rho_s$ represents the density of the adsorbed polymer; $A_s^l$ and $A_s^b$ represent a specific surface area of the medium where layer adsorption occurs and a specific surface area of the medium where bridging adsorption occurs, respectively (there may be $A_s^l = A_s^b = A_s$); $\phi_0$ represents the porosity of the reservoir; $\Gamma_l$ represents the layer adsorption density of the polymer; and $\Gamma_b$ represents the bridging adsorption density of the polymer. Substituting the above two formulas into formula (7) yields the following formula:

$$\frac{\partial N(\vec{r}, t)}{\partial t} + v(\vec{r}, t)\nabla N(\vec{r}, t) = -\chi\rho_s A_s^l \frac{1-\phi}{\phi m} \frac{\partial \Gamma_l}{\partial t} - \rho_s A_s^b \frac{1-\phi}{\phi m} \frac{\partial \Gamma_b}{\partial t}, \quad (13-6)$$

and then dividing both sides of the above formula (13-6) by $N_0$ (i.e., the initial number of the molecular chains of the polymer in the fluid) yields the proportion distribution equation of the molecular chains of the adsorbed polymer expressed by formula (13-4).

Step S13203: determining a layer adsorption density and a bridging adsorption density of the polymer when an adsorption of the polymer does not reach a saturation state, according to the layer adsorption rate and the layer desorption rate, the bridging adsorption rate and the bridging desorption rate, and the law of conservation of kinetic energy.

The adsorption process of the polymer also follows the law of conservation of kinetic energy, i.e., adsorption and desorption of polymer molecules per unit time meets a dynamic equilibrium and finally reach an adsorption saturation state. The desorption and adsorption dynamic equilibrium of layer adsorption and bridging adsorption can be expressed as formulas (13-7) and (13-8).

For part of the step S13203, determining the layer adsorption density of the polymer when the adsorption of the polymer does not reach the saturation state may include: determining the layer adsorption density of the polymer according to the layer adsorption rate and the layer desorption rate and the law of conservation of kinetic energy expressed by the following formula:

$$\frac{\partial \Gamma_l}{\partial t} = \kappa_a^l(\Gamma_l^\infty - \Gamma_l) - \kappa_d^l \Gamma_l, \quad (13-7)$$

where $\kappa_a^l$ is the layer adsorption rate; $\kappa_d^l$ is the layer desorption rate; $\Gamma_l^\infty$ is a saturated layer adsorption density of the polymer when the adsorption of the polymer reaches the saturation state; and $\Gamma_l$ is the layer adsorption density.

For part of the step S13203, determining the bridging adsorption density of the polymer when the adsorption of the polymer does not reach the saturation state may include: determining the bridging adsorption density of the polymer when the adsorption of the polymer does not reach saturation according to the bridging adsorption rate and the bridging desorption rate and the law of conservation of kinetic energy expressed by the following formula:

$$\frac{\partial \Gamma_b}{\partial t} = \kappa_a^b P_{poly}(\Gamma_b^\infty - \Gamma_b) - \kappa_d^b \Gamma_b, \tag{13-8}$$

where $\kappa_a^b$ is the bridging adsorption rate; $\kappa_d^b$ is the bridging desorption rate; $\Gamma_b^\infty$ is a saturated bridging adsorption density of the polymer when the adsorption of the polymer reaches the saturation state; $\Gamma_b$ is the bridging adsorption density; and $P_{poly}$ is the proportion of the number of the molecular chains of the adsorbed polymer in the initial number of the molecular chains of the polymer in the fluid.

In the above two formulas (13-7)-(13-8), on the left side, the term $$\frac{\partial \Gamma_i}{\partial t}$$

represents the layer adsorption density of the polymer per unit time when the adsorption of the polymer does not reach the saturation state, and on the right side, $\kappa_a^i(\Gamma_i^\infty - \Gamma_i)$ represents dynamic adsorption density of the polymer per unit time, and $\kappa_d^i \Gamma_i$ represents dynamic desorption density per unit time, where i=l (layer adsorption), b (bridging adsorption).

Step S13204: determining a spatio-temporal evolution simulation equation of reservoir damage by the polymer according to the balance equation of the mass concentration of the polymer in the fluid, the proportion distribution equation of the molecular chains of the adsorbed polymer, the layer adsorption density and the bridging adsorption density.

Substituting formula (13-2) to the right side of formula (13-3) yields the following formula (13-9):

$$\frac{\partial C(\vec{r}, t)}{\partial t} + \nabla(v(\vec{r}, t)C(\vec{r}, t) - D\nabla C(\vec{r}, t)) = \tag{13-9}$$

$$-\chi \rho_s A_s^l \frac{1-\phi}{\phi} \frac{\partial \Gamma_l}{\partial t} - \rho_s A_s^b \frac{1-\phi}{\phi} \frac{\partial \Gamma_b}{\partial t},$$

and then substituting the above formulas (13-7)-(13-8) into formulas (13-4) and (13-9) yields the spatio-temporal evolution simulation equation of reservoir damage by the polymer. That is, the spatio-temporal evolution simulation equation of reservoir damage by the polymer is equivalent to an equation set composed of formulas (13-4), and (13-7)-(13-9).

In summary, according to the present invention, the balance equation of the mass concentration of the polymer in the fluid and the proportion distribution equation of the molecular chains of adsorbed polymer adsorbed on the reservoir in the polymer is creatively established according to the velocity of the fluid, the number distribution equation of the molecular chains of the polymer in the fluid and the diffusion coefficient of the polymer; the layer adsorption density and the bridging adsorption density of the polymer when the adsorption of the polymer does not reach the saturation state is determined according to the layer adsorption rate and the layer desorption rate, the bridging adsorption rate and the bridging desorption rate, and the law of conservation of kinetic energy; and the spatio-temporal evolution simulation equation of reservoir damage by the polymer is determined according to the balance equation of the mass concentration of the polymer in the fluid, the proportion distribution equation of the molecular chains of the adsorbed polymer, the layer adsorption density and the bridging adsorption density. Thus, by using the determined spatio-temporal evolution simulation equation, a four-dimensional spatio-temporal evolution process of reservoir damage characteristics caused by the polymer can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Figure 13G:
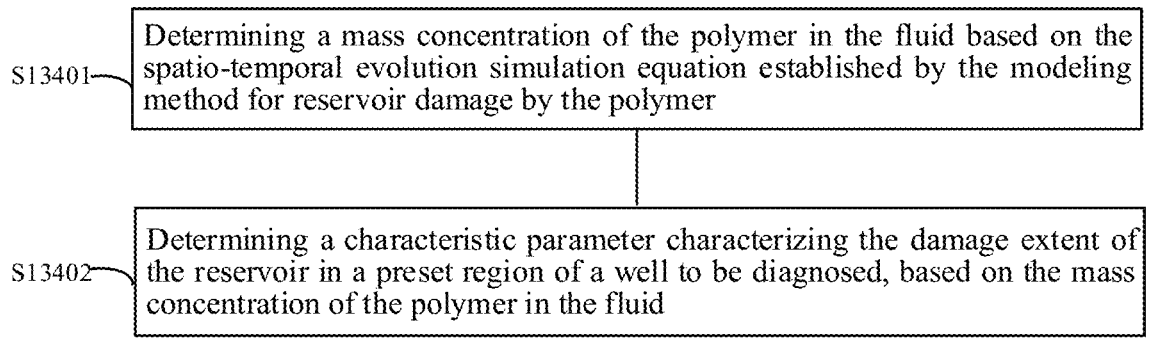
FIG. 13G is a flow diagram of a method for determining a damage extent of a reservoir provided in an embodiment of the present invention.

FIG. 13G is a flow diagram of a method for determining a damage extent of a reservoir provided in an embodiment of the present invention. As shown in FIG. 13G, the method may include steps S13401-S13402.

Step S13401: determining a mass concentration of the polymer in the fluid based on the spatio-temporal evolution simulation equation established by the modeling method for reservoir damage by the polymer.

For the polymer migration equation of reservoir damage by polymer adsorption expressed by the above formula (13-7), the volume concentration $C(\vec{r}, t)$ of the polymer can be calculated by referring to the process of solving the volume concentration of the deposited particles in the above Embodiment 1.

The mass concentration $C(\vec{r}, t)$ of the polymer in the fluid can be calculated by the above method. As the spatio-temporal evolution simulation equation established by the above modeling method of reservoir damage by polymer adsorption comprehensively considers the influence of various physical and chemical factors on reservoir damage during polymer adsorption within the reservoir, the mass concentration of the polymer in the fluid obtained by the step S13401 is very precise.

Step S13402: determining a characteristic parameter characterizing the damage extent of the reservoir in the preset region of the well to be diagnosed, based on the mass concentration of the polymer in the fluid.

Wherein the characteristic parameter is permeability of the reservoir.

For the step S13402, the determining a characteristic parameter characterizing the damage extent of the reservoir in the preset region of the well to be diagnosed may include:

determining the permeability $K(\vec{r}, t)$ of the reservoir based on the mass concentration $C(\vec{r}, t)$ of the polymer in the fluid and formula (13-10):

$$K(\vec{r}, t)/K_0(\vec{r}) = \left(1 - \frac{C_0(\vec{r}, t) - C(\vec{r}, t)}{\phi_0}\right)^{m_K}, \tag{13-10}$$

where $\phi_0$ is an initial value of porosity of the reservoir; $C_0(\vec{r}, t)$ is an initial mass concentration of the polymer in the fluid; $C^\infty$ is a maximum adsorption mass concentration of the polymer; $m_K$ is a second empirical value; and $K_o(\vec{r})$ is an initial value of the permeability of the reservoir.

Wherein the characteristic parameter is a fluid loss coefficient of the reservoir.

For the step S13402, the determining a characteristic parameter characterizing the damage extent of the reservoir in the preset region of the well to be diagnosed may include: determining the fluid loss coefficient $k(\vec{r}, t)$ of the reservoir based on the mass concentration of the polymer in the fluid and formula (13-11):

$$k(\vec{r}, t) = k_0(\vec{r}) \cdot \left(1 - \frac{C_0(\vec{r}, t) - C(\vec{r}, t)}{C^\infty}\right)^{m_k}, \quad (13\text{-}11)$$

where $\phi_0$ is the initial value of the porosity of the reservoir; $C_0(\vec{r}, t)$ is the initial mass concentration of the polymer in the fluid; $C^\infty$ is the maximum adsorption mass concentration of the polymer; $m_k$ is a first empirical value; and $k_0(\vec{r})$ is an initial value of the fluid loss coefficient of the reservoir.

Wherein the characteristic parameter is a skin factor of the reservoir.

For the step S13402, the determining a characteristic parameter characterizing the damage extent of the reservoir in the preset region of the well to be diagnosed includes: determining the permeability $K(\vec{r}, t)$ of the reservoir based on the mass concentration $C(\vec{r}, t)$ of the polymer in the fluid and formula $$K(\vec{r}, t)/K_0(\vec{r}) = \left(1 - \frac{C_0(\vec{r}, t) - C(\vec{r}, t)}{\phi_0}\right)^{m_K};$$

and determining the skin factor $S(\vec{r}, t)$ of the reservoir based on the permeability $K(\vec{r}, t)$ of the reservoir and formula (13-12):

$$S(\vec{r}, t) = \left(\frac{1}{K_d(\vec{r}, t)} - 1\right) \ln\left(\frac{r_{sw}}{r_w}\right), \quad (13\text{-}12)$$

where $K_o(\vec{r})$ is the initial value of the permeability of the reservoir; $\phi_0$ is the initial value of the porosity; $C_0(\vec{r}, t)$ is the initial mass concentration of the polymer in the fluid; $m_K$ is the second empirical value; $K_d(\vec{r}, t) = K(\vec{r}, t)/K_o(\vec{r})$; $r_w$ is a wellbore radius of the well to be diagnosed; and $r_{sw}$ is a damage radius of the reservoir.

Figure 13H:
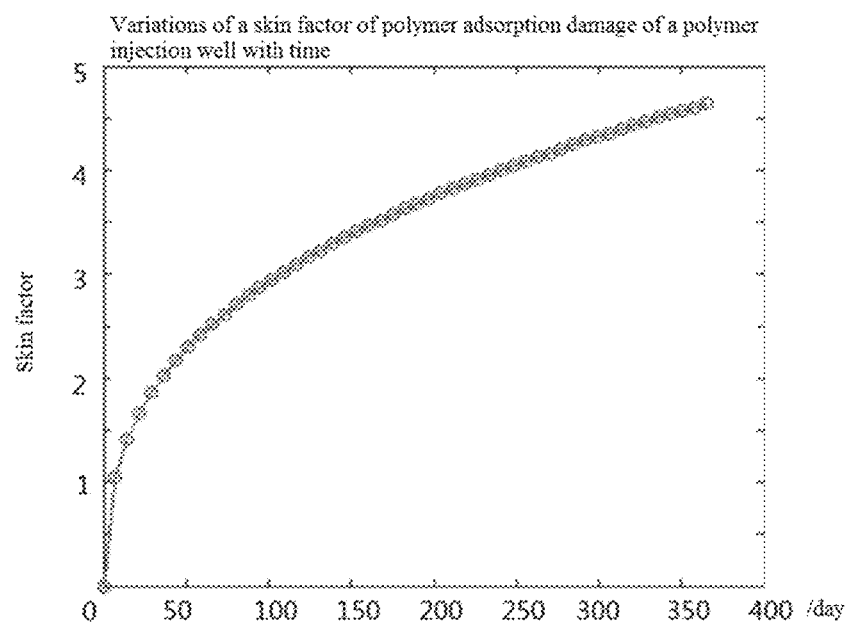
FIG. 13H is a schematic diagram of evolution of a skin factor over time provided in an embodiment of the present invention.
Figure 13I:
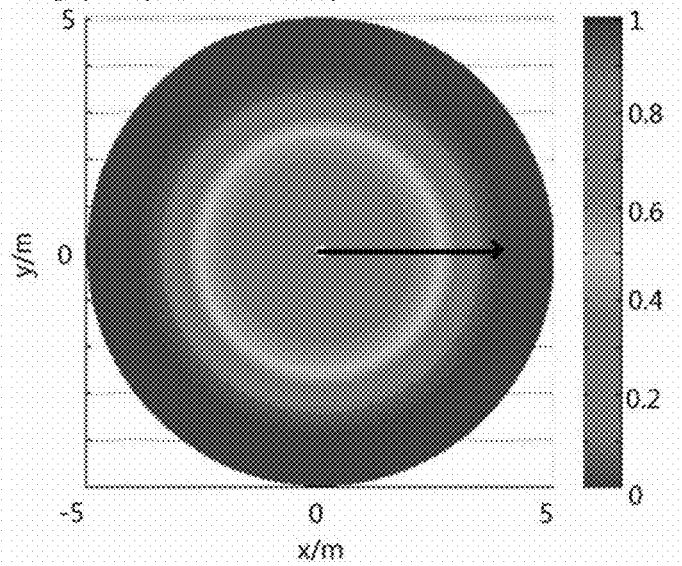
FIG. 13I is a schematic diagram of a radius of reservoir damage by a polymer at day 40 characterized by a permeability damage rate of the reservoir provided in an embodiment of the present invention.

The characteristic parameter (e.g., the permeability $K(\vec{r}, t)$ and the skin factor $S(\vec{r}, t)$ of the reservoir) obtained by the step S13402 is a result of 4D quantitative simulation of spatio-temporal evolution (as shown in FIG. 13H). More specifically, FIG. 13I shows a schematic diagram of a radius (a radius as indicated by an arrow) of reservoir damage by polymer adsorption at day 365 characterized by a permeability damage rate of the reservoir (the permeability damage rate $I(r_i, t)$, of the reservoir is determined based on the permeability $K(\vec{r}, t)$ of the reservoir and formula $$I(\vec{r}, t) = 1 - \frac{K(\vec{r}, t)}{K_{max}(\vec{r}, t)},$$

where $K_{max}(\vec{r}, t)$ is a maximum value of $K(\vec{r}, t)$), and a working person concerned can visually confirm the damage extent of the reservoir from FIG. 13I. Therefore, quantitative prediction of reservoir damage and spatio-temporal deduction of damage laws can be performed according to evolution characteristics of the permeability or the skin factor, which is of scientific guidance significance for preventing or avoiding reservoir damage, and formulating development plans for oil pools and subsequent well stimulation measures.

In the case where the permeability of the reservoir when each factor damages the reservoir is obtained in each of the above embodiments, the skin factor (or permeability damage rate) of the reservoir when each factor damages the reservoir can be obtained according to a relational expression (e.g., formula (3-8) or (5-14)) between the permeability and the skin factor (or permeability damage rate). Then, for various stages of the same diagnostic well, weighted summation is performed on the permeability (or skin factor or permeability damage rate) of the reservoir when each of the plurality of factors damages the reservoir respectively to determine the permeability (or skin factor or permeability damage rate) of the reservoir when the plurality of factors damage the reservoir simultaneously. Further, a contribution proportion of the permeability of the reservoir when each factor damages the reservoir to the total permeability (or total skin factor or total permeability damage rate) can also be determined.

In summary, according to the present invention, the mass concentration of the polymer in the fluid can be calculated creatively by using the determined spatio-temporal evolution simulation equation, then the characteristic parameter (e.g., the permeability and/or the skin factor of the reservoir) characterizing the damage extent of the reservoir in the preset region of the well to be diagnosed can be determined based on the determined mass concentration of the polymer, and thus, a four-dimensional spatio-temporal evolution process of characteristics of reservoir damage caused by polymer adsorption can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Field Verification and Application

Using relevant parameters provided on site, a total skin factor (as shown in FIGS. 14-A to 14-D) of the well to be diagnosed, after some time, is calculated and compared with a measured skin factor to verify the correctness and accuracy of the 4D quantitative simulation technology of spatio-temporal evolution established herein. Since the measured skin factor is the sum of a true skin factor and a pseudo skin factor, the measured skin factor needs to be decomposed, and the true skin factor obtained after decomposition is compared with the calculated skin factor to determine the correctness and accuracy of the 4D quantitative simulation technology.

The following is an example of well G01s1 in Suizhong oilfield 36-1. Relevant parameters and measured skin factors of the well are shown in Table 3.

Table 3 Measured results of basic parameters and skin factors of well G01s1 in Suizhong oilfield 36-1

| Parameter | Value | Parameter | Value |
|---|---|---|---|
| Actual production time (d) | 40 | initial permeability of reservoir ($10^{-3}$ μm$^2$) | 1660 |
| Actual production differential pressure (MPa) | 5.42 | Reservoir temperature (° C.) | 65 |
| wellbore radius (m) | 0.09 | Reservoir depth (m) | 1800 |
| well deviation angle (°) | 40 | initial porosity of reservoir (%) | 32 |
| Reservoir thickness (m) | 38.3 | Average radius of reservoir pore throats (μm) | 14 |
| Actual well completed thickness (m) | 33.7 | Oil-water interfacial tension of reservoir (mN/m) | 13.5 m |
| Liquid withdrawal rate (m$^3$/d) | 45 m$^3$/d | Density of produced sand grains (kg/m$^3$) | 2.65 |
| Oil phase viscosity of reservoir (mPa · s) | 120 | shale content of reservoir (%) | 15.3 |
| Reservoir pressure (MPa) | 13.2 | Dynamic Poisson's ratio of rock | 0.13 |
| Overlying rock layer pressure (MPa) | 1800 m | Bubble point pressure MPa | 11 |
| Rock volume density (kg/m$^3$) | 2.5 | Crude oil density g/cm$^3$ | 0.96 |
| Young's modulus of rock (MPa) | 500 | System coefficient | 1.1 |
| (Static) Poisson's ratio of rock | 0.13 | Colloidal asphaltene content % | 40.9 |
| Compression coefficient of reservoir rock (MPa$^{-1}$) | 5e−3 | Skin factor | 36.5 |

Figure 14A:
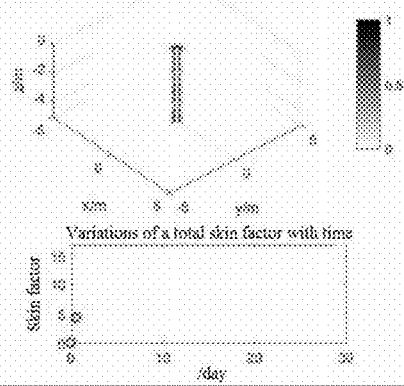
FIGS. 14A to 14D are schematic diagrams of a damage radius and a total skin factor of a reservoir at days 0.6, 2.4, 8.4 and 30 characterized by a permeability damage rate of the reservoir provided in an embodiment of the present invention.
Figure 14B:
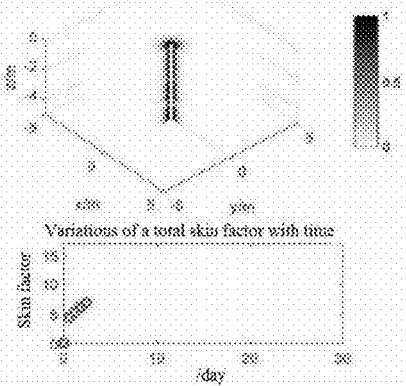
Figure 14C:
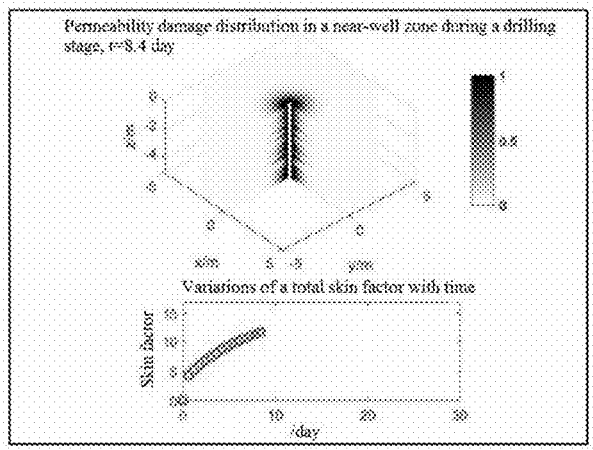
Figure 14D:
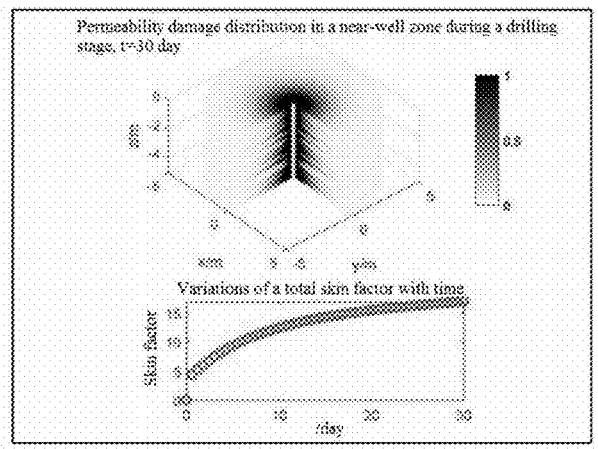
Figure 14E:
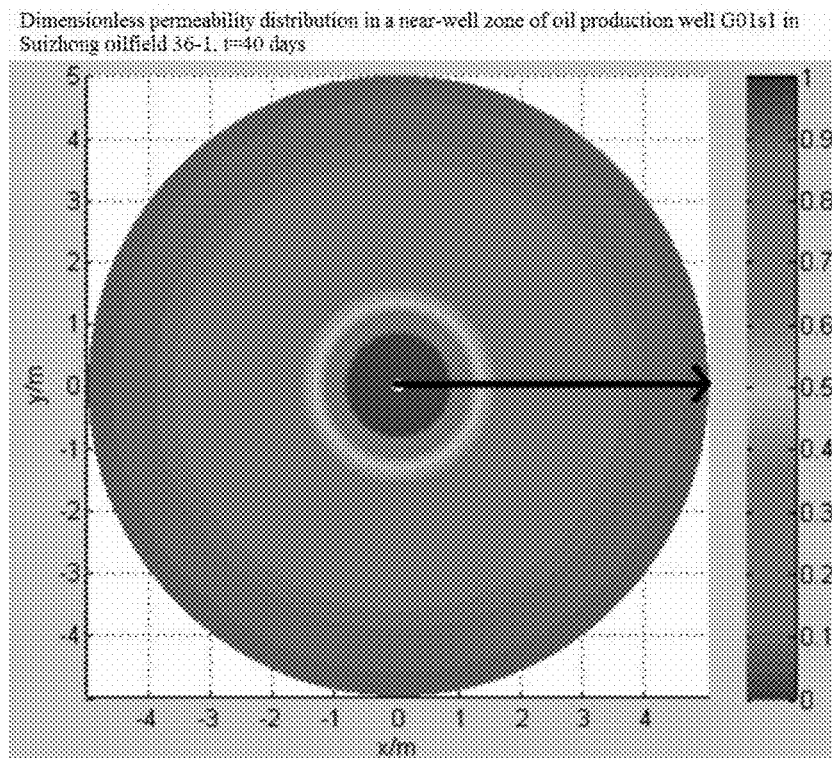
FIG. 14E is a schematic diagram of a total damage radius of a reservoir at day 40 characterized by a permeability damage rate of the reservoir provided in an embodiment of the present invention.
Figure 14F:
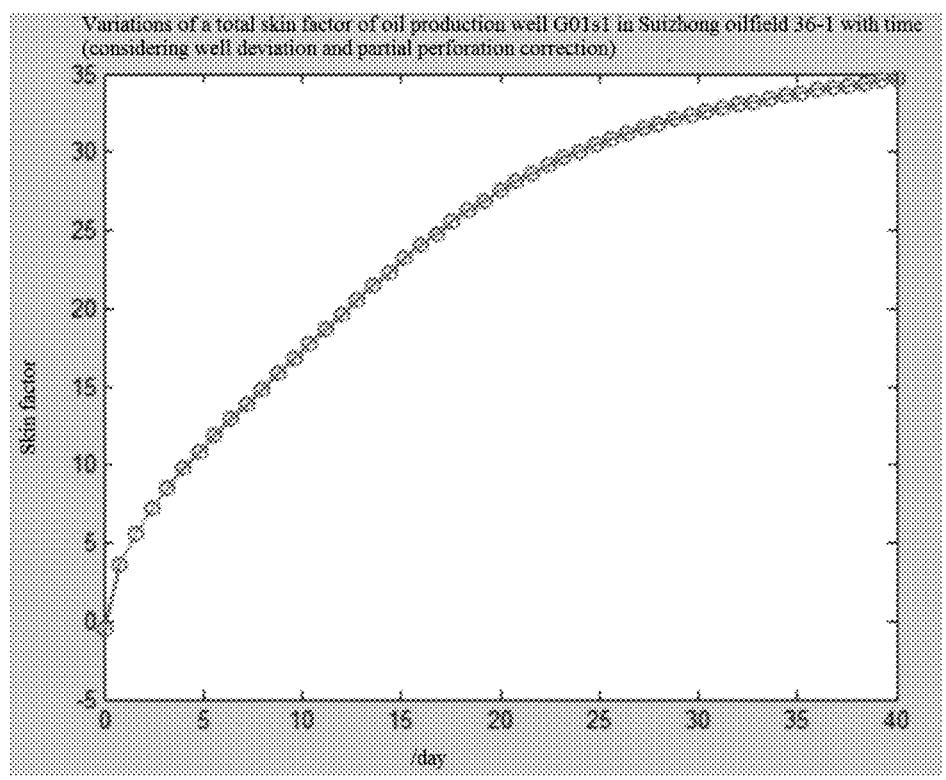
FIG. 14F is a schematic diagram of evolution of a total skin factor over time provided in an embodiment of the present invention.
Figure 14G:
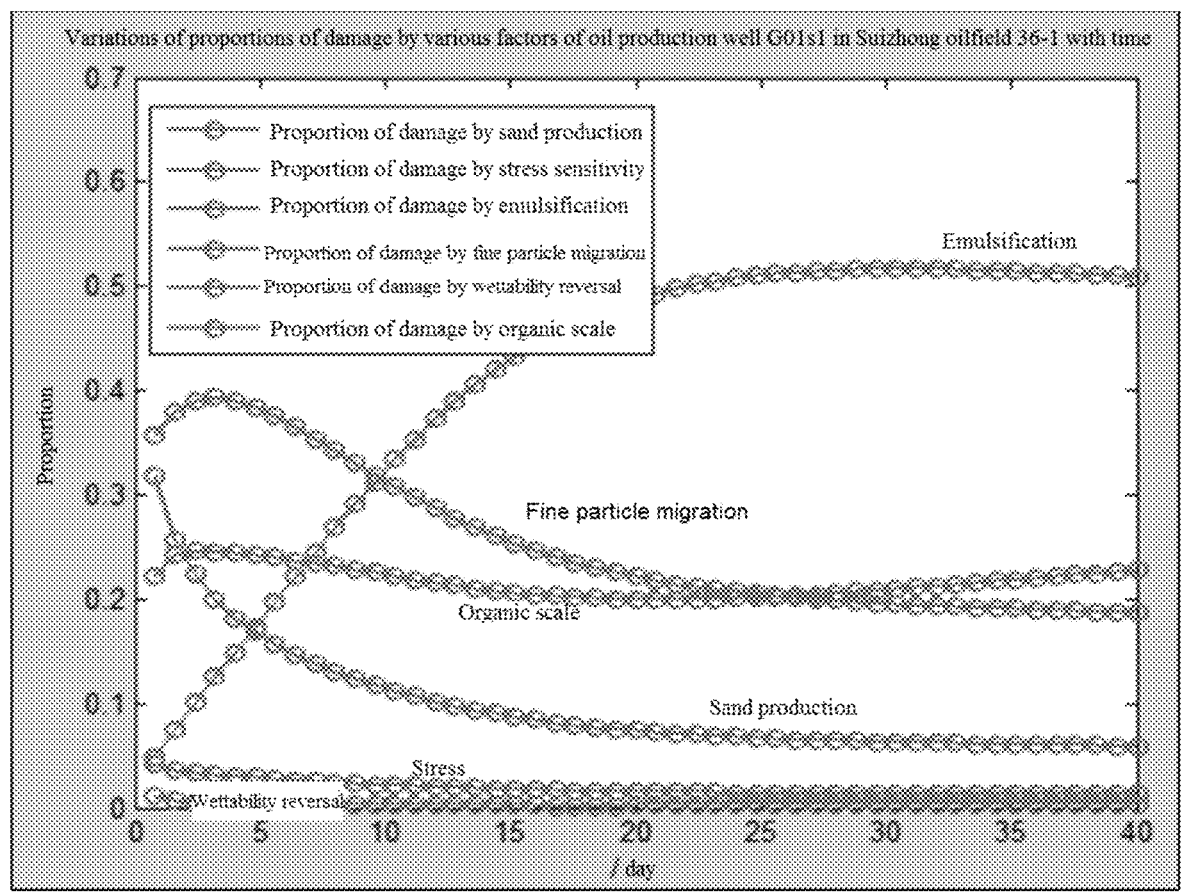
FIG. 14G illustrates an evolution law of a proportion of damage caused by various types of factors in a total damage, over time, provided in an embodiment of the present invention.

The parameters in Table 3 are input into software loaded with the above methods to obtain variations of damaged zone radii and damage extents (e.g., permeability damage rates) caused by six damage types: "sand production, stress sensitivity, emulsification, fine particle migration, wettability reversal, and organic scale" with time (as shown in FIGS. 7D, 6G, 9D, 4E, 8D, and 10F, respectively); and the distribution law of a total damaged zone radius (as shown in FIG. 14E, which is a maximum value of the damage radii corresponding to the damage factors) and the distribution law of a total damage extent (e.g., dimensionless permeability, which is equal to 1-permeability damage rate) over time after 40 days (as shown in FIG. 14F); and evolution laws of the proportions of damage caused by various types of factors in the total damage, over time, are as shown in FIG. 14G.

The simulation results show that at day 40, a total skin factor is 35.65, a measured skin factor is 36.5, and a pseudo skin factor due to well deviation and partial completion is 0.49, with a relative error of only 0.99%, which indicates very high conformity. Analysis based on the damage factors shows that the major damage factors are emulsification, fine particle migration, organic scale, and sand production for reservoir damage, while the damage caused by wettability reversal and stress sensitivity is very small. Of course, it is also possible to simulate the distribution and evolution of any reservoir damage parameter in a 4D space, such as at different depth points and in different directions, as needed.

In addition, the 4D quantitative simulation technology of spatio-temporal evolution established herein has been widely verified and applied in different types of oilfields in China, such as those developed by China National Offshore Oil Corporation, with an average accuracy of 95% or above, which fully proves the reliability, accuracy and practicality of this simulation technology. A comparison of simulation results for some of the wells is shown in Table 4.

Table 4 Comparison of simulation calculated values and measured values of skin factors of some wells

| Serial number | Well number | Operation stage | Actual measurement result | Calculation result | Accuracy rate/% | Major damage factor |
|---|---|---|---|---|---|---|
| 1 | 10a in oilfield LF 13-1 | Well drilling | 30 | 32.84 | 90.53 | Inorganic precipitation, and clay swelling |
| 2 | P10 in oilfield 34-24 of middle part of Bohai sea | Well drilling | 12.4 | 12.03 | 97.02 | Clay swelling |
| 3 | HZ 26-1-20 Sb | Well completion | 4.52 | 4.42 | 97.79 | Water lock effect, and fine particle migration |
| 4 | BZ 34-1 A23 | Oil production | 36.1 | 35.61 | 98.64 | Organic scale, and wettability reversal |
| 5 | JZ 9-3-A7 | Oil production | 12.1 | 11.85 | 97.93 | Early stage: organic scale, and stress sensitivity Mid to late stage: wettability |

-continued

| Serial number | Well number | Operation stage | Actual measurement result | Calculation result | Accuracy rate/% | Major damage factor |
|---|---|---|---|---|---|---|
| 6 | A20H1 in oilfield WC13-2 | Oil production | 12.1 | 13.17 | 91.16 | reversal, and organic scale Organic scale, and wettability reversal |
| 7 | Wen19-1-A6 | Oil production | 22.1 | 21.53 | 97.42 | Organic scale |
| 8 | Wen19-1-B5 | Oil production | 20 | 19.15 | 95.75 | Organic scale, and wettability reversal |
| 9 | M13 in Suizhong oilfield 36-1 | Water injection | 8.38 | 8.76 | 95.47 | Clay swelling, extraneous solid-phase particles, fine particles within the reservoir |

Thus, the embodiments described above can achieve the following advantages.

(1) The field verification shows that the 4D quantitative numerical simulation technology of spatio-temporal evolution of reservoir damage extents caused by 13 common reservoir damage types established by combining continuum mechanics and a probabilistic process can be used for quantitative 4D simulation of reservoir damage causes and extent in the whole process of oil-gas field exploration and development with high accuracy and precision, and strong practicality and operability; furthermore, it is proved that the quantitative simulation study of reservoir damage by combining continuum mechanics and the probabilistic process has higher scientificity, reliability and feasibility, and represents a future development direction.

(2) The 4D quantitative simulation technology of spatio-temporal evolution of reservoir damage established herein not only can achieve simulation of spatio-temporal evolution of various damage types and a total damage extent, but also can provide a sensitivity degree of each damage type to the total damage and quantitatively provide the proportion of each damage type in the total damage extent, and provides core technology for precisely controlling and eliminating reservoir damage and restoring production of oil wells and water injection capacity of water wells.

(3) The established 4D quantitative simulation technology for spatio-temporal evolution of reservoir damage can be used not only for quantitative simulation of reservoir damage but also for quantitative prediction of reservoir damage. For a well with reservoir damage, quantitative simulation and spatial-temporal evolution of reservoir damage are achieved by using historical parameters, which is of great significance for optimal design of a declogging measure and improvement of numerical simulation precision of oil pools; and for a well without reservoir damage, quantitative prediction of reservoir damage and spatio-temporal deduction of damage laws can be performed according to physical property parameters and engineering parameters to be implemented, which is of scientific guidance significance for preventing or avoiding reservoir damage, and formulating development plans for oil pools and subsequent well stimulation measures.

(4) Not only are the reservoir damage causes diverse and dynamically changing, but also the damage factors are mutually associated and mutually constrained, thus influencing the total damage extent of oil and water wells and the spatio-temporal evolution law. The research work on the mutual influences and constraints of the damage types should be strengthened later to further improve and enhance the accuracy of quantitative simulation of reservoir damage.

In summary, according to the present invention, based on a spatio-temporal evolution simulation equation of reservoir damage by each of a plurality of factors, a characteristic parameter characterizing reservoir damage by each of the plurality of factors is creatively determined; and the effective characteristic parameter characterizing the damage extent of the reservoir is determined based on the characteristic parameter characterizing reservoir damage by each of the plurality of factors. Thus, by using the spatio-temporal evolution simulation equations of reservoir damage by the relevant factors, the characteristic parameters (such as permeability) of reservoir damage caused by the factors respectively and a total characteristic parameter (such as total permeability or effective permeability) of reservoir damage caused by the plurality of relevant factors can be quantitatively simulated. Therefore, performing quantitative prediction of reservoir damage and spatio-temporal deduction of damage laws is of scientific guidance significance for preventing or avoiding reservoir damage, and formulating development plans for oil pools and subsequent well stimulation measures for a well without reservoir damage, and is of very great significance for optimal design of a declogging measure and improvement or restoration of oil well production and water well injection capacity for damaged wells, and improvement of numerical simulation precision of oil pools.

Correspondingly, an embodiment of the present invention further provides a system for determining a damage extent of a reservoir, the system including: a first parameter determination device (not shown) configured to, based on a spatio-temporal evolution simulation equation of reservoir damage by each of a plurality of factors, determine a characteristic parameter characterizing reservoir damage by each of the plurality of factors, wherein the reservoir is located in a preset region of a well to be diagnosed; and a second parameter determination device (not shown) configured to determine an effective characteristic parameter characterizing the damage extent of the reservoir based on the characteristic parameter characterizing reservoir damage by each of the plurality of factors.

The system for determining the damage extent of the reservoir has the same advantages as the above-mentioned method for determining the damage extent of the reservoir with respect to the prior art, which will not be described here.

Correspondingly, an embodiment of the present invention further provides a machine-readable storage medium that stores instructions which are configured to cause a machine to execute the method for determining the damage extent of the reservoir.

The machine-readable storage medium includes, but is not limited to, phase-change memory (short for phase change random access memory, PRAM, also called RCM/PCRAM), static random access memory (SRAM), dynamic random access memory (DRAM), other types of random access memory (RAM), read-only memory (ROM), electrically erasable programmable read-only memory (EEPROM), flash memory or other memory technologies, compact disc read-only memory (CD-ROM), digital versatile disk (DVD) or other optical storage, magnetic cartridge tape, magnetic tape disk storage or other magnetic storage devices, and various other media that can store program codes.

The steps in the above embodiments can be performed by a computer, and the processing procedures of various physicochemical quantities involved in certain steps (e.g., steps S1101-S1104) achieve simulation of a spatio-temporal evolution field of reservoir damage by the factors, and the processing procedures of various physicochemical quantities involved in certain steps (e.g., steps S1201-S1202) achieve prediction of spatio-temporal evolution of reservoir damage by the factors. The steps in the above embodiments can be performed by a processor.

Preferred implementations of the present invention are described above in detail with reference to the accompanying drawings. However, the present invention is not limited to the specific details in the above implementations. Within the scope of the technical concept of the present invention, various simple modifications can be made to the technical solutions of the present invention, and these simple modifications are all encompassed within the protection scope of the present invention.

In addition, it should be noted that the specific technical features described in the above specific implementations may be combined in any suitable manner without contradiction. To avoid unnecessary repetition, various possible combinations will not be described separately in the present invention.

In addition, various different implementations of the present invention may also be combined optionally, and the combinations should also be regarded as contents disclosed in the present invention so long as they do not depart from the idea of the present invention.

The invention claimed is:

1. A method for determining a damage extent of a reservoir, comprising:
    drilling a well to be diagnosed to the reservoir;
    applying a pressure to drive a fluid containing flowing particles to continuously intrude from a wellbore of the well to be diagnosed into the reservoir;
    determining a characteristic parameter characterizing reservoir damage by each of a plurality of factors based on a spatio-temporal evolution simulation equation of reservoir damage by each of the plurality of factors, wherein the reservoir is located in a preset region of the well to be diagnosed; and
    determining an effective characteristic parameter characterizing the damage extent of the reservoir based on the characteristic parameter characterizing reservoir damage by each of the plurality of factors,
    wherein the well to be diagnosed is a water injection well, a polymer injection well or an oil production well, the plurality of factors comprise extraneous solid-phase particles, the method further comprising:
        when the well to be diagnosed is in a drilling stage, determining a spatio-temporal evolution simulation equation of reservoir damage by the extraneous solid-phase particles by the following modeling process:
            determining a velocity of the fluid containing flowing particles in the reservoir;
            establishing a mass balance equation between the fluid and deposited particles on rock in the reservoir, based on a convection parameter and a diffusion parameter of the fluid;
            establishing a connection condition equation between a volume concentration of the deposited particles and a volume concentration of the fluid, based on the convection parameter and the diffusion parameter of the fluid; and
            determining the spatio-temporal evolution simulation equation of reservoir damage by the particles according to a relationship between a mass fraction of the flowing particles and a volume concentration of the flowing particles, the velocity of the fluid, the mass balance equation and the connection condition equation, wherein the spatio-temporal evolution simulation equation is used to simulate a four-dimensional spatio-temporal evolution process of characteristics of reservoir damage caused by the extraneous solid-phase particles.

2. The method for determining the damage extent of the reservoir according to claim 1, wherein when the well to be diagnosed is in the drilling stage, the plurality of factors further comprise at least one of: clay swelling, migration of fine particle within the reservoir, inorganic precipitation, and water lock effect;
    wherein when the well to be diagnosed is an oil production well and is in an oil production stage, the plurality of factors further comprise at least two of: migration of fine particle within the reservoir, sand production, emulsification, Jamin effect, stress sensitivity, wettability reversal, and organic scale;
    wherein when the well to be diagnosed is a water injection well and is in a water injection stage, the plurality of factors further comprise at least two of: clay swelling, bacteria, water lock effect, extraneous solid-phase particles, fine particle migration, and inorganic precipitation; or
    wherein when the well to be diagnosed is a polymer injection well and is in a polymer injection stage, the plurality of factors further comprise at least two of: polymer, clay swelling, extraneous solid-phase particles, fine particle migration, and inorganic precipitation.

3. The method for determining the damage extent of the reservoir according to claim 2, further comprising: determining a spatio-temporal evolution simulation equation of reservoir damage by the migration of fine particle within the reservoir by the following modeling process:

determining a velocity of a fluid in the reservoir;

establishing a mass balance equation between the fluid and deposited fine particles on rock in the reservoir, based on a convection parameter and a diffusion parameter of the fluid and a mass change rate of migrating fine particles in the fluid, wherein there is a correlation between the mass change rate of the migrating fine particles and the velocity of the fluid;

establishing a connection condition equation between a volume concentration of the deposited fine particles and a volume concentration of the fluid, based on the convection parameter and the diffusion parameter of the fluid; and determining the spatio-temporal evolution simulation equation of reservoir damage by the migrating fine particles within the reservoir according to a relationship between a mass fraction of the migrating fine particles and a volume concentration of the migrating fine particles, the velocity of the fluid, the mass balance equation and the connection condition equation, wherein the spatio-temporal evolution simulation equation is used to simulate a four-dimensional spatio-temporal evolution process of characteristics of reservoir damage caused by the fine particles.

4. The method for determining the damage extent of the reservoir according to claim 2, further comprising: determining a spatio-temporal evolution simulation equation of reservoir damage by the clay swelling by the following modeling process:

determining a Darcy apparent velocity of a fluid in the reservoir;

establishing a mass balance equation for water molecules in the fluid according to the Darcy apparent velocity of the fluid and a diffusion coefficient of the water molecules in the fluid;

establishing a diffusion equation for diffusion of the water molecules in the fluid to the interior of rock in the reservoir according to Fick's law of diffusion; and determining the spatio-temporal evolution simulation equation of reservoir damage by the clay swelling according to the diffusion equation and the mass balance equation, wherein the spatio-temporal evolution simulation equation is used to simulate a four-dimensional spatio-temporal evolution process of characteristics of reservoir damage caused by the clay swelling, and the clay is a component of the rock.

5. The method for determining the damage extent of the reservoir according to claim 2, further comprising: determining a spatio-temporal evolution simulation equation of reservoir damage by the water lock effect by the following modeling process:

determining a Darcy apparent velocity of a fluid in the reservoir;

establishing an aqueous phase motion equation of the reservoir according to the Darcy apparent velocity of the fluid and a diffusion coefficient of water molecules in the fluid;

establishing a permeability distribution equation of the reservoir according to pore size distribution characteristics of pores of the reservoir and a preset permeability model of the reservoir; and determining the spatio-temporal evolution simulation equation of reservoir damage by the water lock effect according to the permeability distribution equation and the aqueous phase motion equation, wherein the spatio-temporal evolution simulation equation is used to simulate a four-dimensional spatio-temporal evolution process of characteristics of reservoir damage caused by the water lock effect.

6. The method for determining the damage extent of the reservoir according to claim 2, further comprising: determining a spatio-temporal evolution simulation equation of reservoir damage by the inorganic precipitation by the following modeling process:

determining a Darcy apparent velocity of a fluid in the reservoir;

determining an ion concentration loss corresponding to each of a plurality of ions in an extraneous fluid, wherein the ion concentration loss is caused by a precipitation reaction between each of the ions and a corresponding ion in the fluid in the reservoir;

establishing a migration equation for each of the ions according to the Darcy apparent velocity of the fluid, the ion concentration loss corresponding to each of the ions, and a diffusion coefficient of each of the ions; and determining the spatio-temporal evolution simulation equation of reservoir damage by the inorganic precipitation according to the migration equation for each of the ions and a reaction coefficient of a precipitate produced by each of the ions, wherein the spatio-temporal evolution simulation equation is used to simulate a four-dimensional spatio-temporal evolution process of characteristics of reservoir damage caused by the corresponding precipitates produced by the plurality of ions.

7. The method for determining the damage extent of the reservoir according to claim 2, further comprising: determining a spatio-temporal evolution simulation equation of reservoir damage by the sand production by the following modeling process:

determining a velocity of a fluid in the reservoir;

establishing a mass balance equation between the fluid and deposited sand grains on rock in the reservoir, based on a convection parameter and a diffusion parameter of the fluid and a mass change rate of sand grains in the fluid, wherein there is a correlation between the mass change rate of the sand grains and a crude oil production of the reservoir;

establishing a connection condition equation between a volume concentration of the deposited sand grains and a volume concentration of the fluid, based on the convection parameter and the diffusion parameter of the fluid; and determining the spatio-temporal evolution simulation equation of reservoir damage by the sand production according to a relationship between a mass fraction of the sand grains and a volume concentration of the sand grains, the velocity of the fluid, the mass balance equation and the connection condition equation.

8. The method for determining the damage extent of the reservoir according to claim 2, further comprising: determining a spatio-temporal evolution simulation equation of reservoir damage by the emulsification by the following modeling process:

determining a Darcy apparent velocity of a fluid in the reservoir;

determining a viscosity of an oil phase according to a temperature field of the reservoir and a function relationship between the viscosity of the oil phase and a temperature;

determining a radius of an emulsified droplet formed by an emulsification of the fluid according to the Darcy apparent velocity of the fluid, the viscosity of the oil phase, and an emulsification condition of the fluid; and determining the spatio-temporal evolution simulation equation of reservoir damage by emulsification clogging according to a pore size distribution function of pores of the reservoir and the radius of the emulsified droplet, wherein the spatio-temporal evolution simulation equation is used to simulate a four-dimensional spatio-temporal evolution process of characteristics of reservoir damage caused by the emulsification clogging.

9. The method for determining the damage extent of the reservoir according to claim 2, further comprising: determining a spatio-temporal evolution simulation equation of reservoir damage by the Jamin effect by the following modeling process:

determining a Darcy apparent velocity of a fluid in the reservoir, wherein permeability of the reservoir is lower than preset permeability;

establishing an aqueous phase motion equation of the reservoir according to the Darcy apparent velocity of the fluid and a diffusion coefficient of water molecules in the fluid;

establishing a permeability distribution equation of the reservoir according to pore size distribution characteristics of pores of the reservoir and a preset permeability model of the reservoir; and determining the spatio-temporal evolution simulation equation of reservoir damage by the Jamin effect according to the permeability distribution equation and the aqueous phase motion equation, wherein the spatio-temporal evolution simulation equation is used to simulate a four-dimensional spatio-temporal evolution process of characteristics of reservoir damage caused by the Jamin effect.

10. The method for determining the damage extent of the reservoir according to claim 2, further comprising: determining a spatio-temporal evolution simulation equation of reservoir damage by the stress sensitivity by the following modeling process:

determining an effective stress on the reservoir;

determining a flow rate of a fluid in the reservoir according to pore size distribution characteristics of pores of the reservoir, a diameter and length of each capillary bundle of the reservoir under the effective stress, and a fluid flow formula, wherein the capillary bundle is composed of a plurality of solid matrices and pores between the plurality of solid matrices; and determining the spatio-temporal evolution simulation equation of reservoir damage by the stress sensitivity according to a permeability model of the reservoir and the flow rate of the fluid in the reservoir, wherein the spatio-temporal evolution simulation equation is used to simulate a four-dimensional spatio-temporal evolution process of characteristics of reservoir damage caused by the stress sensitivity.

11. The method for determining the damage extent of the reservoir according to claim 2, further comprising: determining a spatio-temporal evolution simulation equation of reservoir damage by the organic scale by the following modeling process:

determining a pressure of the reservoir;

determining a first relational expression in which a maximum dissolved quantity of the organic scale in a crude oil produced from the reservoir varies with the pressure of the reservoir, according to a bubble point pressure of the reservoir, a molar volume of the crude oil at the bubble point pressure, a solubility parameter of the crude oil, a solubility parameter of the organic scale in the crude oil, and a molar volume of the organic scale;

determining a second relational expression in which a mole number of organic scale particles in the crude oil varies with both the pressure of the reservoir and the maximum dissolved quantity of the organic scale in the crude oil, according to a distribution function of organic scale particles in the organic scale and a mole number of the crude oil, wherein the distribution function is a proportional function of a mole number of organic scale particles with a particle size greater than a preset particle size to a total mole number of the organic scale particles; and determining the spatio-temporal evolution simulation equation of reservoir damage by the organic scale according to the second relational expression, the first relational expression and the pressure of the reservoir, wherein the spatio-temporal evolution simulation equation is used to simulate a four-dimensional spatio-temporal evolution process of characteristics of reservoir damage caused by the organic scale.

12. The method for determining the damage extent of the reservoir according to claim 2, further comprising: determining a spatio-temporal evolution simulation equation of reservoir damage by the wettability reversal by the following modeling process:

determining a relationship between a pressure distribution field of an aqueous phase and a pressure distribution field of capillaries in the reservoir according to a pressure distribution equation of the reservoir, wherein the capillaries are formed by the wettability reversal of a contact interface between the aqueous phase and an oil phase in the reservoir;

determining a pressure distribution field of the oil phase according to the relationship between the pressure distribution field of the aqueous phase and the pressure distribution field of the capillaries and a force balance condition of the capillaries;

determining a velocity distribution field of the oil phase according to the pressure distribution field of the oil phase and a Darcy formula; and determining the spatio-temporal evolution simulation equation of reservoir damage by the wettability reversal according to a convection diffusion law of the oil phase, the velocity distribution field and a dispersion coefficient of the oil phase, wherein the spatio-temporal evolution simulation equation is used to simulate a four-dimensional spatio-temporal evolution process of characteristics of reservoir damage caused by the wettability reversal.

13. The method for determining the damage extent of the reservoir according to claim 2, further comprising: determining a spatio-temporal evolution simulation equation of reservoir damage by the bacteria by the following modeling process:

determining a growth rate of the bacteria according to a temperature distribution field of the reservoir and an actual concentration of nutrients in a fluid in the reservoir;

determining a total amount of the bacteria on rock surfaces according to an amount of the bacteria attached to the rock surfaces in the reservoir associated with both an apparent concentration of the bacteria in the fluid and the total amount of the bacteria on the rock surfaces, and the growth rate and a decay rate of the bacteria;

establishing an apparent concentration distribution equation of the bacteria in the fluid according to a Darcy velocity of the fluid, a dispersion coefficient of the bacteria, the growth rate and the decay rate of the bacteria, and the amount of the bacteria attached to the rock surfaces in the reservoir;

establishing an apparent concentration distribution equation of the nutrients according to the Darcy velocity of the fluid, a dispersion coefficient of the nutrients, the total amount of the bacteria on the rock surfaces, and the apparent concentration of the bacteria; and determining the spatio-temporal evolution simulation equation of reservoir damage by the bacteria according to the apparent concentration distribution equation of the nutrients and the apparent concentration distribution equation of the bacteria in the fluid, wherein the spatio-temporal evolution simulation equation is used to simulate a four-dimensional spatio-temporal evolution process of characteristics of reservoir damage caused by the bacteria.

14. The method for determining the damage extent of the reservoir according to claim 2, further comprising determining a spatio-temporal evolution simulation equation of reservoir damage by the polymer by the following modeling process:

determining a velocity of a fluid in the reservoir;

establishing a balance equation of a mass concentration of polymer in the fluid and a proportion distribution equation of molecular chains of adsorbed polymer adsorbed on the reservoir in the polymer according to the velocity of the fluid, a number distribution equation of molecular chains of the polymer in the fluid and a diffusion coefficient of the polymer, wherein the proportion of the molecular chains of the adsorbed polymer is the proportion of a number of the molecular chains of the adsorbed polymer in an initial number of molecular chains of the polymer in the fluid;

determining a layer adsorption density and a bridging adsorption density of the polymer when an adsorption process of the polymer does not reach saturation, according to a layer adsorption rate and a layer desorption rate, a bridging adsorption rate and a bridging desorption rate, and the law of conservation of kinetic energy; and determining the spatio-temporal evolution simulation equation of reservoir damage by the polymer according to the balance equation of the mass concentration of the polymer in the fluid, the proportion distribution equation of the molecular chains of the adsorbed polymer, the layer adsorption density and the bridging adsorption density.

15. The method for determining the damage extent of the reservoir according to claim 1, wherein determining an effective characteristic parameter characterizing the damage extent of the reservoir comprises:

determining an effective characteristic parameter $F(\vec{r}, t)$ characterizing the damage extent of the reservoir based on a characteristic parameter $F_i(\vec{r}, t)$ characterizing reservoir damage by an ith factor of the plurality of factors and the following formula, $$F(\vec{r}, t) = \sum_{i=1}^{n} L_i F_i(\vec{r}, t),$$

where $L_i$ is a weight of $F_i(\vec{r}, t)$; and n is a number of the plurality of factors.

16. A non-transitory machine-readable storage medium, the machine-readable storage medium stores instructions which are configured to enable a machine to execute the method for determining a damage extent of a reservoir according to claim 1.

17. A system for determining a damage extent of a reservoir, comprising:

a drill for drilling a well to be diagnosed to the reservoir;

a pump for applying a pressure to drive a fluid containing flowing particles to continuously intrude from a wellbore of the well to be diagnosed into the reservoir;

a first parameter determination device configured to, based on a spatio-temporal evolution simulation equation of reservoir damage by each of a plurality of factors, determine a characteristic parameter characterizing reservoir damage by each of the plurality of factors, wherein the reservoir is located in a preset region of a well to be diagnosed; and a second parameter determination device configured to determine an effective characteristic parameter characterizing the damage extent of the reservoir based on the characteristic parameter characterizing reservoir damage by each of the plurality of factors, wherein the well to be diagnosed is a water injection well, a polymer injection well or an oil production well, the plurality of factors comprise extraneous solid-phase particles, the system further configured to determine, when the well to be diagnosed is in a drilling stage, a spatio-temporal evolution simulation equation of reservoir damage by the extraneous solid-phase particles by the following modeling process:

determining a velocity of the fluid containing flowing particles in the reservoir;

establishing a mass balance equation between the fluid and deposited particles on rock in the reservoir, based on a convection parameter and a diffusion parameter of the fluid;

establishing a connection condition equation between a volume concentration of the deposited particles and a volume concentration of the fluid, based on the convection parameter and the diffusion parameter of the fluid; and determining the spatio-temporal evolution simulation equation of reservoir damage by the particles according to a relationship between a mass fraction of the flowing particles and a volume concentration of the flowing particles, the velocity of the fluid, the mass balance equation and the connection condition equation, wherein the spatio-temporal evolution simulation equation is used to simulate a four-dimensional spatio-temporal evolution process of characteristics of reservoir damage caused by the extraneous solid-phase particles.

* * * * *